United States Patent
Apgar et al.

(10) Patent No.: US 9,868,733 B2
(45) Date of Patent: *Jan. 16, 2018

(54) AZABENZIMIDAZOLE TETRAHYDROFURAN DERIVATIVES

(71) Applicant: Merck Sharp & Dohme Corp., Rahway, NJ (US)

(72) Inventors: James M. Apgar, Highland, NJ (US); Tesfaye Biftu, Freehold, NJ (US); Ping Chen, Edison, NJ (US); Danqing Feng, Green Brook, NJ (US); Jacqueline D. Hicks, Scotch Plains, NJ (US); Ahmet Kekec, Jersey City, NJ (US); Kenneth J. Leavitt, Mount Laurel, NJ (US); Bing Li, Towaco, NJ (US); Iyassu Sebhat, Jersey City, NJ (US); Xiaoxia Qian, New York, NY (US); Lan Wei, Berkeley Heights, NJ (US); Robert R. Wilkening, Maplewood, NJ (US); Zhicai Wu, Montvale, NJ (US); Ashok Arasappan, Bridgewater, NJ (US)

(73) Assignee: Merck Sharp & Dohme Corp., Rahway, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 14/419,825

(22) PCT Filed: Aug. 19, 2013

(86) PCT No.: PCT/US2013/055531
§ 371 (c)(1),
(2) Date: Feb. 5, 2015

(87) PCT Pub. No.: WO2014/031517
PCT Pub. Date: Feb. 27, 2014

(65) Prior Publication Data
US 2015/0203487 A1   Jul. 23, 2015

Related U.S. Application Data

(60) Provisional application No. 61/692,021, filed on Aug. 22, 2012.

(51) Int. Cl.
| | | |
|---|---|---|
| C07D 471/04 | (2006.01) | |
| C07D 519/00 | (2006.01) | |
| A61K 31/366 | (2006.01) | |
| A61K 31/397 | (2006.01) | |
| A61K 31/4985 | (2006.01) | |
| A61K 31/19 | (2006.01) | |
| A61K 31/437 | (2006.01) | |
| A61K 31/444 | (2006.01) | |
| A61K 31/496 | (2006.01) | |
| A61K 31/5377 | (2006.01) | |
| C07C 53/18 | (2006.01) | |

(52) U.S. Cl.
CPC ............ *C07D 471/04* (2013.01); *A61K 31/19* (2013.01); *A61K 31/366* (2013.01); *A61K 31/397* (2013.01); *A61K 31/437* (2013.01); *A61K 31/444* (2013.01); *A61K 31/496* (2013.01); *A61K 31/4985* (2013.01); *A61K 31/5377* (2013.01); *C07C 53/18* (2013.01); *C07D 519/00* (2013.01)

(58) Field of Classification Search
CPC .......................... C07D 519/00; C07D 471/04
USPC .......................................... 546/118; 514/303
See application file for complete search history.

(56) References Cited

U.S. PATENT DOCUMENTS

| | | | |
|---|---|---|---|
| 6,312,662 B1 | 11/2001 | Erion et al. | |
| 6,489,476 B1 | 12/2002 | Dang et al. | |
| 8,796,258 B2 * | 8/2014 | Anand | A61K 31/5377 514/210.21 |
| 2005/0038068 A1 | 2/2005 | Iyengar et al. | |
| 2005/0090660 A1 | 4/2005 | Watanabe et al. | |
| 2005/0148643 A1 | 7/2005 | Rui et al. | |
| 2006/0287356 A1 | 12/2006 | Iyengar et al. | |
| 2007/0015665 A1 | 1/2007 | Potluri et al. | |
| 2007/0032529 A1 | 2/2007 | Takagi et al. | |
| 2011/0195964 A1 | 8/2011 | Dang et al. | |
| 2011/0218174 A1 | 9/2011 | Bao et al. | |

FOREIGN PATENT DOCUMENTS

| | | |
|---|---|---|
| CA | 2811025 A1 | 3/2012 |
| DE | 3316095 A1 | 5/1983 |
| EP | 0120403 A2 | 10/1984 |
| EP | 120403 A3 | 10/1984 |
| EP | 0126030 A2 | 11/1984 |
| EP | 126030 A3 | 11/1984 |
| EP | 128862 A3 | 12/1984 |
| EP | 129506 A3 | 12/1984 |

(Continued)

OTHER PUBLICATIONS

Ogura Haruo et al, 1978, Sci. Pharm. Si, pp. 221 to 228.*

(Continued)

*Primary Examiner* — Rita J Desai
(74) *Attorney, Agent, or Firm* — Baerbel R. Brown; Catherine D. Fitch

(57) ABSTRACT

Novel compounds of the structural formula (I) are activators of AMP-protein kinase and may be useful in the treatment, prevention and suppression of diseases mediated by the AMPK-activated protein kinase. The compounds of the present invention may be useful in the treatment of Type 2 diabetes, hyperglycemia, metabolic syndrome, obesity, hypercholesterolemia, and hypertension.

(I)

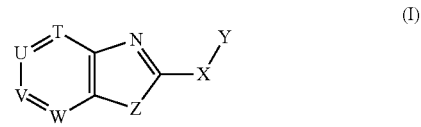

15 Claims, No Drawings

(56) References Cited

FOREIGN PATENT DOCUMENTS

| | | |
|---|---|---|
| EP | 0129506 B1 | 12/1984 |
| JP | 6298731 | 10/1994 |
| WO | WO9307124 A1 | 4/1993 |
| WO | WO1995029897 A1 | 11/1995 |
| WO | WO1998039342 A1 | 9/1998 |
| WO | WO1998039343 A1 | 9/1998 |
| WO | WO2000003997 A1 | 1/2000 |
| WO | WO2000014095 A1 | 3/2000 |
| WO | WO2001053272 A1 | 7/2001 |
| WO | WO2001053291 A1 | 7/2001 |
| WO | WO2002040019 A1 | 5/2002 |
| WO | WO2002092575 A1 | 11/2002 |
| WO | WO2003018061 A1 | 3/2003 |
| WO | WO2005002520 A2 | 1/2005 |
| WO | WO2005002520 A3 | 1/2005 |
| WO | WO05020892 A3 | 3/2005 |
| WO | WO2005018672 A1 | 3/2005 |
| WO | WO2005020892 A2 | 3/2005 |
| WO | WO005051298 A2 | 6/2005 |
| WO | WO05051298 A3 | 6/2005 |
| WO | WO2005051298 A2 | 6/2005 |
| WO | WO06094209 A3 | 9/2006 |
| WO | WO2006094209 A2 | 9/2006 |
| WO | WO2008006432 A1 | 1/2008 |
| WO | WO2010036613 A1 | 4/2010 |
| WO | WO2010047982 A1 | 4/2010 |
| WO | WO2010051176 A1 | 5/2010 |
| WO | WO2010051206 A1 | 5/2010 |
| WO | 2011/106273 * | 9/2011 |
| WO | WO2011106273 A1 | 9/2011 |
| WO | WO2012116145 A1 | 8/2012 |
| WO | WO2014031441 A1 | 2/2014 |
| WO | WO2014031445 A1 | 2/2014 |
| WO | WO2014031465 A1 | 2/2014 |
| WO | WO2014031468 A1 | 2/2014 |
| WO | WO2014031515 A1 | 2/2014 |
| WO | WO2014031517 A1 | 2/2014 |
| WO | WO2012033149 A1 | 3/2015 |

OTHER PUBLICATIONS

Caplus English Abstract DN157:410294 English caplus abstract WO 2012116145 Anand Rajan et al.*

Bergeron, R. et al., Effect of 5-Aminoimidazole-4-Caroboxamide-1-B-D-Ribofuranoside Infusion on In Vivo Glucose and Lipid Metabolism in Lean and Obese Zucker Rats, Diabetes, 2001, p. 1076-1082, vol. 50.

Blazquez, C. et al., The AMP-Activated Protein Kinase Is Involved in the Reulation of Ketone Body Production by Astrocytes, Journal of Neurochemistry, 1999, p. 1674-1682, vol. 73.

Buhl. E. S. et al., Long-Term AICAR Administration Reduces Metabolic Disturbances and Lowers Blood Pressure in Rats Displaying Features of the Insulin Resistance Syndrome, Diabetes, 2002, p. 2199-2206, vol. 51.

Carling, D. et al., A common bicyclic protein kinase cascade inactivates the regulatory enzymes of fatty acid and cholesterol biosynthesis, FEB, 1987, p. 217-222, vol. 223, No. 2.

Chen, Z, P. et al., AMP-activated protein kinase phosphorylation of endothelial NO synthase, FEBS Letters, 1999, p. 285-289, vol. 443.

Halseth, A. E. et al., Acute and chronic treatment of ob/ob and db/db mice with AICAR decreases blood glucose concentrations, Biochemical and Biophysical Research Communications, 2002, p. 798-805, vol. 294.

Minokoshi, Y. et al., Leptin stimulates fatty-acid oxidation by activating AMP-activated protein kinase, Nature, 2002, p. 339-, vol. 415.

Mu, J. et al., A Role for AMP-Activated Protein Kinase in Contraction- and Hypoxia-Regulated Glucose Transport in Skeletal Muscle, Molecular Cell, 2001, p. 1085-1094, vol. 7.

Musi, N. et al., Metofrmin Increases AMP-Activated Protein Kinase Activity in Skeletal Muscle of Subjects With Type 2 Diabetes, Diabetes, 2002, p. 2074-2081, vol. 51.

Song, X. M. et al., 5-Aminoimidazole-4-carboxamide ribonucleoside treatment improve glucose homeostasis in insulin-resistant diabetic (ob/ob) mice, Diabetologia, 2002, p. 56-65, vol. 45.

Zhou, G. et al., Role of AMP-activated protein kinase in mechanism of metformin action, The Journal of Clinical Investigation, 2001, p. 1167-1174, vol. 108, No. 8.

Zhou, M. et al., UCP-3 expression in skeletal muscle: effects of exercise, hypoxia, and AMP-activated protein kinase, Am. J. Physiol Endocrinol Metab, 2000, p. E622-E629, vol. 279.

Ikehara, M. et al, Studies of Nuclieosides and Nucleotides-Liv Purine Cyclonucleosides-19. Further Investigations on the Cleavage of the 8,2-O-Anhydro Linkage. A New Synthesis of 9-B-D-Arabinofuranosyladenine, Tetrohedron, 1972, p. 3695-3704, vol. 28.

Shuman, D. A. et al, Synthesis and Biological Activity of Certain 8-Mercaptopurine and 6-Mercaptopyrimidine S-Nucleosides, J. Med. Chem, 1969, p. 663-657, vol. 12, No. 4.

* cited by examiner

AZABENZIMIDAZOLE TETRAHYDROFURAN DERIVATIVES

CROSS-REFERENCE TO RELATED APPLICATIONS

This application is a U.S. National Phase application under 35 U.S.C. §371 of PCT Application No. PCT/US2013/055531, filed on Aug. 19, 2013, which claims priority from and the benefit of U.S. Provisional Application No. 61/692,021, filed Aug. 22, 2012.

BACKGROUND OF THE INVENTION

Diabetes is characterized by elevated levels of plasma glucose (hyperglycemia) in the fasting state or after administration of glucose during an oral glucose tolerance test. In Type 1 diabetes, or insulin-dependent diabetes mellitus (IDDM), patients produce little or no insulin, the hormone which regulates glucose utilization. In Type 2 diabetes, or noninsulin-dependent diabetes mellitus (NIDDM), insulin is still produced by islet cells in the pancreas. Patients with Type 2 diabetes have a resistance to the effects of insulin in stimulating glucose and lipid metabolism in the main insulin-sensitive tissues, including muscle, liver and adipose tissues. These patients often have normal levels of insulin, and may have hyperinsulinemia (elevated plasma insulin levels), as they compensate for the reduced effectiveness of insulin by secreting increased amounts of insulin (Polonsky, Int. J. Obes. Relat. Metab. Disord. 24 Suppl 2:S29-31, 2000). Insulin resistance is not primarily caused by a diminished number of insulin receptors but rather by a post-insulin receptor binding defect that is not yet completely understood. This lack of responsiveness to insulin results in insufficient insulin-mediated activation of uptake, oxidation and storage of glucose in muscle, and inadequate insulin-mediated repression of lipolysis in adipose tissue and of glucose production and secretion in the liver. Eventually, a patient may be become diabetic due to the inability to properly compensate for insulin resistance. In humans, the beta cells within the pancreatic islets initially compensate for insulin resistance by increasing insulin output. The onset of Type 2 diabetes due to insufficient increases (or actual declines) in beta cell mass is apparently due to increased beta cell apoptosis relative to non-diabetic insulin resistant individuals (Butler et al., Diabetes 52:102-110, 2003).

Persistent or uncontrolled hyperglycemia is associated with increased and premature morbidity and mortality. Often abnormal glucose homeostasis is associated both directly and indirectly with obesity, hypertension, and alterations of the lipid, lipoprotein and apolipoprotein metabolism, as well as other metabolic and hemodynamic disease. Patients with Type 2 diabetes mellitus have a significantly increased risk of macrovascular and microvascular complications, including atherosclerosis, coronary heart disease, stroke, peripheral vascular disease, hypertension, nephropathy, neuropathy, and retinopathy. Therefore, effective therapeutic control of glucose homeostasis, lipid metabolism, obesity, and hypertension are critically important in the clinical management and treatment of diabetes mellitus.

Patients who have insulin resistance often exhibit several symptoms that together are referred to as Syndrome X or Metabolic Syndrome. According to one widely used definition, a patient having Metabolic Syndrome is characterized as having three or more symptoms selected from the following group of five symptoms: (1) abdominal obesity; (2) hypertriglyceridemia; (3) low high-density lipoprotein cholesterol (HDL); (4) high blood pressure; and (5) elevated fasting glucose, which may be in the range characteristic of Type 2 diabetes if the patient is also diabetic. Each of these symptoms is defined clinically in the Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. Patients with Metabolic Syndrome, whether or not they have or develop overt diabetes mellitus, have an increased risk of developing the macrovascular and microvascular complications that occur with Type 2 diabetes, such as atherosclerosis and coronary heart disease.

There are several available treatments for Type 2 diabetes, each of which has its own limitations and potential risks. Physical exercise and a reduction in dietary intake of calories often dramatically improve the diabetic condition and are the usual recommended first-line treatment of Type 2 diabetes and of pre-diabetic conditions associated with insulin resistance. Compliance with this treatment is generally very poor because of well-entrenched sedentary lifestyles and excess food consumption, especially of foods containing high amounts of fat and carbohydrates. Pharmacologic treatments for diabetes have largely focused on three areas of pathophysiology: (1) hepatic glucose production (biguanides, such as phenformin and metformin), (2) insulin resistance (PPAR agonists, such as rosiglitazone, troglitazone, engliazone, balaglitazone, MCC-555, netoglitazone, T-131, LY-300512, LY-818 and pioglitazone), (3) insulin secretion (sulfonylureas, such as tolbutamide, glipizide and glimipiride); (4) incretin hormone mimetics (GLP-1 derivatives and analogs, such as exenatide and liraglutide); and (5) inhibitors of incretin hormone degradation (DPP-4 inhibitors, such as sitagliptin).

Many of the current treatments for diabetes have unwanted side effects. Phenformin and metformin can induce lactic acidosis, nausea/vomiting, and diarrhea. Metformin has a lower risk of side effects than phenformin and is widely prescribed for the treatment of Type 2 diabetes. The currently marketed PPAR gamma agonists are modestly effective in reducing plasma glucose and hemoglobinA1C, and do not greatly improve lipid metabolism or the lipid profile. Sulfonylureas and related insulin secretagogues can cause insulin secretion even if the glucose level is low, resulting in hypoglycemia, which can be fatal in severe cases. The administration of insulin secretagogues must therefore be carefully controlled. There remains a need for treatments for diabetes that work by novel mechanisms of action and that exhibit fewer side effects.

AMP-activated protein kinase (AMPK) has been identified as a regulator of carbohydrate and fatty acid metabolism that helps maintain energy balance in response to environmental and nutritional stress. There is evidence that activation of AMPK results in a number of beneficial effects on lipid and glucose metabolism by reducing glucogenesis and de novo lipogenesis (fatty acid and cholesterol synthesis), and by increasing fatty acid oxidation and skeletal muscle glucose uptake. Inhibition of ACC, by phosphorylation by AMPK, leads to a decrease in fatty acid synthesis and to an increase in fatty acid oxidation, while inhibition of HMG-CoA reductase, by phosphorylation by AMPK, leads to a decrease in cholesterol synthesis (Carling, D. et. al., FEBS Letters 223:217 (1987)).

In the liver, AMPK activation results in a decrease in fatty acid and cholesterol synthesis, inhibiting hepatic glucose production and increasing fatty acid oxidation. It has been shown that AMP-activated protein kinase regulates triacylglycerol synthesis and fatty acid oxidation in liver and muscle via glycerol-3-phosphate acyltransferase (Muoio, D. M. et. al., Biochem. J. 338:783 (1999)). Another substrate of AMPK, hepatocyte nuclear factor-4α, has been shown to be involved in type-1 maturity onset diabetes (Leclerc, I. et. al., Diabetes 50:1515 (2001)). Additional processes believed to be regulated through AMPK activation include the stimulation of glucose transport in skeletal muscle and the regulation of key genes in fatty acid and glucose metabolism in the liver (Hardie, D. G. and Hawley, S. A., Bioessays 23: 1112 (2001), Kemp, B. E. et. al., Biochem. Soc. Transactions 31:162 (2003), Musi, N. and Goodyear, L. J. Current Drug Targets-Immune, Endocrine and Metabolic Disorders 2:119 (2002); Lochhead, P. A. et. al., Diabetes 49:896 (2000); and Zhou, G. et. al., J. of Clin. Invest. 108: 1167 (2001).

In vivo studies have demonstrated the following beneficial effects of both acute and chronic administration of AICAR, an AMPK activator, in rodent models of obesity and type 2 diabetes: 1) an improvement in glucose homeostasis in insulin-resistant diabetic (ob/ob) mice; 2) a decrease in blood glucose concentrations in ob/ob and db/db mice and a blood glucose reduction of 35% following 8 weeks of administration; and 3) a reduction in metabolic disturbances and a reduction of blood pressure in rats displaying characteristics of insulin resistance syndrome (Bergeron, R. et. al., Diabetes 50:1076 (2001); Song, S. M. et. al., Diabetologia 45:56 (2002); Halseth, A. E. et. al., Biochem. and Biophys. Res. Comm. 294:798 (2002); and Buhl, E. S. et. al., Diabetes 51: 2199 (2002)). A further study of 7 week AICAR administration in obese Zucker (fa/fa) rats lead to a reduction in plasma triglycerides and free fatty acids; an increase in HDL cholesterol; and a normalization of glucose metabolism as assessed by an oral glucose tolerance test (Minokoshi, Y. et. al., Nature 415: 339 (2002)). Expression of dominant negative AMPK in skeletal muscle of transgenic mice has demonstrated that the AICAR effect on stimulation of glucose transport is dependent on AMPK activation (Mu, J. et. al., Molecular Cell 7: 1085 (2001)).

Recent data also suggest that AMPK activation is involved in the glucose and lipid-lowering effects of the anti-diabetic drug metformin. It has been shown that the diabetes drug metformin can activate AMPK in vivo at high concentrations (Zhou, G. et. al., J. of Clin. Invest. 108: 1167 (2001); Musi, N. et. al. Diabetes 51: 2074 (2002)).

Based on these studies, it is expected that the in vivo activation of AMPK in the liver may result in the reduction of hepatic glucose output, an improvement in overall glucose homeostasis, a decrease in fatty acid and cholesterol synthesis, and an increase in fatty acid oxidation. Stimulation of AMPK in skeletal muscle is expected to result in an increase in glucose uptake and fatty acid oxidation with resulting improvement of glucose homeostasis, and an improvement in insulin action. Finally, the resulting increase in energy expenditure may lead to a decrease in body weight. The lowering of blood pressure has also been reported to be a consequence of AMPK activation.

Increased fatty acid synthesis is a characteristic of many tumor cells, therefore decreasing the synthesis of fatty acids via AMPK activation may also be useful as a cancer therapy. Activation of AMPK may also be useful to treat ischemic events in the brain (Blazquez, C. et. al., J. Neurochem. 73: 1674 (1999)); to prevent damage from reactive oxygen species (Zhou, M. et. al., Am. J. Physiol. Endocrinol. Metab. 279: E622 (2000)); and to improve local circulatory systems (Chen, Z.-P., et. al. AMP-activated protein kinase phosphorylation of endothelial NO synthase. FEBS Letters 443: 285 (1999)).

Compounds that activate AMPK may be useful to treat type 2 diabetes mellitus, obesity, hypertension, dyslipidemia, cancer, and metabolic syndrome, as well as cardiovascular diseases, such as myocardial infarction and stroke, by improving glucose and lipid metabolism and by reducing body weight. There is a need for potent AMPK activators that have pharmacokinetic and pharmacodynamic properties suitable for use as human pharmaceuticals.

Benzimidazole compounds are disclosed in WO 2010/051206; WO 2010/051176; WO 2010/047982; WO 2010/036613; WO 93/07124; WO 95/29897; WO 98/39342; WO 98/39343; WO 00/03997; WO 00/14095; WO 01/53272; WO 01/53291; WO 02/092575; WO 02/40019; WO 03/018061; WO 05/002520; WO 05/018672; WO 06/094209; U.S. Pat. No. 6,312,662; U.S. Pat. No. 6,489,476; US 2005/0148643; DE 3 316 095; JP 6 298 731; EP 0 126 030; EP 0 128 862; EP 0 129 506; and EP 0 120 403. AMPK activators are disclosed in WO 08/006432; WO 05/051298; WO 05/020892; US 2007/015665; US 2007/032529; US 2006/287356; and US 2005/038068. Azabenzimidazole compounds are disclosed in WO 2012/33149.

SUMMARY OF THE INVENTION

The present invention is concerned with novel benzimidazole derivatives of structural Formula I:

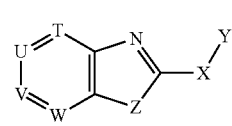

(I)

and pharmaceutically acceptable salts thereof. The compounds of structural formula I, and salts thereof, are activators of AMP-activated protein kinase (AMPK) and are useful in the treatment, prevention and suppression of diseases, disorders and conditions mediated by activation of AMP-activated protein kinase. As AMPK activators, the compounds of structural formula I may be useful to treat Type 2 diabetes mellitus, insulin resistance, hyperglycemia, dyslipidemia, lipid disorders, obesity, hypertension, Metabolic Syndrome and atherosclerosis.

The present invention also relates to pharmaceutical compositions comprising the compounds of the present invention and a pharmaceutically acceptable carrier. The present invention also relates to methods for the treatment, control or prevention of disorders, diseases, and conditions that are responsive to activation of AMP-activated protein kinase in a subject in need thereof by administering the compounds and pharmaceutical compositions of the present invention. The present invention also relates to the use of compounds of the present invention for manufacture of a medicament useful in treating diseases, disorders and conditions are responsive to the activation of AMP-activated protein kinase. The present invention is also concerned with treatment of these diseases, disorders and conditions by administering the compounds of the present invention in combination with a therapeutically effective amount of another agent useful to treat the disease, disorder and condition. The invention is further concerned with processes for preparing the compounds of this invention.

DETAILED DESCRIPTION OF THE INVENTION

The present invention is concerned with novel compounds of structural Formula I:

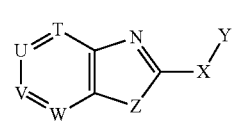

(I)

or a pharmaceutically acceptable salt thereof, wherein:
T is selected from the group consisting of: $CR^3$, N and N-oxide;

U is selected from the group consisting of: $CR^1$, N and N-oxide;
V is selected from the group consisting of: $CR^2$, N and N-oxide;
W is selected from the group consisting of: $CR^4$, N and N-oxide,
provided that at least one of T, U, V and W is N or N-oxide;
X is selected from:
  (1) —$CH_2$—,
  (2) —CHF—,
  (3) —$CF_2$—,
  (4) —S—,
  (5) —O—,
  (6) —O—$CH_2$—,
  (7) —O—$CH_2CH_2$—,
  (8) —NH—,
  (9) —C(O)—,
  (10) —NHC(O)—,
  (11) —C(O)NH—,
  (12) —$NHSO_2$—,
  (13) —$SO_2NH$—, and
  (14) —$CO_2$—,
wherein each $CH_2$ is unsubstituted or substituted with 1 or 2 substituents selected from: hydroxy, halogen, $NH_2$, $C_{1-6}$alkyl, $CO_2H$, $CO_2C_{1-6}$alkyl, $COC_{1-6}$alkyl, phenyl and —$CH_2$phenyl, and wherein each NH is unsubstituted or substituted with 1 substituent selected from: $C_{1-6}$alkyl, $CO_2H$, $CO_2C_{1-6}$alkyl, $COC_{1-6}$alkyl, phenyl and —$CH_2$phenyl;
Y is selected from:

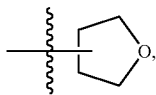

wherein Y is unsubstituted or substituted with 1, 2, 3, 4 or 5 substituents selected from $R^b$;
Z is selected from:
  (1) $NR^5$,
  (2) —S—, and
  (3) —O—;
each $R^1$ and $R^2$ is independently selected from:
  (1) hydrogen,
  (2) halogen,
  (3) CN,
  (4) $CF_3$,
  (5) —$C_{1-6}$alkyl,
  (6) —$C_{2-6}$alkenyl,
  (7) —$C_{2-6}$alkynyl,
  (8) —$(CH_2)_pC_{3-10}$cycloalkyl,
  (9) —$(CH_2)_pC_{3-7}$cycloalkyl-aryl,
  (10) —$(CH_2)_pC_{3-7}$cycloalkyl-heteroaryl,
  (11) —$(CH_2)_pC_{4-10}$cycloalkenyl,
  (12) —$(CH_2)_pC_{4-7}$cycloalkenyl-aryl,
  (13) —$(CH_2)_pC_{4-7}$cycloalkenyl-heteroaryl,
  (14) —$(CH_2)_pC_{2-10}$cycloheteroalkyl,
  (15) —$(CH_2)_pC_{2-10}$cycloheteroalkenyl,
  (16) —$(CH_2)_p$aryl,
  (17) —$(CH_2)_p$aryl-$C_{1-8}$alkyl,
  (18) —$(CH_2)_p$aryl-$C_{2-8}$alkenyl,
  (19) —$(CH_2)_p$aryl-$C_{2-8}$alkynyl-$C_{1-8}$alkyl,
  (20) —$(CH_2)_p$aryl-$C_{2-8}$alkynyl-$C_{3-7}$cycloalkyl,
  (21) —$(CH_2)_p$aryl-$C_{2-8}$alkynyl-$C_{3-7}$cycloalkenyl,
  (22) —$(CH_2)_p$aryl-$C_{2-8}$alkynyl-$C_{2-10}$cycloheteroalkyl,
  (23) —$(CH_2)_p$aryl-$C_{2-8}$alkynyl-$C_{2-10}$cycloheteroalkenyl,
  (24) —$(CH_2)_p$aryl-$C_{2-8}$alkynyl-aryl,
  (25) —$(CH_2)_p$aryl-$C_{2-8}$alkynyl-heteroaryl,
  (26) —$(CH_2)_p$aryl-$C_{3-7}$cycloalkyl,
  (27) —$(CH_2)_p$aryl-$C_{2-10}$cycloheteroalkyl,
  (28) —$(CH_2)_p$aryl-$C_{2-10}$cycloheteroalkenyl,
  (29) —$(CH_2)_p$aryl-aryl,
  (30) —$(CH_2)_p$aryl-heteroaryl,
  (31) —$(CH_2)_p$heteroaryl,
  (32) —$(CH_2)_p$heteroaryl-$C_{3-7}$cycloalkyl,
  (33) —$(CH_2)_p$heteroaryl-$C_{2-10}$cycloheteroalkyl,
  (34) —$(CH_2)_p$heteroaryl-$C_{2-10}$cycloheteroalkenyl,
  (35) —$(CH_2)_p$heteroaryl-aryl,
  (36) —$(CH_2)_p$heteroaryl-heteroaryl,
  (37) —$C_{2-6}$alkenyl-alkyl,
  (38) —$C_{2-6}$alkenyl-aryl,
  (39) —$C_{2-6}$alkenyl-heteroaryl,
  (40) —$C_{2-6}$alkenyl-$C_{3-7}$cycloalkyl,
  (41) —$C_{2-6}$alkenyl-$C_{3-7}$cycloalkenyl,
  (42) —$C_{2-6}$alkenyl-$C_{2-7}$cycloheteroalkyl,
  (43) —$C_{2-6}$alkenyl-$C_{2-7}$cycloheteroalkenyl,
  (44) —$C_{2-6}$ alkynyl-$(CH_2)_{1-3}$—O-aryl,
  (45) —$C_{2-6}$alkynyl-alkyl,
  (46) —$C_{2-6}$alkynyl-aryl,
  (47) —$C_{2-6}$alkynyl-heteroaryl,
  (48) —$C_{2-6}$alkynyl-$C_{3-7}$cycloalkyl,
  (49) —$C_{2-6}$alkynyl-$C_{3-7}$cycloalkenyl,
  (50) —$C_{2-6}$alkynyl-$C_{2-7}$cycloheteroalkyl,
  (51) —$C_{2-6}$alkynyl-$C_{2-7}$cycloheteroalkenyl, and
  (52) —C(O)NH—$(CH_2)_{0-3}$phenyl,
wherein each $CH_2$ is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}$alkyl$)_2$, wherein each alkyl, alkenyl, alkynyl, cycloalkyl, cycloalkenyl, cycloheteroalkyl, cycloheteroalkenyl, phenyl, aryl and heteroaryl is unsubstituted or substituted with 1, 2, 3 or 4 substituents independently selected from $R^a$;
provided that at least one of and only one of $R^1$ and $R^2$ is selected from the group consisting of: hydrogen, halogen, —CN, —$CF_3$, —$C_{1-6}$alkyl, —$C_{2-6}$alkenyl and —$C_{2-6}$alkynyl;
$R^3$ and $R^4$ are each independently selected from:
  (1) hydrogen,
  (2) halogen,
  (3) —$C_{1-6}$alkyl,
  (4) —$C_{2-6}$alkenyl,
  (5) —$C_{2-6}$alkynyl,
  (6) —$C_{3-10}$cycloalkyl,
  (7) —$C_{3-10}$cycloalkenyl,
  (8) aryl,
  (9) heteroaryl,
  (10) —CN,
  (11) —$CF_3$,
  (12) —OH,
  (13) —$OC_{1-6}$alkyl,
  (14) —$NH_2$,
  (15) —$NHC_{1-6}$alkyl,
  (16) —$N(C_{1-6}$alkyl$)_2$,
  (17) —$SC_{1-6}$alkyl,
  (18) —$SOC_{1-6}$alkyl,
  (19) —$SO_2C_{1-6}$alkyl,
  (20) —$NHSO_2C_{1-6}$alkyl,
  (21) —$NHC(O)C_{1-6}$alkyl,
  (22) —$SO_2NHC_{1-6}$alkyl, and
  (23) —$C(O)NHC_{1-6}$alkyl;
$R^5$ is selected from:
  (1) hydrogen,
  (2) —$C_{1-6}$alkyl, (3) —$C_{1-6}$alkenyl,
(4) —$(CH_2)_u$OH,
(5) —$CH_2CO_2H$, and
(6) —$CH_2CO_2C_{1-6}$alkyl;

each $R^a$ is independently selected from the group consisting of:
(1) —$(CH_2)_m$-halogen,
(2) oxo,
(3) —$(CH_2)_m$OH,
(4) —$(CH_2)_mN(R^j)_2$,
(5) —$(CH_2)_mNO_2$,
(6) —$(CH_2)_mCN$,
(7) —$C_{1-6}$alkyl,
(8) —$(CH_2)_mCF_3$,
(9) —$(CH_2)_mOCF_3$,
(10) —O—$(CH_2)_m$—$OC_{1-6}$ alkyl,
(11) —$(CH_2)_mN(R^j)C(O)R^f$,
(12) —$(CH_2)_mN(R^j)CO_2R^f$,
(13) —$(CH_2)_mC(=N—OH)N(R^j)_2$,
(14) —$(CH_2)_mOC_{1-6}$alkyl,
(15) —$(CH_2)_mO$—$(CH_2)_m$—$C_{3-7}$cycloalkyl,
(16) —$(CH_2)_mO$—$(CH_2)_m$—$C_{2-7}$cycloheteroalkyl,
(17) —$(CH_2)_mO$—$(CH_2)_m$-aryl,
(18) —$(CH_2)_mO$—$(CH_2)_m$-heteroaryl,
(19) —$(CH_2)_mSC_{1-6}$alkyl,
(20) —$(CH_2)_mS(O)C_{1-6}$alkyl,
(21) —$(CH_2)_mSO_2C_{1-6}$alkyl,
(22) —$(CH_2)_mSO_2(CH_2)_m$—$C_{3-7}$cycloalkyl,
(23) —$(CH_2)_mSO_2(CH_2)_m$—$C_{2-7}$cycloheteroalkyl,
(24) —$(CH_2)_mSO_2(CH_2)_m$-aryl,
(25) —$(CH_2)_mSO_2(CH_2)_m$-heteroaryl,
(26) —$(CH_2)_mSO_2NH_2$,
(27) —$(CH_2)_mSO_2NHC_{1-6}$alkyl,
(28) —$(CH_2)_mSO_2NHC_{3-7}$cycloalkyl,
(29) —$(CH_2)_mSO_2NHC_{2-7}$cycloheteroalkyl,
(30) —$(CH_2)_mSO_2NH$-aryl,
(31) —$(CH_2)_mSO_2NH$-heteroaryl,
(32) —$(CH_2)_mNHSO_2$—$C_{1-6}$alkyl,
(33) —$(CH_2)_mNHSO_2$—$C_{3-7}$cycloalkyl,
(34) —$(CH_2)_mNHSO_2$—$C_{2-7}$cycloheteroalkyl,
(35) —$(CH_2)_mNHSO_2$-aryl,
(36) —$(CH_2)_mNHSO_2NH$-heteroaryl,
(37) —$(CH_2)_mN(R^j)$—$C_{1-6}$alkyl,
(38) —$(CH_2)_mN(R^j)$—$C_{3-7}$cycloalkyl,
(39) —$(CH_2)_mN(R^j)$—$C_{2-7}$cycloheteroalkyl,
(40) —$(CH_2)_mN(R^j)$—$C_{2-7}$cycloheteroalkenyl,
(41) —$(CH_2)_mN(R^j)$-aryl,
(42) —$(CH_2)_mN(R^j)$-heteroaryl,
(43) —$(CH_2)_mC(O)R^f$,
(44) —$(CH_2)_mC(O)N(R^j)_2$,
(45) —$(CH_2)_mN(R^j)C(O)N(R^j)_2$,
(46) —$(CH_2)_mCO_2H$,
(47) —$(CH_2)_mOCOH$,
(48) —$(CH_2)_mCO_2R^f$,
(49) —$(CH_2)_mOCOR^f$,
(50) —$(CH_2)_mC_{3-7}$cycloalkyl,
(51) —$(CH_2)_mC_{3-7}$cycloalkenyl,
(52) —$(CH_2)_mC_{2-6}$cycloheteroalkyl,
(53) —$(CH_2)_mC_{2-6}$cycloheteroalkenyl,
(54) —$(CH_2)_m$aryl, and
(55) —$(CH_2)_m$heteroaryl, wherein each $CH_2$ is unsubstituted or substituted with 1 or 2 substituents selected from: oxo, —OH, —$(CH_2)_{1-3}$OH, —CN, —$NH_2$, —NH($C_{1-6}$alkyl), —N($C_{1-6}$alkyl)$_2$, oxo, —$C_{1-6}$alkyl, —$C_{1-6}$alkyl substituted with 1-5 OH, —$OC_{1-6}$ alkyl, halogen, —$CH_2F$, —$CHF_2$, —$CF_3$, —$CO_2H$, —$CO_2C_{1-6}$alkyl, —$C_{3-7}$cycloalkyl, phenyl, $CH_2$phenyl, heteroaryl and $CH_2$heteroaryl, and wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —OH, —$(CH_2)_{1-5}$OH, —$(CH_2)_{1-5}$CN, —CN, —$NH_2$, —NH($C_{1-6}$alkyl), —N($C_{1-6}$alkyl)$_2$, —$C_{1-6}$alkyl, —$C_{1-6}$alkyl substituted with 1-5 OH, —$OC_{1-6}$alkyl, halogen, —$CH_2F$, —$CHF_2$, —$CF_3$, —$(CH_2)_{1-5}CF_3$ optionally substituted with 1, 2 or 3 —OH, —$CO_2H$, —$CO_2C_{1-6}$alkyl, —$SO_2C_{1-6}$alkyl, —$C_{3-7}$cycloalkyl, phenyl, $CH_2$phenyl, heteroaryl and $CH_2$heteroaryl;

each $R^b$ is independently selected from:
(1) hydrogen,
(2) —$C_{1-6}$alkyl,
(3) —$C_{1-6}$alkenyl,
(4) —$(CH_2)nC_{3-10}$cycloalkyl,
(5) —$(CH_2)nC_{3-10}$cycloalkenyl,
(6) —$(CH_2)nC_{2-10}$cycloheteroalkyl,
(7) —$(CH_2)nC_{2-10}$cycloheteroalkenyl,
(8) —$(CH_2)n$aryl,
(9) —$(CH_2)n$heteroaryl,
(10) oxo,
(11) —$(CH_2)nCF_3$,
(12) —$(CH_2)nCN$,
(13) —$(CH_2)t$-halogen,
(14) —$(CH_2)s$-OH,
(15) —$(CH_2)_nNO_2$,
(16) —$(CH_2)_nNH_2$,
(17) —$(CH_2)_nNH(C_{1-6}$alkyl$)$,
(18) —$(CH_2)_nN(C_{1-6}$alkyl$)_2$,
(19) —$(CH_2)_nNHCO_2H$,
(20) —$(CH_2)nOC_{1-6}$alkyl,
(21) —$(CH_2)nOC_{1-6}$alkenyl,
(22) —$(CH_2)_nCOC_{1-6}$alkyl,
(23) —$(CH_2)_nCO_2H$,
(24) —$(CH_2)_nOCOH$,
(25) —$(CH_2)_nCO_2R^i$,
(26) —$(CH_2)_nOC(O)R^i$,
(27) —$(CH_2)_qC(O)N(R^e)_2$,
(28) —$(CH_2)_qCO_2N(R^e)_2$,
(29) —$(CH_2)_nC(O)(CH_2)_nN(R^g)_2$,
(30) —$(CH_2)_nOC(O)(CH_2)_nN(R^g)_2$,
(31) —$(CH_2)_nN(R^e)C(O)C_{1-6}$alkyl,
(32) —$(CH_2)_nN(R^e)SO_2R^i$,
(33) —$(CH_2)_nSO_2C_{1-6}$alkyl,
(34) —$(CH_2)_nSO_2N(R^e)R^g$,
(35) —$(CH_2)_nSO_2N(R^e)C(O)R^i$,
(36) —$(CH_2)_nSO_2N(R^e)CO_2R^i$,
(37) —$(CH_2)_nSO_2N(R^e)CON(R^g)_2$,
(38) —$(CH_2)_nC(O)N(R^e)SO_2R^i$,
(39) —$(CH_2)_nN(R^e)C(O)N(R^g)_2$,
(40) =N(OH), and
(41) =N($OC_{1-6}$alkyl), wherein each $CH_2$ is unsubstituted or substituted with 1 or 2 substituents selected from: —$C_{1-6}$alkyl, —OH, halogen and —$NH_2$ wherein each NH is unsubstituted or substituted with 1 substituent selected from $R^c$, and wherein each alkyl, cycloalkyl, cycloalkenyl, cycloheteroalkyl, cycloheteroalkenyl, aryl and heteroaryl is unsubstituted or substituted with 1, 2, 3 or 4 substituents selected from $R^c$, or wherein two $R^b$ substituents and the carbon to which they are attached may form a 3 to 6 membered cycloalkyl ring, a 3-6 membered cycloalkenyl ring, a 3-6 membered cycloheteroalkyl ring or a 3-6 membered cycloheteroalkenyl ring, wherein the ring is unsubstituted or substituted with 1, 2, 3 or 4 substituents selected from $R^c$;

each $R^c$ is independently selected from:
(1) halogen,
(2) oxo,
(3) —$(CH_2)_r$OH,
(4) —$(CH_2)_rN(R^e)_2$, (5) —(CH$_2$)$_r$CN,
(6) —C$_{1-6}$alkyl,
(7) —CF$_3$,
(8) —C$_{1-6}$alkyl-OH,
(9) —OCH$_2$OC$_{1-6}$alkyl,
(10) —(CH$_2$)$_r$OC$_{1-6}$alkyl,
(11) —OCH$_2$aryl,
(12) —(CH$_2$)$_r$SC$_{1-6}$alkyl,
(13) —(CH$_2$)$_r$C(O)R$^f$,
(14) —(CH$_2$)$_r$C(O)N(R$^e$)$_2$,
(15) —(CH$_2$)$_r$CO$_2$H,
(16) —(CH$_2$)$_r$CO$_2$R$^f$,
(17) —(CH$_2$)$_r$C$_{3-7}$cycloalkyl,
(18) —(CH$_2$)$_r$C$_{2-6}$cycloheteroalkyl,
(19) —(CH$_2$)$_r$aryl, and
(20) —(CH$_2$)$_r$heteroaryl, wherein each CH$_2$ is unsubstituted or substituted with 1 or 2 substituents selected from: oxo, —OH, —CN, —N(R$^h$)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl and heteroaryl, and wherein alkyl, cycloalkyl, cycloheteroalkyl, aryl and heteroaryl are unsubstituted or substituted with 1, 2, 3 or 4 substituents selected from: oxo, —OH, —CN, —N(R$^h$)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl and heteroaryl;

each R$^e$, R$^g$ and R$^h$ is independently selected from:
(1) hydrogen,
(2) —C$_{1-6}$alkyl, and
(3) —O—C$_{1-6}$alkyl,
wherein alkyl is unsubstituted or substituted with 1, 2, 3 or 4 substituents selected from: —OH, oxo, halogen, C$_{1-6}$alkyl, —OC$_{1-6}$alkyl, —NH$_2$, —NH(C$_{1-6}$alkyl), and —N(C$_{1-6}$alkyl)$_2$;

each R$^j$ is independently selected from:
(1) hydrogen,
(2) C$_{1-6}$alkyl,
(3) C$_{3-6}$cycloalkyl,
(4) —C(O)R$^i$,
(5) —CO$_2$R$^i$, and
(6) —SO$_2$R$^i$,
wherein alkyl and cycloalkyl are unsubstituted or substituted with 1, 2, 3 or 4 substituents selected from: —OH, oxo, halogen, C$_{1-6}$alkyl, —OC$_{1-6}$alkyl, —NH$_2$, —NH(C$_{1-6}$alkyl), and —N(C$_{1-6}$alkyl)$_2$;

each R$^f$ and R$^i$ is independently selected from:
(1) C$_{1-6}$alkyl,
(2) —(CH$_2$)$_r$C$_{4-7}$cycloalkyl,
(3) —(CH$_2$)$_r$C$_{4-7}$cycloalkenyl,
(4) —(CH$_2$)$_r$C$_{3-7}$cycloheteroalkyl,
(5) —(CH$_2$)$_r$C$_{3-7}$cycloheteroalkenyl,
(6) —(CH$_2$)$_r$aryl, and
(7) —(CH$_2$)$_r$heteroaryl,
wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl, and heteroaryl;

n is 0, 1, 2, 3 or 4;
m is 0, 1, 2, 3 or 4;
p is 0, 1, 2, or 3;
q is 0, 1, 2, 3 or 4;
r is 0, 1 or 2;
s is 0, 1, 2, 3 or 4; and
t is 0, 1, 2, 3 or 4, and
u is 0, 1, 2, 3 or 4.

In one embodiment of the present invention, T is selected from the group consisting of: CR$^3$, N and N-oxide; U is selected from the group consisting of: CR$^1$, N and N-oxide; V is selected from the group consisting of: CR$^2$, N and N-oxide; and W is selected from the group consisting of: CR$^4$, N and N-oxide, provided that at least one of T, U, V and W is N or N-oxide.

In another embodiment of the present invention, T is N; U is CR$^1$; V is CR$^2$; and W is CR$^4$. In a class of this embodiment, R$^2$ is halogen. In another class of this embodiment, R$^2$ is F or Cl. In another class of this embodiment, R$^2$ is F. In another class of this embodiment, R$^2$ is Cl.

In another embodiment of the present invention, T is selected from the group consisting of: —CR$^3$—, N, and N-oxide. In a class of this embodiment, T is —CR$^3$—. In another class of this embodiment, T is selected from the group consisting of: N, and N-oxide. In another class of this embodiment, T is N. In another class of this embodiment, T is N-oxide.

In another embodiment of the present invention, U is selected from the group consisting of: —CR$^1$—, N, and N-oxide. In a class of this embodiment, U is —CR$^1$—. In another class of this embodiment, U is selected from the group consisting of: N, and N-oxide. In another class of this embodiment, U is N. In another class of this embodiment, U is selected from the group consisting of: N-oxide.

In another embodiment of the present invention, V is selected from the group consisting of: —CR$^2$—, N, and N-oxide. In a class of this embodiment, V is —CR$^2$—. In another class of this embodiment, V is selected from the group consisting of: N, and N-oxide. In another class of this embodiment, V is N. In another class of this embodiment, V is N-oxide.

In another embodiment of the present invention, W is selected from the group consisting of: —CR$^4$—, N, and N-oxide. In a class of this embodiment, W is selected from the group consisting of: —CR$^4$—. In another class of this embodiment, W is selected from the group consisting of: N, and N-oxide. In another class of this embodiment, W is N. In another class of this embodiment, W is N-oxide.

In another embodiment of the present invention, one of T and W is N or N-oxide, U is CR$^1$ and V is CR$^2$, provided that if W is N or N-oxide then R$^1$ is selected from hydrogen, halogen, —CN, —CF$_3$, —C$_{1-6}$alkyl, —C$_{2-6}$alkenyl and —C$_{2-6}$alkynyl, and if T is N or N-oxide then R$^2$ is selected from hydrogen, halogen, —CN, —CF$_3$, —C$_{1-6}$alkyl, —C$_{2-6}$alkenyl and —C$_{2-6}$alkynyl.

In another embodiment of the present invention, one of T and W is N or N-oxide, U is CR$^1$ and V is CR$^2$, provided that if W is N or N-oxide then R$^1$ is halogen, and if T is N or N-oxide then R$^2$ is halogen.

In another embodiment of the present invention, T is N or N-oxide; U is —CR$^1$—; V is —CR$^2$—; and W is —CR$^4$—. In a class of this embodiment, T is N or N-oxide; U is —CR$^1$—; V is —CR$^2$—, wherein R$^2$ is halogen; and W is —CR$^4$—. In another class of this embodiment, T is N; U is —CR$^1$—; V is —CR$^2$—, wherein R$^2$ is halogen; and W is —CR$^4$—. In another class of this embodiment, T is N; U is —CR$^1$—; V is —CR$^2$—, wherein R$^2$ is halogen; and W is —CR$^4$—.

In another embodiment of the present invention, X is selected from: —CH$_2$—, —CHF—, —CF$_2$—, —S—, —O—, —O—CH$_2$—, —O—CH$_2$CH$_2$—, —NH—, —C(O)—, —NHC(O)—, —C(O)NH—, —NHSO$_2$—, —SO$_2$NH—, and —CO$_2$—, wherein each CH$_2$ is unsubstituted or substituted with 1 or 2 substituents selected from: hydroxy, halogen, NH$_2$, C$_{1-6}$alkyl, CO$_2$H, CO$_2$C$_{1-6}$alkyl, COC$_{1-6}$alkyl, phenyl and —CH$_2$phenyl, and wherein each NH is unsubstituted or substituted with 1 substituent selected from: C$_{1-6}$alkyl, CO$_2$H, CO$_2$C$_{1-6}$alkyl, COC$_{1-6}$alkyl, phenyl and —CH$_2$phenyl.

In another embodiment of the present invention, X is selected from: —S—, —O—, and —NH—. In another embodiment of the present invention, X is —O—. In another embodiment of the present invention, X is —S—. In another embodiment of the present invention, X is —NH—.

In another embodiment of the present invention, Y is selected from:

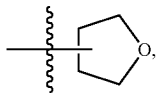

wherein Y is unsubstituted or substituted with 1, 2, 3, 4 or 5 substituents selected from $R^b$.

In another embodiment of the resent invention, Y is selected from:

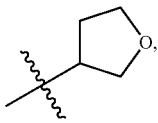

wherein Y is unsubstituted or substituted with 1, 2, 3, 4 or 5 substituents selected from $R^b$. In a class of this embodiment, Y is:

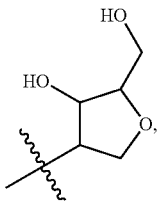

wherein Y is unsubstituted or substituted with 1, 2 or 3 substituents selected from $R^b$. In a class of this embodiment, Y is:

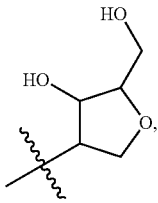

wherein Y is unsubstituted or substituted with 1 or 2 substituents selected from $R^b$. In another class of this embodiment, Y is:

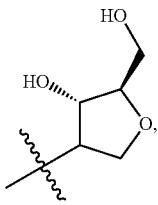

wherein Y is unsubstituted or substituted with 1, 2 or 3 substituents selected from $R^b$. In another class of this embodiment, Y is:

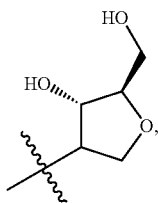

wherein Y is unsubstituted or substituted with 1 or 2 substituents selected from $R^b$.

In another embodiment of the present invention, Z is selected from: $NR^5$, —S—, and —O—. In a class of this embodiment, Z is $NR^5$. In another class of this embodiment, Z is —S—. In another class of this embodiment, Z is —O—.

In another embodiment of the present invention, each $R^1$ and $R^2$ is independently selected from: hydrogen, halogen, CN, $CF_3$, —$C_{1-6}$alkyl, —$C_{2-6}$alkenyl, —$C_{2-6}$alkynyl, —$(CH_2)_pC_{3-10}$cycloalkyl, —$(CH_2)_pC_{3-7}$cycloalkyl-aryl, —$(CH_2)_pC_{3-7}$cycloalkyl-heteroaryl, —$(CH_2)_pC_{4-10}$cycloalkenyl, —$(CH_2)_pC_{4-7}$cycloalkenyl-aryl, —$(CH_2)_pC_{4-7}$cycloalkenyl-heteroaryl, —$(CH_2)_pC_{2-10}$cycloheteroalkyl, —$(CH_2)_pC_{2-10}$cycloheteroalkenyl, —$(CH_2)_p$aryl, —$(CH_2)_p$aryl-$C_{1-8}$alkyl, —$(CH_2)_p$aryl-$C_{2-8}$alkenyl, —$(CH_2)_p$aryl-$C_{2-8}$alkynyl-$C_{1-8}$alkyl, —$(CH_2)_p$aryl-$C_{2-8}$alkynyl-$C_{3-7}$cycloalkyl, —$(CH_2)_p$aryl-$C_{2-8}$alkynyl-$C_{3-7}$cycloalkenyl, —$(CH_2)_p$aryl-$C_{2-8}$alkynyl-$C_{2-10}$cycloheteroalkyl, —$(CH_2)_p$aryl-$C_{2-8}$alkynyl-$C_{2-10}$cycloheteroalkenyl, —$(CH_2)_p$aryl-$C_{2-8}$alkynyl-aryl, —$(CH_2)_p$aryl-$C_{2-8}$alkynyl-heteroaryl, —$(CH_2)_p$aryl-$C_{3-7}$cycloalkyl, —$(CH_2)_p$aryl-$C_{2-10}$cycloheteroalkyl, —$(CH_2)_p$aryl-$C_{2-10}$cycloheteroalkenyl, —$(CH_2)_p$aryl-aryl, —$(CH_2)_p$aryl-heteroaryl, —$(CH_2)_p$heteroaryl, —$(CH_2)_p$heteroaryl-$C_{3-7}$cycloalkyl, —$(CH_2)_p$heteroaryl-$C_{2-10}$cycloheteroalkyl —$(CH_2)_p$heteroaryl-$C_{2-10}$cycloheteroalkenyl, —$(CH_2)_p$heteroaryl-aryl, —$(CH_2)_p$heteroaryl-heteroaryl, —$C_{2-6}$alkenyl-alkyl, —$C_{2-6}$alkenyl-aryl, —$C_{2-6}$alkenyl-heteroaryl, —$C_{2-6}$alkenyl-$C_{3-7}$cycloalkyl, —$C_{2-6}$alkenyl-$C_{3-7}$cycloalkenyl, —$C_{2-6}$alkenyl-$C_{2-7}$cycloheteroalkyl, —$C_{2-6}$alkenyl-$C_{2-7}$cycloheteroalkenyl, —$C_{2-6}$alkynyl-$(CH_2)_{1-3}$—O-aryl, —$C_{2-6}$alkynyl-alkyl, —$C_{2-6}$alkynyl-aryl, —$C_{2-6}$alkynyl-heteroaryl, —$C_{2-6}$alkynyl-$C_{3-7}$cycloalkyl, —$C_{2-6}$alkynyl-$C_{3-7}$cycloalkenyl, —$C_{2-6}$alkynyl-$C_{2-7}$cycloheteroalkyl, —$C_{2-6}$alkynyl-$C_{2-7}$cycloheteroalkenyl, and —$C(O)NH$—$(CH_2)_{0-3}$phenyl, wherein each $CH_2$ is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}alkyl)_2$, and wherein each alkyl, alkenyl, alkynyl, cycloalkyl, cycloalkenyl, cycloheteroalkyl, cycloheteroalkenyl, phenyl, aryl and heteroaryl is unsubstituted or substituted with 1, 2, 3 or 4 substituents independently selected from $R^a$, provided that at least one of and only one of $R^1$ and $R^2$ is selected from the group consisting of: hydrogen, halogen, —CN, —$CF_3$, —$C_{1-6}$alkyl, —$C_{2-6}$alkenyl and —$C_{2-6}$alkynyl. In a class of this embodiment, at least one of and only one of $R^1$ and $R^2$ is selected from halogen. In a subclass of this class, at least one of and only one of $R^1$ and $R^2$ is selected from: F and Cl.

In another embodiment of the present invention, each $R^1$ and $R^2$ is independently selected from: halogen, —$(CH_2)_p$aryl-aryl, and —$(CH_2)_p$aryl-heteroaryl, wherein each $CH_2$ is unsubstituted or substituted with 1 or 2 substituents selected from: halogen, $CF_3$, —OH, —$NH_2$, —$C_{1-6}$alkyl, —$OC_{1-6}$ alkyl, —NHC$_{1-6}$alkyl, and —N(C$_{1-6}$alkyl)$_2$, and wherein each cycloheteroalkyl, aryl and heteroaryl is unsubstituted or substituted with 1, 2, 3 or 4 substituents independently selected from R$^a$, provided that at least one of and only one of R$^1$ and R$^2$ is selected from the group consisting of: halogen.

In another embodiment of the present invention, each R$^1$ and R$^2$ is independently selected from: halogen, —(CH$_2$)$_p$aryl-aryl, and aryl-heteroaryl, wherein each cycloheteroalkyl, aryl and heteroaryl is unsubstituted or substituted with 1, 2, 3 or 4 substituents independently selected from R$^a$, provided that at least one of and only one of R$^1$ and R$^2$ is selected from halogen. In a subclass of this class, at least one of and only one of R$^1$ and R$^2$ is selected from: F and Cl. In another subclass of this class, at least one of and only one of R$^1$ and R$^2$ is Cl. In another embodiment of the present invention, each R$^1$ and R$^2$ is independently selected from: halogen, biphenyl, phenyl-naphthalene, phenyl-pyridine and phenyl-dihydropyrrolopyrazole, wherein each aryl and heteroaryl is unsubstituted or substituted with 1, 2, 3 or 4 substituents independently selected from R$^a$, provided that at least one of and only one of R$^1$ and R$^2$ is selected from halogen. In a subclass of this class, at least one of and only one of R$^1$ and R$^2$ is selected from: F and Cl. In another subclass of this class, at least one of and only one of R$^1$ and R$^2$ is Cl.

In another embodiment of the present invention, each R$^1$ and R$^2$ is independently selected from: halogen and aryl-aryl, wherein each aryl is unsubstituted or substituted with 1, 2, 3 or 4 substituents independently selected from R$^a$, provided that at least one of and only one of R$^1$ and R$^2$ is selected from halogen. In a subclass of this class, at least one of and only one of R$^1$ and R$^2$ is selected from: F and Cl. In another subclass of this class, at least one of and only one of R$^1$ and R$^2$ is Cl. In another subclass of this class, R$^2$ is halogen. In another subclass of this class, R$^2$ is Cl.

In another embodiment of the present invention, each R$^1$ and R$^2$ is independently selected from: halogen and biphenyl, wherein each phenyl is unsubstituted or substituted with 1, 2, 3 or 4 substituents independently selected from R$^a$, provided that at least one of and only one of R$^1$ and R$^2$ is selected from halogen. In a subclass of this class, at least one of and only one of R$^1$ and R$^2$ is selected from: F and Cl. In another subclass of this class, at least one of and only one of R$^1$ and R$^2$ is Cl. In another subclass of this class, R$^2$ is halogen. In another subclass of this class, R$^2$ is Cl.

In another embodiment of the present invention, each R$^1$ is independently selected from: hydrogen, halogen, CN, CF$_3$, —C$_{1-6}$alkyl, —C$_{2-6}$alkenyl, —C$_{2-6}$alkynyl, —(CH$_2$)$_p$C$_{3-10}$cycloalkyl, —(CH$_2$)$_p$C$_{3-7}$cycloalkyl-aryl, —(CH$_2$)$_p$C$_{3-7}$ cycloalkyl-heteroaryl, —(CH$_2$)$_p$C$_{4-10}$cycloalkenyl, —(CH$_2$)$_p$C$_{4-7}$cycloalkenyl-aryl, —(CH$_2$)$_p$C$_{4-7}$cycloalkenyl-heteroaryl, —(CH$_2$)$_p$C$_{2-10}$cycloheteroalkyl, —(CH$_2$)$_p$C$_{2-10}$cycloheteroalkenyl, —(CH$_2$)$_p$aryl, —(CH$_2$)$_p$aryl-C$_{1-8}$alkyl, —(CH$_2$)$_p$aryl-C$_{2-8}$alkenyl, —(CH$_2$)$_p$aryl-C$_{2-8}$alkynyl-C$_{1-8}$alkyl, —(CH$_2$)$_p$aryl-C$_{2-8}$alkynyl-C$_{3-7}$cycloalkyl, —(CH$_2$)$_p$aryl-C$_{2-8}$alkynyl-C$_{3-7}$cycloalkenyl, —(CH$_2$)$_p$aryl-C$_{2-8}$alkynyl-C$_{2-10}$cycloheteroalkyl, —(CH$_2$)$_p$aryl-C$_{2-8}$alkynyl-C$_{2-10}$cycloheteroalkenyl, —(CH$_2$)$_p$aryl-C$_{2-8}$alkynyl-aryl, —(CH$_2$)$_p$aryl-C$_{2-8}$alkynyl-heteroaryl, —(CH$_2$)$_p$aryl-C$_{3-7}$cycloalkyl, —(CH$_2$)$_p$aryl-C$_{2-10}$cycloheteroalkyl, —(CH$_2$)$_p$aryl-C$_{2-10}$cycloheteroalkenyl, —(CH$_2$)$_p$aryl-aryl, —(CH$_2$)$_p$aryl-heteroaryl, —(CH$_2$)$_p$heteroaryl, —(CH$_2$)$_p$heteroaryl-C$_{3-7}$cycloalkyl, —(CH$_2$)$_p$heteroaryl-C$_{2-10}$cycloheteroalkyl —(CH$_2$)$_p$heteroaryl-C$_{2-10}$cycloheteroalkenyl, —(CH$_2$)$_p$heteroaryl-aryl, —(CH$_2$)$_p$heteroaryl-heteroaryl, —C$_{2-6}$alkenyl-alkyl, —C$_{2-6}$alkenyl-aryl, —C$_{2-6}$alkenyl-heteroaryl, —C$_{2-6}$alkenyl-C$_{3-7}$cycloalkyl, —C$_{2-6}$alkenyl-C$_{3-7}$cycloalkenyl, —C$_{2-6}$alkenyl-C$_{2-7}$cycloheteroalkyl, —C$_{2-6}$alkenyl-C$_{2-7}$cycloheteroalkenyl, —C$_{2-6}$ alkynyl-(CH$_2$)$_{1-3}$—O-aryl, —C$_{2-6}$alkynyl-alkyl, —C$_{2-6}$alkynyl-aryl, —C$_{2-6}$alkynyl-heteroaryl, —C$_{2-6}$alkynyl-C$_{3-7}$cycloalkyl, —C$_{2-6}$alkynyl-C$_{3-7}$cycloalkenyl, —C$_{2-6}$alkynyl-C$_{2-7}$cycloheteroalkyl, —C$_{2-6}$alkynyl-C$_{2-7}$cycloheteroalkenyl, and —C(O)NH—(CH$_2$)$_{0-3}$phenyl, wherein each CH$_2$ is unsubstituted or substituted with 1 or 2 substituents selected from: halogen, CF$_3$, —OH, —NH$_2$, —C$_{1-6}$alkyl, —OC$_{1-6}$alkyl, —NHC$_{1-6}$alkyl, and —N(C$_{1-6}$alkyl)$_2$, and wherein each alkyl, alkenyl, alkynyl, cycloalkyl, cycloalkenyl, cycloheteroalkyl, cycloheteroalkenyl, phenyl, aryl and heteroaryl is unsubstituted or substituted with 1, 2, 3 or 4 substituents independently selected from R$^a$.

In another embodiment of the present invention, each R$^1$ is independently selected from: —(CH$_2$)$_p$C$_{3-10}$cycloalkyl, —(CH$_2$)$_p$C$_{3-7}$cycloalkyl-aryl, —(CH$_2$)$_p$C$_{3-7}$cycloalkyl-heteroaryl, —(CH$_2$)$_p$C$_{4-10}$cycloalkenyl, —(CH$_2$)$_p$C$_{4-7}$cycloalkenyl-aryl, —(CH$_2$)$_p$C$_{4-7}$cycloalkenyl-heteroaryl, —(CH$_2$)$_p$C$_{2-10}$cycloheteroalkyl, —(CH$_2$)$_p$C$_{2-10}$cycloheteroalkenyl, —(CH$_2$)$_p$aryl, —(CH$_2$)$_p$aryl-C$_{1-8}$alkyl, —(CH$_2$)$_p$ aryl-C$_{2-8}$alkenyl, —(CH$_2$)$_p$aryl-C$_{2-8}$alkynyl-C$_{1-8}$alkyl, —(CH$_2$)$_p$aryl-C$_{2-8}$alkynyl-C$_{3-7}$cycloalkyl, —(CH$_2$)$_p$aryl-C$_{2-8}$alkynyl-C$_{3-7}$cycloalkenyl, —(CH$_2$)$_p$aryl-C$_{2-8}$alkynyl-C$_{2-10}$cycloheteroalkyl, —(CH$_2$)$_p$aryl-C$_{2-8}$alkynyl-C$_{2-10}$cycloheteroalkenyl, —(CH$_2$)$_p$aryl-C$_{2-8}$alkynyl-aryl, —(CH$_2$)$_p$aryl-C$_{2-8}$alkynyl-heteroaryl, —(CH$_2$)$_p$aryl-C$_{3-7}$cycloalkyl, —(CH$_2$)$_p$aryl-C$_{2-10}$cycloheteroalkyl, —(CH$_2$)$_p$aryl-C$_{2-10}$cycloheteroalkenyl, —(CH$_2$)$_p$aryl-aryl, —(CH$_2$)$_p$aryl-heteroaryl, —(CH$_2$)$_p$heteroaryl, —(CH$_2$)$_p$heteroaryl-C$_{3-7}$cycloalkyl, —(CH$_2$)$_p$heteroaryl-C$_{2-10}$cycloheteroalkyl —(CH$_2$)$_p$heteroaryl-C$_{2-10}$cycloheteroalkenyl, —(CH$_2$)$_p$heteroaryl-aryl, —(CH$_2$)$_p$heteroaryl-heteroaryl, —C$_{2-6}$alkenyl-alkyl, —C$_{2-6}$alkenyl-aryl, —C$_{2-6}$alkenyl-heteroaryl, —C$_{2-6}$alkenyl-C$_{3-7}$cycloalkyl, —C$_{2-6}$alkenyl-C$_{3-7}$cycloalkenyl, —C$_{2-6}$alkenyl-C$_{2-7}$cycloheteroalkyl, —C$_{2-6}$alkenyl-C$_{2-7}$cycloheteroalkenyl, —C$_{2-6}$ alkynyl-(CH$_2$)$_{1-3}$—O-aryl, —C$_{2-6}$alkynyl-alkyl, —C$_{2-6}$alkynyl-aryl, —C$_{2-6}$alkynyl-heteroaryl, —C$_{2-6}$alkynyl-C$_{3-7}$cycloalkyl, —C$_{2-6}$alkynyl-C$_{3-7}$cycloalkenyl, —C$_{2-6}$alkynyl-C$_{2-7}$cycloheteroalkyl, —C$_{2-6}$alkynyl-C$_{2-7}$cycloheteroalkenyl, and —C(O)NH—(CH$_2$)$_{0-3}$phenyl, wherein each CH$_2$ is unsubstituted or substituted with 1 or 2 substituents selected from: halogen, CF$_3$, —OH, —NH$_2$, —C$_{1-6}$alkyl, —OC$_{1-6}$alkyl, —NHC$_{1-6}$alkyl, and —N(C$_{1-6}$alkyl)$_2$, and wherein each alkyl, alkenyl, alkynyl, cycloalkyl, cycloalkenyl, cycloheteroalkyl, cycloheteroalkenyl, phenyl, aryl and heteroaryl is unsubstituted or substituted with 1, 2, 3 or 4 substituents independently selected from R$^a$.

In another embodiment, each R$^1$ is independently selected from: —(CH$_2$)$_p$aryl-aryl-(CH$_2$)$_p$aryl-heteroaryl, —(CH$_2$)$_p$aryl-C$_{3-7}$cycloalkyl, —(CH$_2$)$_p$aryl-C$_{2-10}$cycloheteroalkyl, —(CH$_2$)$_p$aryl-C$_{2-10}$cycloheteroalkenyl and —(CH$_2$)$_p$heteroaryl, wherein each CH$_2$ is unsubstituted or substituted with 1 or 2 substituents selected from: halogen, CF$_3$, —OH, —NH$_2$, —C$_{1-6}$alkyl, —OC$_{1-6}$alkyl, —NHC$_{1-6}$alkyl, and —N(C$_{1-6}$alkyl)$_2$, wherein each cycloalkyl, cycloheteroalkyl, cycloheteroalkenyl, aryl and heteroaryl is unsubstituted or substituted with 1, 2, 3 or 4 substituents independently selected from R$^a$. In a class of this embodiment, each R$^1$ is independently selected from: biphenyl, phenyl-naphthalene, phenyl-pyridine, phenyl-dihydropyrrolopyrazole, phenyl-pyrrolidine, phenyl-azetidine, phenyl-piperazine, phenyl-dihydrothiopyran, phenyl-cyclobutyl and benzodioxane, wherein each phenyl, naphthalene, pyridine, dihydropyrrolopyrazole, pyrrolidine, azetidine, piperazine, dihydrothiopyran, cyclobutyl and benzodioxane is unsubstituted or substituted with 1, 2, 3 or 4 substituents independently selected from $R^a$.

In another embodiment of the present invention, each $R^1$ is independently selected from: aryl-aryl, aryl-$C_{3-7}$cycloalkyl, aryl-$C_{2-10}$cycloheteroalkyl, aryl-$C_{2-10}$cycloheteroalkenyl and heteroaryl, wherein each cycloalkyl, cycloheteroalkyl, cycloheteroalkenyl, aryl and heteroaryl is unsubstituted or substituted with 1, 2, 3 or 4 substituents independently selected from $R^a$, provided that at least one of and only one of $R^1$ and $R^2$ is selected from halogen. In a subclass of this class, at least one of and only one of $R^1$ and $R^2$ is selected from: F and Cl. In another subclass of this class, at least one of and only one of $R^1$ and $R^2$ is Cl.

In another embodiment of the present invention, each $R^1$ is independently selected from: biphenyl, phenyl-pyrrolidine, phenyl-azetidine, phenyl-piperazine, phenyl-dihydrothiopyran, and phenyl-cyclobutyl, wherein each phenyl, pyrrolidine, azetidine, piperazine, dihydrothiopyran, cyclobutyl and benzodioxane, and each $R^1$ is unsubstituted or substituted with 1, 2, 3 or 4 substituents independently selected from $R^a$, provided that at least one of and only one of $R^1$ and $R^2$ is selected from halogen. In a subclass of this class, at least one of and only one of $R^1$ and $R^2$ is selected from: F and Cl. In another subclass of this class, at least one of and only one of $R^1$ and $R^2$ is Cl.

In another embodiment, each $R^1$ is independently selected from: —$(CH_2)_p$aryl-$C_{3-7}$cycloalkyl, —$(CH_2)_p$aryl-$C_{2-10}$cycloheteroalkyl, —$(CH_2)_p$aryl-$C_{2-10}$cycloheteroalkenyl and —$(CH_2)_p$heteroaryl, wherein each $CH_2$ is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}alkyl)_2$, wherein each cycloalkyl, cycloheteroalkyl, cycloheteroalkenyl, aryl and heteroaryl is unsubstituted or substituted with 1, 2, 3 or 4 substituents independently selected from $R^a$.

In another embodiment, each $R^1$ is independently selected from: aryl-$C_{3-7}$cycloalkyl, aryl-$C_{2-10}$cycloheteroalkyl, aryl-$C_{2-10}$cycloheteroalkenyl and -heteroaryl, wherein each cycloalkyl, cycloheteroalkyl, cycloheteroalkenyl, aryl and heteroaryl is unsubstituted or substituted with 1, 2, 3 or 4 substituents independently selected from $R^a$.

In another embodiment, each $R^1$ is independently selected from: phenyl-$C_{3-7}$cycloalkyl, phenyl-$C_{2-10}$cycloheteroalkyl, phenyl-$C_{2-10}$cycloheteroalkenyl and heteroaryl, wherein each cycloalkyl, cycloheteroalkyl, cycloheteroalkenyl, phenyl and heteroaryl is unsubstituted or substituted with 1, 2, 3 or 4 substituents independently selected from $R^a$.

In another embodiment, each $R^1$ is independently selected from: phenyl-pyrrolidine, phenyl-azetidine, phenyl-piperazine, phenyl-dihydrothiopyran, phenyl-cyclobutyl and benzodioxane, wherein each phenyl, pyrrolidine, azetidine, piperazine, dihydrothiopyran, cyclobutyl and benzodioxane is unsubstituted or substituted with 1, 2, 3 or 4 substituents independently selected from $R^a$.

In another embodiment of the present invention, each $R^1$ is independently selected from: —$(CH_2)_p$aryl-aryl, and —$(CH_2)_p$aryl-heteroaryl, wherein each $CH_2$ is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}alkyl)_2$, and wherein each aryl and heteroaryl is unsubstituted or substituted with 1, 2, 3 or 4 substituents independently selected from $R^a$.

In another embodiment of the present invention, each $R^1$ is independently selected from: —$(CH_2)_p$aryl-aryl, and aryl-heteroaryl, wherein each aryl and heteroaryl is unsubstituted or substituted with 1, 2, 3 or 4 substituents independently selected from $R^a$.

In another embodiment of the present invention, each $R^1$ is independently selected from: biphenyl, phenyl-naphthalene, phenyl-pyridine, and phenyl-dihydropyrrolopyrazole, wherein each aryl and heteroaryl is unsubstituted or substituted with 1, 2, 3 or 4 substituents independently selected from $R^a$.

In another embodiment of the present invention, each $R^1$ is independently selected from: aryl-aryl, wherein each aryl is unsubstituted or substituted with 1, 2, 3 or 4 substituents independently selected from $R^a$, provided that at least one of and only one of $R^1$ and $R^2$ is selected from halogen. In a subclass of this class, at least one of and only one of $R^1$ and $R^2$ is selected from: F and Cl. In another subclass of this class, at least one of and only one of $R^1$ and $R^2$ is Cl.

In another embodiment of the present invention, each $R^1$ is independently selected from: biphenyl, wherein each phenyl is unsubstituted or substituted with 1, 2, 3 or 4 substituents independently selected from $R^a$, provided that at least one of and only one of $R^1$ and $R^2$ is selected from halogen. In a subclass of this class, at least one of and only one of $R^1$ and $R^2$ is selected from: F and Cl. In another subclass of this class, at least one of and only one of $R^1$ and $R^2$ is Cl.

In another embodiment of the present invention, each $R^1$ is independently selected from: hydrogen, halogen, —CN, —$CF_3$, —$C_{1-6}$alkyl, —$C_{2-6}$alkenyl and —$C_{2-6}$alkynyl. In another embodiment of the present invention, each $R^1$ is independently selected from: halogen. In another embodiment of the present invention, each $R^1$ is independently selected from: Cl and F. In a class of this embodiment, $R^1$ is Cl. In another class of this embodiment, $R^1$ is F.

In another embodiment of the present invention, $R^2$ is independently selected from: hydrogen, halogen, CN, $CF_3$, —$C_{1-6}$alkyl, —$C_{2-6}$alkenyl, —$C_{2-6}$alkynyl, —$(CH_2)_pC_{3-10}$cycloalkyl, —$(CH_2)_pC_{3-7}$cycloalkyl-aryl, —$(CH_2)_pC_{3-7}$cycloalkyl-heteroaryl, —$(CH_2)_pC_{4-10}$cycloalkenyl, —$(CH_2)_pC_{4-7}$cycloalkenyl-aryl, —$(CH_2)_pC_{4-7}$cycloalkenyl-heteroaryl, —$(CH_2)_pC_{2-10}$cycloheteroalkyl, —$(CH_2)_pC_{2-10}$cycloheteroalkenyl, —$(CH_2)_p$aryl, —$(CH_2)_p$aryl-$C_{1-8}$alkyl, —$(CH_2)_p$aryl-$C_{2-8}$alkenyl, —$(CH_2)_p$aryl-$C_{2-8}$alkynyl-$C_{1-8}$alkyl, —$(CH_2)_p$aryl-$C_{2-8}$alkynyl-$C_{3-7}$cycloalkyl, —$(CH_2)_p$aryl-$C_{2-8}$alkynyl-$C_{3-7}$cycloalkenyl, —$(CH_2)_p$aryl-$C_{2-8}$alkynyl-$C_{2-10}$cycloheteroalkyl, —$(CH_2)_p$aryl-$C_{2-8}$alkynyl-$C_{2-10}$cycloheteroalkenyl, —$(CH_2)_p$aryl-$C_{2-8}$alkynyl-aryl, —$(CH_2)_p$aryl-$C_{2-8}$alkynyl-heteroaryl, —$(CH_2)_p$aryl-$C_{3-7}$cycloalkyl, —$(CH_2)_p$aryl-$C_{2-10}$cycloheteroalkyl, —$(CH_2)_p$aryl-$C_{2-10}$cycloheteroalkenyl, —$(CH_2)_p$aryl-aryl, —$(CH_2)_p$aryl-heteroaryl, —$(CH_2)_p$heteroaryl, —$(CH_2)_p$heteroaryl-$C_{3-7}$cycloalkyl, —$(CH_2)_p$heteroaryl-$C_{2-10}$cycloheteroalkyl —$(CH_2)_p$heteroaryl-$C_{2-10}$cycloheteroalkenyl, —$(CH_2)_p$heteroaryl-aryl, —$(CH_2)_p$heteroaryl-heteroaryl, —$C_{2-6}$alkenyl-alkyl, —$C_{2-6}$alkenyl-aryl, —$C_{2-6}$alkenyl-heteroaryl, —$C_{2-6}$alkenyl-$C_{3-7}$cycloalkyl, —$C_{2-6}$alkenyl-$C_{3-7}$cycloalkenyl, —$C_{2-6}$alkenyl-$C_{2-7}$cycloheteroalkyl, —$C_{2-6}$alkenyl-$C_{2-7}$cycloheteroalkenyl, —$C_{2-6}$ alkynyl-$(CH_2)_{1-3}$—O-aryl, —$C_{2-6}$alkynyl-alkyl, —$C_{2-6}$alkynyl-aryl, —$C_{2-6}$alkynyl-heteroaryl, —$C_{2-6}$alkynyl-$C_{3-7}$cycloalkyl, —$C_{2-6}$alkynyl-$C_{3-7}$cycloalkenyl, —$C_{2-6}$alkynyl-$C_{2-7}$cycloheteroalkyl, —$C_{2-6}$alkynyl-$C_{2-7}$cycloheteroalkenyl, and —$C(O)NH$—$(CH_2)_{0-3}$phenyl, wherein each $CH_2$ is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}alkyl)_2$, and wherein each alkyl, alkenyl, alkynyl, cycloalkyl, cycloalkenyl, cycloheteroalkyl, cycloheteroalkenyl, phenyl, aryl and heteroaryl is unsubstituted or substituted with 1, 2, 3 or 4 substituents independently selected from $R^a$.

In another embodiment of the present invention, $R^2$ is independently selected from: —$(CH_2)_pC_{3-10}$cycloalkyl, —$(CH_2)_pC_{3-7}$cycloalkyl-aryl, —$(CH_2)_pC_{3-7}$cycloalkyl-heteroaryl, —$(CH_2)_pC_{4-10}$cycloalkenyl, —$(CH_2)_pC_{4-7}$cycloalkenyl-aryl, —$(CH_2)_pC_{4-7}$cycloalkenyl-heteroaryl, —$(CH_2)_pC_{2-10}$cycloheteroalkyl, —$(CH_2)_pC_{2-10}$cycloheteroalkenyl, —$(CH_2)_p$aryl, —$(CH_2)_p$aryl-$C_{1-8}$alkyl, —$(CH_2)_p$ aryl-$C_{2-8}$alkenyl, —$(CH_2)_p$aryl-$C_{2-8}$alkynyl-$C_{1-8}$ alkyl, —$(CH_2)_p$aryl-$C_{2-8}$alkynyl-$C_{3-7}$cycloalkyl, —$(CH_2)_p$ aryl-$C_{2-8}$alkynyl-$C_{3-7}$cycloalkenyl, —$(CH_2)_p$aryl-$C_{2-8}$alkynyl-$C_{2-10}$cycloheteroalkyl, —$(CH_2)_p$aryl-$C_{2-8}$alkynyl-$C_{2-10}$ cycloheteroalkenyl, —$(CH_2)_p$aryl-$C_{2-8}$alkynyl-aryl, —$(CH_2)_p$aryl-$C_{2-8}$alkynyl-heteroaryl, —$(CH_2)_p$aryl-$C_{3-7}$cycloalkyl, —$(CH_2)_p$aryl-$C_{2-10}$cycloheteroalkyl, —$(CH_2)_p$ aryl-$C_{2-10}$cycloheteroalkenyl, —$(CH_2)_p$aryl-aryl, —$(CH_2)_p$ aryl-heteroaryl, —$(CH_2)_p$heteroaryl, —$(CH_2)_p$heteroaryl-$C_{3-7}$cycloalkyl, —$(CH_2)_p$heteroaryl-$C_{2-10}$cycloheteroalkyl —$(CH_2)_p$heteroaryl-$C_{2-10}$cycloheteroalkenyl, —$(CH_2)_p$heteroaryl-aryl, —$(CH_2)_p$heteroaryl-heteroaryl, —$C_{2-6}$alkenyl-alkyl, —$C_{2-6}$alkenyl-aryl, —$C_{2-6}$alkenyl-heteroaryl, —$C_{2-6}$ alkenyl-$C_{3-7}$cycloalkyl, —$C_{2-6}$alkenyl-$C_{3-7}$cycloalkenyl, —$C_{2-6}$alkenyl-$C_{2-7}$cycloheteroalkyl, —$C_{2-6}$alkenyl-$C_{2-7}$cycloheteroalkenyl, —$C_{2-6}$ alkynyl-$(CH_2)_{1-3}$—O-aryl, —$C_{2-6}$ alkynyl-alkyl, —$C_{2-6}$alkynyl-aryl, —$C_{2-6}$alkynyl-heteroaryl, —$C_{2-6}$alkynyl-$C_{3-7}$cycloalkyl, —$C_{2-6}$alkynyl-$C_{3-7}$ cycloalkenyl, —$C_{2-6}$alkynyl-$C_{2-7}$cycloheteroalkyl, —$C_{2-6}$ alkynyl-$C_{2-7}$cycloheteroalkenyl, and —$C(O)NH$—$(CH_2)_{0-3}$ phenyl, wherein each $CH_2$ is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}$alkyl$)_2$, and wherein each alkyl, alkenyl, alkynyl, cycloalkyl, cycloalkenyl, cycloheteroalkyl, cycloheteroalkenyl, phenyl, aryl and heteroaryl is unsubstituted or substituted with 1, 2, 3 or 4 substituents independently selected from $R^a$.

In another embodiment, each $R^2$ is independently selected from: —$(CH_2)_p$aryl-aryl-$(CH_2)_p$aryl-heteroaryl, —$(CH_2)_p$ aryl-$C_{3-7}$cycloalkyl, —$(CH_2)_p$aryl-$C_{2-10}$cycloheteroalkyl, —$(CH_2)_p$aryl-$C_{2-10}$cycloheteroalkenyl, and —$(CH_2)_p$heteroaryl, wherein each $CH_2$ is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}$alkyl$)_2$, wherein each cycloalkyl, cycloheteroalkyl, cycloheteroalkenyl, aryl and heteroaryl is unsubstituted or substituted with 1, 2, 3 or 4 substituents independently selected from $R^a$. In a class of this embodiment, each $R^1$ is independently selected from: biphenyl, phenyl-naphthalene, phenyl-pyridine, phenyl-dihydropyrrolopyrazole, phenyl-pyrrolidine, phenyl-azetidine, phenyl-piperazine, phenyl-dihydrothiopyran, and phenyl-cyclobutyl, wherein each phenyl, naphthalene, pyridine, dihydropyrrolopyrazole, pyrrolidine, azetidine, piperazine, dihydrothiopyran, cyclobutyl and benzodioxane is unsubstituted or substituted with 1, 2, 3 or 4 substituents independently selected from $R^a$.

In another embodiment of the present invention, each $R^2$ is independently selected from: aryl-aryl, aryl-$C_{3-7}$cycloalkyl, aryl-$C_{2-10}$cycloheteroalkyl, aryl-$C_{2-10}$cycloheteroalkenyl, and heteroaryl, wherein each cycloalkyl, cycloheteroalkyl, cycloheteroalkenyl, aryl and heteroaryl is unsubstituted or substituted with 1, 2, 3 or 4 substituents independently selected from $R^a$, provided that at least one of and only one of $R^1$ and $R^2$ is selected from halogen. In a subclass of this class, at least one of and only one of $R^1$ and $R^2$ is selected from: F and Cl. In another subclass of this class, at least one of and only one of $R^1$ and $R^2$ is Cl.

In another embodiment of the present invention, each $R^2$ is independently selected from: biphenyl, phenyl-pyrrolidine, phenyl-azetidine, phenyl-piperazine, phenyl-dihydrothiopyran, and phenyl-cyclobutyl, wherein each phenyl, pyrrolidine, azetidine, piperazine, dihydrothiopyran, cyclobutyl and benzodioxane, is unsubstituted or substituted with 1, 2, 3 or 4 substituents independently selected from $R^a$, provided that at least one of and only one of $R^1$ and $R^2$ is selected from halogen. In a subclass of this class, at least one of and only one of $R^1$ and $R^2$ is selected from: F and Cl. In another subclass of this class, at least one of and only one of $R^1$ and $R^2$ is Cl.

In another embodiment, each $R^2$ is independently selected from: —$(CH_2)_p$aryl-$C_{3-7}$cycloalkyl, —$(CH_2)_p$aryl-$C_{2-10}$cycloheteroalkyl, —$(CH_2)_p$aryl-$C_{2-10}$cycloheteroalkenyl and —$(CH_2)_p$heteroaryl, wherein each $CH_2$ is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}$alkyl$)_2$, wherein each cycloalkyl, cycloheteroalkyl, cycloheteroalkenyl, aryl and heteroaryl is unsubstituted or substituted with 1, 2, 3 or 4 substituents independently selected from $R^a$.

In another embodiment, each $R^2$ is independently selected from: aryl-$C_{3-7}$cycloalkyl, aryl-$C_{2-10}$cycloheteroalkyl, aryl-$C_{2-10}$cycloheteroalkenyl and -heteroaryl, wherein each cycloalkyl, cycloheteroalkyl, cycloheteroalkenyl, aryl and heteroaryl is unsubstituted or substituted with 1, 2, 3 or 4 substituents independently selected from $R^a$.

In another embodiment, each $R^2$ is independently selected from: phenyl-$C_{3-7}$cycloalkyl, phenyl-$C_{2-10}$cycloheteroalkyl, phenyl-$C_{2-10}$cycloheteroalkenyl and heteroaryl, wherein each cycloalkyl, cycloheteroalkyl, cycloheteroalkenyl, phenyl and heteroaryl is unsubstituted or substituted with 1, 2, 3 or 4 substituents independently selected from $R^a$.

In another embodiment, each $R^2$ is independently selected from: phenyl-pyrrolidine, phenyl-azetidine, phenyl-piperazine, phenyl-dihydrothiopyran, phenyl-cyclobutyl and benzodioxane, wherein each phenyl, pyrrolidine, azetidine, piperazine, dihydrothiopyran, cyclobutyl and benzodioxane is unsubstituted or substituted with 1, 2, 3 or 4 substituents independently selected from $R^a$.

In another embodiment of the present invention, each $R^2$ is independently selected from: —$(CH_2)_p$aryl-aryl, and —$(CH_2)_p$aryl-heteroaryl, wherein each $CH_2$ is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}$alkyl$)_2$, and wherein each aryl and heteroaryl is unsubstituted or substituted with 1, 2, 3 or 4 substituents independently selected from $R^a$.

In another embodiment of the present invention, each $R^2$ is independently selected from: —$(CH_2)_p$aryl-aryl, and aryl-heteroaryl, wherein each aryl and heteroaryl is unsubstituted or substituted with 1, 2, 3 or 4 substituents independently selected from $R^a$.

In another embodiment of the present invention, each $R^2$ is independently selected from: biphenyl, phenyl-naphthalene, phenyl-pyridine, and phenyl-dihydropyrrolopyrazole, wherein each aryl and heteroaryl is unsubstituted or substituted with 1, 2, 3 or 4 substituents independently selected from $R^a$.

In another embodiment of the present invention, each $R^2$ is independently selected from: aryl-aryl, wherein each aryl is unsubstituted or substituted with 1, 2, 3 or 4 substituents independently selected from $R^a$, provided that at least one of and only one of $R^1$ and $R^2$ is selected from halogen. In a subclass of this class, at least one of and only one of $R^1$ and $R^2$ is selected from: F and Cl. In another subclass of this class, at least one of and only one of $R^1$ and $R^2$ is Cl.

In another embodiment of the present invention, each $R^2$ is independently selected from: biphenyl, wherein each phenyl is unsubstituted or substituted with 1, 2, 3 or 4 substituents independently selected from $R^a$, provided that at least one of and only one of $R^1$ and $R^2$ is selected from halogen. In a subclass of this class, at least one of and only one of $R^1$ and $R^2$ is selected from: F and Cl. In another subclass of this class, at least one of and only one of $R^1$ and $R^2$ is Cl.

In another embodiment of the present invention, each $R^2$ is independently selected from: hydrogen, halogen, —CN, —CF$_3$, —C$_{1-6}$alkyl, —C$_{2-6}$alkenyl and —C$_{2-6}$alkynyl. In another embodiment of the present invention, each $R^2$ is halogen. In another embodiment of the present invention, each $R^2$ is independently selected from: Cl and F. In a class of this embodiment, $R^2$ is Cl. In another class of this embodiment, $R^2$ is F.

In another embodiment of the present invention, $R^3$ and $R^4$ are each independently selected from: hydrogen, halogen, —C$_{1-6}$alkyl, —C$_{2-6}$alkenyl, —C$_{2-6}$alkynyl, —C$_{3-10}$cycloalkyl, —C$_{3-10}$cycloalkenyl, aryl, heteroaryl, —CN, —CF$_3$, —OH, —OC$_{1-6}$alkyl, —NH$_2$, —NHC$_{1-6}$alkyl, —N(C$_{1-6}$alkyl)$_2$, —SC$_{1-6}$alkyl, —SOC$_{1-6}$alkyl, —SO$_2$C$_{1-6}$alkyl, —NHSO$_2$C$_{1-6}$alkyl, —NHC(O)C$_{1-6}$alkyl, —SO$_2$NHC$_{1-6}$alkyl, and —C(O)NHC$_{1-6}$alkyl.

In another embodiment of the present invention, each $R^3$ is independently selected from: hydrogen, halogen, —C$_{1-6}$alkyl, —C$_{2-6}$alkenyl, —C$_{2-6}$alkynyl, —C$_{3-10}$cycloalkyl, —C$_{3-10}$ cycloalkenyl, aryl, heteroaryl, —CN, —CF$_3$, —OH, —OC$_{1-6}$alkyl, —NH$_2$, —NHC$_{1-6}$alkyl, —N(C$_{1-6}$alkyl)$_2$, —SC$_{1-6}$alkyl, —SOC$_{1-6}$alkyl, —SO$_2$C$_{1-6}$alkyl, —NHSO$_2$C$_{1-6}$alkyl, —NHC(O)C$_{1-6}$alkyl, —SO$_2$NHC$_{1-6}$alkyl, and —C(O)NHC$_{1-6}$alkyl.

In another embodiment of the present invention, $R^3$ is selected from hydrogen, halogen, and —C$_{1-6}$alkyl. In a class of this embodiment, $R^3$ is hydrogen. In a class of this embodiment, $R^3$ is halogen. In another class of this embodiment of the present invention, $R^3$ is absent.

In another embodiment of the present invention, each $R^4$ is absent or independently selected from: hydrogen, halogen, —C$_{1-6}$alkyl, —C$_{2-6}$alkenyl, —C$_{2-6}$alkynyl, —C$_{3-10}$cycloalkyl, —C$_{3-10}$cycloalkenyl, aryl, heteroaryl, —CN, —CF$_3$, —OH, —OC$_{1-6}$alkyl, —NH$_2$, —NHC$_{1-6}$alkyl, —N(C$_{1-6}$alkyl)$_2$, —SC$_{1-6}$alkyl, —SOC$_{1-6}$alkyl, —SO$_2$C$_{1-6}$alkyl, —NHSO$_2$C$_{1-6}$alkyl, —NHC(O)C$_{1-6}$alkyl, —SO$_2$NHC$_{1-6}$alkyl, and —C(O)NHC$_{1-6}$alkyl.

In another embodiment of the present invention, $R^4$ is selected from hydrogen, halogen, and —C$_{1-6}$alkyl. In a class of this embodiment, $R^4$ is hydrogen. In another class of this embodiment, $R^4$ is halogen. In another class of this embodiment of the present invention, $R^4$ is absent.

In another embodiment of the present invention, $R^5$ is selected from: hydrogen, —C$_{1-6}$alkyl, —C$_{1-6}$alkenyl, —(CH$_2$)$_u$OH, —CH$_2$CO$_2$H, and —CH$_2$CO$_2$C$_{1-6}$alkyl. In a class of this embodiment, $R^5$ is hydrogen.

In another embodiment of the present invention, each $R^a$ is independently selected from the group consisting of: —(CH$_2$)$_m$-halogen, oxo, —(CH$_2$)$_m$OH, —(CH$_2$)$_m$N(R$^j$)$_2$, —(CH$_2$)$_m$NO$_2$, —(CH$_2$)$_m$CN, —C$_{1-6}$alkyl, —(CH$_2$)$_m$CF$_3$, —(CH$_2$)$_m$OCF$_3$, —O—(CH$_2$)$_m$—OC$_{1-6}$alkyl, —(CH$_2$)$_m$N(R$^j$)C(O)R$^f$, —(CH$_2$)$_m$N(R$^j$)CO$_2$R$^f$, —(CH$_2$)$_m$C(=N—OH)N(R$^j$)$_2$, —(CH$_2$)$_m$OC$_{1-6}$alkyl, —(CH$_2$)$_m$O—(CH$_2$)$_m$—C$_{3-7}$cycloalkyl, —(CH$_2$)$_m$O—(CH$_2$)$_m$—C$_{2-7}$cycloheteroalkyl, —(CH$_2$)$_m$O—(CH$_2$)$_m$-aryl, —(CH$_2$)$_m$O—(CH$_2$)$_m$-heteroaryl, —(CH$_2$)$_m$SC$_{1-6}$alkyl, —(CH$_2$)$_m$S(O)C$_{1-6}$alkyl, —(CH$_2$)$_m$SO$_2$C$_{1-6}$alkyl, —(CH$_2$)$_m$SO$_2$(CH$_2$)$_m$—C$_{3-7}$cycloalkyl, —(CH$_2$)$_m$SO$_2$(CH$_2$)$_m$—C$_{2-7}$cycloheteroalkyl, —(CH$_2$)$_m$SO$_2$(CH$_2$)$_m$-aryl, —(CH$_2$)$_m$SO$_2$(CH$_2$)$_m$-heteroaryl, —(CH$_2$)$_m$SO$_2$NH$_2$, —(CH$_2$)$_m$SO$_2$NHC$_{1-6}$alkyl, —(CH$_2$)$_m$SO$_2$NHC$_{3-7}$cycloalkyl, —(CH$_2$)$_m$SO$_2$NHC$_{2-7}$cycloheteroalkyl, —(CH$_2$)$_m$SO$_2$NH-aryl, —(CH$_2$)$_m$SO$_2$NH-heteroaryl, —(CH$_2$)$_m$NHSO$_2$C$_{1-6}$alkyl, —(CH$_2$)$_m$NHSO$_2$—C$_{3-7}$cycloalkyl, —(CH$_2$)$_m$NHSO$_2$—C$_{2-7}$cycloheteroalkyl, —(CH$_2$)$_m$NHSO$_2$-aryl, —(CH$_2$)$_m$NHSO$_2$NH-heteroaryl, —(CH$_2$)$_m$N(R$^j$)—C$_{1-6}$alkyl, —(CH$_2$)$_m$N(R$^j$)—C$_{3-7}$cycloalkyl, —(CH$_2$)$_m$N(R$^j$)—C$_{2-7}$cycloheteroalkyl, —(CH$_2$)$_m$N(R$^j$)—C$_{2-7}$cycloheteroalkenyl, —(CH$_2$)$_m$N(R$^j$)-aryl, —(CH$_2$)$_m$N(R$^j$)-heteroaryl, —(CH$_2$)$_m$C(O)R$^f$, —(CH$_2$)$_m$C(O)N(R$^j$)$_2$, —(CH$_2$)$_m$N(R$^j$)C(O)N(R$^j$)$_2$, —(CH$_2$)$_m$CO$_2$H, —(CH$_2$)$_m$OCOH, —(CH$_2$)$_m$CO$_2$R$^f$, —(CH$_2$)$_m$OCOR$^f$, —(CH$_2$)$_m$C$_{3-7}$cycloalkyl, —(CH$_2$)$_m$C$_{3-7}$cycloalkenyl, —(CH$_2$)$_m$C$_{2-6}$cycloheteroalkyl, —(CH$_2$)$_m$C$_{2-6}$cycloheteroalkenyl, —(CH$_2$)$_m$aryl, and —(CH$_2$)$_m$heteroaryl, wherein each CH$_2$ is unsubstituted or substituted with 1 or 2 substituents selected from: oxo, —OH, —(CH$_2$)$_{1-3}$OH, —CN, —NH$_2$, —NH(C$_{1-6}$alkyl), —N(C$_{1-6}$alkyl)$_2$, oxo, —C$_{1-6}$alkyl, —C$_{1-6}$alkyl substituted with 1-5 OH, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl, phenyl, CH$_2$phenyl, heteroaryl and CH$_2$heteroaryl, and wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —OH, —(CH$_2$)$_{1-5}$OH, —(CH$_2$)$_{1-5}$CN, —CN, —NH$_2$, —NH(C$_{1-6}$alkyl), —N(C$_{1-6}$alkyl)$_2$, —C$_{1-6}$alkyl, —C$_{1-6}$alkyl substituted with 1-5 OH, —OC$_{1-6}$alkyl, halogen, —CH$_2$F, —CHF$_2$, —CF$_3$, —(CH$_2$)$_{1-5}$CF$_3$ optionally substituted with 1, 2 or 3 —OH, —CO$_2$H, —CO$_2$C$_{1-6}$alkyl, —SO$_2$C$_{1-6}$alkyl, —C$_{3-7}$cycloalkyl, phenyl, CH$_2$phenyl, heteroaryl and CH$_2$heteroaryl.

In another embodiment of the present invention, each $R^a$ is independently selected from the group consisting of: —(CH$_2$)$_m$-halogen, —(CH$_2$)$_m$OH, —(CH$_2$)$_m$C(O)R$^f$, —(CH$_2$)$_m$C$_{2-6}$cycloheteroalkyl, and —(CH$_2$)$_m$heteroaryl, wherein each CH$_2$ is unsubstituted or substituted with 1 or 2 substituents selected from: oxo, —OH, —(CH$_2$)$_{1-3}$OH, —CN, —NH$_2$, —NH(C$_{1-6}$alkyl), —N(C$_{1-6}$alkyl)$_2$, oxo, —C$_{1-6}$alkyl, —C$_{1-6}$alkyl substituted with 1-5 OH, —OC$_{1-6}$ alkyl, halogen, —CH$_2$F, —CHF$_2$, —CF$_3$, —CO$_2$H, and —CO$_2$C$_{1-6}$alkyl, and wherein cycloheteroalkyl and heteroaryl are unsubstituted or substituted with 1, 2, 3 or 4 substituents selected from: oxo, —OH, —(CH$_2$)$_{1-5}$OH, —(CH$_2$)$_{1-5}$CN, —CN, —NH$_2$, —NH(C$_{1-6}$alkyl), —N(C$_{1-6}$ alkyl)$_2$, —C$_{1-6}$alkyl, —C$_{1-6}$alkyl substituted with 1-5 OH, —OC$_{1-6}$alkyl, halogen, —CH$_2$F, —CHF$_2$, —CF$_3$, —(CH$_2$)$_{1-5}$CF$_3$ optionally substituted with 1, 2 or 3 —OH, —CO$_2$H, —CO$_2$C$_{1-6}$alkyl, and —SO$_2$C$_{1-6}$alkyl.

In another embodiment of the present invention, each $R^a$ is independently selected from the group consisting of: —(CH$_2$)$_m$-halogen, —(CH$_2$)$_m$OH, —(CH$_2$)$_m$C(O)R$^f$, —(CH$_2$)$_m$C$_{2-6}$cycloheteroalkyl, —(CH$_2$)$_m$SO$_2$(CH$_2$)$_m$—C$_{3-7}$cycloalkyl and —(CH$_2$)$_m$heteroaryl, wherein each CH$_2$ is unsubstituted or substituted with 1 or 2 substituents selected from: oxo, —OH, —(CH$_2$)$_{1-3}$OH, —CN, —NH$_2$, —NH(C$_{1-6}$alkyl), —N(C$_{1-6}$alkyl)$_2$, oxo, —C$_{1-6}$alkyl, —C$_{1-6}$alkyl substituted with 1-5 OH, —OC$_{1-6}$alkyl, halogen, —CH$_2$F, —CHF$_2$, —CF$_3$, —CO$_2$H, and —CO$_2$C$_{1-6}$alkyl, and wherein cycloheteroalkyl and heteroaryl are unsubstituted or substituted with 1, 2, 3 or 4 substituents selected from: oxo, —OH, —(CH$_2$)$_{1-5}$OH, —(CH$_2$)$_{1-5}$CN, —CN, —NH$_2$, —NH(C$_{1-6}$alkyl), —N(C$_{1-6}$alkyl)$_2$, —C$_{1-6}$alkyl, —C$_{1-6}$alkyl substituted with 1-5 OH, —OC$_{1-6}$alkyl, halogen, —CH$_2$F, —CHF$_2$, —CF$_3$, —(CH$_2$)$_{1-5}$CF$_3$ optionally substituted with 1, 2 or 3 —OH, —CO$_2$H, —CO$_2$C$_{1-6}$alkyl, and —SO$_2$C$_{1-6}$alkyl.

In another embodiment of the present invention, each R$^a$ is independently selected from the group consisting of: halogen, —(CH$_2$)$_m$OH, —C(O)R$^f$, —C$_{2-6}$cycloheteroalkyl, —SO$_2$—C$_{3-7}$cycloalkyl and -heteroaryl, wherein each CH$_2$ is unsubstituted or substituted with 1 or 2 substituents selected from: oxo, —OH, —(CH$_2$)$_{1-3}$OH, —CN, —NH$_2$, —NH(C$_{1-6}$alkyl), —N(C$_{1-6}$alkyl)$_2$, oxo, —C$_{1-6}$alkyl, —C$_{1-6}$alkyl substituted with 1-5 OH, —OC$_{1-6}$alkyl, halogen, —CH$_2$F, —CHF$_2$, —CF$_3$, —CO$_2$H, and —CO$_2$C$_{1-6}$alkyl, and wherein cycloheteroalkyl and heteroaryl are unsubstituted or substituted with 1, 2, 3 or 4 substituents selected from: oxo, —OH, —(CH$_2$)$_{1-5}$OH, —(CH$_2$)$_{1-5}$CN, —CN, —NH$_2$, —NH(C$_{1-6}$alkyl), —N(C$_{1-6}$alkyl)$_2$, —C$_{1-6}$alkyl, —C$_{1-6}$alkyl substituted with 1-5 OH, —OC$_{1-6}$alkyl, halogen, —CH$_2$F, —CHF$_2$, —CF$_3$, —(CH$_2$)$_{1-5}$CF$_3$ optionally substituted with 1, 2 or 3 —OH, —CO$_2$H, —CO$_2$C$_{1-6}$alkyl, and —SO$_2$C$_{1-6}$alkyl.

In another embodiment of the present invention, each R$^a$ is independently selected from the group consisting of: halogen, —(CH$_2$)$_m$OH, —C(O)R$^f$, —C$_{2-6}$cycloheteroalkyl, and -heteroaryl, wherein each CH$_2$ is unsubstituted or substituted with 1 or 2 substituents selected from: oxo, —OH, —(CH$_2$)$_{1-3}$OH, —CN, —NH$_2$, —NH(C$_{1-6}$alkyl), —N(C$_{1-6}$alkyl)$_2$, oxo, —C$_{1-6}$alkyl, —C$_{1-6}$alkyl substituted with 1-5 OH, —OC$_{1-6}$alkyl, halogen, —CH$_2$F, —CHF$_2$, —CF$_3$, —CO$_2$H, and —CO$_2$C$_{1-6}$alkyl, and wherein cycloheteroalkyl and heteroaryl are unsubstituted or substituted with 1, 2, 3 or 4 substituents selected from: oxo, —OH, —(CH$_2$)$_{1-5}$OH, —(CH$_2$)$_{1-5}$CN, —CN, —NH$_2$, —NH(C$_{1-6}$alkyl), —N(C$_{1-6}$alkyl)$_2$, —C$_{1-6}$alkyl, —C$_{1-6}$alkyl substituted with 1-5 OH, —OC$_{1-6}$alkyl, halogen, —CH$_2$F, —CHF$_2$, —CF$_3$, —(CH$_2$)$_{1-5}$CF$_3$ optionally substituted with 1, 2 or 3 —OH, —CO$_2$H, —CO$_2$C$_{1-6}$alkyl, and —SO$_2$C$_{1-6}$alkyl. In a class of this embodiment, CH$_2$ is unsubstituted or substituted with 1 or 2 substituents selected from: —C$_{1-6}$alkyl and halogen, and wherein cycloheteroalkyl and heteroaryl are unsubstituted or substituted with 1, 2, 3 or 4 substituents selected from: —OH, —(CH$_2$)$_{1-5}$CN, and —C$_{1-6}$alkyl substituted with 1-5 OH.

In another embodiment of the present invention, each R$^a$ is independently selected from the group consisting of: Br, Cl, F, —CH$_2$C(CH$_3$)$_2$OH, —CH$_2$C(CH$_3$)$_2$F, —C(O)pyrrolidine, —SO$_2$cyclopropyl, morpholine, pyrazole, triazole, and tetrazole, wherein cycloheteroalkyl and heteroaryl are unsubstituted or substituted with 1, 2, 3 or 4 substituents selected from: oxo, —OH, —(CH$_2$)$_{1-5}$OH, —(CH$_2$)$_{1-5}$CN, —CN, —NH$_2$, —NH(C$_{1-6}$alkyl), —N(C$_{1-6}$alkyl)$_2$, —C$_{1-6}$alkyl, —C$_{1-6}$alkyl substituted with 1-5 OH, —OC$_{1-6}$alkyl, halogen, —CH$_2$F, —CHF$_2$, —CF$_3$, —(CH$_2$)$_{1-5}$CF$_3$ optionally substituted with 1, 2 or 3 —OH, —CO$_2$H, —CO$_2$C$_{1-6}$alkyl, and —SO$_2$C$_{1-6}$alkyl.

In another embodiment of the present invention, each R$^a$ is independently selected from the group consisting of: Br, Cl, F, —CH$_2$C(CH$_3$)$_2$OH, —CH$_2$C(CH$_3$)$_2$F, —C(O)pyrrolidine, morpholine, pyrazole, triazole, and tetrazole, wherein cycloheteroalkyl and heteroaryl are unsubstituted or substituted with 1, 2, 3 or 4 substituents selected from: oxo, —OH, —(CH$_2$)$_{1-5}$OH, —(CH$_2$)$_{1-5}$CN, —CN, —NH$_2$, —NH(C$_{1-6}$alkyl), —N(C$_{1-6}$alkyl)$_2$, —C$_{1-6}$alkyl, —C$_{1-6}$alkyl substituted with 1-5 OH, —OC$_{1-6}$alkyl, halogen, —CH$_2$F, —CHF$_2$, —CF$_3$, —(CH$_2$)$_{1-5}$CF$_3$ optionally substituted with 1, 2 or 3 —OH, —CO$_2$H, —CO$_2$C$_{1-6}$alkyl, and —SO$_2$C$_{1-6}$alkyl. In a class of this embodiment, each R$^a$ is independently selected from the group consisting of: Br, Cl, F, —CH$_2$C(CH$_3$)$_2$OH, —CH$_2$C(CH$_3$)$_2$F, —C(O)pyrrolidine, morpholine, pyrazole, triazole, and tetrazole, wherein cycloheteroalkyl and heteroaryl are unsubstituted or substituted with 1, 2, 3 or 4 substituents selected from: —OH, —(CH$_2$)$_{1-5}$CN, and —C$_{1-6}$alkyl substituted with 1-5 OH. In another class of this embodiment, each R$^a$ is independently selected from the group consisting of: Br, Cl, F, —CH$_2$C(CH$_3$)$_2$OH, —CH$_2$C(CH$_3$)$_2$F, —C(O)pyrrolidine, morpholine, pyrazole, triazole, and tetrazole.

In another embodiment of the present invention, each R$^a$ is independently selected from the group consisting of: —(CH$_2$)$_m$-halogen, —(CH$_2$)$_m$C(O)R$^f$, —(CH$_2$)$_m$C$_{2-6}$cycloheteroalkyl and —(CH$_2$)$_m$heteroaryl, wherein each CH$_2$ is unsubstituted or substituted with 1 or 2 substituents selected from: oxo, —OH, —(CH$_2$)$_{1-3}$OH, —CN, —NH$_2$, —NH(C$_{1-6}$alkyl), —N(C$_{1-6}$alkyl)$_2$, oxo, —C$_{1-6}$alkyl, —C$_{1-6}$alkyl substituted with 1-5 OH, —OC$_{1-6}$alkyl, halogen, —CH$_2$F, —CHF$_2$, —CF$_3$, —CO$_2$H, and —CO$_2$C$_{1-6}$alkyl, and wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —OH, —(CH$_2$)$_{1-5}$OH, —(CH$_2$)$_{1-5}$CN, —CN, —NH$_2$, —NH(C$_{1-6}$alkyl), —N(C$_{1-6}$alkyl)$_2$, —C$_{1-6}$alkyl, —C$_{1-6}$alkyl substituted with 1-5 OH, —OC$_{1-6}$alkyl, halogen, —CH$_2$F, —CHF$_2$, —CF$_3$, —(CH$_2$)$_{1-5}$CF$_3$ optionally substituted with 1, 2 or 3 —OH, —CO$_2$H, —CO$_2$C$_{1-6}$alkyl, and —SO$_2$C$_{1-6}$alkyl. In a class of this embodiment, CH$_2$ is unsubstituted or substituted with 1 or 2 substituents selected from: —C$_{1-6}$alkyl and halogen, and wherein cycloheteroalkyl and heteroaryl are unsubstituted or substituted with 1, 2, 3 or 4 substituents selected from: —OH, —(CH$_2$)$_{1-5}$CN, and —C$_{1-6}$alkyl substituted with 1-5 OH. In another embodiment of the present invention, each R$^a$ is independently selected from the group consisting of: halogen, —C(O)R$^f$, —C$_{2-6}$cycloheteroalkyl and heteroaryl, wherein cycloheteroalkyl and heteroaryl are unsubstituted or substituted with 1, 2, 3 or 4 substituents selected from: oxo, —OH, —(CH$_2$)$_{1-5}$OH, —(CH$_2$)$_{1-5}$CN, —CN, —NH$_2$, —NH(C$_{1-6}$alkyl), —N(C$_{1-6}$alkyl)$_2$, —C$_{1-6}$alkyl, —C$_{1-6}$alkyl substituted with 1-5 OH, —OC$_{1-6}$alkyl, halogen, —CH$_2$F, —CHF$_2$, —CF$_3$, —(CH$_2$)$_{1-5}$CF$_3$ optionally substituted with 1, 2 or 3 —OH, —CO$_2$H, —CO$_2$C$_{1-6}$alkyl, and —SO$_2$C$_{1-6}$alkyl. In a class of this embodiment, cycloheteroalkyl and heteroaryl are unsubstituted or substituted with 1, 2, 3 or 4 substituents selected from: —OH, —(CH$_2$)$_{1-5}$CN, —C$_{1-6}$alkyl substituted with 1-5 OH.

In another embodiment of the present invention, each R$^a$ is independently selected from the group consisting of: F, —C(O)pyrrolidine, morpholine, pyrazole, triazole and tetrazole, wherein cycloheteroalkyl and heteroaryl are unsubstituted or substituted with 1, 2, 3 or 4 substituents selected from: oxo, —OH, —(CH$_2$)$_{1-5}$OH, —(CH$_2$)$_{1-5}$CN, —CN, —NH$_2$, —NH(C$_{1-6}$alkyl), —N(C$_{1-6}$alkyl)$_2$, —C$_{1-6}$alkyl, —C$_{1-6}$alkyl substituted with 1-5 OH, —OC$_{1-6}$alkyl, halogen, —CH$_2$F, —CHF$_2$, —CF$_3$, —(CH$_2$)$_{1-5}$CF$_3$ optionally substituted with 1, 2 or 3 —OH, —CO$_2$H, —CO$_2$C$_{1-6}$alkyl, and —SO$_2$C$_{1-6}$alkyl. In a class of this embodiment, cycloheteroalkyl and heteroaryl are unsubstituted or substituted with 1, 2, 3 or 4 substituents selected from: —OH, —(CH$_2$)$_{1-5}$CN, —C$_{1-6}$alkyl substituted with 1-5 OH.

In another embodiment of the present invention, each R$^b$ is independently selected from: hydrogen, —C$_{1-6}$alkyl, —C$_{1-6}$alkenyl, —(CH$_2$)nC$_{3-10}$cycloalkyl, —(CH$_2$)nC$_{3-10}$cycloalkenyl, —(CH$_2$)nC$_{2-10}$cycloheteroalkyl, —(CH$_2$)nC$_{2-10}$cycloheteroalkenyl, —(CH$_2$)naryl, —(CH$_2$)nheteroaryl, oxo, —(CH$_2$)nCF$_3$, —(CH$_2$)nCN, —(CH$_2$)t-halogen, —(CH$_2$)s-OH, —(CH$_2$)nNO$_2$, —(CH$_2$)nNH$_2$, —(CH$_2$)nNH(C$_{1-6}$alkyl), —(CH$_2$)nN(C$_{1-6}$alkyl)$_2$, —(CH$_2$)nNHCO$_2$H, —(CH$_2$)nOC$_{1-6}$alkyl, —(CH$_2$)nOC$_{1-6}$alkenyl, —(CH$_2$)$_n$COC$_{1-6}$alkyl, —(CH$_2$)$_n$CO$_2$H, —(CH$_2$)$_n$OCOH, —(CH$_2$)$_n$CO$_2$R$^i$, —(CH$_2$)$_n$OC(O)R$^i$, —(CH$_2$)$_q$C(O)N(R$^e$)$_2$, —(CH$_2$)$_q$CO$_2$N(R$^e$)$_2$, —(CH$_2$)$_q$C(O)(CH$_2$)$_n$N(R$^g$)$_2$, —(CH$_2$)$_n$OC(O)(CH$_2$)$_n$N(R$^g$)$_2$, —(CH$_2$)nN(R$^e$)C(O)C$_{1-6}$alkyl, —(CH$_2$)$_n$N(R$^e$)SO$_2$R$^i$, —(CH$_2$)$_n$SO$_2$C$_{1-6}$alkyl, —(CH$_2$)$_n$SO$_2$N(R$^e$)R$^g$, —(CH$_2$)$_n$SO$_2$N(R$^e$)C(O)R$^i$, —(CH$_2$)$_n$SO$_2$N(R$^e$)CO$_2$R$^i$, —(CH$_2$)$_n$SO$_2$N(R$^e$)CON(R$^g$)$_2$, —(CH$_2$)$_n$C(O)N(R$^e$)SO$_2$R$^i$, —(CH$_2$)$_n$N(R$^e$)C(O)N(R$^g$)$_2$, =N(OH), and =N(OC$_{1-6}$alkyl), wherein each CH$_2$ is unsubstituted or substituted with 1 or 2 substituents selected from: —C$_{1-6}$alkyl, —OH, halogen and —NH$_2$ wherein each NH is unsubstituted or substituted with 1 substituent selected from R$^c$, and wherein each alkyl, cycloalkyl, cycloalkenyl, cycloheteroalkyl, cycloheteroalkenyl, aryl and heteroaryl is unsubstituted or substituted with 1, 2, 3 or 4 substituents selected from R$^c$, or wherein two R$^b$ substituents and the carbon to which they are attached may form a 3 to 6 membered cycloalkyl ring, a 3-6 membered cycloalkenyl ring, a 3-6 membered cycloheteroalkyl ring or a 3-6 membered cycloheteroalkenyl ring, wherein the ring is unsubstituted or substituted with 1, 2, 3 or 4 substituents selected from R$^c$. In a class of this embodiment, two R$^b$ substituents and the carbon to which they are attached may form a 3-6 membered cycloheteroalkyl ring, wherein the ring is unsubstituted or substituted with 1, 2, 3 or 4 substituents selected from R$^c$.

In another embodiment of the present invention, each R$^b$ is independently selected from: —C$_{1-6}$alkyl, —(CH$_2$)s-OH, —(CH$_2$)$_n$CO$_2$H, and —(CH$_2$)$_q$CO$_2$N(R$^e$)$_2$, wherein each CH$_2$ is unsubstituted or substituted with 1 or 2 substituents selected from: —C$_{1-6}$alkyl, —OH, halogen and —NH$_2$ wherein each NH is unsubstituted or substituted with 1 substituent selected from R$^c$, and wherein each alkyl is unsubstituted or substituted with 1, 2, 3 or 4 substituents selected from R$^c$, or wherein two R$^b$ substituents and the carbon to which they are attached may form a 3 to 6 membered cycloalkyl ring, a 3-6 membered cycloalkenyl ring, a 3-6 membered cycloheteroalkyl ring or a 3-6 membered cycloheteroalkenyl ring, wherein the ring is unsubstituted or substituted with 1, 2, 3 or 4 substituents selected from R$^c$. In a class of this embodiment, two R$^b$ substituents and the carbon to which they are attached may form a 3-6 membered cycloheteroalkyl ring, wherein the ring is unsubstituted or substituted with 1, 2, 3 or 4 substituents selected from R$^c$.

In another embodiment of the present invention, each R$^b$ is independently selected from: —C$_{1-6}$alkyl, —(CH$_2$)s-OH, —CO$_2$H, and —CO$_2$N(R$^e$)$_2$, wherein each CH$_2$ is unsubstituted or substituted with 1 or 2 substituents selected from: —C$_{1-6}$alkyl, —OH, halogen and —NH$_2$ wherein each NH is unsubstituted or substituted with 1 substituent selected from R$^c$, and wherein each alkyl is unsubstituted or substituted with 1, 2, 3 or 4 substituents selected from R$^c$. In a class of this embodiment, each R$^b$ is independently selected from: —CH$_3$, —OH, —CH$_2$OH, —CO$_2$H and —CO$_2$NH$_2$.

In another embodiment of the present invention, each R$^b$ is independently selected from: —(CH$_2$)s-OH. In another embodiment of the present invention, each R$^b$ is independently selected from: —OH and —CH$_2$OH.

In another embodiment of the present invention, each R$^c$ is independently selected from: halogen, oxo, —(CH$_2$)$_r$OH, —(CH$_2$)$_r$N(R$^e$)$_2$, —(CH$_2$)$_r$CN, —C$_{1-6}$alkyl, —CF$_3$, —C$_{1-6}$alkyl-OH, —OCH$_2$OC$_{1-6}$alkyl, —(CH$_2$)$_r$OC$_{1-6}$alkyl, —OCH$_2$aryl, —(CH$_2$)$_r$SC$_{1-6}$alkyl, —(CH$_2$)$_r$C(O)R$^f$, —(CH$_2$)$_r$C(O)N(R$^e$)$_2$, —(CH$_2$)$_r$CO$_2$H, —(CH$_2$)$_r$CO$_2$R$^f$, —(CH$_2$)$_r$C$_{3-7}$cycloalkyl, —(CH$_2$)$_r$C$_{2-6}$cycloheteroalkyl, —(CH$_2$)$_r$aryl, and —(CH$_2$)$_r$heteroaryl, wherein each CH$_2$ is unsubstituted or substituted with 1 or 2 substituents selected from: oxo, —OH, —CN, —N(R$^h$)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl and heteroaryl, and wherein alkyl, cycloalkyl, cycloheteroalkyl, aryl and heteroaryl are unsubstituted or substituted with 1, 2, 3 or 4 substituents selected from: oxo, —OH, —CN, —N(R$^h$)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl and heteroaryl. In a class of this embodiment, each R$^c$ is independently selected from: oxo, —(CH$_2$)$_r$OH, —(CH$_2$)$_r$CO$_2$H, and —(CH$_2$)$_r$CO$_2$R$^f$, wherein each CH$_2$ is unsubstituted or substituted with 1 or 2 substituents selected from: oxo, —OH, —CN, —N(R$^h$)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl and heteroaryl. In a subclass of this class, each R$^c$ is independently selected from: oxo, —OH, —CO$_2$H and —CO$_2$R$^f$.

In another embodiment of the present invention, each R$^c$ is independently selected from: halogen, oxo, —(CH$_2$)$_r$OH, —(CH$_2$)$_r$N(R$^e$)$_2$, —(CH$_2$)$_r$CN, —C$_{1-6}$alkyl, —CF$_3$, —C$_{1-6}$alkyl-OH, —OCH$_2$OC$_{1-6}$alkyl, —(CH$_2$)$_r$OC$_{1-6}$alkyl, —OCH$_2$aryl, —(CH$_2$)$_r$SC$_{1-6}$alkyl, —(CH$_2$)$_r$C(O)R$^f$, —(CH$_2$)$_r$C(O)N(R$^e$)$_2$, —(CH$_2$)$_r$CO$_2$H, and —(CH$_2$)$_r$CO$_2$R$^f$, wherein each CH$_2$ is unsubstituted or substituted with 1 or 2 substituents selected from: oxo, —OH, —CN, —N(R$^h$)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl and heteroaryl, and wherein alkyl, cycloalkyl, cycloheteroalkyl, aryl and heteroaryl are unsubstituted or substituted with 1, 2, 3 or 4 substituents selected from: oxo, —OH, —CN, —N(R$^h$)$_2$, —C$_{1-6}$alkyl, —OC$_{1-6}$alkyl, halogen, —CH$_2$F, —CHF$_2$, —CF$_3$, —CO$_2$H, and —CO$_2$C$_{1-6}$alkyl.

In another embodiment of the present invention, each R$^c$ is independently selected from: halogen, oxo, —(CH$_2$)$_r$OH, —(CH$_2$)$_r$N(R$^e$)$_2$, —(CH$_2$)$_r$CN, —C$_{1-6}$alkyl, —CF$_3$, and —C$_{1-6}$alkyl-OH.

In another embodiment of the present invention, each R$^c$ is independently selected from: halogen, oxo, and —C$_{1-6}$alkyl.

In another embodiment of the present invention, each R$^c$ is independently selected from: —C$_{1-6}$alkyl.

In another embodiment of the present invention, each R$^e$, R$^g$ and R$^h$ is independently selected from: hydrogen, —C$_{1-6}$alkyl, and —O—C$_{1-6}$alkyl, wherein alkyl is unsubstituted or substituted with 1, 2, 3 or 4 substituents selected from: —OH, oxo, halogen, C$_{1-6}$alkyl, —OC$_{1-6}$alkyl, —NH$_2$, —NH(C$_{1-6}$alkyl), and —N(C$_{1-6}$alkyl)$_2$. In another embodiment of the present invention, each R$^e$, R$^g$ and R$^h$ is hydrogen.

In another embodiment of the present invention, each R$^e$ is independently selected from: hydrogen, —C$_{1-6}$alkyl, and —O—C$_{1-6}$alkyl, wherein alkyl is unsubstituted or substituted with 1, 2, 3 or 4 substituents selected from: —OH, oxo, halogen, C$_{1-6}$alkyl, —OC$_{1-6}$alkyl, —NH$_2$, —NH(C$_{1-6}$alkyl), and —N(C$_{1-6}$alkyl)$_2$. In another embodiment of the present invention, each R$^e$ is hydrogen.

In another embodiment of the present invention, each R$^g$ is independently selected from: hydrogen, —C$_{1-6}$alkyl, and —O—C$_{1-6}$alkyl, wherein alkyl is unsubstituted or substituted with 1, 2, 3 or 4 substituents selected from: —OH, oxo, halogen, C$_{1-6}$alkyl, —OC$_{1-6}$alkyl, —NH$_2$, —NH(C$_{1-6}$alkyl), and —N(C$_{1-6}$alkyl)$_2$. In another embodiment of the present invention, each R$^g$ is hydrogen.

In another embodiment of the present invention, each $R^h$ is independently selected from: hydrogen, —$C_{1-6}$alkyl, and —O—$C_{1-6}$alkyl, wherein alkyl is unsubstituted or substituted with 1, 2, 3 or 4 substituents selected from: —OH, oxo, halogen, $C_{1-6}$alkyl, —$OC_{1-6}$alkyl, —$NH_2$, —NH($C_{1-6}$alkyl), and —N($C_{1-6}$alkyl)$_2$. In another embodiment of the present invention, each $R^h$ is hydrogen.

In another embodiment of the present invention, each $R^j$ is independently selected from: hydrogen, —$C_{1-6}$alkyl, —$C_{3-6}$cycloalkyl, —C(O)$R^i$, —$CO_2R^i$, and —$SO_2R^i$, wherein alkyl and cycloalkyl are unsubstituted or substituted with 1, 2, 3 or 4 substituents selected from: —OH, oxo, halogen, $C_{1-6}$alkyl, —$OC_{1-6}$alkyl, —$NH_2$, —NH($C_{1-6}$alkyl), and —N($C_{1-6}$alkyl)$_2$. In another embodiment of the present invention, each $R^j$ is independently selected from: hydrogen, —$C_{1-6}$alkyl. In another embodiment of the present invention, each $R^j$ is hydrogen.

In another embodiment of the present invention, each $R^f$ and $R^i$ is independently selected from: —$C_{1-6}$alkyl, —(CH$_2$)$_r$$C_{4-7}$cycloalkyl, —(CH$_2$)$_r$$C_{4-7}$cycloalkenyl, —(CH$_2$)$_r$$C_{3-7}$cycloheteroalkyl, —(CH$_2$)$_r$$C_{3-7}$cycloheteroalkenyl, —(CH$_2$)$_r$aryl, and —(CH$_2$)$_r$heteroaryl, wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —OH, —CN, —$NH_2$, —NH($C_{1-6}$alkyl), —N($C_{1-6}$alkyl)$_2$, —$C_{1-6}$alkyl, —$OC_{1-6}$alkyl, halogen, —$CH_2F$, —$CHF_2$, —$CF_3$, —$CO_2H$, —$CO_2C_{1-6}$alkyl, —$C_{3-7}$cycloalkyl, and heteroaryl. In a class of this embodiment, alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —OH, —CN, —$NH_2$, —NH($C_{1-6}$alkyl), —N($C_{1-6}$alkyl)$_2$, —$C_{1-6}$alkyl, —$OC_{1-6}$alkyl, halogen, —$CH_2F$, —$CHF_2$, —$CF_3$, —$CO_2H$, and —$CO_2C_{1-6}$alkyl.

In another embodiment of the present invention, each $R^f$ and $R^i$ is independently selected from: $C_{3-7}$cycloheteroalkyl, wherein cycloheteroalkyl is unsubstituted or substituted with 1, 2, 3 or 4 substituents selected from: oxo, —OH, —CN, —$NH_2$, —NH($C_{1-6}$alkyl), —N($C_{1-6}$alkyl)$_2$, —$C_{1-6}$alkyl, —$OC_{1-6}$alkyl, halogen, —$CH_2F$, —$CHF_2$, —$CF_3$, —$CO_2H$, and —$CO_2C_{1-6}$alkyl. In a class of this embodiment, each $R^f$ and $R^i$ is independently selected from: pyrrolidine, wherein pyrrolidine is unsubstituted or substituted with 1, 2, 3 or 4 substituents selected from: oxo, —OH, —CN, —$NH_2$, —NH($C_{1-6}$alkyl), —N($C_{1-6}$alkyl)$_2$, —$C_{1-6}$alkyl, —$OC_{1-6}$alkyl, halogen, —$CH_2F$, —$CHF_2$, —$CF_3$, —$CO_2H$, and —$CO_2C_{1-6}$alkyl.

In another embodiment of the present invention, each $R^f$ is independently selected from: —$C_{1-6}$alkyl, —(CH$_2$)$_r$$C_{4-7}$cycloalkyl, —(CH$_2$)$_r$$C_{4-7}$cycloalkenyl, —(CH$_2$)$_r$$C_{3-7}$cycloheteroalkyl, —(CH$_2$)$_r$$C_{3-7}$cycloheteroalkenyl, —(CH$_2$)$_r$aryl, and —(CH$_2$)$_r$heteroaryl, wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —OH, —CN, —$NH_2$, —NH($C_{1-6}$alkyl), —N($C_{1-6}$alkyl)$_2$, —$C_{1-6}$alkyl, —$OC_{1-6}$alkyl, halogen, —$CH_2F$, —$CHF_2$, —$CF_3$, —$CO_2H$, —$CO_2C_{1-6}$alkyl, —$C_{3-7}$cycloalkyl, and heteroaryl. In a class of this embodiment, alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —OH, —CN, —$NH_2$, —NH($C_{1-6}$alkyl), —N($C_{1-6}$alkyl)$_2$, —$C_{1-6}$alkyl, —$OC_{1-6}$alkyl, halogen, —$CH_2F$, —$CHF_2$, —$CF_3$, —$CO_2H$, and —$CO_2C_{1-6}$alkyl.

In another embodiment of the present invention, each $R^f$ is independently selected from: $C_{3-7}$cycloheteroalkyl, wherein cycloheteroalkyl is unsubstituted or substituted with 1, 2, 3 or 4 substituents selected from: oxo, —OH, —CN, —$NH_2$, —NH($C_{1-6}$alkyl), —N($C_{1-6}$alkyl)$_2$, —$C_{1-6}$alkyl, —$OC_{1-6}$alkyl, halogen, —$CH_2F$, —$CHF_2$, —$CF_3$, —$CO_2H$, and —$CO_2C_{1-6}$alkyl. In a class of this embodiment, each $R^f$ and $R^i$ is independently selected from: pyrrolidine, wherein pyrrolidine is unsubstituted or substituted with 1, 2, 3 or 4 substituents selected from: oxo, —OH, —CN, —$NH_2$, —NH($C_{1-6}$alkyl), —N($C_{1-6}$alkyl)$_2$, —$C_{1-6}$alkyl, —$OC_{1-6}$alkyl, halogen, —$CH_2F$, —$CHF_2$, —$CF_3$, —$CO_2H$, and —$CO_2C_{1-6}$alkyl.

In another embodiment of the present invention, each $R^i$ is independently selected from: —$C_{1-6}$alkyl, —(CH$_2$)$_r$$C_{4-7}$cycloalkyl, —(CH$_2$)$_r$$C_{4-7}$cycloalkenyl, —(CH$_2$)$_r$$C_{3-7}$cycloheteroalkyl, —(CH$_2$)$_r$$C_{3-7}$cycloheteroalkenyl, —(CH$_2$)$_r$aryl, and —(CH$_2$)$_r$heteroaryl, wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —OH, —CN, —$NH_2$, —NH($C_{1-6}$alkyl), —N($C_{1-6}$alkyl)$_2$, —$C_{1-6}$alkyl, —$OC_{1-6}$alkyl, halogen, —$CH_2F$, —$CHF_2$, —$CF_3$, —$CO_2H$, —$CO_2C_{1-6}$alkyl, —$C_{3-7}$cycloalkyl, and heteroaryl. In a class of this embodiment, alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —OH, —CN, —$NH_2$, —NH($C_{1-6}$alkyl), —N($C_{1-6}$alkyl)$_2$, —$C_{1-6}$alkyl, —$OC_{1-6}$alkyl, halogen, —$CH_2F$, —$CHF_2$, —$CF_3$, —$CO_2H$, and —$CO_2C_{1-6}$alkyl.

In another embodiment of the present invention, each $R^i$ is independently selected from: $C_{3-7}$cycloheteroalkyl, wherein cycloheteroalkyl is unsubstituted or substituted with 1, 2, 3 or 4 substituents selected from: oxo, —OH, —CN, —$NH_2$, —NH($C_{1-6}$alkyl), —N($C_{1-6}$alkyl)$_2$, —$C_{1-6}$alkyl, —$OC_{1-6}$alkyl, halogen, —$CH_2F$, —$CHF_2$, —$CF_3$, —$CO_2H$, and —$CO_2C_{1-6}$alkyl. In a class of this embodiment, each $R^f$ and $R^i$ is independently selected from: pyrrolidine, wherein pyrrolidine is unsubstituted or substituted with 1, 2, 3 or 4 substituents selected from: oxo, —OH, —CN, —$NH_2$, —NH($C_{1-6}$alkyl), —N($C_{1-6}$alkyl)$_2$, —$C_{1-6}$alkyl, —$OC_{1-6}$alkyl, halogen, —$CH_2F$, —$CHF_2$, —$CF_3$, —$CO_2H$, and —$CO_2C_{1-6}$alkyl.

In another embodiment of the present invention, n is 0, 1, 2, 3 or 4. In a class of this embodiment, n is 1, 2 or 3. In another class of this embodiment, n is 0, 1 or 2. In another class of this embodiment, n is 0. In another class of this embodiment, n is 1. In another class of this embodiment, n is 2.

In another embodiment of the present invention, m is 0, 1, 2, 3, or 4. In a class of this embodiment, m is 0, 1, 2 or 3. In another class of this embodiment, m is 1, 2 or 3. In another class of this embodiment, m is 0, 1 or 2. In another class of this embodiment, m is 0 or 1. In another class of this embodiment, m is 0. In another class of this embodiment, m is 1.

In another embodiment of the present invention, p is 0, 1, 2 or 3. In a class of this embodiment, p is 1, 2 or 3. In another class of this embodiment, p is 0, 1 or 2. In another class of this embodiment, p is 0 or 2. In another class of this embodiment, p is 0. In another class of this embodiment, p is 1. In another class of this embodiment, p is 2.

In another embodiment of the present invention, q is 0, 1, 2, 3 or 4. In a class of this embodiment, q is 1, 2 or 3. In another class of this embodiment, q is 0, 1 or 2. In another class of this embodiment, q is 1 or 2. In another class of this embodiment, q is 0. In another class of this embodiment, q is 1. In another class of this embodiment, q is 2.

In another embodiment of the present invention, r is 0, 1 or 2. In a class of this embodiment, r is 0 or 1. In another class of this embodiment, r is 0. In another class of this embodiment, r is 1. In another class of this embodiment, r is 2.

In another embodiment of the present invention, s is 0, 1, 2, 3 or 4. In a class of this embodiment, s is 0, 1, 2 or 3. In a class of this embodiment, s is 0, 1 or 2. In another class of this embodiment, s is 0 or 1. In another class of this embodiment, s is 1 or 2. In another class of this embodiment, s is 0 or 2. In another class of this embodiment, s is 0. In another class of this embodiment, s is 1. In another class of this embodiment, s is 2. In another class of this embodiment, s is 3.

In another embodiment of the present invention, t is 0, 1, 2, 3 or 4. In a class of this embodiment, t is 0, 1, 2 or 3. In a class of this embodiment, t is 0, 1 or 2. In another class of this embodiment, t is 0 or 1. In another class of this embodiment, t is 1 or 2. In another class of this embodiment, t is 0 or 2. In another class of this embodiment, t is 0. In another class of this embodiment, t is 1. In another class of this embodiment, t is 2. In another class of this embodiment, t is 3.

In another embodiment of the present invention, u is 0, 1, 2, 3 or 4. In a class of this embodiment, u is 0, 1, 2 or 3. In a class of this embodiment, u is 0, 1 or 2. In another class of this embodiment, u is 0 or 1. In another class of this embodiment, u is 1 or 2. In another class of this embodiment, u is 0 or 2. In another class of this embodiment, u is 0. In another class of this embodiment, u is 1. In another class of this embodiment, u is 2. In another class of this embodiment, u is 3. In another class of this embodiment, u is 4.

Another embodiment of the present invention relates to compounds of structural formula I wherein:
T is N;
U is —$CR^1$—;
V is —$CR^2$—;
W is —$CR^4$—;
X is —O—;
Y is selected from:

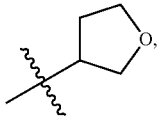

wherein Y is unsubstituted or substituted with 1, 2, 3, 4 or 5 substituents selected from $R^b$;
Z is $NR^5$;
each $R^1$ is independently selected from:
(1) —$(CH_2)_p$aryl-aryl, and
(2) aryl-heteroaryl,
wherein each aryl and heteroaryl is unsubstituted or substituted with 1, 2, 3 or 4 substituents independently selected from $R^a$;
$R^2$ is halogen;
$R^4$ is hydrogen;
$R^5$ is hydrogen;
or a pharmaceutically acceptable salt thereof.

Another embodiment of the present invention relates to compounds of structural formula I wherein:
T is N;
U is —$CR^1$—;
V is —$CR^2$—;
W is —$CR^4$—;
X is —O—;
Y is:

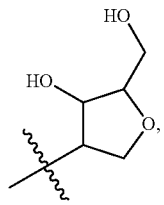

wherein Y is unsubstituted or substituted with 1, 2 or 3 substituents selected from $R^b$;
Z is $NR^5$;
each $R^1$ is independently selected from:
(1) biphenyl,
(2) phenyl-naphthalene,
(3) phenyl-pyridine, and
(4) phenyl-dihydropyrrolopyrazole,
wherein each phenyl, naphthalene, pyridine and dihydropyrrolopyrazole is unsubstituted or substituted with 1, 2, 3 or 4 substituents independently selected from $R^a$;
$R^2$ is halogen;
$R^4$ is hydrogen; and
$R^5$ is hydrogen;
or a pharmaceutically acceptable salt thereof.

Another embodiment of the present invention relates to compounds of structural formula I wherein:
T is N;
U is —$CR^1$—;
V is —$CR^2$—;
W is —$CR^4$—;
X is —O—;
Y is:

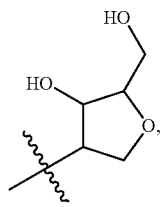

wherein Y is unsubstituted or substituted with 1, 2 or 3 substituents selected from $R^b$;
Z is NR;
each $R^1$ is independently selected from: aryl-aryl, wherein each aryl is unsubstituted or substituted with 1, 2, 3 or 4 substituents independently selected from $R^a$;
$R^2$ is halogen;
$R^4$ is hydrogen; and
$R^5$ is hydrogen;
or a pharmaceutically acceptable salt thereof.

In another embodiment of the present invention, the invention relates to compounds of structural formula Ia:

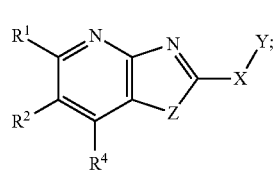

(Ia)

or a pharmaceutically acceptable salt thereof.

In another embodiment of the present invention, the invention relates to compounds of structural formula Ib:

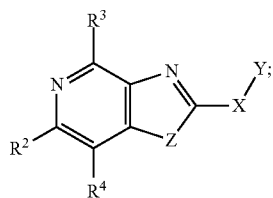

(Ib)

or a pharmaceutically acceptable salt thereof.

In another embodiment of the present invention, the invention relates to compounds of structural formula Ic:

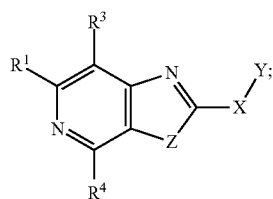

(Ic)

or a pharmaceutically acceptable salt thereof.

In another embodiment of the present invention, the invention relates to compounds of structural formula Id:

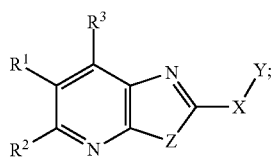

(Id)

or a pharmaceutically acceptable salt thereof.

In another embodiment of the present invention, the invention relates to compounds of structural formula Ie:

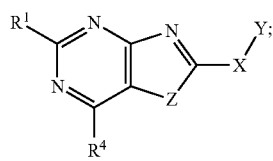

(Ie)

or a pharmaceutically acceptable salt thereof.

In another embodiment of the present invention, the invention relates to compounds of structural formula If:

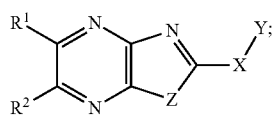

(If)

or a pharmaceutically acceptable salt thereof.

In another embodiment of the present invention, the invention relates to compounds of structural formula Ig:

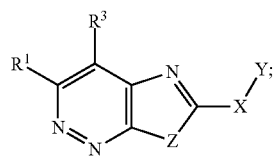

(Ig)

or a pharmaceutically acceptable salt thereof.

The compound of structural formula I, includes the compounds of structural formulas Ia, Ib, Ic, Id, Ie, If and Ig and pharmaceutically acceptable salts, hydrates and solvates thereof.

Illustrative, but non-limiting, examples of the compounds of the present invention that are useful as activators of AMP-protein kinase are the following compounds:

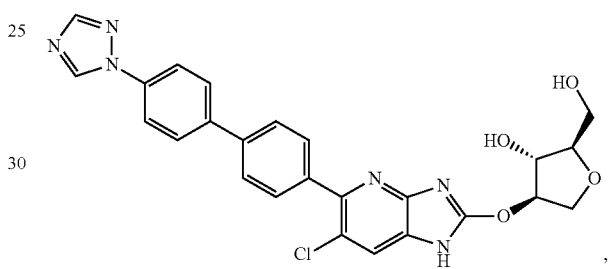

,

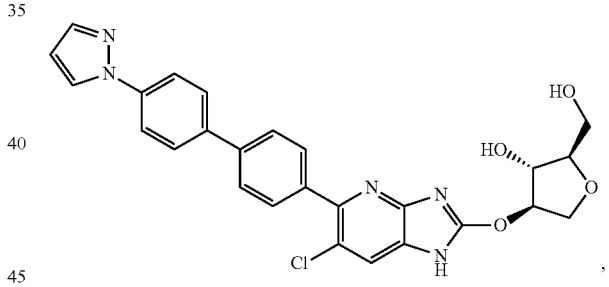

,

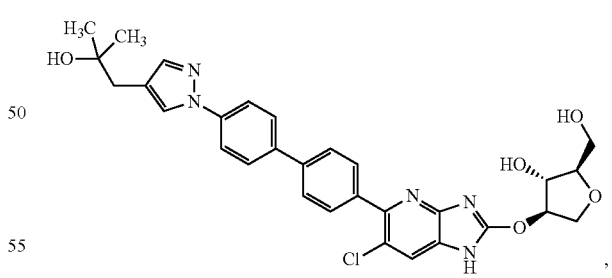

,

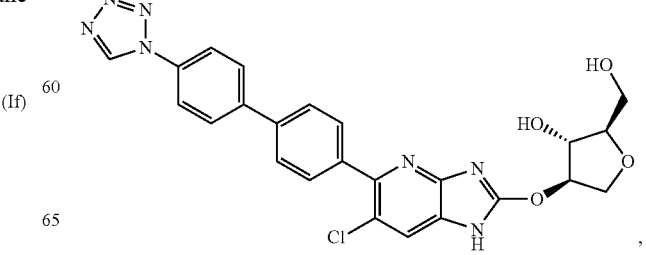

,

-continued

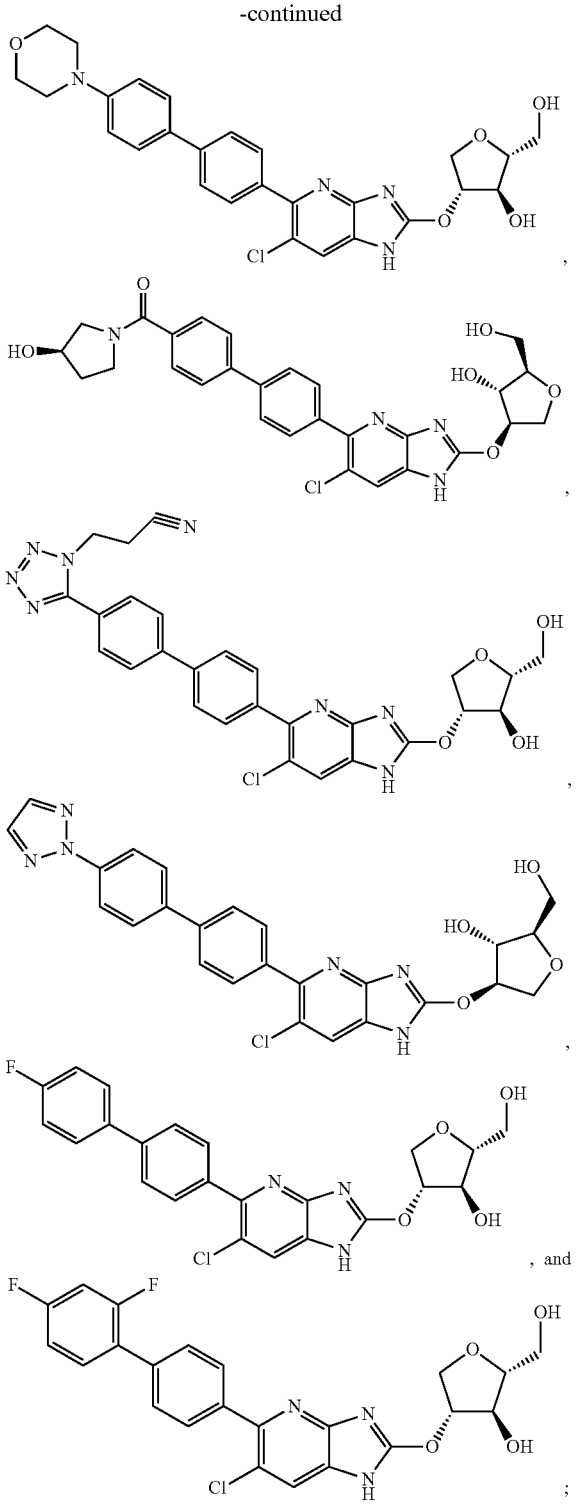

and pharmaceutically acceptable salts thereof.

"Alkyl", as well as other groups having the prefix "alk", such as alkoxy, alkanoyl, means carbon chains of up to 10 carbons which may be linear or branched or combinations thereof. Examples of alkyl groups include methyl, ethyl, n-propyl, isopropyl, butyl, isobutyl, sec- and tert-butyl, pentyl, hexyl, heptyl, octyl, nonyl, and the like.

"Alkenyl" means carbon chains up to 10 carbons which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like. In one embodiment of the present invention, alkenyl is vinyl.

"Alkynyl" means carbon chains up to 10 carbons which contain at least one carbon-carbon triple bond, and which may be linear or branched or combinations thereof. In one embodiment, $C_{2-8}$alkynyl means a carbon chain with 2 to 8 carbons that contains one carbon-carbon triple bond. Examples of alkynyl include ethynyl, propargyl, 3-methyl-1-pentynyl, 2-heptynyl and the like. In one embodiment of the present invention, alkynyl is ethynyl. In another embodiment, alkynyl is propargyl.

"Cycloalkyl" means mono- or bicyclic, spiro or bridged saturated carbocyclic rings, each having from 3 to 14 carbon atoms. Examples of cycloalkyl include cyclopropyl, cyclobutyl, cyclopentyl, cyclohexyl, cycloheptyl, cyclooctyl, and decahydronaphthyl, and the like. In one embodiment of the present invention, cycloalkyl is selected from cyclopentyl and cyclohexyl. In another embodiment of the present invention, cycloalkyl is selected from cyclopropyl, cyclopentyl, and cyclohexyl. In another embodiment of the present invention, cycloalkyl is selected from: cyclopropyl, cyclobutyl, cyclopentyl, and cyclohexyl. In another embodiment of the present invention, cycloalkyl is selected from: cyclopropyl, cyclobutyl, and cyclopentyl.

"Cycloalkenyl" means nonaromatic, mono- or bicyclic, spiro or bridged carbocyclic rings, each having from 3 to 14 carbon atoms and containing at least one double bond. Examples of cycloalkyl include cyclopropenyl, cyclobutenyl, cyclopentenyl, cyclohexenyl, cycloheptenyl, cyclooxtenyl, decahydronaphthyl, bicyclo[2.2.1]hept-5-en-2-yl, and the like.

"Cycloheteroalkyl" means nonaromatic, monocyclic, bicyclic, spiro or bridged saturated carbocyclic rings, each having from 2 to 14 carbon atoms and containing 1, 2, 3, 4 or 5 heteroatoms selected from N, NH, O and S. In one embodiment, $C_{2-10}$cycloheteroalkyl means non-aromatic, mono- or bicyclic, spiro or bridged saturated carbocyclic rings, having from 2 to 10 carbon atoms and containing, 1, 2, 3, 4 or 5 heteroatoms selected from N, NH, O and S. In one embodiment, $C_{2-6}$cycloheteroalkyl means non-aromatic, mono- or bicyclic, spiro or bridged saturated carbocyclic rings, having from 2 to 6 carbon atoms and containing, 1, 2, 3, 4 or 5 heteroatoms selected from N, NH, O and S. In one embodiment, $C_{3-7}$cycloheteroalkyl means non-aromatic, mono- or bicyclic, spiro or bridged saturated carbocyclic rings, having from 3 to 7 carbon atoms and containing, 1, 2, 3, 4 or 5 heteroatoms selected from N, NH, O and S. Examples of cycloheteroalkyl include tetrahydrofuranyl, azetidinyl, perhydroazepinyl, dihydrofuranyl, dioxanyl, oxanyl, morpholinyl, 1,4-dithianyl, piperazinyl, piperidinyl, 1,3-dioxolanyl, imidazolidinyl, imidazolinyl, pyrrolinyl, pyrrolidinyl, pyranyl, tetrahydropyranyl, dihydropyranyl, oxathiolanyl, dithiolanyl, 1,3-dithianyl, oxathianyl, thiomorpholinyl, dioxidoisothiazolidinyl, azacycloheptyl, diazobicyclo[3.2.1]-octane, and hexahydroindazolyl. The cycloheteroalkyl ring may be substituted on the ring carbons and/or the ring nitrogens. In one embodiment of the present invention, cycloheteroalkyl is selected from piperidine, pyrrolidine, oxazolidine, 1,3-oxazolidine-2,4-dione, thiazolidine, 1,3-thiazolidine-2,4-dione, imidazolidine, and hydantoin, and the like. In another embodiment of the present invention cycloheteroalkyl is selected from: morpholine, pyrrolidine, piperazine, and piperidine. In another embodiment of the present invention, cycloheteroalkyl is pyrrolidine.

In another embodiment, $C_{2-10}$cycloheteroalkyl is a non-aromatic monocyclic, bicyclic, spiro or bridged carbocyclic ring having from 2 to 10 carbon atoms, and containing 1 or 2 heteroatoms selected from O. In another embodiment of the present invention, cycloheteroalkyl is dianhydro-mannitol. In another embodiment of the present invention, cycloheteroalkyl is 1,4:3,6-dianhydro-mannitol. In another embodiment of the present invention, cycloheteroalkyl is 1,4:3,6-dianhydro-D-mannitol. In another embodiment of the present invention, cycloheteroalkyl is hexahydrofuro[3,2-b]furan. In a class of this embodiment, cycloheteroalkyl is 2,3,3a,5,6,6a-hexahydrofuro[3,2-b]furan.

In another embodiment, $C_{3-7}$cycloheteroalkyl is pyrrolidine. In another embodiment, $C_{2-6}$cycloheteroalkyl is morpholine.

In another embodiment, $C_{2-10}$cycloheteroalkyl is pyrrolidine, piperazine and azetidine.

"Cycloheteroalkenyl" means aromatic monocyclic, bicyclic, spiro or bridged rings each having from 2 to 14 carbon atoms containing at least one double bond and containing 1, 2, 3, 4 or 5 heteroatoms selected from N, NH, O and S. Examples of cycloheteroalkenyl include 1,2,4-oxadiazol-5-one, 1,2,4-thiadiazol-5-one, 1,2,4-triazol-3-one, and 1,2,3,6-tetrahydropyridine, dihydro-1,3,4-oxadiazole, and [1,6]-dihydropyridine and the like. In one embodiment of the present invention, cycloheteroalkenyl is dihydro-1,3,4-oxadiazole. In another embodiment of the present invention, cycloheteroalkenyl is [1,6]-dihydropyridine. In another embodiment of the present invention, cycloheteroalkenyl is dihydrothiophene and dihydrothiopyran. In another embodiment of the present invention, cycloheteroalkenyl is 2,5-dihydrothiophene and 3,6-dihydrothiopyran. In another embodiment of the present invention, cycloheteroalkenyl is dihydrothiopyran. In another embodiment of the present invention, cycloheteroalkenyl is 3,6-dihydrothiopyran.

In another embodiment, $C_{2-10}$cycloheteroalkenyl is a non-aromatic, bicyclic carbocyclic ring having from 2 to 10 carbon atoms, and containing 1, 2 or 3 heteroatoms selected from N, and NH. In a class of this embodiment, cycloheteroalkenyl is dihydropyrrolo[3,4-c]pyrazole. In another class of this embodiment, cycloheteroalkenyl is 4,6-dihydropyrrolo[3,4-c]pyrazole.

In another embodiment, $C_{2-6}$cycloheteroalkenyl is a non-aromatic, bicyclic carbocyclic ring having from 2 to 6 carbon atoms, and containing 1 or 2 heteroatoms selected from N, and NH. In a class of this embodiment, cycloheteroalkenyl is dihydroimidazole or tetrahydropyrimidine. In another class of this embodiment, cycloheteroalkenyl is 2,5 dihydro-1H-imidazole or 1,4,5,6-tetrahydropyrimidine. In another class of this embodiment, cycloheteroalkenyl is dihydroimidazole. In another class of this embodiment, cycloheteroalkenyl is 2,5 dihydro-1H-imidazole. In another class of this embodiment, cycloheteroalkenyl is tetrahydropyrimidine. In another class of this embodiment, cycloheteroalkenyl is 1,4,5,6-tetrahydropyrimidine.

"Aryl" means a monocyclic, bicyclic or tricyclic ring system containing 5-14 carbon atoms, wherein at least one of the rings is aromatic. Aryl thus includes ring systems in which an aromatic ring is fused to a non-aromatic ring, such as a cycloalkyl or cycloalkenyl ring. Examples of aryl include phenyl, naphthalene, biphenyl, indane and 5,6,7,8-tetrahydronaphthalene, and the like. In one embodiment of the present invention, aryl is phenyl, naphthalene, biphenyl, indane, and 5,6,7,8-tetrahydronaphthalene. In another embodiment of the present invention, aryl is phenyl, naphthalene, indane and 5,6,7,8-tetrahydronaphthalene. In one class of this embodiment, aryl is phenyl and naphthalene. In another class of this embodiment, aryl is phenyl. In another class of this embodiment, aryl is naphthalene.

"Heteroaryl" means a monocyclic, bicyclic or tricyclic ring system containing 5-14 carbon atoms and containing 1, 2, 3, 4 or 5 heteroatoms selected from N, NH, O and S wherein at least one of the heteroatom containing rings is aromatic. Heteroaryl thus includes ring systems in which an aromatic heteroatom containing ring is fused to a non-aromatic ring, such as a cycloalkyl, cycloalkenyl, cycloheteroalkyl or cycloheteroalkenyl ring, and also includes ring systems in which an aryl ring is fused to a non-aromatic heteroatom containing ring, such as acycloheteroalkyl or cycloheteroalkenyl ring. Examples of heteroaryls include: pyrazole, pyridine, pyrazine, pyrimidine, thiazole, thiophene, benzoimidazole, quinoline, isoquinoline, indole, indazole, carbazole, benzotriazole, benzofuran, benzothiazole, benzothiophene, benzoisooxazole, oxazole, furan, benzoxazole, isoxazole, indoline, isoindoline, tetrazole, imidazole, oxadiazole, thiadiazole, triazole, benzothiazole, bernzopyrazole, imidazopyridine, benzodioxole, dihydropyridine, dihydropyrrolopyridine, dihydrobenzooxazine, benzodioxole, benzodioxine, pyrrolopyridine, triazolopyridine, dihydropyridooxazine, dihydrobenzoxazine, dihydroindole, dihydroisoindole, dihydrobenzoimidazole, dihydroquinoline, tetrahydroisoquinoline, tetrahydrocyclopentaindole, tetrahydroquinoxaline, and tetrahydropyridine. In one embodiment of the present invention, heteroaryl is selected from: imidazole, pyrazole, pyridine, pyrazine, pyrimidine, thiazole, thiophene, benzoimidazole, quinoline, isoquinoline, indole, indazole, carbazole, benzotriazole, benzofuran, benzothiazole, benzo[b]thiophene, benzo[d]isooxazole, 3,4-dihydro-2H-benzo[1,4]oxazine, benzo[1,3]dioxole, benzo[1,4]dioxine, 1H-pyrrolo[2,3-b]pyridine, 1,6-dihydro-pyridine, [1,2,4]triazolo[4,3-a]pyridine, 3,4 dihydropyrido[3,2-b][1,4]oxazine, 3,4-dihydro-2H-1,4-benzoxazine, 2,3-dihydro-1H-indole, 2,3-dihydro-1H-isoindole, 2,3-dihydrobenzoimidazole, 1,2-dihydroquinoline, 1,2,3,4-tetrahydroisoquinoline, 1,2,3,4-tetrahydrocyclopenta[b]indole, 1,2,3,4-tetrahydroquinoxaline, and 1,2,3,6-tetrahydropyridine. In another embodiment of the present invention, heteroaryl is tetrazole. In another embodiment, heteroaryl is selected from: pyrazole, pyridine, pyrimidine, isoxazole, imidazole, oxazole, triazole, tetrazole, oxadiazole, thiazole, thiadiazole, benzodioxane and benzoxazole. In another embodiment, heteroaryl is selected from: pyrazole, pyridine, pyrimidine, isoxazole, imidazole, oxazole, triazole, tetrazole, oxadiazole, thiazole, thiadiazole, and benzoxazole. In another embodiment of this invention, heteroaryl is tetrazole.

In another embodiment, heteroaryl is pyridine or dihydropyrrolopyrazole. In another embodiment, heteroaryl is pyrazole, triazole, or tetrazole.

In another embodiment of the present invention, dihydropyrrolopyrazole is 4,6-dihydropyrrolo[3,4-c]pyrazole, In another embodiment of the present invention, dihydroimidazole is 4,5-dihydro-1H-imidazole.

"Halogen" includes fluorine, chlorine, bromine and iodine. In one embodiment of the present invention, halogen is selected from fluorine, chlorine, and bromine. In another embodiment of the present invention, halogen is selected from fluorine, and chlorine. In another embodiment of the present invention, halogen is fluorine. In another embodiment of the present invention, halogen is chlorine.

When any variable (e.g., $R^1$, $R^a$, etc.) occurs more than one time in any constituent or in formula I, its definition on each occurrence is independent of its definition at every other occurrence. Also, combinations of substituents and/or variables are permissible only if such combinations result in stable compounds. A squiggly line across a bond in a substituent variable represents the point of attachment.

Under standard nomenclature used throughout this disclosure, the terminal portion of the designated side chain is described first, followed by the adjacent functionality toward the point of attachment. For example, a $C_{1-5}$ alkylcarbonylamino $C_{1-6}$ alkyl substituent is equivalent to:

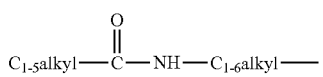

In choosing compounds of the present invention, one of ordinary skill in the art will recognize that the various substituents, i.e. $R^1$, $R^2$, etc., are to be chosen in conformity with well-known principles of chemical structure connectivity and stability.

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

Compounds of Formula I may contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Tautomers are defined as compounds that undergo rapid proton shifts from one atom of the compound to another atom of the compound. Some of the compounds described herein may exist as tautomers with different points of attachment of hydrogen. Such an example may be a ketone and its enol form known as keto-enol tautomers. The individual tautomers as well as mixture thereof are encompassed with compounds of Formula I.

Examples of tautomers include, but are not limited to:

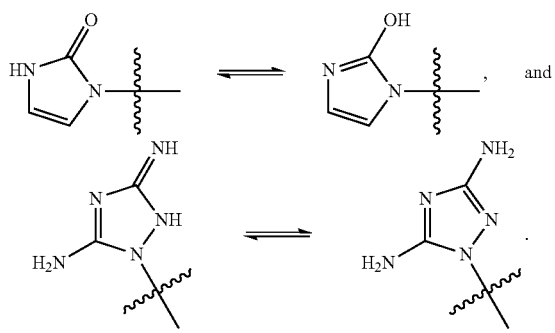

In the compounds of general formula I, the atoms may exhibit their natural isotopic abundances, or one or more of the atoms may be artificially enriched in a particular isotope having the same atomic number, but an atomic mass or mass number different from the atomic mass or mass number predominately found in nature. The present invention is meant to include all suitable isotopic variations of the compounds of structural formula I. For example, different isotopic forms of hydrogen (H) include protium (1H) and deuterium (2H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within structural formula I, can be prepared without undue experimentation by conventional techniques well known to those skilled in the art or by processes analogous to those described in the Schemes and Examples herein using appropriate isotopically-enriched reagents and/or intermediates.

Compounds of the Formula I may be separated into diastereoisomeric pairs of enantiomers by, for example, fractional crystallization from a suitable solvent, for example MeOH or ethyl acetate or a mixture thereof. The pair of enantiomers thus obtained may be separated into individual stereoisomers by conventional means, for example by the use of an optically active amine as a resolving agent or on a chiral HPLC column.

Alternatively, any enantiomer of a compound of the general Formula I may be obtained by stereospecific synthesis using optically pure starting materials or reagents of known configuration.

Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

It is generally preferable to administer compounds of the present invention as enantiomerically pure formulations. Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. The term "pharmaceutically acceptable salt" further includes all acceptable salts such as acetate, trifluoroacetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate, valerate, and the like which can be used as a dosage form for modifying the solubility or hydrolysis characteristics or can be used in sustained release or pro-drug formulations.

It will be understood that, as used herein, references to the compounds of Formula I are meant to also include the pharmaceutically acceptable salts.

Compounds of the present invention are activators of the AMP-activated protein kinase. The methods of treatment of this invention comprise a method of activating AMPK-activated protein kinase and treating AMPK-activated protein kinase mediated diseases by administering to a patient in need of such treatment a non-toxic therapeutically effective amount of a compound of this invention that activates AMPK-activated protein kinase.

AMP-activated protein kinase (AMPK) is a heterotrimeric enzyme composed of a catalytic a subunit and regulatory β and γ subunits. There are two genes encoding isoforms of both the α and β subunits (α1, α2, β1 and β2) and three genes encoding isoforms of the γ subunit (γ1, γ2 and γ3) leading to 12 possible heterotrimeric combinations. The α2 isoform is predominately found in skeletal and cardiac muscle AMPK; both the al and α2 isoforms are found in hepatic AMPK; while in pancreatic islet β-cells the al isoform AMPK predominates. In particular, the compounds of structural formula I are activators of at least one heterotrimeric isoform of AMP-activated protein kinase.

An "activator" is a compound that either increases the activity (phosphorylation of downstream substrates) of fully phosphorylated AMPK or that increases the phosphorylation of AMPK.

The compounds of the present invention are efficacious in the treatment and prevention of diseases, disorders and conditions that are responsive to the activation of AMP-activated protein kinase. As AMPK activators, the compounds of the present invention may be useful for the treatment of Type 2 diabetes, insulin resistance, hyperglycemia, obesity, hyperinsulinemia, glucose intolerance, atherosclerosis, Metabolic Syndrome, hypertension, high hepatic glucose output, high blood glucose concentrations, nonalcoholic steatohepatitis, protection against ischemia and reperfusion damage, and lipid disorders, such as dyslipidemia, elevated levels of plasma triglycerides, elevated levels of free fatty acids, elevated levels of cholesterol, high levels of low density lipoprotein (LDL) and low levels of high density lipoprotein (HDL). The compounds of the present invention may also be useful for the treatment of cancer, hypoxia and glucocorticoid-induced apoptosis. The compounds of the present invention may also be useful for the treatment of sarcopenia by treating or preventing the loss of skeletal muscle mass, including but not limited to a loss of skeletal muscle mass due to aging.

One or more of the following diseases may be treated by the administration of a therapeutically effective amount of a compound of Formula I, or a pharmaceutically acceptable salt thereof, to a patient in need of treatment or prevention of: (1) non-insulin dependent diabetes mellitus (Type 2 diabetes); (2) hyperglycemia; (3) Metabolic Syndrome; (4) obesity; (5) hypercholesterolemia; (6) hypertriglyceridemia (elevated levels of triglyceride-rich-lipoproteins); (7) mixed or diabetic dyslipidemia; (8) low HDL cholesterol; (9) high LDL cholesterol; (10) atherosclerosis; (11) atherosclerosis, (12) hypertension, and (13) sarcopenia.

In one embodiment of the present invention, the compounds of Formula I may be useful for the treatment of one or more of the following diseases by administering a therapeutically effective amount to a patient in need of treatment: (1) Type 2 diabetes; (2) hyperglycemia; (3) Metabolic Syndrome; (4) obesity; (5) hypercholesterolemia; and (6) hypertension.

The compounds of structural Formula I may also be used for manufacturing a medicament for use in the treatment of one or more of the above diseases.

The compounds may also be effective in lowering glucose and lipids in diabetic patients and in non-diabetic patients who have impaired glucose tolerance and/or are in a pre-diabetic condition. The compounds may ameliorate hyperinsulinemia, which often occurs in diabetic or pre-diabetic patients, by modulating the swings in the level of serum glucose that often occurs in these patients. The compounds may also be effective in treating or reducing insulin resistance. The compounds may be effective in treating or preventing gestational diabetes.

The compounds, compositions, methods and medicaments as described herein may also be effective in: a) reducing the risks of adverse sequelae associated with metabolic syndrome, b) reducing the risk of developing atherosclerosis, c) delaying the onset of atherosclerosis, and/or d) reducing the risk of sequelae of atherosclerosis. Sequelae of atherosclerosis include angina, claudication, heart attack, stroke, and others. By keeping hyperglycemia under control, the compounds may also be effective in delaying or preventing vascular restenosis and diabetic retinopathy.

The compounds of this invention may also have utility in improving or restoring 3-cell function, and may be useful in treating type 1 diabetes, and in delaying or preventing a patient with Type 2 diabetes from needing insulin therapy.

Other possible outcomes of treatment with the compounds of the present invention may be: 1) a decrease in fatty acid synthesis; 2) an increase in fatty acid oxidation and ketogenesis; 3) a decrease in cholesterol synthesis, lipogenesis, and triglyceride synthesis; 4) a decrease in blood glucose levels and concentration; 5) an improvement in glucose homeostasis; 6) a normalization of glucose metabolism; 7) a decrease in blood pressure; 8) an increase in HDL; 9) a decrease in LDL; 10) a decrease in plasma triglycerides; 11) a decrease in free fatty acids; 12) a decrease in hepatic glucose output; 13) an improvement in insulin action; 14) a decrease in blood pressure; 15) an improvement in insulin sensitivity; 16) a suppression of hepatic glucose output; 17) an inhibition of de novo lipogenesis; 18) stimulation of muscle glucose uptake; 19) modulation of insulin secretion by pancreatic 3 cells; 20) a decrease in body weight; 21) an increase in skeletal muscle mass; and 22) a prevention in the loss of skeletal muscle mass.

The compounds of the present invention may be efficacious in treating one or more of the following diseases: (1) Type 2 diabetes (also known as non-insulin dependent diabetes mellitus, or NIDDM), (2) hyperglycemia, (3) impaired glucose tolerance, (4) insulin resistance, (5) obesity, (6) lipid disorders, (7) dyslipidemia, (8) hyperlipidemia, (9) hypertriglyceridemia, (10) hypercholesterolemia, (11) low HDL levels, (12) high LDL levels, (13) atherosclerosis and its sequelae, (14) vascular restenosis, (15) abdominal obesity, (16) retinopathy, (17) metabolic syndrome, (18) high blood pressure (hypertension), and (19) insulin resistance.

One aspect of the invention provides potential methods for the treatment and control of mixed or diabetic dyslipidemia, hypercholesterolemia, atherosclerosis, low HDL levels, high LDL levels, hyperlipidemia, and/or hypertriglyceridemia, which comprises administering to a patient in need of such treatment a therapeutically effective amount of a compound of formula I alone or with a cholesterol biosynthesis inhibitor, particularly an HMG-CoA reductase inhibitor such as lovastatin, simvastatin, rosuvastatin, pravastatin, fluvastatin, atorvastatin, rivastatin, itavastatin, or ZD-4522. The compound of formula I may also be used advantageously in combination with other lipid lowering drugs such as cholesterol absorption inhibitors (for example stanol esters, sterol glycosides such as tiqueside, and azetidinones such as ezetimibe), ACAT inhibitors (such as avasimibe), CETP inhibitors (for example anacetrapib, torcetrapib, and those described in published applications WO2005/100298, WO2006/014413, and WO2006/014357), niacin and niacin receptor agonists, bile acid sequestrants, microsomal triglyceride transport inhibitors, and bile acid reuptake inhibitors. These combination treatments may be effective for the treatment or control of one or more related conditions selected from the group consisting of hypercholesterolemia, atherosclerosis, hyperlipidemia, hypertriglyceridemia, dyslipidemia, high LDL, and low HDL.

The present invention also provides potential methods and medicaments for the treatment, control, or prevention of Type 2 diabetes by administering the compounds and pharmaceutical compositions of the present invention alone or in combination with a therapeutically effective amount of another agent known to be useful to treat the condition. The present invention also relates to potential methods and medicaments for the treatment, control, or prevention of diabetes related disorders by administering the compounds and pharmaceutical compositions of the present invention alone, or in combination. The present invention also relates to potential methods and medicaments for the treatment and prevention of diabetes in pre-diabetic subject by administering the compounds and pharmaceutical compositions of the present invention alone, or in combination.

The present invention also relates to potential methods and medicaments for the treatment, control, or prevention of obesity by administering the compounds and pharmaceutical compositions of the present invention, alone or in combination with a therapeutically effective amount of another agent known to be useful to treat the condition. The present invention also relates to potential methods and medicaments for the treatment, control, or prevention of obesity related disorders by administering the compounds and pharmaceutical compositions of the present invention alone, or in combination. The present invention also relates to potential methods and medicaments for the treatment and prevention of obesity in overweight subject by administering the compounds and pharmaceutical compositions of the present invention alone, or in combination. The compounds may also be useful for the treatment of obesity related disorders.

The present invention also relates to potential methods and medicaments for the treatment, control, or prevention of hyperglycemia by administering the compounds and pharmaceutical compositions of the present invention, alone or in combination with a therapeutically effective amount of another agent known to be useful to treat the condition.

The present invention also relates to potential methods and medicaments for the treatment, control, or prevention of insulin resistance by administering the compounds and pharmaceutical compositions of the present invention, alone or in combination with a therapeutically effective amount of another agent known to be useful to treat the condition.

The present invention also relates to potential methods and medicaments for the treatment, control, or prevention of lipid disorders by administering the compounds and pharmaceutical compositions of the present invention, alone or in combination with a therapeutically effective amount of another agent known to be useful to treat the condition. The present invention also relates to potential methods and medicaments for the treatment, control, or prevention of dyslipidemia related disorders and lipid disorder-related disorders by administering the compounds and pharmaceutical compositions of the present invention alone, or in combination.

The present invention also relates to potential methods and medicaments for the treatment, control, or prevention of atherosclerosis by administering the compounds and pharmaceutical compositions of the present invention, alone or in combination with a therapeutically effective amount of another agent known to be useful to treat the condition.

The present invention also relates to potential methods and medicaments for the treatment, control, or prevention of hypertension by administering the compounds and pharmaceutical compositions of the present invention, alone or in combination with a therapeutically effective amount of another agent known to be useful to treat the condition. The present invention also relates to potential methods and medicaments for the treatment and prevention of hypertension in pre-hypertensive subject by administering the compounds and pharmaceutical compositions of the present invention alone, or in combination.

The present invention also relates to potential methods and medicaments for the treatment, control, or prevention of Metabolic Syndrome by administering the compounds and pharmaceutical compositions of the present invention, alone or in combination with a therapeutically effective amount of another agent known to be useful to treat the condition.

The compounds of the present invention wherein Y is a tetrahydrofuran derivative have the unexpected benefit of reduced inhibition of recombinant CYP2C9 or CYP2C8 isozymes, compared to analogous compounds wherein Y is phenyl. In particular, the compounds of the present invention wherein Y is a tetrahydrofuran derivative have the unexpected benefit of reduced inhibition of recombinant CYP2C9 or CYP2C8 isozymes, compared to analogous compounds wherein Y is benzoic acid.

Inhibition of a recombinant CYP isozyme is measured by using a probe substrate, which upon oxidation by human liver microsome, is converted to a metabolite which is monitored by LC-MS/MS. NADPH or NADPH regenerating system are used as electron donors for the microsome catalytic cycle. Control incubations containing no inhibitors performed to evaluate the 100% activities. The activity of the enzyme is evaluated in the presence of various concentrations of test compounds. Standard specific enzyme inhibitors are used as positive controls. Inhibition curves are generated and IC50 values are calculated for tested compounds.

Co-administration of CYP inhibitors with pharmaceutical agents that are metabolized by the enzyme can result in elevated circulating concentrations of the pharmaceutical agents. This can lead to adverse events.

Additionally, the compounds of the present invention wherein at least one of T, U, V and W is N or N-oxide have the unexpected benefit of reduced binding to human plasma proteins compared to compounds wherein T is $CR^3$, U is $CR^1$—, V is $CR^2$ and W is $CR^4$. Pharmacological activity in vivo is associated with the concentration of drug unbound to plasma proteins. Plasma proteins, by virtue of their high concentration, control the concentration of drug unbound to plasma proteins in plasma and in compartments in equilibrium with plasma, thereby, effectively attenuating drug potency in vivo (See Trainor, G. L. (2007), Expert Opin. Drug Discov. 2(1), 51-64). A higher concentration of drug unbound to plasma proteins results in an increase in pharmacological activity in vivo. Due to their increased potency and their higher unbound fraction in plasma, the compounds of the present invention are expected to exhibit glucose lowering efficacy at reduced plasma exposures.

The term "diabetes," as used herein, includes both insulin-dependent diabetes mellitus (i.e., IDDM, also known as type 1 diabetes) and non-insulin-dependent diabetes mellitus (i.e., NIDDM, also known as Type 2 diabetes). Type 1 diabetes, or insulin-dependent diabetes, is the result of an absolute deficiency of insulin, the hormone which regulates glucose utilization. Type 2 diabetes, or insulin-independent diabetes (i.e., non-insulin-dependent diabetes mellitus), often occurs in the face of normal, or even elevated levels of insulin and appears to be the result of the inability of tissues to respond appropriately to insulin. Most of the Type 2 diabetics are also obese. The compositions of the present invention may be useful for treating both Type 1 and Type 2 diabetes. The term "diabetes associated with obesity" refers to diabetes caused by obesity or resulting from obesity. The compositions may be especially effective for treating Type 2 diabetes. The compositions of the present invention may also be useful for treating and/or preventing gestational diabetes mellitus.

Diabetes is characterized by a fasting plasma glucose level of greater than or equal to 126 mg/dl. A diabetic subject has a fasting plasma glucose level of greater than or equal to 126 mg/dl. A pre diabetic subject is someone suffering from prediabetes. Prediabetes is characterized by an impaired fasting plasma glucose (FPG) level of greater than or equal to 110 mg/dl and less than 126 mg/dl; or impaired glucose tolerance; or insulin resistance. A prediabetic subject is a subject with impaired fasting glucose (a fasting plasma glucose (FPG) level of greater than or equal to 110 mg/dl and less than 126 mg/dl); or impaired glucose tolerance (a 2 hour plasma glucose level of >140 mg/dl and <200 mg/dl); or insulin resistance, resulting in an increased risk of developing diabetes.

Treatment of diabetes mellitus refers to the administration of a compound or combination of the present invention to treat a diabetic subject. One outcome of treatment may be decreasing the glucose level in a subject with elevated glucose levels. Another outcome of treatment may be decreasing insulin levels in a subject with elevated insulin levels. Another outcome of treatment may be decreasing plasma triglycerides in a subject with elevated plasma triglycerides. Another outcome of treatment is decreasing LDL cholesterol in a subject with high LDL cholesterol levels. Another outcome of treatment may be increasing HDL cholesterol in a subject with low HDL cholesterol levels. Another outcome of treatment is increasing insulin sensitivity. Another outcome of treatment may be enhancing glucose tolerance in a subject with glucose intolerance. Yet another outcome of treatment may be decreasing insulin resistance in a subject with increased insulin resistance or elevated levels of insulin. Prevention of diabetes mellitus, in particular diabetes associated with obesity, refers to the administration of a compound or combination of the present invention to prevent the onset of diabetes in a subject in need thereof. A subject in need of preventing diabetes is a prediabetic subject that is overweight or obese.

The term "diabetes related disorders" should be understood to mean disorders that are associated with, caused by, or result from diabetes. Examples of diabetes related disorders include retinal damage, kidney disease, and nerve damage.

The term "atherosclerosis" as used herein encompasses vascular diseases and conditions that are recognized and understood by physicians practicing in the relevant fields of medicine. Atherosclerotic cardiovascular disease, coronary heart disease (also known as coronary artery disease or ischemic heart disease), cerebrovascular disease and peripheral vessel disease are all clinical manifestations of atherosclerosis and are therefore encompassed by the terms "atherosclerosis" and "atherosclerotic disease." The combination comprised of a therapeutically effective amount of an anti-obesity agent in combination with a therapeutically effective amount of an anti-hypertensive agent may be administered to prevent or reduce the risk of occurrence, or recurrence where the potential exists, of a coronary heart disease event, a cerebrovascular event, or intermittent claudication. Coronary heart disease events are intended to include CHD death, myocardial infarction (i.e., a heart attack), and coronary revascularization procedures. Cerebrovascular events are intended to include ischemic or hemorrhagic stroke (also known as cerebrovascular accidents) and transient ischemic attacks. Intermittent claudication is a clinical manifestation of peripheral vessel disease. The term "atherosclerotic disease event" as used herein is intended to encompass coronary heart disease events, cerebrovascular events, and intermittent claudication. It is intended that persons who have previously experienced one or more non-fatal atherosclerotic disease events are those for whom the potential for recurrence of such an event exists. The term "atherosclerosis related disorders" should be understood to mean disorders associated with, caused by, or resulting from atherosclerosis.

The term "hypertension" as used herein includes essential, or primary, hypertension wherein the cause is not known or where hypertension is due to greater than one cause, such as changes in both the heart and blood vessels; and secondary hypertension wherein the cause is known. Causes of secondary hypertension include, but are not limited to obesity; kidney disease; hormonal disorders; use of certain drugs, such as oral contraceptives, corticosteroids, cyclosporin, and the like. The term "hypertension" encompasses high blood pressure, in which both the systolic and diastolic pressure levels are elevated (>140 mmHg/>90 mmHg), and isolated systolic hypertension, in which only the systolic pressure is elevated to greater than or equal to 140 mm Hg, while the diastolic pressure is less than 90 mm Hg. Normal blood pressure may be defined as less than 120 mmHg systolic and less than 80 mmHg diastolic. A hypertensive subject is a subject with hypertension. A pre-hypertensive subject is a subject with a blood pressure that is between 120 mmHg over 80 mmHg and 139 mmHg over 89 mmHg. One outcome of treatment is decreasing blood pressure in a subject with high blood pressure. Treatment of hypertension refers to the administration of the compounds and combinations of the present invention to treat hypertension in a hypertensive subject. Treatment of hypertension-related disorder refers to the administration of a compound or combination of the present invention to treat the hypertension-related disorder. Prevention of hypertension, or a hypertension related disorder, refers to the administration of the combinations of the present invention to a pre-hypertensive subject to prevent the onset of hypertension or a hypertension related disorder. The hypertension-related disorders herein are associated with, caused by, or result from hypertension. Examples of hypertension-related disorders include, but are not limited to: heart disease, heart failure, heart attack, kidney failure, and stroke.

Dyslipidemias and lipid disorders are disorders of lipid metabolism including various conditions characterized by abnormal concentrations of one or more lipids (i.e. cholesterol and triglycerides), and/or apolipoproteins (i.e., apolipoproteins A, B, C and E), and/or lipoproteins (i.e., the macromolecular complexes formed by the lipid and the apolipoprotein that allow lipids to circulate in blood, such as LDL, VLDL and IDL). Hyperlipidemia is associated with abnormally high levels of lipids, LDL and VLDL cholesterol, and/or triglycerides. Treatment of dyslipidemia refers to the administration of the combinations of the present invention to a dyslipidemic subject. Prevention of dyslipidemia refers to the administration of the combinations of the present invention to a pre-dyslipidemic subject. A pre-dyslipidemic subject is a subject with higher than normal lipid levels, that is not yet dyslipidemic.

The terms "dyslipidemia related disorders" and "lipid disorder related disorders" should be understood to mean disorders associated with, caused by, or resulting from dyslipidemia or lipid disorders. Examples of dylipidemia related disorder and lipid disorder related disorders include, but are not limited to: hyperlipidemia, hypertriglyceridemia, hypercholesterolemia, low high density lipoprotein (HDL) levels, high plasma low density lipoprotein (LDL) levels, atherosclerosis and its sequelae, coronary artery or carotid artery disease, heart attack, and stroke.

The term "obesity" as used herein is a condition in which there is an excess of body fat. The operational definition of obesity is based on the Body Mass Index (BMI), which is calculated as body weight per height in meters squared ($kg/m^2$). "Obesity" refers to a condition whereby an otherwise healthy subject has a Body Mass Index (BMI) greater than or equal to 30 $kg/m^2$, or a condition whereby a subject with at least one co-morbidity has a BMI greater than or equal to 27 $kg/m^2$. An "obese subject" is an otherwise healthy subject with a Body Mass Index (BMI) greater than or equal to 30 $kg/m^2$ or a subject with at least one co-morbidity with a BMI greater than or equal to 27 $kg/m^2$. An overweight subject is a subject at risk of obesity. A "subject at risk of obesity" is an otherwise healthy subject with a BMI of 25 $kg/m^2$ to less than 30 $kg/m^2$ or a subject with at least one co-morbidity with a BMI of 25 $kg/m^2$ to less than 27 $kg/m^2$.

The increased risks associated with obesity occur at a lower Body Mass Index (BMI) in Asians. In Asian countries, including Japan, "obesity" refers to a condition whereby a subject with at least one obesity-induced or obesity-related co-morbidity, that requires weight reduction or that would be improved by weight reduction, has a BMI greater than or equal to 25 $kg/m^2$. In Asian countries, including Japan, an "obese subject" refers to a subject with at least one obesity-induced or obesity-related co-morbidity that requires weight reduction or that would be improved by weight reduction, with a BMI greater than or equal to 25 $kg/m^2$. In Asia-Pacific, a "subject at risk of obesity" is a subject with a BMI of greater than 23 $kg/m^2$ to less than 25 $kg/m^2$.

As used herein, the term "obesity" is meant to encompass all of the above definitions of obesity.

Obesity-induced or obesity-related co-morbidities include, but are not limited to, diabetes mellitus, non-insulin dependent diabetes mellitus—type 2, diabetes associated with obesity, impaired glucose tolerance, impaired fasting glucose, insulin resistance syndrome, dyslipidemia, hypertension, hypertension associated with obesity, hyperuricacidemia, gout, coronary artery disease, myocardial infarction, angina pectoris, sleep apnea syndrome, Pickwickian syndrome, fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, and other obesity-related conditions.

Treatment of obesity and obesity-related disorders refers to the administration of the compounds of the present invention to reduce or maintain the body weight of an obese subject. One outcome of treatment may be reducing the body weight of an obese subject relative to that subject's body weight immediately before the administration of the compounds of the present invention. Another outcome of treatment may be preventing body weight regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate; and in weight reduction in patients in need thereof. The treatment may also result in an alteration of metabolic rate, such as an increase in metabolic rate, rather than or in addition to an inhibition of the reduction of metabolic rate; and/or in minimization of the metabolic resistance that normally results from weight loss.

Prevention of obesity and obesity-related disorders refers to the administration of the compounds of the present invention to reduce or maintain the body weight of a subject at risk of obesity. One outcome of prevention may be reducing the body weight of a subject at risk of obesity relative to that subject's body weight immediately before the administration of the compounds of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, Type II diabetes, polycystic ovarian disease, cardiovascular diseases, osteoarthritis, dermatological disorders, hypertension, insulin resistance, hypercholesterolemia, hypertriglyceridemia, and cholelithiasis.

The obesity-related disorders herein are associated with, caused by, or result from obesity. Examples of obesity-related disorders include overeating and bulimia, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrythmias, myocardial infarction, congestive heart failure, coronary heart disease, sudden death, stroke, polycystic ovarian disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia. Further examples of obesity-related disorders are metabolic syndrome, also known as syndrome X, insulin resistance syndrome, sexual and reproductive dysfunction, such as infertility, hypogonadism in males and hirsutism in females, gastrointestinal motility disorders, such as obesity-related gastro-esophageal reflux, respiratory disorders, such as obesity-hypoventilation syndrome (Pickwickian syndrome), cardiovascular disorders, inflammation, such as systemic inflammation of the vasculature, arteriosclerosis, hypercholesterolemia, hyperuricaemia, lower back pain, gallbladder disease, gout, and kidney cancer.

The compounds of formula I may also be useful for treating or preventing obesity and obesity-related disorders in cats and dogs. As such, the term "mammal" includes companion animals such as cats and dogs.

The term "metabolic syndrome", also known as syndrome X, is defined in the Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. E. S. Ford et al., JAMA, vol. 287 (3), Jan. 16, 2002, pp 356-359. Briefly, a person is defined as having metabolic syndrome if the person has three or more of the following disorders: abdominal obesity, hypertriglyceridemia, low HDL cholesterol, high blood pressure, and high fasting plasma glucose. The criteria for these are defined in ATP-III. Treatment of metabolic syndrome refers to the administration of the combinations of the present invention to a subject with metabolic syndrome. Prevention of metabolic syndrome refers to the administration of the combinations of the present invention to a subject with two of the disorders that define metabolic syndrome. A subject with two of the disorders that define metabolic syndrome is a subject that has developed two of the disorders that define metabolic syndrome, but has not yet developed three or more of the disorders that define metabolic syndrome.

The terms "administration of" and or "administering a" compound should be understood to mean providing a compound of the invention or a prodrug of a compound of the invention to the individual or mammal in need of treatment.

The administration of the compound of structural formula I in order to practice the present methods of therapy is carried out by administering an effective amount of the compound of structural formula I to the mammal in need of such treatment or prophylaxis. The need for a prophylactic administration according to the methods of the present invention is determined via the use of well known risk factors. The effective amount of an individual compound is determined, in the final analysis, by the physician or veterinarian in charge of the case, but depends on factors such as the exact disease to be treated, the severity of the disease and other diseases or conditions from which the patient suffers, the chosen route of administration other drugs and treatments which the patient may concomitantly require, and other factors in the physician's judgment.

The usefulness of the present compounds in these diseases or disorders may be demonstrated in animal disease models that have been reported in the literature.

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it may be necessary to use dosages outside these limits in some cases.

For use where a composition for intravenous administration is employed, a suitable dosage range is from about 0.001 mg to about 100 mg in one embodiment from about 0.01 mg to about 50 mg, and in another embodiment from 0.1 mg to 10 mg of a compound of Formula I per kg of body weight per day.

In the case where an oral composition is employed, a suitable dosage range is, e.g. from about 0.01 mg to about 1000 mg of a compound of Formula I per day. In one embodiment, the range is from about 0.1 mg to about 10 mg per day. For oral administration, the compositions are preferably provided in the form of tablets containing from 0.01 to 1,000 mg, preferably 0.01, 0.05, 0.1, 0.5, 1, 2, 2.5, 3, 4, 5, 6, 7, 8, 9, 10, 12, 12.5, 15, 20, 25, 30, 40, 50, 100, 250, 500, 750 or 1000 milligrams of the active ingredient for the symptomatic adjustment of the dosage to the patient to be treated.

Another aspect of the present invention provides pharmaceutical compositions which comprises a compound of Formula I and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

Any suitable route of administration may be employed for providing a mammal, particularly a human or a companion animal such as a dog or cat, with an effective dosage of a compound of the present invention. For example, oral, rectal, topical, parenteral, ocular, pulmonary, and nasal routes of administration, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. By "pharmaceutically acceptable" it is meant the carrier, diluent or excipient must be compatible with the other ingredients of the formulation and not deleterious to the recipient thereof. The compositions include compositions suitable for oral, rectal, topical, parenteral (including subcutaneous, intramuscular, and intravenous), ocular (ophthalmic), pulmonary (aerosol inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulizers, or as powders which may be formulated and the powder composition may be inhaled with the aid of an insufflation powder inhaler device. The preferred delivery systems for inhalation are metered dose inhalation (MDI) aerosol, which may be formulated as a suspension or solution of a compound of Formula I in suitable propellants, such as fluorocarbons or hydrocarbons and dry powder inhalation (DPI) aerosol, which may be formulated as a dry powder of a compound of Formula I with or without additional excipients.

Suitable topical formulations of a compound of formula I include transdermal devices, aerosols, creams, solutions, ointments, gels, lotions, dusting powders, and the like. The topical pharmaceutical compositions containing the compounds of the present invention ordinarily include about 0.005% to 5% by weight of the active compound in admixture with a pharmaceutically acceptable vehicle. Transdermal skin patches useful for administering the compounds of the present invention include those known to those of ordinary skill in that art.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules (including timed release and sustained release formulations), pills, cachets, powders, granules or tablets each containing a predetermined amount of the active ingredient, as a powder or granules or as a solution or a suspension in an aqueous liquid, a non-aqueous liquid, an oil-in-water emulsion or a water-in-oil liquid emulsion, including elixirs, tinctures, solutions, suspensions, syrups and emulsions. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet cachet or capsule contains from about 0.01 to 1,000 mg, particularly 0.01, 0.05, 0.1, 0.5, 1.0, 2, 2.5, 3, 4, 5, 6, 7, 8, 9, 10, 12, 15, 25, 30, 40, 50, 75, 100, 125, 150, 175, 180, 200, 225, 250, 500, 750 and 1,000 milligrams of the active ingredient for the symptomatic adjustment of the dosage to the patient to be treated.

Additional suitable means of administration of the compounds of the present invention include injection, intravenous bolus or infusion, intraperitoneal, subcutaneous, intramuscular, intranasal, and topical, with or without occlusion.

Exemplifying the invention is a pharmaceutical composition comprising any of the compounds described above and a pharmaceutically acceptable carrier. Also exemplifying the invention is a pharmaceutical composition made by combining any of the compounds described above and a pharmaceutically acceptable carrier. An illustration of the invention is a process for making a pharmaceutical composition comprising combining any of the compounds described above and a pharmaceutically acceptable carrier.

The dose may be administered in a single daily dose or the total daily dosage may be administered in divided doses of two, three or four times daily. Furthermore, based on the properties of the individual compound selected for administration, the dose may be administered less frequently, e.g., weekly, twice weekly, monthly, etc. The unit dosage will, of course, be correspondingly larger for the less frequent administration.

When administered via intranasal routes, transdermal routes, by rectal or vaginal suppositories, or through a continual intravenous solution, the dosage administration will, of course, be continuous rather than intermittent throughout the dosage regimen.

The following are examples of representative pharmaceutical dosage forms for the compounds of Formula I:

| Injectable Suspension (I.M.) | mg/mL | Tablet | mg/tablet |
| --- | --- | --- | --- |
| Compound of Formula I | 10 | Compound of Formula I | 25 |
| Methylcellulose | 5.0 | Microcrystalline Cellulose | 415 |
| Tween 80 | 0.5 | Povidone | 14.0 |
| Benzyl alcohol | 9.0 | Pregelatinized Starch | 43.5 |
| Benzalkonium chloride | 1.0 | Magnesium Stearate | 2.5 |
| Water for injection to a total volume of 1 mL | | | 500 |

| Capsule | mg/ capsule | Aerosol | Per canister |
| --- | --- | --- | --- |
| Compound of Formula I | 25 | Compound of Formula I | 24 mg |
| Lactose Powder | 573.5 | Lecithin, NF Liq. Conc. | 1.2 mg |
| Magnesium Stearate | 1.5 | Trichlorofluoromethane, NF | 4.025 g |
| | 600 | Dichlorodifluoromethane, NF | 12.15 g |

Compounds of Formula I may be used in combination with other drugs that are used in the treatment/prevention/suppression or amelioration of the diseases, disorders or conditions for which compounds of Formula I may be useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I. Examples of other active ingredients that may be combined with a compound of Formula I include, but are not limited to: other anti-diabetic agents, anti-dylipidemic agents, and anti-hypertensive agents, anti-obesity agents, and anorectic agents, which may be administered separately or in the same pharmaceutical compositions.

The present invention also provides a method for the treatment or prevention of an AMPK-activated protein kinase (AMPK) mediated disease, which method comprises administration to a patient in need of such treatment or at risk of developing an AMPK mediated disease of an amount of an AMPK activator and an amount of one or more active ingredients, such that together they give effective relief.

In a further aspect of the present invention, there is provided a pharmaceutical composition comprising an AMPK activator and one or more active ingredients, together with at least one pharmaceutically acceptable carrier or excipient.

Thus, according to a further aspect of the present invention there is provided the use of an AMPK activator and one or more active ingredients for the manufacture of a medicament for the treatment or prevention of an AMPK mediated disease. In a further or alternative aspect of the present invention, there is provided a product comprising an AMPK activator and one or more active ingredients as a combined preparation for simultaneous, separate or sequential use in the treatment or prevention of an AMPK mediated disease. Such a combined preparation may be, for example, in the form of a twin pack.

It will be appreciated that for the potential treatment or prevention of diabetes, obesity, hypertension, Metabolic Syndrome, dyslipidemia, cancer, atherosclerosis, and related disorders thereof, a compound of the present invention may be used in conjunction with another pharmaceutical agent effective to treat that disorder.

The present invention also provides a potential method for the treatment or prevention of diabetes, obesity, hypertension, Metabolic Syndrome, dyslipidemia, cancer, atherosclerosis, and related disorders thereof, which method comprises administration to a patient in need of such treatment an amount of a compound of the present invention and an amount of another pharmaceutical agent effective to threat that disorder, such that together they give effective relief.

The present invention also provides a potential method for the treatment or prevention of diabetes, obesity, hypertension, Metabolic Syndrome, dyslipidemia, cancer, atherosclerosis, and related disorders thereof, which method comprises administration to a patient in need of such treatment an amount of a compound of the present invention and an amount of another pharmaceutical agent useful in treating that particular condition, such that together they give effective relief.

Examples of other active ingredients that may be administered separately or in the same pharmaceutical composition in combination with a compound of the formulas described herein include, but are not limited to:

(1) dipeptidyl peptidase-IV (DPP-4) inhibitors (e.g., sitagliptin, alogliptin, linagliptin, vildagliptin, saxagliptin, teneligliptin, omarigliptin);

(2) insulin sensitizers, including (i) PPARγ agonists, such as the glitazones (e.g. pioglitazone, AMG 131, MBX2044, mitoglitazone, lobeglitazone, IDR-105, rosiglitazone, and balaglitazone), and other PPAR ligands, including (1) PPARα/γ dual agonists (e.g., ZYH2, ZYH1, GFT505, chiglitazar, muraglitazar, aleglitazar, sodelglitazar, and naveglitazar); (2) PPARα agonists such as fenofibric acid derivatives (e.g., gemfibrozil, clofibrate, ciprofibrate, fenofibrate, bezafibrate), (3) selective PPARγ modulators (SPPARγM's), (e.g., such as those disclosed in WO 02/060388, WO 02/08188, WO 2004/019869, WO 2004/020409, WO 2004/020408, and WO 2004/066963); and (4) PPARγ partial agonists; (ii) biguanides, such as metformin and its pharmaceutically acceptable salts, in particular, metformin hydrochloride, and extended-release formulations thereof, such as Glumetza™, Fortamet™, and GlucophageXR™; and (iii) protein tyrosine phosphatase-1B (PTP-1B) inhibitors (e.g., ISIS-113715 and TTP814);

(3) insulin or insulin analogs (e.g., insulin detemir, insulin glulisine, insulin degludec, insulin glargine, insulin lispro, SBS 1000 and oral and inhalable formulations of insulin and insulin analogs);

(4) leptin and leptin derivatives and agonists;

(5) amylin and amylin analogs (e.g., pramlintide);

(6) sulfonylurea and non-sulfonylurea insulin secretagogues (e.g., tolbutamide, glyburide, glipizide, glimepiride, mitiglinide, meglitinides, nateglinide and repaglinide);

(7) α-glucosidase inhibitors (e.g., acarbose, voglibose and miglitol);

(8) glucagon receptor antagonists (e.g., NOXG15, LY2409021);

(9) incretin mimetics, such as GLP-1, GLP-1 analogs, derivatives, and mimetics; and GLP-1 receptor agonists (e.g., dulaglutide, semaglutide, albiglutide, exenatide, liraglutide, lixisenatide, taspoglutide, GSK2374697, ADX72231, RG7685, NN9924, ZYOG1, CJC-1131, and BIM-51077, including intranasal, transdermal, and once-weekly formulations thereof), and oxyntomodulin and oxyntomodulin analogs and derivatives;

(10) LDL cholesterol lowering agents such as (i) HMG-CoA reductase inhibitors (e.g., simvastatin, lovastatin, pravastatin, crivastatin, fluvastatin, atorvastatin, pitavastatin and rosuvastatin), (ii) bile acid sequestering agents (e.g., colestilan, colestimide, colesevalam hydrochloride, colestipol, cholestyramine, and dialkylaminoalkyl derivatives of a cross-linked dextran), (iii) inhibitors of cholesterol absorption, (e.g., ezetimibe), and (iv) acyl CoA:cholesterol acyltransferase inhibitors, (e.g., avasimibe);

(11) HDL-raising drugs, (e.g., niacin and nicotinic acid receptor agonists, and extended-release versions thereof; MK-524A, which is a combination of niacin extended-release and the DP-1 antagonist MK-524);

(12) antiobesity compounds;

(13) agents intended for use in inflammatory conditions, such as aspirin, non-steroidal anti-inflammatory drugs or NSAIDs, glucocorticoids, and selective cyclooxygenase-2 or COX-2 inhibitors;

(14) antihypertensive agents, such as ACE inhibitors (e.g., lisinopril, enalapril, ramipril, captopril, quinapril, and tandolapril), A-II receptor blockers (e.g., losartan, candesartan, irbesartan, olmesartan medoxomil, valsartan, telmisartan, and eprosartan), renin inhibitors (e.g., aliskiren), beta blockers, and calcium channel blockers;

(15) glucokinase activators (GKAs) (e.g., AZD6370);

(16) inhibitors of 1β-hydroxysteroid dehydrogenase type 1, (e.g., such as those disclosed in U.S. Pat. No. 6,730,690, and LY-2523199);

(17) CETP inhibitors (e.g., anacetrapib, evacetrapib and torcetrapib);

(18) inhibitors of fructose 1,6-bisphosphatase, (e.g., such as those disclosed in U.S. Pat. Nos. 6,054,587; 6,110,903; 6,284,748; 6,399,782; and 6,489,476);

(19) inhibitors of acetyl CoA carboxylase-1 or 2 (ACC1 or ACC2);

(20) AMP-activated Protein Kinase (AMPK) activators, such as MB 1055, ETC 1002;

(21) other agonists of the G-protein-coupled receptors: (i) GPR-109, (ii) GPR-119 (e.g., MBX2982, APD597, GSK1292263, HM47000, and PSN821), and (iii) GPR-40 (e.g., TAK875, MR 1704, TUG 469, TUG499, ASP 4178);

(22) SSTR3 antagonists (e.g., such as those disclosed in WO 2009/001836);

(23) neuromedin U receptor agonists (e.g., such as those disclosed in WO 2009/042053, including, but not limited to, neuromedin S (NMS));

(24) SCD inhibitors;

(25) GPR-105 antagonists (e.g., such as those disclosed in WO 2009/000087);

(26) SGLT inhibitors (e.g., ASP1941, SGLT-3, empagliflozin, dapagliflozin, canagliflozin, BI-10773, PF-04971729, remogloflozin, TS-071, tofogliflozin, ipragliflozin, and LX-4211);

(27) inhibitors of acyl coenzyme A:diacylglycerol acyltransferase 1 and 2 (DGAT-1 and DGAT-2);

(28) inhibitors of fatty acid synthase;

(29) inhibitors of acyl coenzyme A:monoacylglycerol acyltransferase 1 and 2 (MGAT-1 and MGAT-2);

(30) agonists of the TGR5 receptor (also known as GPBAR1, BG37, GPCR19, GPR131, and M-BAR);

(31) ileal bile acid transporter inhibitors;

(32) PACAP, PACAP mimetics, and PACAP receptor 3 agonists;

(33) PPAR agonists;

(34) protein tyrosine phosphatase-1B (PTP-1B) inhibitors;

(35) IL-1b antibodies, (e.g., XOMA052 and canakinumab);

(36) bromocriptine mesylate and rapid-release formulations thereof;

(37) GPR 120 agonists (such as KDT501.

Other suitable pharmaceutical agents of use in combination with a compound of the present invention, include, but are not limited to:

(a) anti-diabetic agents such as (1) PPARγ agonists such as glitazones (e.g. ciglitazone; darglitazone; englitazone; isaglitazone (MCC-555); pioglitazone (ACTOS); rosiglitazone (AVANDIA); troglitazone; rivoglitazone, BRL49653; CLX-0921; 5-BTZD, GW-0207, LG-100641, R483, and LY-300512, and the like and compounds disclosed in WO97/10813, 97/27857, 97/28115, 97/28137, 97/27847, 03/000685, and 03/027112 and SPPARMS (selective PPAR gamma modulators) such as T131 (Amgen), FK614 (Fujisawa), netoglitazone, and metaglidasen; (2) biguanides such as buformin; metformin; and phenformin, and the like; (3) protein tyrosine phosphatase-1B (PTP-1B) inhibitors such as ISIS 113715, A-401674, A-364504, IDD-3, IDD 2846, KP-40046, KR61639, MC52445, MC52453, C7, OC-060062, OC-86839, OC29796, TTP-277BC1, and those agents disclosed in WO 04/041799, 04/050646, 02/26707, 02/26743, 04/092146, 03/048140, 04/089918, 03/002569, 04/065387, 04/127570, and US 2004/167183; (4) sulfonylureas such as acetohexamide; chlorpropamide; diabinese; glibenclamide; glipizide; glyburide; glimepiride; gliclazide; glipentide; gliquidone; glisolamide; tolazamide; and tolbutamide, and the like; (5) meglitinides such as repaglinide, metiglinide (GLUFAST) and nateglinide, and the like; (6) alpha glucoside hydrolase inhibitors such as acarbose; adiposine; camiglibose; emiglitate; miglitol; voglibose; pradimicin-Q; salbostatin; CKD-711; MDL-25,637; MDL-73,945; and MOR 14, and the like; (7) alpha-amylase inhibitors such as tendamistat, trestatin, and Al-3688, and the like; (8) insulin secreatagogues such as linogliride nateglinide, mitiglinide (GLUFAST), ID 1101 A-4166, and the like; (9) fatty acid oxidation inhibitors, such as clomoxir, and etomoxir, and the like; (10) A2 antagonists, such as midaglizole; isaglidole; deriglidole; idazoxan; earoxan; and fluparoxan, and the like; (11) insulin or insulin mimetics, such as biota, LP-100, novarapid, insulin detemir, insulin lispro, insulin glargine, insulin zinc suspension (lente and ultralente); Lys-Pro insulin, GLP-1 (17-36), GLP-1 (73-7) (insulintropin); GLP-1 (7-36)-$NH_2$) exenatide/Exendin-4, Exenatide LAR, Linaglutide, AVE0010, CJC 1131, BIM51077, CS 872, THO318, BAY-694326, GPO10, ALBUGON (GLP-1 fused to albumin), HGX-007 (Epac agonist), S-23521, and compounds disclosed in WO 04/022004, WO 04/37859, and the like; (12) non-thiazolidinediones such as JT-501, and farglitazar (GW-2570/GI-262579), and the like; (13) PPARα/γ dual agonists such as AVE 0847, CLX-0940, GW-1536, GW1929, GW-2433, KRP-297, L-796449, LBM 642, LR-90, LY510919, MK-0767, ONO 5129, SB 219994, TAK-559, TAK-654, 677954 (GlaxoSmithkline), E-3030 (Eisai), LY510929 (Lilly), AK109 (Asahi), DRF2655 (Dr. Reddy), DRF8351 (Dr. Reddy), MC3002 (Maxocore), TY51501 (ToaEiyo), farglitazar, naveglitazar, muraglitazar, peliglitazar, tesaglitazar (GALIDA), reglitazar (JT-501), chiglitazar, and those disclosed in WO 99/16758, WO 99/19313, WO 99/20614, WO 99/38850, WO 00/23415, WO 00/23417, WO 00/23445, WO 00/50414, WO 01/00579, WO 01/79150, WO 02/062799, WO 03/033481, WO 03/033450, WO 03/033453; and (14), insulin, insulin mimetics and other insulin sensitizing drugs; (15) VPAC2 receptor agonists; (16) GLK modulators, such as PSN105, RO 281675, RO 274375 and those disclosed in WO 03/015774, WO 03/000262, WO 03/055482, WO 04/046139, WO 04/045614, WO 04/063179, WO 04/063194, WO 04/050645, and the like; (17) retinoid modulators such as those disclosed in WO 03/000249; (18) GSK 3beta/GSK 3 inhibitors such as 4-[2-(2-bromophenyl)-4-(4-fluorophenyl-1H-imidazol-5-yl]pyridine, CT21022, CT20026, CT-98023, SB-216763, SB410111, SB-675236, CP-70949, XD4241 and those compounds disclosed in WO 03/037869, 03/03877, 03/037891, 03/024447, 05/000192, 05/019218 and the like; (19) glycogen phosphorylase (HGLPa) inhibitors, such as AVE 5688, PSN 357, GPi-879, those disclosed in WO 03/037864, WO 03/091213, WO 04/092158, WO 05/013975, WO 05/013981, US 2004/0220229, and JP 2004-196702, and the like; (20) ATP consumption promotors such as those disclosed in WO 03/007990; (21) fixed combinations of PPAR γ agonists and metformin such as AVANDAMET; (22) PPAR pan agonists such as GSK 677954; (23) GPR40 (G-protein coupled receptor 40) also called SNORF 55 such as BG 700, and those disclosed in WO 04/041266, 04/022551, 03/099793; (24) GPR119 (G-protein coupled receptor 119, also called RUP3; SNORF 25) such as RUP3, HGPRBMY26, PFI 007, SNORF 25; (25) adenosine receptor 2B antagonists such as ATL-618, AT1-802, E3080, and the like; (26) carnitine palmitoyl transferase inhibitors such as ST 1327, and ST 1326, and the like; (27) Fructose 1,6-bisphospohatase inhibitors such as CS-917, MB7803, and the like; (28) glucagon antagonists such as AT77077, BAY 694326, GW 4123X, NN2501, and those disclosed in WO 03/064404, WO 05/00781, US 2004/0209928, US 2004/029943, and the like; (30) glucose-6-phosphase inhibitors; (31) phosphoenolpyruvate carboxykinase (PEPCK) inhibitors; (32) pyruvate dehydrogenase kinase (PDK) activators; (33) RXR agonists such as MC1036, CS00018, JNJ 10166806, and those disclosed in WO 04/089916, U.S. Pat. No. 6,759,546, and the like; (34) SGLT inhibitors such as AVE 2268, KGT 1251, T1095/RWJ 394718; (35) BLX-1002; (36) alpha glucosidase inhibitors; (37) glucagon receptor agonists; (38) glucokinase activators; 39) GIP-1; 40) insulin secretagogues; 41) GPR-40 agonists, such as TAK-875, 5-[4-[[(1R)-4-[6-(3-hydroxy-3-methylbutoxy)-2-methylpyridine-3-yl]-2,3-dihydro-1H-indene-1-yl]oxy]phenyl]isothiazole-3-ol 1-oxide, 5-(4-((3-(2,6-dimethyl-4-(3-(methylsulfonyl)propoxy)phenyl)phenyl)methoxy)phenyl)iso, 5-(4-((3-(2-methyl-6-(3-hydroxypropoxyl)pyridine-3-yl)-2-methylphenyl)methoxy)phenyl)isothiazole-3-ol 1-oxide, and 5-[4-[[3-[4-(3-aminopropoxy)-2,6-dimethylphenyl]phenyl]methoxy]phenyl]isothiazole-3-ol 1-oxide), and those disclosed in WO 11/078371.

(b) anti-dyslipidemic agents such as (1) bile acid sequestrants such as, cholestyramine, colesevelem, colestipol, dialkylaminoalkyl derivatives of a cross-linked dextran; Colestid®; LoCholest®; and Questran®, and the like; (2) HMG-CoA reductase inhibitors such as atorvastatin, itavastatin, pitavastatin, fluvastatin, lovastatin, pravastatin, rivastatin, simvastatin, rosuvastatin (ZD-4522), and other statins, particularly simvastatin; (3) HMG-CoA synthase inhibitors; (4) cholesterol absorption inhibitors such as FMVP4 (Forbes Medi-Tech), KT6-971 (Kotobuki Pharmaceutical), FM-VA12 (Forbes Medi-Tech), FM-VP-24 (Forbes Medi-Tech), stanol esters, beta-sitosterol, sterol glycosides such as tiqueside; and azetidinones such as ezetimibe, and those disclosed in WO 04/005247 and the like; (5) acyl coenzyme A-cholesterol acyl transferase (ACAT) inhibitors such as avasimibe, eflucimibe, pactimibe (KY505), SMP 797 (Sumitomo), SM32504 (Sumitomo), and those disclosed in WO 03/091216, and the like; (6) CETP inhibitors such as anacetrapib, JTT 705 (Japan Tobacco), torcetrapib, CP 532, 632, BAY63-2149 (Bayer), SC 591, SC 795, and the like; (7) squalene synthetase inhibitors; (8) anti-oxidants such as probucol, and the like; (9) PPARc agonists such as beclofibrate, bezafibrate, ciprofibrate, clofibrate, etofibrate, fenofibrate, gemcabene, and gemfibrozil, GW 7647, BM 170744 (Kowa), LY518674 (Lilly), GW590735 (GlaxoSmithkline), KRP-101 (Kyorin), DRF10945 (Dr. Reddy), NS-220/R1593 (Nippon Shinyaku/Roche, ST1929 (Sigma Tau) MC3001/MC3004 (MaxoCore Pharmaceuticals, gemcabene calcium, other fibric acid derivatives, such as Atromid®, Lopid® and Tricor®, and those disclosed in U.S. Pat. No. 6,548,538, and the like; (10) FXR receptor modulators such as GW 4064 (GlaxoSmithkline), SR 103912, QRX401, LN-6691 (Lion Bioscience), and those disclosed in WO 02/064125, WO 04/045511, and the like; (11) LXR receptor modulators such as GW 3965 (GlaxoSmithkline), T9013137, and XTCO 179628 (X-Ceptor Therapeutics/Sanyo), and those disclosed in WO 03/031408, WO 03/063796, WO 04/072041, and the like; (12) lipoprotein synthesis inhibitors such as niacin; (13) renin angiotensin system inhibitors; (14) PPAR δ partial agonists, such as those disclosed in WO 03/024395; (15) bile acid reabsorption inhibitors, such as BARI 1453, SC435, PHA384640, S8921, AZD7706, and the like; and bile acid sequesterants such as colesevelam (WELCHOL/CHOLESTAGEL), colestipol, cholestyramine, and dialkylaminoalkyl derivatives of a cross-linked dextran, (16) PPARδ agonists such as GW 501516 (Ligand, GSK), GW 590735, GW-0742 (GlaxoSmithkline), T659 (Amgen/Tularik), LY934 (Lilly), NNC610050 (Novo Nordisk) and those disclosed in WO97/28149, WO 01/79197, WO 02/14291, WO 02/46154, WO 02/46176, WO 02/076957, WO 03/016291, WO 03/033493, WO 03/035603, WO 03/072100, WO 03/097607, WO 04/005253, WO 04/007439, and JP10237049, and the like; (17) triglyceride synthesis inhibitors; (18) microsomal triglyceride transport (MTTP) inhibitors, such as implitapide, LAB687, JTT130 (Japan Tobacco), CP346086, and those disclosed in WO 03/072532, and the like; (19) transcription modulators; (20) squalene epoxidase inhibitors; (21) low density lipoprotein (LDL) receptor inducers; (22) platelet aggregation inhibitors; (23) 5-LO or FLAP inhibitors; and (24) niacin receptor agonists including HM74A receptor agonists; (25) PPAR modulators such as those disclosed in WO 01/25181, WO 01/79150, WO 02/79162, WO 02/081428, WO 03/016265, WO 03/033453; (26) niacin-bound chromium, as disclosed in WO 03/039535; (27) substituted acid derivatives disclosed in WO 03/040114; (28) infused HDL such as LUV/ETC-588 (Pfizer), APO-A1 Milano/ETC216 (Pfizer), ETC-642 (Pfizer), ISIS301012, D4F (Bruin Pharma), synthetic trimeric ApoA1, Bioral Apo A1 targeted to foam cells, and the like; (29) IBAT inhibitors such as BARI143/HMR145A/HMR1453 (Sanofi-Aventis, PHA384640E (Pfizer), S8921 (Shionogi) AZD7806 (AstrZeneca), AK105 (Asah Kasei), and the like; (30) Lp-PLA2 inhibitors such as SB480848 (GlaxoSmithkline), 659032 (GlaxoSmithkline), 677116 (GlaxoSmithkline), and the like; (31) other agents which affect lipic composition including ETC 1001/ESP31015 (Pfizer), ESP-55016 (Pfizer), AGI1067 (AtheroGenics), AC3056 (Amylin), AZD4619 (AstrZeneca); and (c) anti-hypertensive agents such as (1) diuretics, such as thiazides, including chlorthalidone, chlorthiazide, dichlorophenamide, hydroflumethiazide, indapamide, and hydrochlorothiazide; loop diuretics, such as bumetanide, ethacrynic acid, furosemide, and torsemide; potassium sparing agents, such as amiloride, and triamterene; and aldosterone antagonists, such as spironolactone, epirenone, and the like; (2) beta-adrenergic blockers such as acebutolol, atenolol, betaxolol, bevantolol, bisoprolol, bopindolol, carteolol, carvedilol, celiprolol, esmolol, indenolol, metaprolol, nadolol, nebivolol, penbutolol, pindolol, propanolol, sotalol, tertatolol, tilisolol, and timolol, and the like; (3) calcium channel blockers such as amlodipine, aranidipine, azelnidipine, barnidipine, benidipine, bepridil, cinaldipine, clevidipine, diltiazem, efonidipine, felodipine, gallopamil, isradipine, lacidipine, lemildipine, lercanidipine, nicardipine, nifedipine, nilvadipine, nimodepine, nisoldipine, nitrendipine, manidipine, pranidipine, and verapamil, and the like; (4) angiotensin converting enzyme (ACE) inhibitors such as benazepril; captopril; cilazapril; delapril; enalapril; fosinopril; imidapril; losinopril; moexipril; quinapril; quinaprilat; ramipril; perindopril; perindropril; quanipril; spirapril; tenocapril; trandolapril, and zofenopril, and the like; (5) neutral endopeptidase inhibitors such as omapatrilat, cadoxatril and ecadotril, fosidotril, sampatrilat, AVE7688, ER4030, and the like; (6) endothelin antagonists such as tezosentan, A308165, and YM62899, and the like; (7) vasodilators such as hydralazine, clonidine, minoxidil, and nicotinyl alcohol, nicotinic acid or salt thereof, and the like; (8) angiotensin II receptor antagonists such as candesartan, eprosartan, irbesartan, losartan, pratosartan, tasosartan, telmisartan, valsartan, and EXP-3137, FI6828K, and RNH6270, and the like; (9) a/(3 adrenergic blockers as nipradilol, arotinolol and amosulalol, and the like; (10) alpha 1 blockers, such as terazosin, urapidil, prazosin, bunazosin, trimazosin, doxazosin, naftopidil, indoramin, WHIP 164, and XENO10, and the like; (11) alpha 2 agonists such as lofexidine, tiamenidine, moxonidine, rilmenidine and guanobenz, and the like; (12) aldosterone inhibitors, and the like; (13) angiopoietin-2-binding agents such as those disclosed in WO 03/030833; and (d) anti-obesity agents, such as (1) 5HT (serotonin) transporter inhibitors, such as paroxetine, fluoxetine, fenfluramine, fluvoxamine, sertraline, and imipramine, and those disclosed in WO 03/00663, as well as serotonin/noradrenaline re uptake inhibitors such as sibutramine (MERIDIA/REDUCTIL) and dopamine uptake inhibitor/Norepenephrine uptake inhibitors such as radafaxine hydrochloride, 353162 (GlaxoSmithkline), and the like; (2) NE (norepinephrine) transporter inhibitors, such as GW 320659, despiramine, talsupram, and nomifensine; (3) CB1 (cannabinoid-1 receptor) antagonist/inverse agonists, such as taranabant, rimonabant (ACCOMPLIA Sanofi Synthelabo), SR-147778 (Sanofi Synthelabo), AVE1625 (Sanofi-Aventis), BAY 65-2520 (Bayer), SLV 319 (Solvay), SLV326 (Solvay), CP945598 (Pfizer), E-6776 (Esteve), 01691 (Organix), ORG14481 (Organon), VER24343 (Vernalis), NESS0327 (Univ of Sassari/Univ of Cagliari), and those disclosed in U.S. Pat. Nos. 4,973,587, 5,013,837, 5,081,122, 5,112,820, 5,292,736, 5,532,237, 5,624,941, 6,028,084, and 6,509367; and WO 96/33159, WO97/29079, WO98/31227, WO 98/33765, WO98/37061, WO98/41519, WO98/43635, WO98/43636, WO99/02499, WO00/10967, WO00/10968, WO 01/09120, WO 01/58869, WO 01/64632, WO 01/64633, WO 01/64634, WO 01/70700, WO 01/96330, WO 02/076949, WO 03/006007, WO 03/007887, WO 03/020217, WO 03/026647, WO 03/026648, WO 03/027069, WO 03/027076, WO 03/027114, WO 03/037332, WO 03/040107, WO 04/096763, WO 04/111039, WO 04/111033, WO 04/111034, WO 04/111038, WO 04/013120, WO 05/000301, WO 05/016286, WO 05/066126 and EP-658546 and the like; (4) ghrelin agonists/antagonists, such as BVT81-97 (BioVitrum), RC1291 (Rejuvenon), SRD-04677 (Sumitomo), unacylated ghrelin (TheraTechnologies), and those disclosed in WO 01/87335, WO 02/08250, WO 05/012331, and the like; (5) H3 (histamine H3) antagonist/inverse agonists, such as thioperamide, 3-(1H-imidazol-4-yl)propyl N-(4-pentenyl)carbamate), clobenpropit, iodophenpropit, imoproxifan, GT2394 (Gliatech), and A331440, and those disclosed in WO 02/15905; and O-[3-(1H-imidazol-4-yl)propanol]carbamates (Kiec-Kononowicz, K. et al., Pharmazie, 55:349-55 (2000)), piperidine-containing histamine H3-receptor antagonists (Lazewska, D. et al., Pharmazie, 56:927-32 (2001), benzophenone derivatives and related compounds (Sasse, A. et al., Arch. Pharm. (Weinheim) 334:45-52 (2001)), substituted N-phenylcarbamates (Reidemeister, S. et al., Pharmazie, 55:83-6 (2000)), and proxifan derivatives (Sasse, A. et al., J. Med. Chem. 43:3335-43 (2000)) and histamine H3 receptor modulators such as those disclosed in WO 03/024928 and WO 03/024929; (6) melanin-concentrating hormone 1 receptor (MCH1R) antagonists such as T-226296 (Takeda), T71 (Takeda/Amgen), AMGN-608450, AMGN-503796 (Amgen), 856464 (GlaxoSmithkline), A224940 (Abbott), A798 (Abbott), ATC0175/AR224349 (Arena Pharmaceuticals), GW803430 (GlaxoSmithkine), NBI-1A (Neurocrine Biosciences), NGX-1 (Neurogen), SNP-7941 (Synaptic), SNAP9847 (Synaptic), T-226293 (Schering Plough), TPI-1361-17 (Saitama Medical School/University of California Irvine), and those disclosed WO 01/21169, WO 01/82925, WO 01/87834, WO 02/051809, WO 02/06245, WO 02/076929, WO 02/076947, WO 02/04433, WO 02/51809, WO 02/083134, WO 02/094799, WO 03/004027, WO 03/13574, WO 03/15769, WO 03/028641, WO 03/035624, WO 03/033476, WO 03/033480, WO 04/004611, WO 04/004726, WO 04/011438, WO 04/028459, WO 04/034702, WO 04/039764, WO 04/052848, WO 04/087680; and Japanese Patent Application Nos. JP 13226269, JP 1437059, JP2004315511, and the like; (7) MCH$_2$R (melanin concentrating hormone 2R) agonist/antagonists; (8) NPY1 (neuropeptide Y Y1) antagonists, such as BMS205749, BIBP3226, J-115814, BIBO 3304, LY-357897, CP-671906, and GI-264879A; and those disclosed in U.S. Pat. No. 6,001,836; and WO 96/14307, WO 01/23387, WO 99/51600, WO 01/85690, WO 01/85098, WO 01/85173, and WO 01/89528; (9) NPY5 (neuropeptide Y Y5) antagonists, such as 152,804, S2367 (Shionogi), E-6999 (Esteve), GW-569180A, GW-594884A (GlaxoSmithkline), GW-587081X, GW-548118X; FR 235,208; FR226928, FR 240662, FR252384; 1229U91, GI-264879A, CGP71683A, C-75 (Fasgen) LY-377897, LY366377, PD-160170, SR-120562A, SR-120819A, S2367 (Shionogi), JCF-104, and H409/22; and those compounds disclosed in U.S. Pat. Nos. 6,140,354, 6,191,160, 6,258,837, 6,313,298, 6,326,375, 6,329,395, 6,335,345, 6,337,332, 6,329,395, and 6,340,683; and EP-01010691, EP-01044970, and FR252384; and PCT Publication Nos. WO 97/19682, WO 97/20820, WO 97/20821, WO 97/20822, WO 97/20823, WO 98/27063, WO 00/107409, WO 00/185714, WO 00/185730, WO 00/64880, WO 00/68197, WO 00/69849, WO 01/09120, WO 01/14376, WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/20488, WO 02/22592, WO 02/48152, WO 02/49648, WO 02/051806, WO 02/094789, WO 03/009845, WO 03/014083, WO 03/022849, WO 03/028726, WO 05/014592, WO 05/01493; and Norman et al., J. Med. Chem. 43:4288-4312 (2000); (10) leptin, such as recombinant human leptin (PEG-OB, Hoffman La Roche) and recombinant methionyl human leptin (Amgen); (11) leptin derivatives, such as those disclosed in U.S. Pat. Nos. 5,552, 524; 5,552,523; 5,552,522; 5,521,283; and WO 96/23513; WO 96/23514; WO 96/23515; WO 96/23516; WO 96/23517; WO 96/23518; WO 96/23519; and WO 96/23520; (12) opioid antagonists, such as nalmefene (Revex®), 3-methoxynaltrexone, naloxone, and naltrexone; and those disclosed in WO 00/21509; (13) orexin antagonists, such as SB-334867-A (GlaxoSmithkline); and those disclosed in WO 01/96302, 01/68609, 02/44172, 02/51232, 02/51838, 02/089800, 02/090355, 03/023561, 03/032991, 03/037847, 04/004733, 04/026866, 04/041791, 04/085403, and the like; (14) BRS3 (bombesin receptor subtype 3) agonists; (15) CCK-A (cholecystokinin-A) agonists, such as AR-R 15849, GI 181771, JMV-180, A-71378, A-71623, PD170292, PD 149164, SR146131, SR$^{125180}$, butabindide, and those disclosed in U.S. Pat. No. 5,739,106; (16) CNTF (ciliary neurotrophic factors), such as GI-181771 (GlaxoSmithKline); SR146131 (Sanofi Synthelabo); butabindide; and PD170,292, PD 149164 (Pfizer); (17) CNTF derivatives, such as axokine (Regeneron); and those disclosed in WO 94/09134, WO 98/22128, and WO 99/43813; (18) GHS (growth hormone secretagogue receptor) agonists, such as NN703, hexarelin, MK-0677, SM-130686, CP-424,391, L-692,429 and L-163,255, and those disclosed in U.S. Pat. No. 6,358,951, U.S. Patent Application Nos. 2002/049196 and 2002/022637; and WO 01/56592, and WO 02/32888; (19) 5HT2c (serotonin receptor 2c) agonists, such as APD3546/AR10A (Arena Pharmaceuticals), ATH88651 (Athersys), ATH88740 (Athersys), BVT933 (Biovitrum/GSK), DPCA37215 (BMS), IK264; LY448100 (Lilly), PNU 22394; WAY 470 (Wyeth), WAY629 (Wyeth), WAY 161503 (Biovitrum), R-1065, VR1065 (Vernalis/Roche) YM 348; and those disclosed in U.S. Pat. No. 3,914,250; and PCT Publications 01/66548, 02/36596, 02/48124, 02/10169, 02/44152; 02/51844, 02/40456, 02/40457, 03/057698, 05/000849, and the like; (20) Mc3r (melanocortin 3 receptor) agonists; (21) Mc4r (melanocortin 4 receptor) agonists, such as CHIR86036 (Chiron), CHIR915 (Chiron); ME-10142 (Melacure), ME-10145 (Melacure), HS-131 (Melacure), NBI72432 (Neurocrine Biosciences), NNC 70-619 (Novo Nordisk), TTP2435 (Transtech) and those disclosed in PCT Publications WO 99/64002, 00/74679, 01/991752, 01/0125192, 01/52880, 01/74844, 01/70708, 01/70337, 01/91752, 01/010842, 02/059095, 02/059107, 02/059108, 02/059117, 02/062766, 02/069095, 02/12166, 02/11715, 02/12178, 02/15909, 02/38544, 02/068387, 02/068388, 02/067869, 02/081430, 03/06604, 03/007949, 03/009847, 03/009850, 03/013509, 03/031410, 03/094918, 04/028453, 04/048345, 04/050610, 04/075823, 04/083208, 04/089951, 05/000339, and EP 1460069, and US 2005049269, and JP2005042839, and the like; (22) monoamine reuptake inhibitors, such as sibutratmine (Meridia®/Reductil®) and salts thereof, and those compounds disclosed in U.S. Pat. Nos. 4,746,680, 4,806,570, and 5,436,272, and U.S. Patent Publication No. 2002/0006964, and WO 01/27068, and WO 01/62341; (23) serotonin reuptake inhibitors, such as dexfenfluramine, fluoxetine, and those in U.S. Pat. No. 6,365,633, and WO 01/27060, and WO 01/162341; (24) GLP-1 (glucagon-like peptide 1) agonists; (25) Topiramate (Topimax®); (26) phytopharm compound 57 (CP 644,673); (27) ACC2 (acetyl-CoA carboxylase-2) inhibitors; (28) 33 (beta adrenergic receptor 3) agonists, such as rafebergron/AD9677/TAK677 (Dainippon/Takeda), CL-316,243, SB 418790, BRL-37344, L-796568, BMS-196085, BRL-35135A, CGP12177A, BTA-243, GRC1087 (Glenmark Pharmaceuticals) GW 427353 (solabegron hydrochloride), Trecadrine, Zeneca D7114, N-5984 (Nisshin Kyorin), LY-377604 (Lilly), KT07924 (Kissei), SR 59119A, and those disclosed in U.S. Pat. No. 5,705,515, U.S. Pat. No. 5,451,677; and WO94/18161, WO95/29159, WO97/46556, WO98/04526 WO98/32753, WO 01/74782, WO 02/32897, WO 03/014113, WO 03/016276, WO 03/016307, WO 03/024948, WO 03/024953, WO 03/037881, WO 04/108674, and the like; (29) DGAT1 (diacylglycerol acyltransferase 1) inhibitors; (30) DGAT2 (diacylglycerol acyltransferase 2) inhibitors; (31) FAS (fatty acid synthase) inhibitors, such as Cerulenin and C75; (32) PDE (phosphodiesterase) inhibitors, such as theophylline, pentoxifylline, zaprinast, sildenafil, amrinone, milrinone, cilostamide, rolipram, and cilomilast, as well as those described in WO 03/037432, WO 03/037899; (33) thyroid hormone P agonists, such as KB-2611 (KaroBioBMS), and those disclosed in WO 02/15845; and Japanese Patent Application No. JP 2000256190; (34) UCP-1 (uncoupling protein 1), 2, or 3 activators, such as phytanic acid, 4-[(E)-2-(5,6,7,8-tetrahydro-5,5,8,8-tetramethyl-2-napthalenyl)-1-propenyl]benzoic acid (TTNPB), and retinoic acid; and those disclosed in WO 99/00123; (35) acyl-estrogens, such as oleoyl-estrone, disclosed in del Mar-Grasa, M. et al., Obesity Research, 9:202-9 (2001); (36) glucocorticoid receptor antagonists, such as CP472555 (Pfizer), KB 3305, and those disclosed in WO 04/000869, WO 04/075864, and the like; (37) 11β HSD-1 (11-beta hydroxy steroid dehydrogenase type 1) inhibitors, such as BVT 3498 (AMG 331), BVT 2733, 3-(1-adamantyl)-4-ethyl-5-(ethylthio)-4H-1,2,4-triazole, 3-(1-adamantyl)-5-(3,4,5-trimethoxyphenyl)-4-methyl-4H-1,2,4-triazole, 3-adamantanyl-4,5,6,7,8,9,10,11,12,3a-decahydro-1,2,4-triazolo[4,3-a][11]annulene, and those compounds disclosed in WO 01/90091, 01/90090, 01/90092, 02/072084, 04/011410, 04/033427, 04/041264, 04/027047, 04/056744, 04/065351, 04/089415, 04/037251, and the like; (38) SCD-1 (stearoyl-CoA desaturase-1) inhibitors; (39) dipeptidyl peptidase IV (DPP-4) inhibitors, such as isoleucine thiazolidide, valine pyrrolidide, sitagliptin (Januvia), saxagliptin, alogliptin, NVP-DPP728, LAF237 (vildagliptin), P93/01, TSL 225, TMC-2A/2B/2C, FE 999011, P93 10/K364, VIP 0177, SDZ 274-444, GSK 823093, E 3024, SYR 322, TS021, SSR 162369, GRC 8200, K579, NN7201, CR 14023, PHX 1004, PHX 1149, PT-630, SK-0403; and the compounds disclosed in WO 02/083128, WO 02/062764, WO 02/14271, WO 03/000180, WO 03/000181, WO 03/000250, WO 03/002530, WO 03/002531, WO 03/002553, WO 03/002593, WO 03/004498, WO 03/004496, WO 03/005766, WO 03/017936, WO 03/024942, WO 03/024965, WO 03/033524, WO 03/055881, WO 03/057144, WO 03/037327, WO 04/041795, WO 04/071454, WO 04/0214870, WO 04/041273, WO 04/041820, WO 04/050658, WO 04/046106, WO 04/067509, WO 04/048532, WO 04/099185, WO 04/108730, WO 05/009956, WO 04/09806, WO 05/023762, US 2005/043292, and EP 1 258 476; (40) lipase inhibitors, such as tetrahydrolipstatin (orlistat/XENICAL), ATL962 (Alizyme/Takeda), GT389255 (Genzyme/Peptimmune) Triton WR1339, RHC80267, lipstatin, teasaponin, and diethylumbelliferyl phosphate, FL-386, WAY-121898, Bay-N-3176, valilactone, esteracin, ebelactone A, ebelactone B, and RHC 80267, and those disclosed in WO 01/77094, WO 04/111004, and U.S. Pat. Nos. 4,598,089, 4,452,813, 5,512,565, 5,391,571, 5,602,151, 4,405,644, 4,189,438, and 4,242,453, and the like; (41) fatty acid transporter inhibitors; (42) dicarboxylate transporter inhibitors; (43) glucose transporter inhibitors; and (44) phosphate transporter inhibitors; (45) anorectic bicyclic compounds such as 1426 (Aventis) and 1954 (Aventis), and the compounds disclosed in WO 00/18749, WO 01/32638, WO 01/62746, WO 01/62747, and WO 03/015769; (46) peptide YY and PYY agonists such as PYY336 (Nastech/Merck), AC162352 (IC Innovations/Curis/Amylin), TM30335/TM30338 (7TM Pharma), PYY336 (Emisphere Tehcnologies), pegylated peptide YY3-36, those disclosed in WO 03/026591, 04/089279, and the like; (47) lipid metabolism modulators such as maslinic acid, erythrodiol, ursolic acid uvaol, betulinic acid, betulin, and the like and compounds disclosed in WO 03/011267; (48) transcription factor modulators such as those disclosed in WO 03/026576; (49) Mc5r (melanocortin 5 receptor) modulators, such as those disclosed in WO 97/19952, WO 00/15826, WO 00/15790, US 20030092041, and the like; (50) Brain derived neutotropic factor (BDNF), (51) Mc1r (melanocortin 1 receptor modulators such as LK-184 (Proctor & Gamble), and the like; (52) 5HT6 antagonists such as BVT74316 (BioVitrum), BVT5182c (BioVitrum), E-6795 (Esteve), E-6814 (Esteve), SB399885 (GlaxoSmithkline), SB271046 (GlaxoSmithkline), RO-046790 (Roche), and the like; (53) fatty acid transport protein 4 (FATP4); (54) acetyl-CoA carboxylase (ACC) inhibitors such as CP640186, CP610431, CP640188 (Pfizer); (55) C-terminal growth hormone fragments such as AOD9604 (Monash Univ/Metabolic Pharmaceuticals), and the like; (56) oxyntomodulin; (57) neuropeptide FF receptor antagonists such as those disclosed in WO 04/083218, and the like; (58) amylin agonists such as Symlin/pramlintide/AC137 (Amylin); (59) Hoodia and trichocaulon extracts; (60) BVT74713 and other gut lipid appetite suppressants; (61) dopamine agonists such as bupropion (WELLBUTRIN/GlaxoSmithkline); (62) zonisamide (ZONEGRAN/Dainippon/Elan), and the like; and (e) anorectic agents suitable for use in combination with a compound of the present invention include, but are not limited to, aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine; and pharmaceutically acceptable salts thereof. A particularly suitable class of anorectic agent are the halogenated amphetamine derivatives, including chlorphentermine, cloforex, clortermine, dexfenfluramine, fenfluramine, picilorex and sibutramine; and pharmaceutically acceptable salts thereof. Particular halogenated amphetamine derivatives of use in combination with a compound of the present invention include: fenfluramine and dexfenfluramine, and pharmaceutically acceptable salts thereof.

Specific compounds of use in combination with a compound of the present invention include: simvastatin, mevastatin, ezetimibe, atorvastatin, sitagliptin, metformin, sibutramine, orlistat, Qnexa, topiramate, naltrexone, bupriopion, phentermine, and losartan, losartan with hydrochlorothiazide. Specific CB1 antagonists/inverse agonists of use in combination with a compound of the present invention include: those described in WO03/077847, including: N-[3-(4-chlorophenyl)-2(S)-phenyl-1(S)-methylpropyl]-2-(4-trifluoromethyl-2-pyrimidyloxy)-2-methylpropanamide, N-[3-(4-chlorophenyl)-2-(3-cyanophenyl)-1-methylpropyl]-2-(5-trifluoromethyl-2-pyridyloxy)-2-methylpropanamide, N-[3-(4-chlorophenyl)-2-(5-chloro-3-pyridyl)-1-methylpropyl]-2-(5-trifluoromethyl-2-pyridyloxy)-2-methylpropanamide, and pharmaceutically acceptable salts thereof; as well as those in WO05/000809, which includes the following: 3-{1-[bis(4-chlorophenyl)methyl]azetidin-3-ylidene}-3-(3,5-difluorophenyl)-2,2-dimethylpropanenitrile, 1-{1-[1-(4-chlorophenyl)pentyl]azetidin-3-yl}-1-(3,5-difluorophenyl)-2-methylpropan-2-ol. 3-((S)-(4-chlorophenyl) {3-[(1S)-1-(3,5-difluorophenyl)-2-hydroxy-2-methylpropyl]azetidin-1-yl}methyl)benzonitrile, 3-((S)-(4-chlorophenyl) {3-[(1S)-1-(3,5-difluorophenyl)-2-fluoro-2-methylpropyl]azetidin-1-yl}methyl)benzonitrile, 3-((4-chlorophenyl) {3-[1-(3,5-difluorophenyl)-2,2-dimethylpropyl]azetidin-1-yl}methyl) benzonitrile, 3-((1S)-1-{1-[(S)-(3-cyanophenyl)(4-cyanophenyl)methyl]azetidin-3-yl}-2-fluoro-2-methylpropyl)-5-fluorobenzonitrile, 3-[(S)-(4-chlorophenyl)(3-{(1S)-2-fluoro-1-[3-fluoro-5-(4H-1,2,4-triazol-4-yl)phenyl]-2-methylpropyl}azetidin-1-yl)methyl]benzonitrile, and 5-((4-chlorophenyl) {3-[(1S)-1-(3,5-difluorophenyl)-2-fluoro-2-methylpropyl]azetidin-1-yl}methyl)thiophene-3-carbonitrile, and pharmaceutically acceptable salts thereof; as well as: 3-[(S)-(4-chlorophenyl)(3-{(1S)-2-fluoro-1-[3-fluoro-5-(5-oxo-4,5-dihydro-1,3,4-oxadiazol-2-yl)phenyl]-2-methylpropyl}azetidin-1-yl)methyl]benzonitrile, 3-[(S)-(4-chlorophenyl)(3-{(1S)-2-fluoro-1-[3-fluoro-5-(1,3,4-oxadiazol-2-yl)phenyl]-2-methylpropyl}azetidin-1-yl)methyl]benzonitrile, 3-[(S)-(3-{(1S)-1-[3-(5-amino-1,3,4-oxadiazol-2-yl)-5-fluorophenyl]-2-fluoro-2-methylpropyl}azetidin-1-yl)(4-chlorophenyl)methyl]benzonitrile, 3-[(S)-(4-cyanophenyl)(3-{(1S)-2-fluoro-1-[3-fluoro-5-(5-oxo-4,5-dihydro-1,3,4-oxadiazol-2-yl)phenyl]-2-methylpropyl}azetidin-1-yl)methyl]benzonitrile, 3-[(S)-(3-{(1S)-1-[3-(5-amino-1,3,4-oxadiazol-2-yl)-5-fluorophenyl]-2-fluoro-2-methylpropyl}azetidin-1-yl)(4-cyanophenyl)methyl]benzonitrile, 3-[(S)-(4-cyanophenyl)(3-{(1S)-2-fluoro-1-[3-fluoro-5-(1,3,4-oxadiazol-2-yl)phenyl]-2-methylpropyl}azetidin-1-yl)methyl]benzonitrile, 3-[(S)-(4-chlorophenyl)(3-{(1S)-2-fluoro-1-[3-fluoro-5-(1,2,4-oxadiazol-3-yl)phenyl]-2-methylpropyl}azetidin-1-yl) methyl]benzonitrile, 3-[(1S)-1-(1-{(S)-(4-cyanophenyl)[3-(1,2,4-oxadiazol-3-yl)phenyl]-methyl}azetidin-3-yl)-2-fluoro-2-methylpropyl]-5-fluorobenzonitrile, 5-(3-{1-[1-(diphenylmethyl)azetidin-3-yl]-2-fluoro-2-methylpropyl}-5-fluorophenyl)-1H-tetrazole, 5-(3-{1-[1-(diphenylmethyl)azetidin-3-yl]-2-fluoro-2-methylpropyl}-5-fluorophenyl)-1-methyl-1H-tetrazole, 5-(3-{1-[1-(diphenylmethyl)azetidin-3-yl]-2-fluoro-2-methylpropyl}-5-fluorophenyl)-2-methyl-2H-tetrazole, 3-[(4-chlorophenyl)(3-{2-fluoro-1-[3-fluoro-5-(2-methyl-2H-tetrazol-5-yl)phenyl]-2-methylpropyl}azetidin-1-yl)methyl]benzonitrile, 3-[(4-chlorophenyl)(3-{2-fluoro-1-[3-fluoro-5-(1-methyl-1H-tetrazol-5-yl)phenyl]-2-methylpropyl}azetidin-1-yl)methyl]benzonitrile, 3-[(4-cyanophenyl)(3-{2-fluoro-1-[3-fluoro-5-(1-methyl-1H-tetrazol-5-yl)phenyl]-2-methylpropyl}azetidin-1-yl)methyl]benzonitrile, 3-[(4-cyanophenyl)(3-{2-fluoro-1-[3-fluoro-5-(2-methyl-2H-tetrazol-5-yl)phenyl]-2-methylpropyl}azetidin-1-yl)methyl]benzonitrile, 5-{3-[(S)-{3-[(1S)-1-(3-bromo-5-fluorophenyl)-2-fluoro-2-methylpropyl]azetidin-1-yl}(4-chlorophenyl)methyl]phenyl}-1,3,4-oxadiazol-2(3H)-one, 3-[(1S)-1-(1-{(S)-(4-chlorophenyl)[3-(5-oxo-4,5-dihydro-1,3,4-oxadiazol-2-yl)phenyl]methyl}azetidin-3-yl)-2-fluoro-2-methylpropyl]-5-fluorobenzonitrile, 3-[(1S)-1-(1-{(S)-(4-cyanophenyl)[3-(5-oxo-4,5-dihydro-1,3,4-oxadiazol-2-yl)phenyl]methyl}azetidin-3-yl)-2-fluoro-2-methylpropyl]-5-fluorobenzonitrile, 3-[(1S)-1-(1-{(S)-(4-cyanophenyl)[3-(1,3,4-oxadiazol-2-yl)phenyl]methyl}azetidin-3-yl)-2-fluoro-2-methylpropyl]-5-fluorobenzonitrile, 3-[(1S)-1-(1-{(S)-(4-chlorophenyl)[3-(1,3,4-oxadiazol-2-yl)phenyl]methyl}azetidin-3-yl)-2-fluoro-2-methylpropyl]-5-fluorobenzonitrile, 3-((1S)-1-{1-[(S)-[3-(5-amino-1,3,4-oxadiazol-2-yl)phenyl](4-chlorophenyl)methyl]azetidin-3-yl}-2-fluoro-2-methylpropyl)-5-fluorobenzonitrile, 3-((1S)-1-{1-[(S)-[3-(5-amino-1,3,4-oxadiazol-2-yl)phenyl](4-cyanophenyl)methyl]azetidin-3-yl}-2-fluoro-2-methylpropyl)-5-fluorobenzonitrile, 3-[(1S)-1-(1-{(S)-(4-cyanophenyl)[3-(1,2,4-oxadiazol-3-yl)phenyl]methyl}azetidin-3-yl)-2-fluoro-2-methylpropyl]-5-fluorobenzonitrile, 3-[(1S)-1-(1-{(S)-(4-chlorophenyl)[3-(1,2,4-oxadiazol-3-yl)phenyl]methyl}azetidin-3-yl)-2-fluoro-2-methylpropyl]-5-fluorobenzonitrile, 5-[3-((S)-(4-chlorophenyl) {3-[(1S)-1-(3,5-difluorophenyl)-2-fluoro-2-methylpropyl]azetidin-1-yl}methyl)phenyl]-1,3,4-oxadiazol-2(3H)-one, 5-[3-((S)-(4-chlorophenyl) {3-[(1S)-1-(3,5-difluorophenyl)-2-fluoro-2-methylpropyl]azetidin-1-yl}methyl)phenyl]-1,3,4-oxadiazol-2(3H)-one, 4-{(S)-{3-[(1S)-1-(3,5-difluorophenyl)-2-fluoro-2-methylpropyl]azetidin-1-yl}[3-(5-oxo-4,5-dihydro-1,3,4-oxadiazol-2-yl)phenyl]methyl}-benzonitrile, and pharmaceutically acceptable salts thereof.

Specific NPY5 antagonists of use in combination with a compound of the present invention include: 3-oxo-N-(5- phenyl-2-pyrazinyl)-spiro[isobenzofuran-1(3H),4'-piperidine]-1'-carboxamide, 3-oxo-N-(7-trifluoromethylpyrido[3,2-b]pyridin-2-yl)spiro-[isobenzofuran-1(3H),4'-piperidine]-1'-carboxamide, N-[5-(3-fluorophenyl)-2-pyrimidinyl]-3-oxospiro-[isobenzofuran-1(3H),4'-piperidine]-1'-carboxamide, trans-3'-oxo-N-(5-phenyl-2-pyrimidinyl)spiro [cyclohexane-1,1'(3'H)-isobenzofuran]-4-carboxamide, trans-3'-oxo-N-[1-(3-quinolyl)-4-imidazolyl]spiro[cyclohexane-1,1'(3' H)-isobenzofuran]-4-carboxamide, trans-3-oxo-N-(5-phenyl-2-pyrazinyl)spiro[4-azaiso-benzofuran-1 (3H),1'-cyclohexane]-4'-carboxamide, trans-N-[5-(3-fluorophenyl)-2-pyrimidinyl]-3-oxospiro[5-azaisobenzofuran-1(3H),1'-cyclohexane]-4'-carboxamide, trans-N-[5-(2-fluorophenyl)-2-pyrimidinyl]-3-oxospiro[5-azaisobenzofuran-1(3H),1'-cyclohexane]-4'-carboxamide, trans-N-[1-(3,5-difluorophenyl)-4-imidazolyl]-3-oxospiro [7-azaisobenzofuran-1(3H),1'-cyclohexane]-4'-carboxamide, trans-3-oxo-N-(1-phenyl-4-pyrazolyl)spiro[4-azaisobenzofuran-1(3H),1'-cyclohexane]-4'-carboxamide, trans-N-[1-(2-fluorophenyl)-3-pyrazolyl]-3-oxospiro[6-azaisobenzofuran-1(3H),1'-cyclohexane]-4'-carboxamide, trans-3-oxo-N-(1-phenyl-3-pyrazolyl)spiro[6-azaisobenzofuran-1(3H),1'-cyclohexane]-4'-carboxamide, trans-3-oxo-N-(2-phenyl-1,2,3-triazol-4-yl)spiro[6-azaisobenzofuran-1 (3H),1'-cyclohexane]-4'-carboxamide, and pharmaceutically acceptable salts and esters thereof.

Specific ACC-1/2 inhibitors of use in combination with a compound of the present invention include: 1'-[(4,8-dimethoxyquinolin-2-yl)carbonyl]-6-(1H-tetrazol-5-yl)spiro [chroman-2,4'-piperidin]-4-one; (5-{1'-[(4,8-dimethoxyquinolin-2-yl)carbonyl]-4-oxospiro[chroman-2,4'-piperidin]-6-yl}-2H-tetrazol-2-yl)methyl pivalate; 5-{1'-[(8-cyclopropyl-4-methoxyquinolin-2-yl)carbonyl]-4-oxospiro[chroman-2,4'-piperidin]-6-yl}nicotinic acid; 1'-(8-methoxy-4-morpholin-4-yl-2-naphthoyl)-6-(1H-tetrazol-5-yl)spiro [chroman-2,4'-piperidin]-4-one; and 1'-[(4-ethoxy-8-ethylquinolin-2-yl)carbonyl]-6-(1H-tetrazol-5-yl)spiro [chroman-2,4'-piperidin]-4-one; and pharmaceutically acceptable salts and esters thereof. Specific MCH1R antagonist compounds of use in combination with a compound of the present invention include: 1-{4-[(1-ethylazetidin-3-yl) oxy]phenyl}-4-[(4-fluorobenzyl)oxy]pyridin-2(1H)-one, 4-[(4-fluorobenzyl)oxy]-1-{4-[(1-isopropylazetidin-3-yl) oxy]phenyl}pyridin-2(1H)-one, 1-[4-(azetidin-3-yloxy)phenyl]-4-[(5-chloropyridin-2-yl)methoxy]pyridin-2(1H)-one, 4-[(5-chloropyridin-2-yl)methoxy]-1-{4-[(1-ethylazetidin-3-yl)oxy]phenyl}pyridin-2(1H)-one, 4-[(5-chloropyridin-2-yl)methoxy]-1-{4-[(1-propylazetidin-3-yl)oxy] phenyl}pyridin-2(1H)-one, and 4-[(5-chloropyridin-2-yl) methoxy]-1-(4-{[(2S)-1-ethylazetidin-2-yl] methoxy}phenyl)pyridin-2(1H)-one, or a pharmaceutically acceptable salt thereof.

Specific DP-IV inhibitors of use in combination with a compound of the present invention are selected from Januvia, 7-[(3R)-3-amino-4-(2,4,5-trifluorophenyl)butanoyl]-3-(trifluoromethyl)-5,6,7,8-tetrahydro-1,2,4-triazolo[4,3-a] pyrazine. In particular, the compound of formula I is favorably combined with 7-[(3R)-3-amino-4-(2,4,5-trifluorophenyl)butanoyl]-3-(trifluoromethyl)-5,6,7,8-tetrahydro-1,2,4-triazolo[4,3-a]pyrazine, and pharmaceutically acceptable salts thereof.

Specific H3 (histamine H3) antagonists/inverse agonists of use in combination with a compound of the present invention include: those described in WO005/077905, including: 3-{4-[(1-cyclobutyl-4-piperidinyl)oxy]phenyl}-2-ethylpyrido[2,3-d]-pyrimidin-4(3H)-one, 3-{4-[(1-cyclobutyl-4-piperidinyl)oxy]phenyl}-2-methylpyrido[4,3-d] pyrimidin-4(3H)-one, 2-ethyl-3-(4-{3-[(3S)-3-methylpiperidin-1-yl]propoxy}phenyl)pyrido[2,3-d] pyrimidin-4(3H)-one 2-methyl-3-(4-{3-[(3S)-3-methylpiperidin-1-yl]propoxy}phenyl)pyrido[4,3-d] pyrimidin-4(3H)-one, 3-{4-[(1-cyclobutyl-4-piperidinyl) oxy]phenyl}-2,5-dimethyl-4(3H)-quinazolinone, 3-{4-[(1-cyclobutyl-4-piperidinyl)oxy]phenyl}-2-methyl-5-trifluoromethyl-4(3H)-quinazolinone, 3-{4-[(1-cyclobutyl-4-piperidinyl)oxy]phenyl}-5-methoxy-2-methyl-4(3H)-quinazolinone, 3-{4-[(1-cyclobutylpiperidin-4-yl)oxy] phenyl}-5-fluoro-2-methyl-4(3H)-quinazolinone, 3-{4-[(1-cyclobutylpiperidin-4-yl)oxy]phenyl}-7-fluoro-2-methyl-4 (3H)-quinazolinone, 3-{4-[(1-cyclobutylpiperidin-4-yl)oxy] phenyl}-6-methoxy-2-methyl-4(3H)-quinazolinone, 3-{4-[(1-cyclobutylpiperidin-4-yl)oxy]phenyl}-6-fluoro-2-methyl-4(3H)-quinazolinone, 3-{4-[(1-cyclobutylpiperidin-4-yl)oxy]phenyl}-8-fluoro-2-methyl-4(3H)-quinazolinone, 3-{4-[(1-cyclopentyl-4-piperidinyl)oxy]phenyl}-2-methyl-pyrido[4,3-d]pyrimidin-4(3H)-one, 3-{4-[(1-cyclobutylpiperidin-4-yl)oxy]phenyl}-6-fluoro-2-methylpyrido[3,4-d]pyrimidin-4(3H)-one, 3-{4-[(1-cyclobutyl-4-piperidinyl)oxy] phenyl}-2-ethylpyrido[4,3-d]pyrimidin-4(3H)-one, 6-methoxy-2-methyl-3-{4-[3-(1-piperidinyl)propoxy] phenyl}pyrido[3,4-d]pyrimidin-4(3H)-one, 6-methoxy-2-methyl-3-{4-[3-(1-pyrrolidinyl)propoxy]phenyl}pyrido[3,4-d]pyrimidin-4(3H)-one, 2,5-dimethyl-3-{4-[3-(1-pyrrolidinyl)propoxy]phenyl}-4(3H)-quinazolinone, 2-methyl-3-{4-[3-(1-pyrrolidinyl)propoxy]phenyl}-5-trifluoromethyl-4(3H)-quinazolinone, 5-fluoro-2-methyl-3-{4-[3-(1-piperidinyl)propoxy]phenyl}-4(3H)-quinazolinone, 6-methoxy-2-methyl-3-{4-[3-(1-piperidinyl)propoxy]phenyl}-4(3H)-quinazolinone, 5-methoxy-2-methyl-3-(4-{3-[(3S)-3-methylpiperidin-1-yl]propoxy}phenyl)-4(3H)-quinazolinone, 7-methoxy-2-methyl-3-(4-{3-[(3S)-3-methylpiperidin-1-yl]propoxy}phenyl)-4(3H)-quinazolinone, 2-methyl-3-(4-{3-[(3S)-3-methylpiperidin-1-yl]propoxy}phenyl)pyrido[2,3-d]pyrimidin-4(3H)-one, 5-fluoro-2-methyl-3-(4-{3-[(2R)-2-methylpyrrolidin-1-yl] propoxy}phenyl)-4(3H)-quinazolinone, 2-methyl-3-(4-{3-[(2R)-2-methylpyrrolidin-1-yl]propoxy}phenyl)pyrido[4,3-d]pyrimidin-4(3H)-one, 6-methoxy-2-methyl-3-(4-{3-[(2R)-2-methylpyrrolidin-1-yl]propoxy}phenyl)-4(3H)-quinazolinone, 6-methoxy-2-methyl-3-(4-{3-[(2S)-2-methylpyrrolidin-1-yl]propoxy}phenyl)-4(3H)-quinazolinone, and pharmaceutically acceptable salts thereof.

Specific CCK1R agonists of use in combination with a compound of the present invention include: 3-(4-{[1-(3-ethoxyphenyl)-2-(4-methylphenyl)-1H-imidazol-4-yl]carbonyl}-1-piperazinyl)-1-naphthoic acid; 3-(4-{[1-(3-ethoxyphenyl)-2-(2-fluoro-4-methylphenyl)-1H-imidazol-4-yl]carbonyl}-1-piperazinyl)-1-naphthoic acid; 3-(4-{[1-(3-ethoxyphenyl)-2-(4-fluorophenyl)-1H-imidazol-4-yl] carbonyl}-1-piperazinyl)-1-naphthoic acid; 3-(4-{[1-(3-ethoxyphenyl)-2-(2,4-difluorophenyl)-1H-imidazol-4-yl] carbonyl}-1-piperazinyl)-1-naphthoic acid; and 3-(4-{[1-(2,3-dihydro-1,4-benzodioxin-6-yl)-2-(4-fluorophenyl)-1H-imidazol-4-yl]carbonyl}-1-piperazinyl)-1-naphthoic acid; and pharmaceutically acceptable salts thereof.

Specific MC4R agonists of use in combination with a compound of the present invention include: 1) (5S)-1'-{[(3R,4R)-1-tert-butyl-3-(2,3,4-trifluorophenyl)piperidin-4-yl]carbonyl}-3-chloro-2-methyl-5-[1-methyl-1-(1-methyl-1H-,2,4-triazol-5-yl)ethyl]-5H-spiro[furo[3,4-b]pyridine-7, 4'-piperidine]; 2) (5R)-1'-{[(3R,4R)-1-tert-butyl-3-(2,3,4-trifluorophenyl)-piperidin-4-yl]carbonyl}-3-chloro-2-methyl-5-[1-methyl-1-(1-methyl-1H-,2,4-triazol-5-yl)

ethyl]-5H-spiro[furo[3,4-b]pyridine-7,4'-piperidine]; 3) 2-(1'-{[(3S,4R)-1-tert-butyl-4-(2,4-difluorophenyl)pyrrolidin-3-yl]carbonyl}-3-chloro-2-methyl-5H-spiro[furo[3,4-b]pyridine-7,4'-piperidin]-5-yl)-2-methylpropanenitrile; 4) 1'-{[(3S,4R)-1-tert-butyl-4-(2,4-difluorophenyl)pyrrolidin-3-yl]carbonyl}-3-chloro-2-methyl-5-[1-methyl-1-(1-methyl-1H-1,2,4-triazol-5-yl)ethyl]-5H-spiro[furo[3,4-b]pyridine-7,4'-piperidine]; 5)N-[(3R,4R)-3-({3-chloro-2-methyl-5-[1-methyl-1-(1-methyl-1H-1,2,4-triazol-5-yl)ethyl]-1'H,5H-spiro[furo-[3,4-b]pyridine-7,4'-piperidin]-1'-yl}carbonyl)-4-(2,4-difluorophenyl)-cyclopentyl]-N-methyltetrahydro-2H-pyran-4-amine; 6) 2-[3-chloro-1'-({(1R,2R)-2-(2,4-difluorophenyl)-4-[methyl(tetrahydro-2H-pyran-4-yl)amino]-cyclopentyl}-carbonyl)-2-methyl-5H-spiro[furo[3,4-b]pyridine-7,4'-piperidin]-5-yl]-2-methyl-propane-nitrile; and pharmaceutically acceptable salts thereof.

Suitable neurokinin-1 (NK-1) receptor antagonists may be favorably employed with the AMP-kinase activators of the present invention. NK-1 receptor antagonists of use in the present invention are fully described in the art. Specific neurokinin-1 receptor antagonists of use in the present invention include: (±)-(2R3R,2S3S)—N-{[2-cyclopropoxy-5-(trifluoromethoxy)-phenyl]methyl}-2-phenylpiperidin-3-amine; 2-(R)-(1-(R)-(3,5-bis(trifluoromethyl)-phenyl)ethoxy)-3-(S)-(4-fluorophenyl)-4-(3-(5-oxo-1H,4H-1,2,4-triazolo)methyl)morpholine; aperpitant; CJ17493; GW597599; GW679769; R673; RO67319; R1124; R1204; SSR146977; SSR240600; T-2328; and T2763; or a pharmaceutically acceptable salts thereof.

The term "therapeutically effective amount" means the amount the compound of structural formula I that will elicit the biological or medical response of a tissue, system, animal or human that is being sought by the researcher, veterinarian, medical doctor or other clinician, which includes alleviation of the symptoms of the disorder being treated. The novel methods of treatment of this invention are for disorders known to those skilled in the art. The term "mammal" includes humans, and companion animals such as dogs and cats.

The weight ratio of the compound of the Formula I to the second active ingredient may be varied and will depend upon the effective dose of each ingredient. Generally, an effective dose of each will be used. Thus, for example, when a compound of the Formula I is combined with a DPIV inhibitor the weight ratio of the compound of the Formula I to the DPIV inhibitor will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

The compounds of structural formula I of the present invention can be prepared according to the procedures of the following Schemes, Intermediates and Examples, using appropriate materials and are further exemplified by the following specific examples. Moreover, by utilizing the procedures described in the disclosure contained herein, one of ordinary skill in the art can readily prepare additional compounds of the present invention claimed herein. The compounds illustrated in the examples are not, however, to be construed as forming the only genus that is considered as the invention. The Examples further illustrate details for the preparation of the compounds of the present invention. Those skilled in the art will readily understand that known variations of the conditions and processes of the following preparative procedures can be used to prepare these compounds. The instant compounds are generally isolated in the form of their pharmaceutically acceptable salts, such as those previously described herein. The use of protecting groups for the amine and carboxylic acid functionalities to facilitate the desired reaction and minimize undesired reactions is well documented. Conditions required to remove protecting groups are found in standard textbooks such as Greene, T, and Wuts, P. G. M., Protective Groups in Organic Synthesis, John Wiley & Sons, Inc., New York, N.Y., 1991. CBZ and BOC are commonly used protecting groups in organic synthesis, and their removal conditions are known to those skilled in the art. All temperatures are degrees Celsius unless otherwise noted. Mass spectra (MS) were measured by electron-spray ion-mass spectroscopy.

Abbreviations used in the description of the preparation of the compounds of the present invention: ACN is acetonitrile; AcOH is acetic acid; aq or aq. is aqueous; $Boc_2O$ is t-butoxycarbonyl anhydride; n-BuLi is n-butyllithium; C is carbon; CPME is cyclopentyl methyl ether; CV is column volume(s); DAST is (diethylamino)sulfur trifluoride; DBU is 1,8-diazabicyclo[5.4.0]-undec-7-ene; DIBAL-H is di-isobutyl aluminum hydride; DCE is dichloroethane; DCM is dichloromethane; DEAD is diethyl azodicarboxylate; DIAD is diisopropyl azodicarboxylate; DIEA and DIPEA is diisopropylethyl amine; DMA is dimethyl acetal; DMAP is 4-(Dimethylamino)pyridine; DME is 1,2-dimethoxyethane; DMF is dimethyl formamide; DMSO is dimethyl sulfoxide; dppf DCM complex is 1,1'-bis(diphenylphosphino)ferrocene dichloromethane complex; DPPP is diphenyl phosphinopropane; EDC is N-(3-Dimethylaminopropyl)-N'-ethylcarbodiimide; $Et_2O$ is diethyl ether; EtOAc is ethyl acetate; dppf is 1,1'-Bis(diphenyl-phosphino)ferrocene; EtOH is ethanol; $Et_3N$ is triethyl amine; h is hour(s); HATU is O-(7-Azabenzotriazol-1-yl)-N,N,N',N'-tetramethyluronium hexafluorophosphate; Hex or hex is hexanes; HOBT is 1-Hydroxybenzotriazole; HPLC is high pressure liquid chromatography; ISCO $R_f$ is the Rf determined via medium pressure liquid chromatography using a Teledyne ISCO RediSep® column; isomannide is 1,4:3,6-Di-anhydro-mannitol; KOAc is potassium acetate; L is liter; LC/MS and LC-MS is liquid chromatography/mass spectroscopy; KOTMS is potassium trimethylsilanolate; LAH is lithium aluminum hydride; M is molar; ml and mL is milliliter; Me is methyl, MeCN is acetonitrile; MeI is methyl iodide; MeMgBr is methyl magnesium bromide; MeOH is methanol; MgBr is magnesium bromide; min is minutes; mmol is millimole(s); m-CPBA is meta chloro per benzoic acid; MPLC is medium pressure liquid chromatography; MS is molecular sieves; MTBE is tert-butyl methyl ether; N is normal; NaOAc is sodium acetate; NBS is N-bromo succinamide; NIS is N-iodo succinamide; $Pd_2(dba)_3$ is tris(dibenzylideneacetone)-dipalladium(0); $[PdCl_2(dppf)]CH_2Cl_2$ or $PdCl_2(dppf)$-DCM is 1,1'-Bis(diphenylphosphino)-ferrocene-palladium(II)dichloride dichloromethane complex; $PPh_3$ is triphenyl phosphine; PhSiH is phenyl silane; wt % is weight percent; psi is pounds per square inch; RT and rt is room temperature; Rt is retention time; Rochelles' Salt is potassium sodium tartrate; RuPhos is 2-Dicyclohexyl-phosphino-2',6'-diisopropoxybiphenyl; sat or sat. is saturated; SEM is 2-(trimethylsilyl)ethoxymethyl; SEM-Cl and SEMCl is 2-(trimethylsilyl)-ethoxymethyl chloride; TBAF is tetrabutyl ammonium fluoride; TBSCl and TBDMSCl is tert-butyldimethylsilyl chloride; TEA is triethylamine; TESCl is chlorotriethylsilane; TFA is trifluoro acetic acid; THF is tetrahydrofuran; TMS is trimethylsilyl; Tosyl-Cl is p-toluene-sulfonyl chloride; and XPhos is 2-Dicyclohexylphosphino-2',4',6'-triisopropylbiphenyl.

Microwave (MW) reactions were performed with a single mode operating Biotage Emrys Optimizer in sealed reaction vials at the indicated fixed temperature held constant for the designated reaction time. The medium pressure liquid chromatography (MPLC) purifications were performed with Teledyne ISCO RediSep® normal-phase columns pre-packed with 35-60 micron silica gel. The LC-MS system contained an Applied Biosystems API150EX MS operating in a positive ion mode receiving 0.1 mL/min flowrate with a Shimadzu UV detector receiving 0.1 mL/min flowrate. Unless specified, the LC conditions were solvent A=0.05% TFA in acetonitrile; solvent B=0.05% TFA in water; flow-rate=10 mL/min; column: Chromolith Performance RP-18e, 100×4.6 mm. Unless specified, the $^1$H NMRs were obtained in $CD_3OD$ at 500 MHz and spectra were recorded in units δ. C, H, N microanalyses were performed by Robertson Microlit Laboratories, Inc., Madison, N.J.

The following reaction schemes illustrate methods which may be employed for the synthesis of the compounds of structural formula I described in this invention. All substituents are as defined above unless indicated otherwise. Several strategies based upon synthetic transformations known in the literature of organic synthesis may be employed for the preparation of the compounds of general formula I.

SCHEME 1

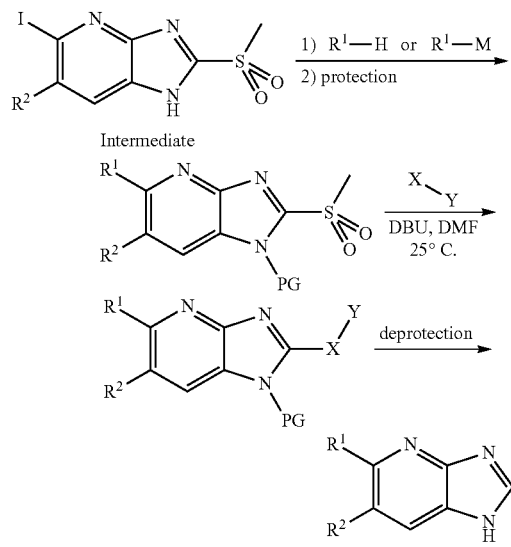

PG = SEM or allyl

General Scheme

SCHEME 2

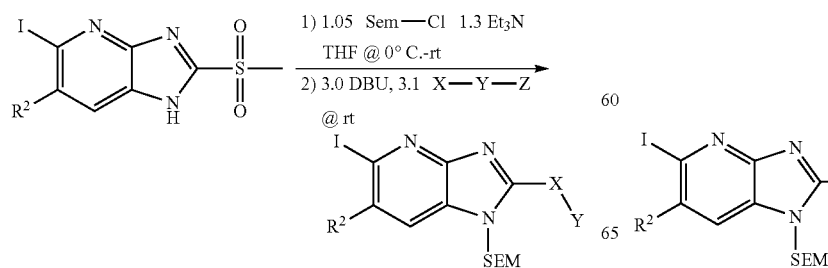

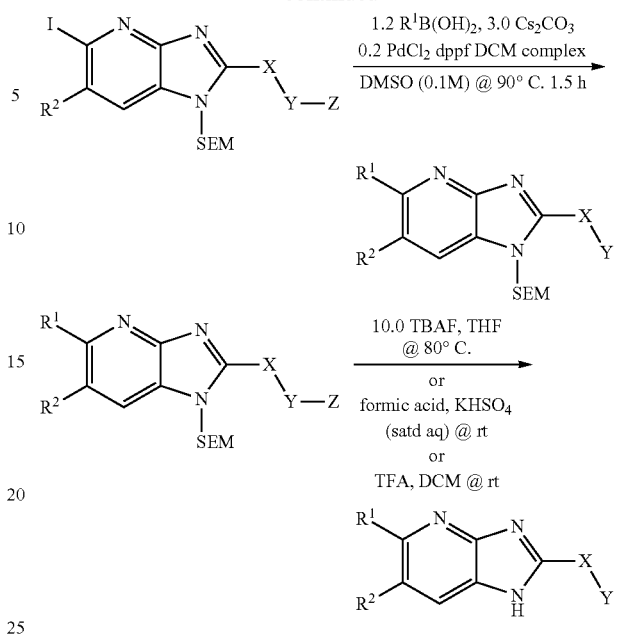

SCHEME 3

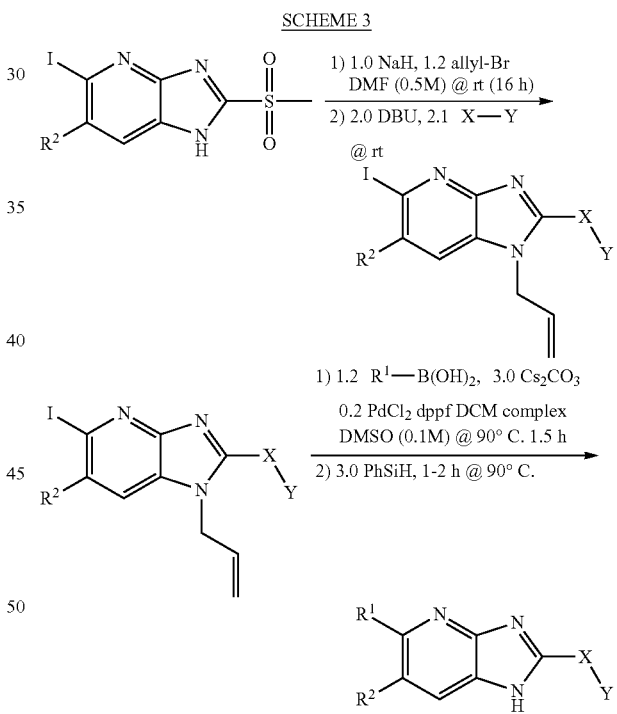

SCHEME 4

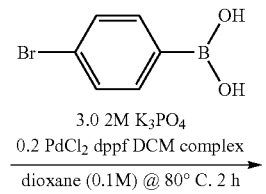

-continued

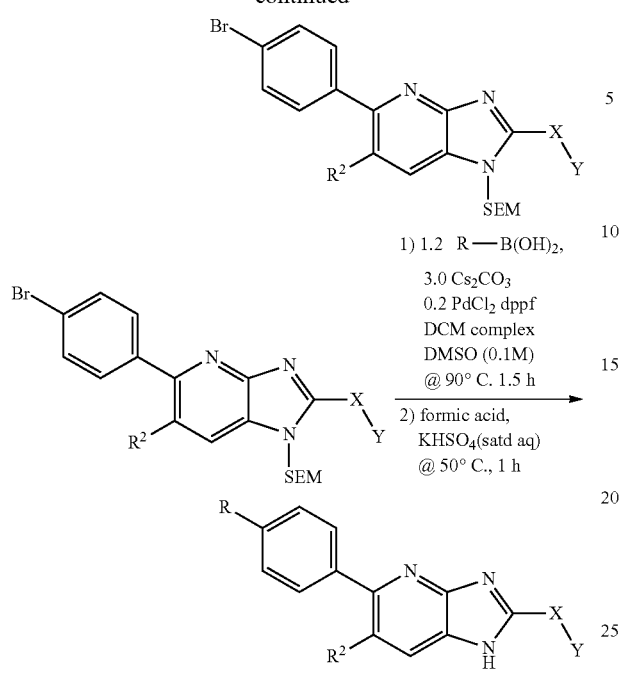

Intermediate 1

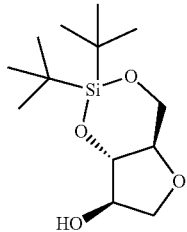 [SMILES: CC(C)(C)[Si]1(C(C)(C)C)OC[C@H]2OC[C@@H](O)[C@@H]2O1]

(4aR,7R,7aS)-2,2-ditert-butyl-4a,6,7,7a-tetrahydro-4H-furo[3,2-d][1,3,2]dioxasilin-7-ol Step A (4aR,7aR)-2,2-ditert-butyl-4a,7a-dihydro-4H-furo[3,2-d][1,3,2]dioxasilin-7-one Dess-Martin periodinane (22.81 g, 53.8 mmol) was added to a stirred solution of (4aR,7S,7aS)-2,2-ditert-butyl-4a,6,7,7a-tetrahydro-4H-furo[3,2-d][1,3,2]dioxasilin-7-ol (7.36 g, 26.8 mmol) in dichloromethane (134.0 ml) in four portions over 8 minutes. The reaction mixture was a white suspension that was stirred at room temperature. After 3.5 hours, additional Dess-Martin periodinane (17.05 g, 40.2 mmol) was added to the reaction mixture. After 3 more hours, the reaction mixture was placed in the refrigerator overnight. The next morning the reaction mixture was allowed to warm to room temperature. After 4 hours, the reaction mixture was partitioned between EtOAc (600 ml) and water (150 ml). The resulting biphasic suspension was filtered through a pad of Celite™. The solid on the Celite™ pad was washed with EtoAc (1×100 ml, 2×50 ml, 1×200 ml). All of the EtOAc washes were combined with the original biphasic filtrate and additional water (150 ml) was added before the filtrate was re-partitioned. The organic layer was washed with water (2×200 ml) and brine (1×200 ml). The solid that remained in the original reaction flask was suspended in EtOAc and filtered through a new pad of Celite™. The solid was washed with EtOAc (1×150 ml). The EtOAc wash was combined with the organic layer from the first part of the workup, dried over $Na_2SO_4$, filtered, and evaporated under reduced pressure to give a colorless oil. Flash chromatography of the oil utilizing a 330 g silica RediSep $R_f$® column and employing a 0-13.3% EtOAc/hexane gradient afforded the desired product as a white solid. $^1$H NMR δ (ppm) (CDCl$_3$): 4.52 (dd, J=5.3 Hz, J=9.5 Hz, 1H), 4.38 (dd, J=1.4 Hz, J=10.9 Hz, 1H), 4.24 (d, J=17.3 Hz, 1H), 4.15 (t, J=9.8 Hz, 1H), 4.04 (d, J=17.2 Hz, 1H), 3.95 (ddd, J=5.1 Hz, J=10.5 Hz, 1H), 1.11 (s, 9H), 1.04 (s, 9H).

Step B (4aR,7R,7aS)-2,2-ditert-butyl-4a,6,7,7a-tetrahydro-4H-furo[3,2-d][1,3,2]dioxasilin-7-ol A stirred solution of (4aR,7aR)-2,2-ditert-butyl-4a,7a-dihydro-4H-furo[3,2-d][1,3,2]dioxasilin-7-one (2.88 g, 10.57 mmol) in MeOH (43.0 ml) was cooled to 0° C. in an ice bath. Sodium borohydride (885.5 mg, 23.41 mmol) was added to the reaction mixture in portions over 8 minutes, resulting in gas evolution. The reaction mixture was a colorless solution. After 3.5 hours, the reaction mixture was removed from the ice bath and allowed to warm to room temperature. The reaction mixture was then partitioned between EtOAc (400 ml) and brine (200 ml). The aqueous layer was extracted with EtOAc (2×100 ml). The organic layers were combined, dried over $Na_2SO_4$, filtered, and evaporated under reduced pressure to give a white solid. Flash chromatography of the solid utilizing a 120 g silica RediSep $R_f$® column and employing a 0-15% EtOAc/hexane gradient followed by a 15% EtOAc/hexane hold afforded the title compound as a white solid. $^1$H NMR δ (ppm) (CDCl$_3$): 4.41-4.45 (m, 1H), 4.35 (dd, J=5.2 Hz, J=9.3 Hz, 1H), 4.22 (t, J=9.0 Hz, 1H), 4.01 (dd, J=7.2 Hz, J=9.6 Hz, 1H), 3.96 (t, J=9.9 Hz, 1H), 3.78 (dd, J=6.2 Hz, J=9.6 Hz, 1H), 3.68 (ddd, J=5.1 Hz, J=10.0 Hz, 1H), 1.10 (s, 9H), 1.03 (s, 9H).

Intermediate 2

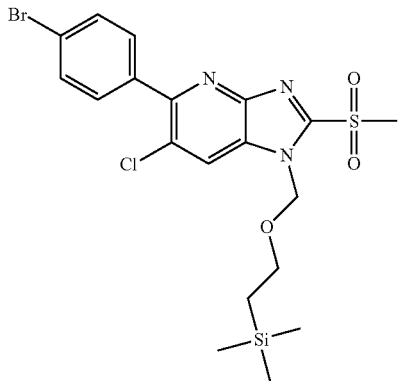 [SMILES: C[Si](C)(C)CCOCn1c(S(C)(=O)=O)nc2nc(-c3ccc(Br)cc3)c(Cl)cc21]

2-[[5-(4-bromophenyl)-6-chloro-2-methylsulfonyl-imidazo[4,5-b]pyridin-1-yl]methoxy]ethyl-trimethyl-silane Step A 5-(4-bromophenyl)-6-chloro-2-(methylsulfonyl)-1H-imidazo[4,5-b]pyridine Palladium tetrakis (1.63 g, 1.411 mmol) was added to a stirred hazy solution of intermediate 1 (10.08 g, 28.2 mmol), 4-bromophenylboronic acid (6.23 g, 31.0 mmol), and potassium phosphate (18.44 g, 87 mmol) in dioxane (150.0 ml) and water (30.0 ml). The reaction mixture was degassed (3×) and placed under nitrogen before being heated to 100° C. After 17 hours, the reaction mixture was cooled to room temperature before being evaporated under reduced pressure. The resulting residue was stripped with toluene (2×60 ml) to afford the product as a brown/white solid, which was used in the next step without further purification. LC-MS: calculated for $C_{13}H_9BrClN_3O_2S$ 384.93, 386.93. observed m/e: 385.81, 387.84 (M+H)$^+$ (Rt 1.15/2 min).

Step B 2-[[5-(4-bromophenyl)-6-chloro-2-methyl-sulfonyl-imidazo[4,5-b]pyridin-1-yl]methoxy]ethyl-trimethyl-silane N,N-diisopropylethylamine (15.0 ml, 86 mmol) was added to a stirred suspension of the unpurified 5-(4-bromophenyl)-6-chloro-2-(methylsulfonyl)-1H-imidazo[4,5-b]pyridine from Step A in THF (150.0 ml). The reaction mixture was cooled to 0° C. in an ice bath prior to the slow addition of SEM-Cl (10.0 ml, 56.4 mmol) over 9 minutes. Ten minutes after the addition was complete, the reaction mixture was removed from the ice bath and allowed to warm to room temperature. 16 hours, the reaction mixture was partitioned following the addition of water (200 ml). The aqueous layer was extracted with EtOAc (3×200 ml). The organic layers were combined, washed with brine (1×100 ml), dried over $Na_2SO_4$, filtered, and evaporated under reduced pressure to give a yellow/brown solid. Flash chromatography of the solid utilizing two (the material was divided in half) 330 g silica RediSep $R_f$® columns and employing a 0-30% EtOAc/hexane gradient with a 30% EtOAc/hexane hold afforded the title compound as a yellow solid. LC-MS: calculated for $C_{19}H_{23}BrClN_3O_3SSi$ 515.01, 517.01. observed m/e: 515.85, 517.86 (M+H)$^+$ (Rt 1.33/2 min).

Intermediate 3

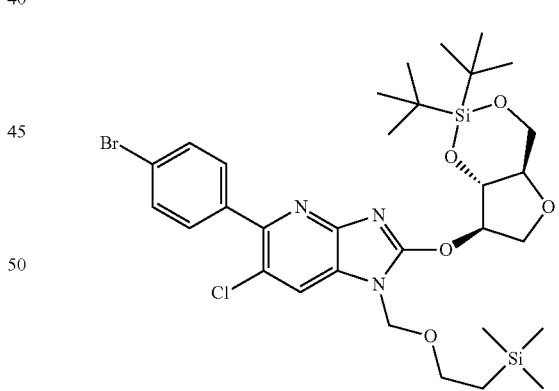

2-[[2-[[(4aR,7R,7aR)-2,2-ditert-butyl-4a,6,7,7a-tetrahydro-4H-furo[3,2-d][1,3,2]dioxasilin-7-yl]oxy]-5-(4-bromophenyl)-6-chloro-imidazo[4,5-b]pyridin-1-yl]methoxy]ethyl-trimethyl-silane Cesium carbonate (2.84 g, 8.72 mmol) was added to a stirred suspension of 2-[[5-(4-bromophenyl)-6-chloro-2-methylsulfonyl-imidazo[4,5-b]pyridin-1-yl]methoxy]ethyl-trimethyl-silane (3.00 g, 5.80 mmol) and (4aR,7R,7aS)-2,2- ditert-butyl-4a,6,7,7a-tetrahydro-4H-furo[3,2-d][1,3,2]dioxasilin-7-ol (1.71 g, 6.23 mmol) in DMF (30.0 ml). The reaction mixture was a yellow suspension that was stirred at room temperature. After 20 hours, the reaction mixture was partitioned between EtOAc (400 ml) and water (150 ml). The organic layer was washed with water (4×100 ml) and brine (1×100 ml), dried over $Na_2SO_4$, filtered, and evaporated under reduced pressure to give a yellow foam. The foam was purified by flash chromatography utilizing a 120 g silica RediSep $R_f$® column and employing a 0-15% EtOAc/hexane gradient with a 15% EtOAc/hexane hold followed by a 15-50% EtOAc/hexane gradient with a 50% EtOAc/hexane hold. The product fractions were combined, evaporated under reduced pressure, and lyophilized from ethanol and benzene to give the title compound as a pale yellow solid. LC-MS: calculated for $C_{31}H_{45}BrClN_3O_5Si_2$ 709.18, 711.18. observed m/e: 709.96, 711.99 $(M+H)^+$ (Rt 1.56/2 min).

Intermediate 4

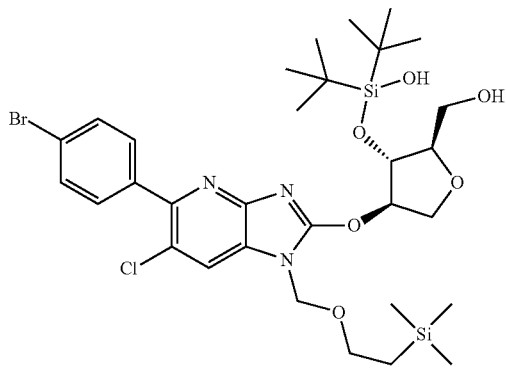 [SMILES: CC(C)(C)[Si](O)(O[C@@H]1[C@@H](CO)OC[C@H]1Oc1nc2nc(-c3ccc(Br)cc3)c(Cl)cc2n1COCC[Si](C)(C)C)C(C)(C)C]

[(2R,3R,4R)-4-[5-(4-bromophenyl)-6-chloro-1-(2-trimethylsilylethoxymethyl)imidazo-[4,5-b]pyridin-2-yl]oxy-3-[ditert-butyl(hydroxy)silyl]oxy-tetrahydrofuran-2-yl]methanol Cesium carbonate (2.84 g, 8.72 mmol) was added to a stirred suspension of 2-[[5-(4-bromophenyl)-6-chloro-2-methylsulfonyl-imidazo[4,5-b]pyridin-1-yl]methoxy]ethyl-trimethyl-silane (3.00 g, 5.80 mmol) and (4aR,7R,7aS)-2,2-ditert-butyl-4a,6,7,7a-tetrahydro-4H-furo[3,2-d][1,3,2]dioxasilin-7-ol (1.71 g, 6.23 mmol) in DMF (30.0 ml). The reaction mixture was a yellow suspension that was stirred at room temperature. After 20 hours, the reaction mixture was partitioned between EtOAc (400 ml) and water (150 ml). The organic layer was washed with water (4×100 ml) and brine (1×100 ml), dried over $Na_2SO_4$, filtered, and evaporated under reduced pressure to give a yellow foam. The foam was purified by flash chromatography utilizing a 120 g silica RediSep $R_f$® column and employing a 0-15% EtOAc/hexane gradient with a 15% EtOAc/hexane hold followed by a 15-50% EtOAc/hexane gradient with a 50% EtOAc/hexane hold. The product fractions were combined, evaporated under reduced pressure, and lyophilized from ethanol and benzene to give the title compound as a yellow solid. LC-MS: calculated for $C_{31}H_{47}BrClN_3O_6Si_2$ 727.19, 729.19. observed m/e: 728.09, 730.07 $(M+H)^+$ (Rt 1.48/2 min).

Intermediate 5

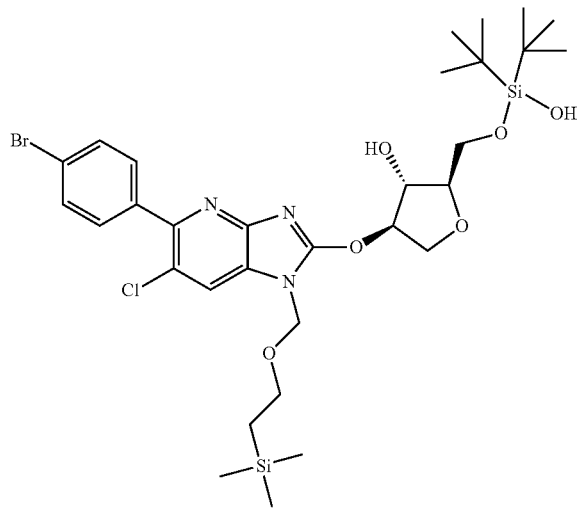 [SMILES: CC(C)(C)[Si](O)(OC[C@H]1OC[C@@H](Oc2nc3nc(-c4ccc(Br)cc4)c(Cl)cc3n2COCC[Si](C)(C)C)[C@@H]1O)C(C)(C)C]

(2R,3R,4R)-4-[5-(4-bromophenyl)-6-chloro-1-(2-trimethylsilylethoxymethyl)imidazo-[4,5-b]pyridin-2-yl]oxy-2-[[ditert-butyl(hydroxy)silyl]oxymethyl]-tetrahydrofuran-3-ol Cesium carbonate (2.84 g, 8.72 mmol) was added to a stirred suspension of 2-[[5-(4-bromophenyl)-6-chloro-2-methylsulfonyl-imidazo[4,5-b]pyridin-1-yl]methoxy]ethyl-trimethyl-silane (3.00 g, 5.80 mmol) and (4aR,7R,7aS)-2,2-ditert-butyl-4a,6,7,7a-tetrahydro-4H-furo[3,2-d][1,3,2]dioxasilin-7-ol (1.71 g, 6.23 mmol) in DMF (30.0 ml). The reaction mixture was a yellow suspension that was stirred at room temperature. After 20 hours, the reaction mixture was partitioned between EtOAc (400 ml) and water (150 ml). The organic layer was washed with water (4×100 ml) and brine (1×100 ml), dried over $Na_2SO_4$, filtered, and evaporated under reduced pressure to give a yellow foam. The foam was purified by flash chromatography utilizing a 120 g silica RediSep $R_f$® column and employing a 0-15% EtOAc/hexane gradient with a 15% EtOAc/hexane hold followed by a 15-50% EtOAc/hexane gradient with a 50% EtOAc/hexane hold. The product fractions were combined, evaporated under reduced pressure, and lyophilized from ethanol and benzene to give the desired product as a pale yellow solid. LC-MS: calculated for $C_{31}H_{47}BrClN_3O_6Si_2$ 727.19, 729.19. observed m/e: 728.08, 730.08 $(M+H)^+$ (Rt 1.44/2 min).

Intermediate 6

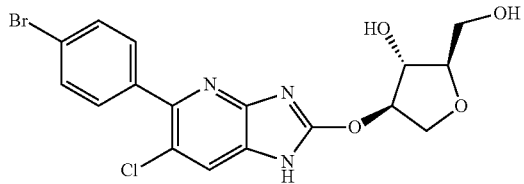 [SMILES: OC[C@H]1OC[C@@H](Oc2nc3nc(-c4ccc(Br)cc4)c(Cl)cc3[nH]2)[C@@H]1O]

(2R,3R,4R)-4-[[5-(4-bromophenyl)-6-chloro-1H-imidazo[4,5-b]pyridin-2-yl]oxy]-2-(hydroxymethyl)tetrahydrofuran-3-ol Combined [(2R,3R,4R)-4-[5-(4-bromophenyl)-6-chloro-1-(2-trimethylsilylethoxymethyl)imidazo[4,5-b]pyridin-2- yl]oxy-3-[ditert-butyl(hydroxy)silyl]-oxy-tetrahydrofuran-2-yl]methanol (127.9 mg, 0.175 mmol), formic acid (1.5 ml, 39.1 mmol), and saturated aqueous $KHSO_4$ (0.1 ml) in a 25 ml flask. The reaction mixture was a hazy white suspension that was heated to 40° C. with stirring. After 17.5 hours, the reaction mixture was cooled to room temperature. The reaction mixture was then cooled to 0° C. in an ice bath. The pH of the reaction mixture was adjusted to pH 14 through the addition of 5 N NaOH (9.0 ml, 45.0 mmol). THF (2.0 ml) was added to the reaction mixture, which was removed from the ice bath and allowed to warm to room temperature. After 30 minutes, the pH of the reaction mixture was adjusted to pH 7 through the addition of 2 N HCl. Then the reaction mixture was partitioned between EtOAc (40 ml) and water (40 ml). The aqueous layer was extracted with EtOAc (2×20 ml). The organic layers were combined, washed with brine (1×20 ml), dried over $Na_2SO_4$, filtered, and evaporated under reduced pressure to give a pale yellow residue. TBAF 1.0 M in THF (1.5 ml, 1.500 mmol) was combined with the residue in a 25 ml flask. The reaction mixture was heated to 60° C. with stirring. After 1.5 hours, the reaction mixture was cooled to room temperature before being partitioned between EtOAc (40 ml) and water (40 ml). The aqueous layer was extracted with EtOAc (2×20 ml). The organic layers were combined, washed with brine (1×20 ml), dried over $Na_2SO_4$, filtered, and evaporated under reduced pressure to give a yellow residue. This material was purified by preparative HPLC reverse phase (C-18), using a 30×150 mm Sunfire™ column and eluting with a 20%-100% acetonitrile/water+0.05% TFA gradient followed by a 100% acetonitrile+0.05% TFA flush. The product fractions were combined and evaporated under reduced pressure to give the title compound as a colorless residue. LC-MS: calculated for $C_{17}H_{15}BrClN_3O_4$ 438.99, 440.99. observed m/e: 439.77, 441.75 $(M+H)^+$ (Rt 1.12/2 min).

Intermediate 7

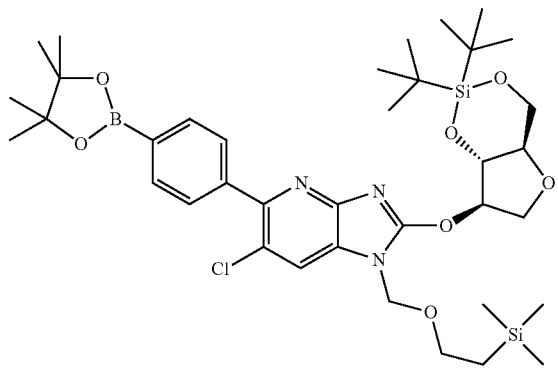 [SMILES: CC1(C)OB(c2ccc(-c3nc4nc(O[C@@H]5CO[C@@H]6CO[Si](C(C)(C)C)(C(C)(C)C)O[C@H]65)n(COCC[Si](C)(C)C)c4cc3Cl)cc2)OC1(C)C]

2-[[2-[[(4aR,7R,7aR)-2,2-ditert-butyl-4a,6,7,7a-tetrahydro-4H-furo[3,2-d][1,3,2]-dioxasilin-7-yl]oxy]-6-chloro-5-[4-(4,4,5,5-tetramethyl-1,3,2-dioxaborolan-2-yl)phenyl]-imidazo[4,5-b]pyridin-1-yl]methoxyl]ethyl-trimethyl-silane 1,1'-bis(diphenylphos-phino)ferrocene-palladium(II) dichloride dichloromethane complex (50.1 mg, 0.061 mmol) was added to a stirred suspension of 2-[[2-[[(4aR,7R,7aR)-2,2-ditert-butyl-4a,6,7,7a-tetrahydro-4H-furo[3,2-d][1,3,2]dioxasilin-7-yl]oxy]-5-(4-bromophenyl)-6-chloro-imidazo[4,5-b]pyridin-1-yl]methoxy]ethyl-trimethyl-silane (402.0 mg, 0.565 mmol), bis(pinacolato)diboron (445.2 mg, 1.753 mmol), and potassium acetate (268.3 mg, 2.73 mmol) in dioxane (5.6 ml). The reaction mixture was degassed (3×) and placed under nitrogen before being heated to 80° C. After 10 minutes, the reaction mixture had turned dark. After 4.5 hours, the reaction mixture was cooled to room temperature. The reaction mixture was partitioned between EtOAc (100 ml) and water (100 ml). The aqueous layer was extracted with EtOAc (2×50 ml). The organic layers were combined, washed with brine (1×50 ml), dried over $Na_2SO_4$, filtered, and evaporated under reduced pressure to give a brown foam. The foam was purified by flash chromatography utilizing a 12 g silica RediSep $R_f$® column and employing a 0-15% EtOAc/hexane gradient followed by a 15% EtOAc/hexane hold. The product fractions were combined, evaporated under reduced pressure, and lyophilized from ethanol and benzene to give the title compound as a white solid. LC-MS: calculated for $C_{37}H_{57}BClN_3O_7Si_2$ 757.35. observed m/e: 758.15 $(M+H)^+$ (Rt 1.59/2 min).

Intermediate 8

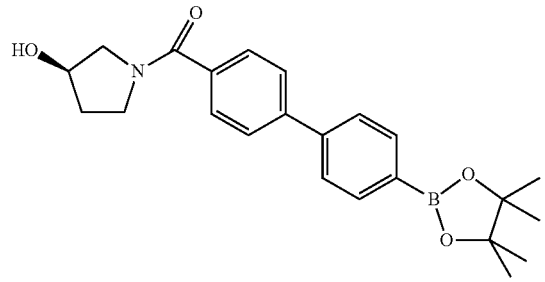 [SMILES: CC1(C)OB(c2ccc(-c3ccc(C(=O)N4CC[C@@H](O)C4)cc3)cc2)OC1(C)C]

[(3R)-3-hydroxypyrrolidin-1-yl]-[4-[4-(4,4,5,5-tetramethyl-1,3,2-dioxaborolan-2-yl)phenyl]phenyl]methanone Step A 4-(4-bromophenyl)benzoic acid Palladium tetrakis (0.500 g, 0.433 mmol), 4-(4,4,5,5-tetramethyl-1,3,2-dioxaborolan-2-yl)benzoic acid (2 g, 8.06 mmol), and 1-bromo-4-iodo-benzene (2.4 g, 8.48 mmol) were dissolved in DMF (40 ml). 1.0 M aqueous potassium carbonate (20 ml, 20.00 ml) was added to the reaction mixture, which was microwaved at 90° C. for 4 hours. The reaction mixture was evaporated under reduced pressure and the resulting residue was used in the next step without further purification or characterization.

Step B [4-(4-bromophenyl)phenyl]-[(3R)-3-hydroxypyrrolidin-1-yl]methanone

Triethylamine (4 ml, 28.7 mmol) was added to a stirred solution of O-(-7azabenzotriazol-1-yl)-N,N,N',N'-tetramethyluronium hexafluorophosphate (5.5 g, 14.46 mmol), (3R)-pyrrolidin-3-ol (1.3 g, 14.92 mmol), and 4-(4-bromophenyl)benzoic acid (2 g, 7.22 mmol) in DMF (60 ml). The reaction mixture was stirred under nitrogen for 24 hours. The reaction mixture was partitioned between EtOAc (200 ml) and water (300 ml). The aqueous layer was extracted with EtOAc (2×100 ml). The organic layers were combined, washed with 1 N HCl (2×200 ml), saturated aqueous NaHCO₃ (6×200 ml), and brine, dried over Na₂SO₄, filtered, and evaporated under reduced pressure. The resulting residue was purified by flash chromatography eluting with 3% MeOH/DCM to give the desired product. LC-MS: calculated for $C_{17}H_{16}BrNO_2$ 345.04, 347.04. observed m/e: 346.05, 348.05 (M+H)⁺ (Rt 1.56/4 min).

Step C [(3R)-3-hydroxypyrrolidin-1-yl]-[4-[4-(4,4,5,5-tetramethyl-1,3,2-dioxaborolan-2-yl)phenyl]phenyl]methanone 1,1'-bis(diphenylphosphino)ferrocene-palladium (II) dichloride (0.102 g, 0.140 mmol), bis(pinacolato)diboron (1.25 g, 4.92 mmol), potassium acetate (1.4 g, 14.26 mmol), and [4-(4-bromophenyl)phenyl]-[(3R)-3-hydroxypyrrolidin-1-yl]methanone (1.61 g, 4.65 mmol) were combined and dissolved in DMSO (9 ml). The resulting mixture was degassed (5×) and placed under nitrogen before being heated to 80° C. with stirring. After 24 hours, the reaction mixture was partitioned between diethyl ether (200 ml) and water (200 ml). The aqueous layer was extracted with diethyl ether (2×100 ml). The organic layers were combined, washed with brine, dried over Na₂SO₄, filtered, and evaporated under reduced pressure. The resulting residue was purified by column chromatography using a 120 g silica column and eluting with 3% MeOH/DCM to give the title compound. LC-MS: calculated for $C_{23}H_{28}BNO_4$ 393.21. observed m/e: 394.24 (M+H)⁺ (Rt 2.01/4 min).

Intermediate 9 nitrogen and heated to 80° C. After 2 hours, the reaction mixture was partitioned between EtOAc and saturated aqueous NH₄Cl. The aqueous layer was extracted with EtOAc (2×). The organic layers were combined, washed with brine, dried over Na₂SO₄, filtered, and evaporated under reduced pressure to give the desired product. The crude product was used in the next step without further purification. LC-MS: calculated for $C_{24}H_{21}ClN_4O_4S$ 496.1. observed m/e: 497.18 (M+H)⁺ (Rt 1.66/4 min).

Step B [4-[4-[6-chloro-2-methylsulfonyl-1-(2-trimethylsilylethoxymethyl)imidazo[4,5-b]pyridin-5-yl]phenyl]phenyl]-[(3R)-3-hydroxypyrrolidin-1-yl]methanone Triethylamine (0.9 ml, 6.46 mmol) and 2-(trimethylsilyl)ethoxymethyl chloride (1.1 ml, 6.20 mmol) were added to a solution of [4-[4-(6-chloro-2-methylsulfonyl-1H-imidazo[4,5-b]pyridin-5-yl)phenyl]phenyl]-[(3R)-3-hydroxypyrrolidin-1-yl]methanone (all of the crude product from the previous step) in DMF (20.0 ml). The reaction mixture was stirred at room temperature. After 1.5 hours, the reaction mixture was partitioned between EtOAc (200 ml) and water (200 ml). The aqueous layer was extracted with EtOAc (2×100 ml). The organic layers were combined, washed with brine, dried over Na₂SO₄, filtered, and evaporated under reduced pressure. The resulting residue was purified by column chromatography, eluting with 3% MeOH/DCM to give the desired product. LC-MS: calculated for $C_{30}H_{35}ClN_4O_5SSi$ 626.18. observed m/e: 627.32 (M+H)⁺ (Rt 2.36/4 min).

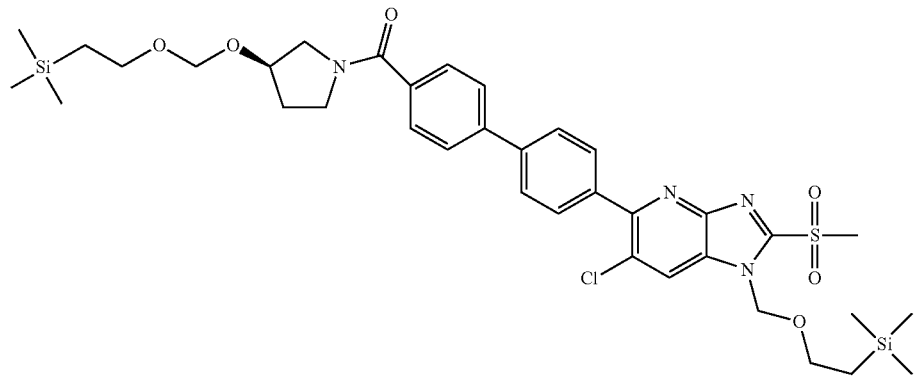

[4-[4-[6-chloro-2-methylsulfonyl-1-(2-trimethylsilylethoxymethyl)imidazo[4,5-b]pyridin-5-yl]phenyl]phenyl]-[(3R)-3-(2-trimethylsilylethoxymethoxy)pyrrolidin-1-yl]methanone Step A [4-[4-(6-chloro-2-methylsulfonyl-1H-imidazo[4,5-b]pyridin-5-yl)phenyl]phenyl]-[(3R)-3-hydroxypyrrolidin-1-yl]methanone

[(3R)-3-hydroxypyrrolidin-1-yl]-[4-[4-(4,4,5,5-tetramethyl-1,3,2-dioxaborolan-2-yl)phenyl]phenyl]methanone (1.1 g, 2.80 mmol) and 6-chloro-5-iodo-2-methylsulfonyl-1H-imidazo[4,5-b]pyridine (1 g, 2.80 mmol) were dissolved in dioxane (14 ml) and purged with nitrogen. 3 M lithium hydroxide (2.80 ml, 8.39 mmol), water (3.73 ml), and 1,1'-bis(diphenylphosphino)-ferrocene-palladium(II)dichloride dichloromethane complex (0.205 g, 0.280 mmol) were added to the reaction mixture, which was purged with Step C [4-[4-[6-chloro-2-methylsulfonyl-1-(2-trimethylsilylethoxymethyl)imidazo[4,5-b]pyridin-5-yl]phenyl]phenyl]-[(3R)-3-(2-trimethylsilylethoxymethoxy)pyrrolidin-1-yl]methanone Tetrabutylammonium iodide (602 mg, 1.631 mmol), N,N-diisopropyl-ethylamine (0.5 ml, 2.86 mmol), and 2-(trimethylsilyl)ethoxymethyl chloride (0.28 ml, 1.579 mmol) were added to a stirred solution of [4-[4-[6-chloro-2-methylsulfonyl-1-(2-trimethylsilylethoxymethyl)imidazo[4,5-b]pyridin-5-yl]phenyl]phenyl]-[(3R)-3-hydroxypyrrolidin-1-yl]methanone (930 mg, 1.483 mmol) in DMF (10 ml). The reaction mixture was stirred at 45° C. overnight. Then the reaction mixture was partitioned between EtOAc (200 ml) and water (200 ml). The aqueous layer was extracted with EtOAc (2×100 ml). The organic layers were combined, washed with brine, dried over Na₂SO₄, filtered, and evaporated under reduced pressure. The resulting residue was purified by column chromatography, eluting with 3% MeOH/DCM to give the title compound. LC-MS: calculated for $C_{36}H_{49}ClN_4O_6SSi_2$ 756.26. observed m/e: 757.33 $(M+H)^+$ (Rt 2.89/4 min).

Intermediate 10

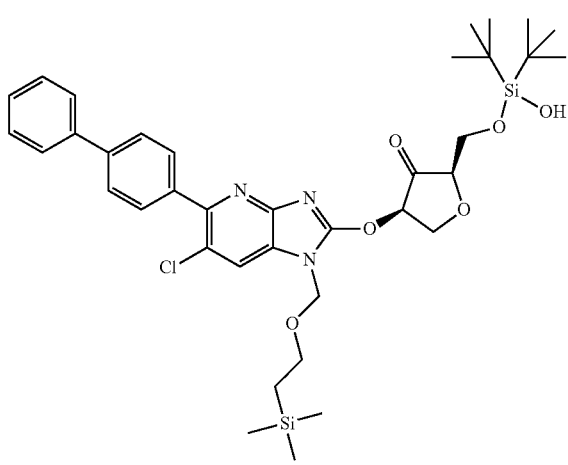 [SMILES: CC(C)(C)[Si](O)(OC[C@H]1OC[C@@H](Oc2nc3nc(-c4ccc(-c5ccccc5)cc4)c(Cl)cc3n2COCC[Si](C)(C)C)C1=O)C(C)(C)C]

(2R,4R)-4-[6-chloro-5-(4-phenylphenyl)-1-(2-trimethylsilylethoxymethyl)imidazo[4,5-b]pyridin-2-yl]oxy-2-[[ditert-butyl(hydroxy)silyl]oxymethyl]tetrahydrofuran-3-one Step A (2R,3R,4R)-4-[6-chloro-5-(4-phenylphenyl)-1-(2-trimethylsilylethoxymethyl)-imidazo[4,5-b]pyridin-2-yl]oxy-2-[[ditertbutyl(hydroxy)silyl]oxymethyl]tetrahydrofuran-3-ol Chloro(2-dicyclohexylphosphino-2',6'-dimethoxy-1,1'-biphenyl)[2-(2-aminoethylphenyl)]-palladium(II)-methyl-t-butyl (43.8 mg, 0.058 mmol) was added to a stirred suspension of (2R,3R,4R)-4-[5-(4-bromophenyl)-6-chloro-1-(2-trimethylsilyl-ethoxymethyl)imidazo[4,5-b]pyridin-2-yl]oxy-2-[[ditert-butyl(hydroxy)silyl]oxymethyl]-tetrahydrofuran-3-ol (419.3 mg, 0.575 mmol), phenylboronic acid (96.0 mg, 0.787 mmol), and tripotassium phosphate (413.7 mg, 1.949 mmol) in dioxane (5.8 ml). The reaction mixture was degassed (3×) and placed under nitrogen before being heated to 80° C. After 4.5 hours, the reaction mixture was cooled to room temperature. Additional chloro(2-dicyclohexylphosphino-2',6'-dimethoxy-1,1'-biphenyl)[2-(2-aminoethylphenyl)]-palladium (II)-methyl-t-butyl (49.8 mg, 0.065 mmol) was added to the reaction mixture, which was degassed (3×) and placed under nitrogen. Then the reaction mixture was heated to 80° C. After an additional hour, 2.0 M aqueous $K_3PO_4$ (0.80 ml, 0.160 mmol) was added to the reaction mixture, which became a hazy yellow solution. After 30 minutes, the reaction mixture was cooled to room temperature overnight. Then additional chloro(2-dicyclohexyl-phosphino-2',6'-dimethoxy-1,1'-biphenyl)[2-(2-aminoethyl-phenyl)]palladium (II)-methyl-t-butyl (47.7 mg, 0.063 mmol) was added to the reaction mixture, which was degassed (3×) and placed under nitrogen before being heated to 80° C. After 3 hours, the reaction mixture was cooled to room temperature before being partitioned between EtOAc (100 ml) and water (100 ml). The aqueous layer was extracted with EtOAc (2×50 ml). The organic layers were combined, washed with brine (1×30 ml), dried over $MgSO_4$, filtered, and evaporated under reduced pressure to give a yellow residue. The residue was purified by flash chromatography utilizing a 40 g silica RediSep $R_f$® column and employing a 0-40% EtOAc/hexane gradient followed by a 40% EtOAc/hexane hold. The product fractions were combined and evaporated under reduced pressure to give the desired product as a pale amber foam. LC-MS: calculated for $C_{37}H_{52}ClN_3O_6Si_2$ 725.31. observed m/e: 726.46 $(M+H)^+$ (Rt 1.50/2 min).

Step B (2R,4R)-4-[6-chloro-5-(4-phenylphenyl)-1-(2-trimethylsilylethoxymethyl)-imidazo[4,5-b]pyridin-2-yl]oxy-2-[[ditert-butyl(hydroxy)silyl]oxymethyl]-tetrahydrofuran-3-one A hazy solution of Dess-MartinPeriodinane (538.1 mg, 1.269 mmol) in DCM (5.6 ml) was added to a flask containing (2R,3R,4R)-4-[6-chloro-5-(4-phenylphenyl)-1-(2-trimethylsilylethoxymethyl)-imidazo[4,5-b]pyridin-2-yl] oxy-2-[[ditert-butyl(hydroxy)silyl]oxymethyl] tetrahydrofuran-3-ol (347.7 mg, 0.479 mmol). The reaction mixture was a yellow solution that was stirred at room temperature. After 2 days, the reaction mixture was diluted with saturated aqueous sodium thiosulfate (10 ml), saturated aqueous $NaHCO_3$ (10 ml), and EtOAc (10 ml). The reaction mixture was stirred for 20 minutes before being partitioned between EtOAc (30 ml) and water (20 ml). The aqueous layer was extracted with EtOAc (3×30 ml). The organic layers were combined, washed with brine (1×30 ml), dried over $MgSO_4$, filtered, and evaporated under reduced pressure to give a yellow residue. The residue was purified by flash chromatography utilizing a 24 g silica RediSep $R_f$® column and employing a 0-30% EtOAc/hexane gradient followed by a 30% EtOAc/hexane hold. The product fractions were combined, evaporated under reduced pressure, and lyophilized from ethanol and benzene to give the title compound as a yellow solid. LC-MS: calculated for $C_{37}H_{50}ClN_3O_6Si_2$ 723.29. observed m/e: 724.49 $(M+H)^+$ (Rt 1.49/2 min).

Intermediate 11

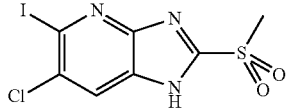

6-chloro-5-iodo-2-(methylsulfonyl)-1H-imidazo[4,5-b]pyridine

Step A 5,6-dichloro-3-nitropyridin-2-amine

To a solution of 5-chloro-3-nitropyridin-2-amine (16 g, 92 mmol) in AcOH (70 mL) was added N-chlorosuccinimide (14.8 g 111 mmol). The mixture was stirred overnight at 80° C. for 3 h, cooled to rt, diluted with MeOH (30 mL) and filtered. The solid residue was washed with AcOH, water, and then dried to afford the desired product as a white solid, which was used in the next step without further purification. LC-MS: calculated for $C_5H_3Cl_2N_3O_2$ 208.0. observed m/e: 208.07 $(M+H)^+$ (Rt 1.48/5 min).

Step B 5-chloro-6-iodo-3-nitropyridin-2-amine

To a solution of 5,6-dichloro-3-nitropyridin-2-amine (15 g, 72.1 mmol) in AcOH (70 mL) was added sodium iodide (43.2 g 149.9 mmol). The mixture was stirred at 90° C. for 2 h, cooled to rt, diluted with water (70 mL) and filtered. The solid residue was washed with water, and then dried under vacuum to afford the desired product as a pale yellow solid, which was used in the next step without further purification. LC-MS: calculated for $C_5H_3ClIN_3O_2$ 299.45. observed m/e: 299.94 (M+H)$^+$ (Rt 2.18/5 min).

Step C 5-chloro-6-iodopyridine-2,3-diamine

To a suspension of 5-chloro-6-iodo-3-nitropyridin-2-amine (18.9 g, 63.1 mmol) in EtOH (100 mL) was added tin (II) chloride dihydrate (57 g, 252 mmol). The mixture was heated at 70° C. for 0.5 h. The rxn was warmed to rt and treated with a slurry of 150 mL water and 60 g KF and stirred for 0.5 h. The mixture was then partitioned between ethyl acetate (300 mL) and water (300 mL). The ethyl acetate layer was washed with brine, dried over magnesium sulfate and filtered through a 100 g pad of silica gel. The filtrate was concentrated and dried under vacuum to give an off-white solid, which was used in next step without further purification. LC-MS: calculated for $C_5H_5ClIN_3$ 269.47. observed m/e: 269.99 (M+H)$^+$ (Rt 1.35/5 min).

Step D 6-chloro-5-iodo-1,3-dihydro-2H-imidazo[4,5-b]pyridine-2-thione

DMAP (15.4 g, 126 mmol) was added to a THF (200 mL) solution of 5-chloro-6-iodopyridine-2,3-diamine (17 g, 63.1 mmol). Thiophosgene (4.9 mL, 63.1 mmol) was then added drop-wise via addition funnel under nitrogen and allowed to stir at rt for 1 h. The mixture was then partitioned between ethyl acetate (500 mL) and 2N HCl (100 mL). The ethyl acetate layer was washed with brine, dried over magnesium sulfate and concentrated to give the desired product as a white powder, which was used in the next step without further purification. LC-MS: calculated for $C_6H_3ClIN_3S$ 311.5. observed m/e: 311.91 (M+H)$^+$ (Rt 1.69/5 min).

Step E 6-chloro-5-iodo-2-(methylsulfanyl)-1H-imidazo[4,5-b]pyridine

A suspension of 6-chloro-5-iodo-1,3-dihydro-2H-imidazo[4,5-b]pyridine-2-thione (11.0 g, 35.3 mmol) and KOH (2.38 g, 42.4 mmol) in ethanol (200 mL) was stirred at rt for 0.5 h. Iodomethane (2.2 mL, 35.3 mmol) was then added and the reaction was allowed to stir for 1 h at rt. The ethanol was removed in vacuo and the resulting residue was partitioned between ethyl acetate (250 mL) and 2N HCl (50 mL). The ethyl acetate layer was washed with brine, dried over magnesium sulfate, filtered through a 100 g pad of silica gel and concentrated to give the desired product as a white solid. LC-MS: calculated for $C_7H_5ClIN_3S$ 325.56. observed m/e: 325.88 (M+H)$^+$ (Rt 2.05/5 min).

Step F 6-chloro-5-iodo-2-(methylsulfonyl)-1H-imidazo[4,5-b]pyridine

Oxone (20.8 g, 33.8 mmol) was added to an acetonitrile (100 mL)/water (100 mL) suspension of 6-chloro-5-iodo-2-(methysulfanyl)-1H-imidazo[4,5-b]pyridine (5.0 g, 15.4 mmol) and the reaction was allowed to stir for 18 h at rt. The suspension was filtered through a sintered glass funnel and the filtrate was partitioned between ethyl acetate and saturated sodium bisulfate. The ethyl acetate layer was washed with brine, dried over magnesium sulfate and concentrated to afford the title compound as a white solid that was used in subsequent steps without further purification. LC-MS: calculated for $C_7H_5ClIN_3O_2S$ 357.56. observed m/e: 357.07 (M+H)$^+$ (Rt 1.36/4 min). $^1$H NMR δ (ppm)(DMSO-d$_6$): 8.44 (1H, s), 3.53 (3H, s).

Intermediate 12

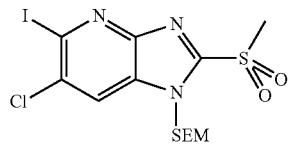 [SMILES: C[Si](C)(C)CCOCn1c(S(C)(=O)=O)nc2nc(I)c(Cl)cc21]

6-chloro-5-iodo-2-(methylsulfonyl)-1-{[2-(trimethylsilyl)ethoxy]methyl}-imidazo[4,5-b]pyridine SEM-Cl (2.48 mL, 14 mmol) was added to a THF (100 mL) solution of Intermediate 11 (5.0 g, 14 mmol) and triethylamine (2.92 mL, 21 mmol) at 0° C. under nitrogen atmosphere. The reaction was warmed to rt over 30 min. The reaction was partitioned between ethyl acetate and saturated aqueous ammonium chloride. The organic layer was washed with water, brine, dried over magnesium sulfate and concentrated. Flash chromatography of the resulting residue utilizing a Biotage™ 100G SNAP cartridge and employing a linear gradient: 0-20% EtOAc/hexane and then 20-100% EtOAc/hexane; afforded the title compound as a clear oil. LC-MS: calculated for $C_{13}H_{19}ClN_3O_3SSi$ 487.8. observed m/e: 428.9 (M+H)$^+$ (Rt 2.54/4 min).

Intermediate 13

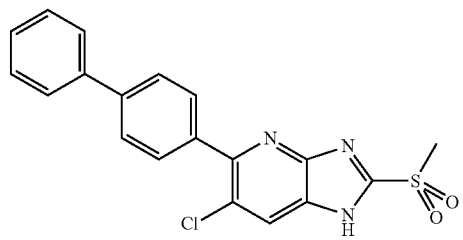 [SMILES: CS(=O)(=O)c1nc2nc(-c3ccc(-c4ccccc4)cc3)c(Cl)cc2[nH]1]

5-(biphenyl-4-yl)-6-chloro-2-(methylsulfonyl)-1H-imidazo[4,5-b]pyridine

Intermediate 11 (50 g, 140 mmol), 4-Biphenylboronic acid (33.2 g, 168 mmol) and tripotassium phosphate (89 g, 212.3 mmol) were dissolved in THF (500 mL) and water (50 mL), then sparged with $N_2$ for 20 min. A solution of palladium acetate (3.14 g, 14.0 mmol) and n-butyldiadamantylphosphine (Cataxcium A, 10 g, 28 mmol) in THF (30 mL) was sparged with $N_2$ for 20 minutes, and then added to the mixture of Intermediate 11, biphenylboronic acid and base. The reaction was heated to 45° C. for 18 h. An additional aliquot of palladium acetate (3.14 g, 14.0 mmol) and n-butyldiadamantylphosphine (Cataxcium A, 10 g, 28 mmol) in THF (30 mL) was sparged with $N_2$ for 20 minutes and added to the reaction mixture. After 24 h at 45° C., the reaction was cooled to rt and diluted with EtOAc and brine. The organic layer was concentrated and triturated with THF/MTBE to provide the title compound as a tan solid. LC-MS: calculated for $C_{19}H_{14}ClN_3O_2S$ 383.05. observed m/e: 383.9 (M+H)$^+$ (Rt 2.01/4 min).

Intermediate 14

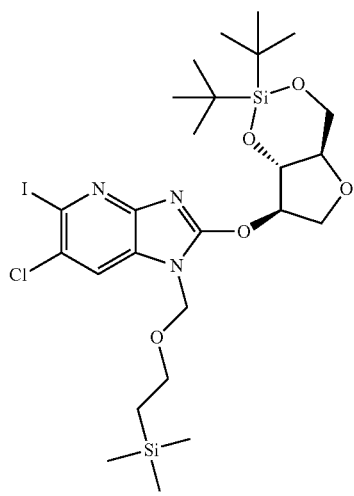 [SMILES: CC(C)(C)[Si]1(C(C)(C)C)OC[C@H]2OC[C@@H](Oc3nc4nc(I)c(Cl)cc4n3COCC[Si](C)(C)C)[C@@H]2O1]

2-[[2-[[(4aR,7R,7aR)-2,2-ditert-butyl-4a,6,7,7a-tetrahydro-4H-furo[3,2-d][1,3,2]dioxasilin-7-yl]oxy]-6-chloro-5-iodo-imidazo[4,5-b]pyridin-1-yl]methoxy]ethyl-trimethyl-silane DBU (0.71 ml, 4.71 mmol) was added to a stirred solution of 2-[(6-chloro-5-iodo-2-methylsulfonyl-imidazo[4,5-b]pyridin-1-yl)methoxy]ethyl-trimethyl-silane (1.52 g, 3.12 mmol) and (4aR,7R,7aS)-2,2-ditert-butyl-4a,6,7,7a-tetrahydro-4H-furo[3,2-d][1,3,2]dioxasilin-7-ol (1.04 g, 3.79 mmol) in DMF (12.0 ml). The reaction mixture was stirred at room temperature. After 16 hours, the reaction mixture was partitioned between EtOAc (300 ml) and water (100 ml). The organic layer was separated, washed with water (3×75 ml) and brine (1×50 ml), dried over MgSO$_4$, filtered, and evaporated under reduced pressure to give a yellow foam. The foam was dissolved in DCM and loaded onto a 25 g silica solid load cartridge. The foam was purified using an ISCO R$_f$ and an 80 g silica column (CV=125 ml), and eluted as follows: 100% Hex (1 CV), 0-12% EtOAc/Hex gradient (11.4 CV) at 60 ml/min. The product fractions were combined and evaporated under reduced pressure to give the title compound as a white foam. LC-MS: calculated for $C_{25}H_{41}ClIN_3O_5Si_2$ 681.13. observed m/e: 682.26 (M+H)$^+$ (Rt 2.00/2 min).

Intermediate 15

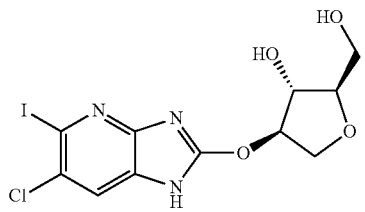 [SMILES: OC[C@H]1OC[C@@H](Oc2nc3nc(I)c(Cl)cc3[nH]2)[C@@H]1O]

(2R,3R,4R)-4-[(6-chloro-5-iodo-1H-imidazo[4,5-b]pyridin-2-yl)oxy]-2-(hydroxymethyl)tetrahydrofuran-3-ol Trifluoroacetic acid (5.0 ml, 64.9 mmol) was added to a stirred solution of 2-[[2-[[(4aR,7R,7aR)-2,2-ditert-butyl-4a,6,7,7a-tetrahydro-4H-furo[3,2-d][1,3,2]dioxasilin-7-yl]oxy]-6-chloro-5-iodo-imidazo[4,5-b]pyridin-1-yl]methoxy]ethyl-trimethyl-silane (1.3387 g, 1.963 mmol) in DCM (5.0 ml). The reaction mixture was stirred at room temperature for 2 hours, then evaporated under reduced pressure to give a yellow foam. Tetrabutylammonium fluoride 1.0 M in THF (10.0 ml, 10.00 mmol) was added to a stirred solution of the foam in THF (10 ml). The reaction mixture was a pale yellow solution that was heated to 50° C. After 2 hours, the reaction mixture was cooled to room temperature. The reaction mixture was partitioned between EtOAc (150 ml) and water (150 m). The aqueous layer was separated and extracted with EtOAc (2×75 ml). The organic layers were combined, dried over MgSO$_4$, filtered, and evaporated under reduced pressure to give a white foam. The foam was dissolved in DCM and loaded onto a 25 g silica solid load cartridge. The foam was purified using an ISCO R$_f$ and an 80 g silica column (CV=125 ml) and eluted as follows: 100% DCM (1 CV), 0-6% MeOH/DCM gradient (15 CV), 6-8% MeOH/DCM gradient (2 CV), 8% MeOH/DCM (2 CV) at 60 ml/min. The product fractions were combined and evaporated under reduced pressure to give the title compound as a white foam. LC-MS: calculated for $C_{11}H_{11}ClIN_3O_4$ 410.95. observed m/e: 412.01 (M+H)$^+$ (Rt 0.73/2 min).

Intermediate 16

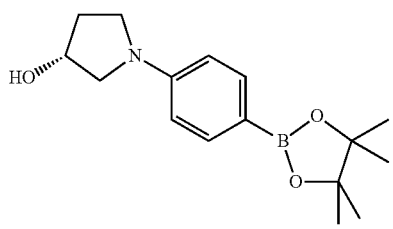 [SMILES: CC1(C)OB(c2ccc(N3CC[C@@H](O)C3)cc2)OC1(C)C]

(3R)-1-[4-(4,4,5,5-tetramethyl-1,3,2-dioxaborolan-2-yl)phenyl]pyrrolidin-3-ol

Palladium(II) acetate (31.1 mg, 0.139 mmol) was added to a stirred suspension of (3R)-1-(4-bromophenyl)pyrrolidin-3-ol (211.5 mg, 1.070 mmol), bis(pinacolato)diboron (438.1 mg, 1.725 mmol), potassium acetate (326.8 mg, 3.33 mmol), and dicyclohexyl(2',4',6'-triisopropyl-[1,1'-biphenyl]-2-yl)phosphine (113.1 mg, 0.237 mmol) in dioxane (10.5 ml). The reaction mixture was degassed (3×) and placed under nitrogen before being heated to 100° C. After 4 hours the reaction mixture was allowed to cool to room temperature. The reaction mixture was partitioned between EtOAc (75 ml) and water (50 ml). The aqueous layer was extracted with EtOAc (2×50 ml). The organic layers were combined, washed with brine (1×30 ml), dried over MgSO$_4$, filtered, and evaporated under reduced pressure to give a dark residue. This material was dissolved in DCM and loaded onto a 5 g silica solid load cartridge. The residue was purified using an ISCO R$_f$ and a 24 g silica gold column (CV=35.9 ml). The column was eluted as follows: 100% Hex (1 CV), 0-40% EtOAc/Hex gradient (20 CV), 40% EtOAc/Hex (5 CV) at 35 ml/min. The product fractions were combined and evaporated under reduced pressure to give the title compound as a white residue. LC-MS: calculated for C$_{16}$H$_{24}$BNO$_3$ 289.18. observed m/e: 290.22 (M+H)$^+$ (Rt 1.15/2 min).

Example 1

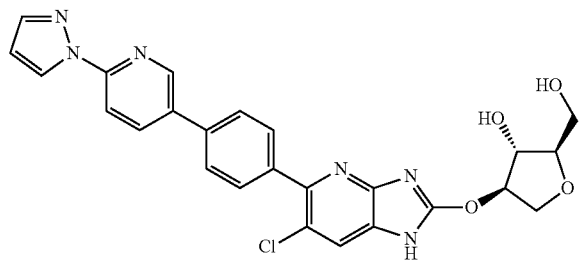

(2R,3R,4R)-4-[[6-chloro-5-[4-(6-pyrazol-1-yl-3-pyridyl)phenyl]-1H-imidazo[4,5-b]pyridin-2-yl]oxy]-2-(hydroxymethyl)tetrahydrofuran-3-ol Step A 2-[[2-[[(4aR,7R,7aR-2,2-ditert-butyl-4a,6,7,7a-tetrahydro-4H-furo[3,2-d][1,3,2]dioxasilin-7-yl]oxy]-6-chloro-5-[4-(6-pyrazol-1-yl-3-pyridyl)phenyl]imidazo-[4,5-b]pyridin-1-yl]methoxy]ethyl-trimethyl-silane Palladium tetrakis (12.0 mg, 10.38 μmol) was added to a hazy stirred solution of 2-[[2-[[(4aR,7R,7aR)-2,2-ditert-bu-

TABLE A

Intermediates 17-19 were prepared according to the methods in Intermediate 16.
Minor variations in conditions are noted.

| Intermediate | Structure | HPLC-mass spectum m/e | Conditions |
|---|---|---|---|
| 17 | 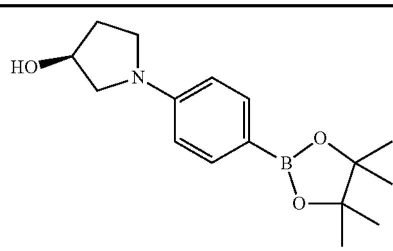 | 289.94 | Chloro(2-dicyclohexylphosphino-2',4',6'-triisopropyl-1,1'-biphenyl)[2-(2'-amino-1,1'-biphenyl)]palladium(II) |
| 18 | 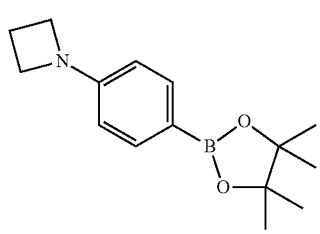 [SMILES: CC1(C)OB(c2ccc(N3CCC3)cc2)OC1(C)C] | 260.35 | Chloro(2-dicyclohexylphosphino-2',4',6'-triisopropyl-1,1'-biphenyl)[2-(2'-amino-1,1'-biphenyl)]palladium(II) |
| 19 | | 276.24 | Chloro(2-dicyclohexylphosphino-2',4',6'-triisopropyl-1,1'-biphenyl)[2-(2'-amino-1,1'-biphenyl)]palladium(II) | tyl-4a,6,7,7a-tetrahydro-4H-furo[3,2-d][1,3,2]dioxasilin-7-yl]oxy]-5-(4-bromophenyl)-6-chloro-imidazo[4,5-b]pyridin-1-yl]methoxy]ethyl-trimethyl-silane (68.5 mg, 0.096 mmol), 2-pyrazol-1-yl-5-(4,4,5,5-tetramethyl-1,3,2-dioxaborolan-2-yl)pyridine (33.3 mg, 0.123 mmol), and potassium phosphate (62.7 mg, 0.295 mmol) in dioxane (0.80 ml) and water (0.2 ml). The reaction mixture was degassed (3×) and placed under nitrogen before being heated to 80° C. After 3.5 hours, the reaction mixture was cooled to room temperature (2:05 pm) before being partitioned between EtOAc (40 ml) and water (40 ml). The aqueous layer was extracted with EtOAc (2×20 ml). The organic layers were combined, washed with brine (1×20 ml), dried over $Na_2SO_4$, filtered, and evaporated under reduced pressure to give a yellow residue. The residue was dissolved in EtOAc/MeOH/DCM and loaded onto two 500 micron 20 cm×20 cm silica gel plates, which were developed using 25% EtOAc/Hex. The silica containing the product band was collected and eluted with EtOAc (80 ml). The solvent was evaporated under reduced pressure to give the desired product as a colorless residue. LC-MS: calculated for $C_{39}H_{51}ClN_6O_5Si_2$ 774.31. observed m/e: 775.12 (M+H)$^+$ (Rt 1.58/2 min).

Step B (2R,3R,4R)-4-[[6-chloro-5-[4-(6-pyrazol-1-yl-3-pyridyl)phenyl]-1H-imidazo[4,5-b]pyridin-2-yl]oxy]-2-(hydroxymethyl)tetrahydrofuran-3-ol Combined 2-[[2-[[(4aR,7R,7aR)-2,2-ditert-butyl-4a,6,7,7a-tetrahydro-4H-furo[3,2-d][1,3,2]dioxasilin-7-yl]oxy]-6-chloro-5-[4-(6-pyrazol-1-yl-3-pyridyl)phenyl]imidazo[4,5-b]pyridin-1-yl]methoxy]ethyl-trimethyl-silane (67.0 mg, 0.086 mmol), formic acid (1.2 ml, 31.3 mmol), and saturated aqueous KHSO$_4$ (0.05 ml) in a 25 ml flask. The reaction mixture was a colorless solution that was heated to 40° C. with stirring. After 17.5 hours, the reaction mixture was cooled to room temperature before being cooled to 0° C. in an ice bath. The pH of the reaction mixture was adjusted to pH 14 through the addition of 5 N NaOH (7.0 ml, 35.0 mmol). THF (2.0 ml) was added to the reaction mixture, which was removed from the ice bath and allowed to warm to room temperature. After 30 minutes, the pH of the reaction mixture was adjusted to pH 7 through the addition of 2 N HCl. The reaction mixture was partitioned between EtOAc (40 ml) and water (30 ml). The aqueous layer was extracted with EtOAc (2×20 ml). The organic layers were combined, washed with brine (1×20 ml), dried over Na$_2$SO$_4$, filtered, and evaporated under reduced pressure to give a white residue. TBAF 1.0 M in THF (2.0 ml, 2.000 mmol) was combined with the residue and heated to 60° C. with stirring. After 1.5 hours, the reaction mixture was cooled to room temperature before being partitioned between EtOAc (40 ml), water (40 ml), and brine. The aqueous layer was extracted with EtOAc (2×20 ml). The organic layers were combined, washed with brine (1×20 ml), dried over Na$_2$SO$_4$, filtered, and evaporated under reduced pressure to give a white/opaque residue. This material was purified by preparative HPLC reverse phase (C-18), using a 30×150 mm Sunfire™ column and eluting with a 20%-100% acetonitrile/water+0.05% TFA gradient followed by a 100% acetonitrile+0.05% TFA flush. The product fractions were combined, evaporated under reduced pressure, and lyophilized from ethanol and benzene to give the title compound as a white solid. LC-MS: calculated for $C_{25}H_{21}ClN_6O_4$ 504.13. observed m/e: 504.93 (M+H)$^+$ (Rt 1.14/2 min). $^1$H NMR δ (ppm) ((CD$_3$)$_2$SO): 8.89 (s, 1H), 8.68 (s, 1H), 8.38 (d, J=8.6 Hz, 1H), 8.04 (d, J=8.5 Hz, 1H), 8.02 (broad s, 1H), 7.87-7.90 (m, 3H), 7.80 (d, J=7.8 Hz, 2H), 6.62 (s, 1H), 5.67 (broad s, 1H), 5.29 (broad s, 1H), 4.82 (t, J=6.8 Hz, 1H), 4.19 (broad s, 1H), 4.09 (dd, J=3.8 Hz, J=10.4 Hz, 1H), 4.02 (d, J=11.0 Hz, 1H), 3.67-3.69 (m, 1H), 3.48-3.57 (m, 2H).

TABLE 1

Compound 2 was prepared according to the methods in Example 1.

| Example Number | Structure | HPLC-mass spectrum m/e |
|---|---|---|
| 2 | (structure shown) | 503.87 |

Example 3

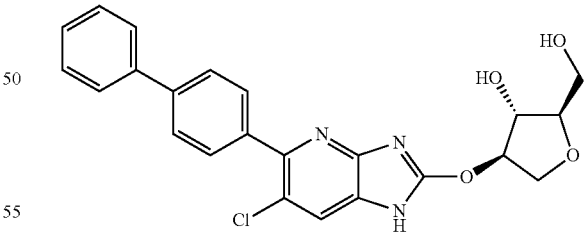

(2R,3R,4R)-4-[[6-chloro-5-(4-phenylphenyl-1H-imidazo[4,5-b]pyridin-2-yl]oxy]-2-(hydroxymethyl)tetrahydrofuran-3-ol Palladium tetrakis (12.4 mg, 10.73 µmol) was added to a stirred hazy solution of (2R,3R,4R)-4-[[5-(4-bromophenyl)-6-chloro-1H-imidazo[4,5-b]pyridin-2-yl]oxy]-2-(hydroxymethyl)tetrahydrofuran-3-ol (39.0 mg, 0.089 mmol), phenylboronic acid (16.9 mg, 0.139 mmol), and potassium phosphate (62.0 mg, 0.292 mmol) in dioxane (0.71 ml) and water (0.18 ml). The reaction mixture was degassed (3×) and placed under nitrogen before being heated to 80° C. After 2.5 hours, the reaction mixture was heated to 100° C. After an additional hour, potassium phosphate 2 M aqueous solution (0.14 ml, 0.28 mmol) was added to the reaction mixture. After 4 additional hours, the reaction mixture was cooled to room temperature. The reaction mixture was then partitioned between EtOAc (40 ml) and water (40 ml). The aqueous layer was extracted with EtOAc (2×20 ml). The organic layers were combined, washed with brine (1×20 ml), dried over $Na_2SO_4$, filtered, and evaporated under reduced pressure to give a yellow residue. The residue was purified by preparative HPLC reverse phase (C-18), using a 30×150 mm Sunfire™ column and eluting with a 20%-100% acetonitrile/water+0.05% TFA gradient followed by a 100% acetonitrile+0.05% TFA flush. The product fractions were combined and evaporated under reduced pressure to give a colorless residue, which was dissolved in EtOAc/MeOH and loaded onto a 500 micron 20 cm×20 cm silica gel plate, which was developed using 10% MeOH/DCM. The silica containing the product band was collected and eluted with 10% MeOH/DCM (80 ml). The solvent was evaporated under reduced pressure and the resulting residue was lyophilized from ethanol and benzene to give the title compound as a white solid. LC-MS: calculated for $C_{23}H_{20}ClN_3O_4$ 437.11. observed m/e: 437.91 (M+H)$^+$ (Rt 1.16/2 min). $^1$H NMR δ (ppm) (CD$_3$OD): 7.85 (s, 1H), 7.72-7.76 (m, 4H), 7.70 (d, J=7.4 Hz, 2H), 7.47 (t, J=7.7 Hz, 2H), 7.37 (t, J=7.4 Hz, 1H), 5.33-5.35 (m, 1H), 4.33 (broad d, J=3.7 Hz, 1H), 4.24 (dd, J=4.3 Hz, J=11.1 Hz, 1H), 4.18 (d, J=11.0 Hz, 1H), 3.85 (qt, J=5.0 Hz, 1H), 3.76 (dd, J=4.5 Hz, J=11.7 Hz, 1H), 3.70 (dd, J=6.0 Hz, J=11.7 Hz, 1H).

Example 4

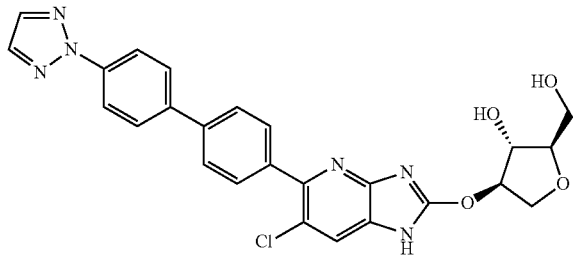 [SMILES: OC[C@H]1OC[C@@H](Oc2nc3nc(-c4ccc(-c5ccc(-n6nccn6)cc5)cc4)c(Cl)cc3[nH]2)[C@@H]1O]

(2R,3R,4R)-4-[[6-chloro-5-[4-[4-(triazol-2-yl)phenyl]phenyl]-1H-imidazo[4,5-b]pyridin-2-yl]oxy]2-(hydroxymethyl)tetrahydrofuran-3-ol LiOH (0.13 ml, 0.390 mmol) and 1,1'-bis(diphenylphosphino)ferrocene-palladium (II) dichloride dichloromethane complex (8.6 mg, 10.53 μmol) were added to a stirred hazy solution of (2R,3R,4R)-4-[[5-(4-bromophenyl)-6-chloro-1H-imidazo[4,5-b]pyridin-2-yl]oxy]-2-(hydroxymethyl)-tetrahydrofuran-3-ol (38.0 mg, 0.086 mmol) and 2-[4-(4,4,5,5-tetramethyl-1,3,2-dioxaborolan-2-yl)phenyl]triazole (31.1 mg, 0.115 mmol) in dioxane (0.69 ml) and water (0.04 ml). The reaction mixture was degassed (3×) and placed under nitrogen before being heated to 80° C. After 3.5 hours, the reaction mixture was cooled to room temperature before being partitioned between EtOAc (40 ml), water (40 ml), and brine (a few milliliters). The organic layer was filtered and the solids were collected. The aqueous layer was extracted with EtOAc (2×20 ml). The organic layers were combined, washed with brine (1×20 ml), dried over $Na_2SO_4$, filtered, and evaporated under reduced pressure to give a pale yellow residue. The residue was purified by preparative HPLC reverse phase (C-18), using a 30×150 mm Sunfire™ column and eluting with a 20%-100% acetonitrile/water+0.05% TFA gradient followed by a 100% acetonitrile+0.05% TFA flush. The product fractions were combined, evaporated under reduced pressure, and lyophilized from ethanol and benzene to give the title compound as a pale yellow solid. LC-MS: calculated for $C_{25}H_{21}ClN_6O_4$ 504.13. observed m/e: 504.92 (M+H)$^+$ (Rt 1.17/2 min). $^1$H NMR δ (ppm) (CD$_3$OD): 8.20 (d, J=8.7 Hz, 2H), 7.97 (s, 1H), 7.96 (s, 2H), 7.89 (d, J=8.7 Hz, 2H), 7.81 (abqt, J=8.3 Hz, J=23.7 Hz, 4H), 5.37-5.38 (m, 1H), 4.34 (broad d, J=4.5 Hz, 1H), 4.24 (dd, J=4.2 Hz, J=11.1 Hz, 1H), 3.85 (qt, J=4.7 Hz, J=10.3 Hz, 1H), 3.77 (dd, J=4.5 Hz, J=11.8 Hz, 1H), 3.71 (dd, J=6.0 Hz, J=11.7 Hz, 1H).

Example 5

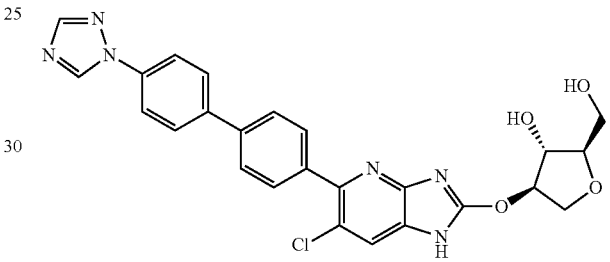

(2R,3R,4R)-4-[[6-chloro-5-[4-[4-(1,2,4-triazol-1-yl)phenyl]phenyl]-1H-imidazo[4,5-b]pyridin-2-yl]oxy]-2-(hydroxymethyl)tetrahydrofuran-3-ol Step A 2-[[2-[[(4aR,7R,7aR)-2,2-ditert-butyl-4a,6,7,7a-tetrahydro-4H-furo[3,2-d][1,3,2]dioxasilin-7-yl]oxy]-6-chloro-5-[4-[4-(1,2,4-triazol-1-yl)phenyl]phenyl]-imidazo[4,5-b]pyridin-1-yl]methoxy]ethyl-trimethyl-silane Palladium tetrakis (14.8 mg, 0.013 mmol) was added to a hazy stirred solution of 2-[[2-[[(4aR,7R,7aR)-2,2-ditert-butyl-4a,6,7,7a-tetrahydro-4H-furo[3,2-d][1,3,2]dioxasilin-7-yl]oxy]-6-chloro-5-[4-(4,4,5,5-tetramethyl-1,3,2-dioxaborolan-2-yl)phenyl]imidazo[4,5-b]pyridin-1-yl]methoxy]ethyl-trimethyl-silane (86.3 mg, 0.114 mmol), 1-(4-bromophenyl)-1,2,4-triazole (37.6 mg, 0.168 mmol), and potassium phosphate (80.7 mg, 0.380 mmol) in dioxane (0.91 ml) and water (0.23 ml). The reaction mixture was degassed (3×) and placed under nitrogen before being heated to 80° C. After 6.5 hours, the reaction mixture was cooled to room temperature. The reaction mixture was partitioned between EtOAc (40 ml) and water (40 ml). The aqueous layer was extracted with EtOAc (2×20 ml). The organic layers were combined, washed with brine (1×20 ml), dried over $Na_2SO_4$, filtered, and evaporated under reduced pressure to give a pale yellow residue. The residue was dissolved in EtOAc/MeOH/DCM and loaded onto three 500 micron 20 cm×20 cm silica gel plates, which were developed using 50% EtOAc/Hex. The silica containing the product band was collected and eluted with EtOAc (100 ml). The solvent was evaporated under reduced pressure to give the desired product as a colorless residue. LC-MS: calculated for $C_{39}H_{51}ClN_6O_5Si_2$ 774.31. observed m/e: 775.20 $(M+H)^+$ (Rt 1.50/2 min).

Step B (2R,3R,4R)-4-[[6-chloro-5-[4-[4-(1,2,4-triazol-1-yl)phenyl]phenyl]-1H-imidazo[4,5-b]pyridin-2-yl]oxy]-2-(hydroxymethyl)tetrahydrofuran-3-ol Combined 2-[[2-[[(4aR,7R,7aR)-2,2-ditert-butyl-4a,6,7,7a-tetrahydro-4H-furo[3,2-d][1,3,2]-dioxasilin-7-yl]oxy]-6-chloro-5-[4-[4-(1,2,4-triazol-1-yl)phenyl]phenyl]-imidazo[4,5-b]pyridin-1-yl]methoxy]ethyl-trimethyl-silane (51.8 mg, 0.067 mmol), formic acid (1.0 ml, 26.1 mmol), and saturated aqueous $KHSO_4$ (0.05 ml) in a 25 ml flask. The reaction mixture was a colorless solution that was heated to 40° C. with stirring. After 17.5 hours, the reaction mixture was cooled to room temperature. The reaction mixture was cooled to 0° C. in an ice bath. The pH of the reaction mixture was adjusted to 14 through the addition of 5 N NaOH (5.8 ml, 29.0 mmol). THF (2.0 ml) was added to the reaction mixture, which was removed from the ice bath and allowed to warm to room temperature. After 5 hours, the pH of the reaction mixture was adjusted to ~pH 6 through the addition of 2 N HCl. The reaction mixture was partitioned between EtOAc (40 ml) and water (40 ml). The aqueous layer was extracted with EtOAc (2×20 ml). The organic layers were combined, washed with brine (1×20 ml), dried over $Na_2SO_4$, filtered, and evaporated under reduced pressure to give a white residue. TBAF 1.0 M in THF (1.0 ml, 1.000 mmol) was combined with the residue in a 25 ml flask. The reaction mixture was a pale yellow solution that was heated to 60° C. with stirring. After 2 hours, the reaction mixture was cooled to room temperature before being partitioned between EtOAc (40 ml) and water (40 ml). The aqueous layer was extracted with EtOAc (2×20 ml). The organic layers were combined, washed with brine (1×20 ml), dried over $Na_2SO_4$, filtered, and evaporated under reduced pressure to give a white/opaque residue. This material was purified by preparative HPLC reverse phase (C-18), using a 30×150 mm Sunfire™ column and eluting with a 20%-100% acetonitrile/water+0.05% TFA gradient followed by a 100% acetonitrile+0.05% TFA flush. The product fractions were combined, evaporated under reduced pressure, and lyophilized from ethanol and benzene to give the title compound as a white solid. LC-MS: calculated for $C_{25}H_{21}ClN_6O_4$ 504.13. observed m/e: 505.27 $(M+H)^+$ (Rt 1.09/2 min). $^1H$ NMR δ (ppm) (($CD_3)_2SO$): 9.38 (s, 1H), 8.27 (s, 1H), 7.98 (broad s, 1H), 7.97 (abqt, J=8.8 Hz, J=20.5 Hz, 4H), 7.81 (abqt, J=8.3 Hz, J=40.2 Hz, 4H), 5.67 (broad s, 1H), 5.27-5.30 (m, 1H), 4.81 (t, J=5.7 Hz, 1H), 4.18 (broad s, 1H), 4.09 (dd, J=4.4 Hz, J=10.9 Hz, 1H), 4.01 (d, J=11.2 Hz, 1H), 3.68 (qt, J=5.4 Hz, J=10.1 Hz, 1H), 3.47-3.57 (m, 2H).

TABLE 2

Compound 6 was prepared according to the methods in Example 5.

| Example Number | Structure | HPLC-mass spectrum m/e |
|---|---|---|
| 6 | 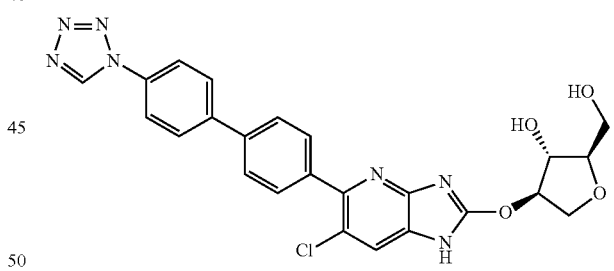 | 576.22 |

Example 7

(2R,3R,4R)-4-[[6-chloro-5-[4-[4-(tetrazol-1-yl)phenyl]phenyl]-1H-imidazo[4,5-b]pyridin-2-yl]oxy]-2-(hydroxymethyl)tetrahydrofuran-3-ol Step A 2-[[2-[[(4aR,7R,7aR)-2,2-ditert-butyl-4a,6,7,7a-tetrahydro-4H-furo[3,2-d][1,3,2]-dioxasilin-7-yl]oxy]-6-chloro-5-[4-[4-(tetrazol-1-yl)phenyl]phenyl]imidazo[4,5-b]pyridin-1-yl]methoxy]ethyl-trimethyl-silane Palladium tetrakis (17.3 mg, 0.015 mmol) was added to a stirred hazy solution of 2-[[2-[[(4aR,7R,7aR)-2,2-ditert-butyl-4a,6,7,7a-tetrahydro-4H-furo[3,2-d][1,3,2]dioxasilin-7-yl]oxy]-6-chloro-5-[4-(4,4,5,5-tetramethyl-1,3,2-dioxaborolan-2-yl)-phenyl]imidazo[4,5-b]pyridin-1-yl]methoxy]

ethyl-trimethyl-silane (85.2 mg, 0.112 mmol), 1-(4-bromophenyl)-1H-tetrazole (35.0 mg, 0.156 mmol), and potassium phosphate (85.3 mg, 0.402 mmol) in dioxane (0.90 ml) and water (0.22 ml). The reaction mixture was degassed (3×) and placed under nitrogen before being heated to 80° C. After 3 hours, the reaction mixture was cooled to room temperature. The reaction mixture was partitioned between EtOAc (40 ml) and water (40 ml). The aqueous layer was extracted with EtOAc (2×20 ml). The organic layers were combined, washed with brine (1×20 ml), dried over $Na_2SO_4$, filtered, and evaporated under reduced pressure to give a pale yellow residue. The residue was dissolved in EtOAc/MeOH and loaded onto three 1000 micron 20 cm×20 cm silica gel plates, which were developed using 40% EtOAc/Hex. The silica containing the product band was collected and eluted with EtOAc (100 ml). The solvent was evaporated under reduced pressure to give the desired product as a colorless residue. LC-MS: calculated for $C_{38}H_{50}ClN_7O_5Si_2$ 775.31. observed m/e: 776.61 $(M+H)^+$ (Rt 1.48/2 min).

Step B (2R,3R,4R)-4-[[6-chloro-5-[4-[4-(tetrazol-1-yl)phenyl]phenyl]-1H-imidazo[4,5-b]pyridin-2-yl]oxy]-2-(hydroxymethyl)tetrahydrofuran-3-ol 2-[[2-[[(4aR,7R,7aR)-2,2-ditert-butyl-4a,6,7,7a-tetrahydro-4H-furo[3,2-d][1,3,2]dioxasilin-7-yl]oxy]-6-chloro-5-[4-[4-(tetrazol-1-yl)phenyl]phenyl]imidazo[4,5-b]pyridin-1-yl]methoxy]ethyl-trimethyl-silane (26.6 mg, 0.034 mmol), formic acid (1.0 ml, 26.1 mmol), and saturated aqueous $KHSO_4$ (0.05 ml) were combined in a 25 ml flask. The reaction mixture was a colorless solution that was heated to 40° C. with stirring. After 19 hours, the reaction mixture was cooled to room temperature before being cooled to 0° C. in an ice bath. The pH of the reaction mixture was adjusted to pH 14 through the addition of 5 N NaOH (5.8 ml, 29.0 mmol). Then THF (2.0 ml) was added to the reaction mixture, which was removed from the ice bath and allowed to warm to room temperature. After 2.5 hr, the pH of the reaction mixture was adjusted to ~pH 7 through the addition of 2 N HCl. The reaction mixture was partitioned between EtOAc (40 ml) and water (30 ml). The aqueous layer was extracted with EtOAc (2×20 ml). The organic layers were combined, washed with brine (1×20 ml), dried over $Na_2SO_4$, filtered, and evaporated under reduced pressure to give a white residue. The residue was purified by preparative HPLC reverse phase (C-18), using a 30×150 mm Sunfire™ column and eluting with a 20%-100% acetonitrile/water+0.05% TFA gradient followed by a 100% acetonitrile+0.05% TFA flush. The product fractions were combined, evaporated under reduced pressure, and lyophilized from ethanol and benzene to give the title compound as a white solid. LC-MS: calculated for $C_{24}H_{20}ClN_7O_4$ 505.13. observed m/e: 506.21 $(M+H)^+$ (Rt 1.10/2 min). $^1H$ NMR δ (ppm) ($CD_3OD$): 9.83 (s, 1H), 7.98-8.02 (m, 4H), 7.92 (s, 1H), 7.83 (abqt, J=8.3 Hz, J=18.4 Hz, 4H), 5.35-5.36 (m, 1H), 4.33 (broad d, J=4.1 Hz, 1H), 4.24 (dd, J=4.4 Hz, J=11.1 Hz, 1H), 4.18 (d, J=10.8 Hz, 1H), 3.84 (qt, J=4.7 Hz, J=10.4 Hz, 1H), 3.76 (dd, J=4.5 Hz, J=11.8 Hz, 1H), 3.70 (dd, J=6.0 Hz, J=11.8 Hz, 1H).

Example 8

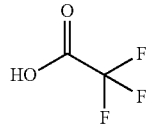

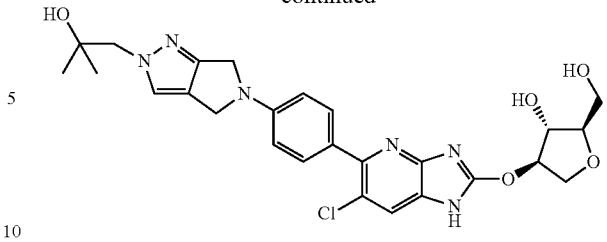

(2R,3R,4R)-4-[[6-chloro-5-[4-[2-(2-hydroxy-2-methyl-propy)-4,6-dihydropyrrolo[3,4-c]pyrazol-5-yl]phenyl]-1H-imidazo[4,5-b]pyridin-2-yl]oxy]-2-(hydroxymethyl)-tetrahydrofuran-3-ol; 2,2,2-trifluoroacetic acid Step A (2R,3R,4R)-4-[6-chloro-5-[4-[2-(2-hydroxy-2-methyl-propyl)-4,6-dihydropyrrolo[3,4-c]pyrazol-5-yl]phenyl]-1-(2-trimethylsilylethoxymethyl)imidazo[4,5-b]pyridin-2-yl]oxy-2-[[ditert-butyl(hydroxy)silyl]oxymethyl]tetrahydrofuran-3-ol $Pd_2(dba)_3$ (11.2 mg, 0.012 mmol) and 2-(di-tert-butylphosphino)-1-phenyl-1H-pyrrole (9.2 mg, 0.032 mmol) were combined in an 8 ml vial, which was evacuated and backfilled with nitrogen (3×). Dioxane (0.25 ml) was added to the vial to give a dark catalyst suspension that was stirred at room temperature. Then (2R,3R,4R)-4-[5-(4-bromophenyl)-6-chloro-1-(2-trimethylsilylethoxymethyl)imidazo[4,5-b]pyridin-2-yl]oxy-2-[[ditert-butyl(hydroxy)silyl]oxymethyl]tetrahydrofuran-3-ol (135.9 mg, 0.186 mmol), 1-(5,6-dihydro-4H-pyrrolo[3,4-c]pyrazol-2-yl)-2-methyl-propan-2-ol; 2,2,2-trifluoroacetic acid (114.4 mg, 0.387 mmol), tripotassium phosphate 2.0 M aqueous (0.56 ml, 1.120 mmol), and dioxane (1.25 ml) were combined in a separate 8 ml vial. After 1 hour, the resulting solution was added to the catalyst suspension, which was degassed (3×) and placed under nitrogen before being heated to 110° C. After 16.5 hours, the reaction mixture was cooled to room temperature before being partitioned between EtOAc (40 ml) and water (40 ml). The aqueous layer was extracted with EtOAc (2×20 ml). The organic layers were combined, washed with brine (1×20 ml), dried over $Na_2SO_4$, filtered, and evaporated under reduced pressure to give a yellow residue. The residue was dissolved in EtOAc/MeOH and loaded onto three 500 micron 20 cm×20 cm silica gel plates, which were developed using 85% EtOAc/Hex. The silica containing the product band was collected and eluted with EtOAc (100 ml). The solvent was evaporated under reduced pressure to give the desired product as a pale yellow residue. LC-MS: calculated for $C_{40}H_{61}ClN_6O_7Si_2$ 828.38. observed m/e: 829.54 $(M+H)^+$ (Rt 1.35/2 min).

Step B (2R,3R,4R)-4-[[6-chloro-5-[4-[2-(2-hydroxy-2-methyl-propyl-4,6-dihydropyrrolo[3,4-c]pyrazol-5-yl]phenyl]-1H-imidazo[4,5-b]pyridin-2-yl]oxy]-2-(hydroxymethyl)tetrahydrofuran-3-ol; 2,2,2-trifluoroacetic acid (2R,3R,4R)-4-[6-chloro-5-[4-[2-(2-hydroxy-2-methyl-propyl)-4,6-dihydropyrrolo[3,4-c]pyrazol-5-yl]phenyl]-1-(2-trimethylsilylethoxymethyl)imidazo[4,5-b]pyridin-2-yl]oxy-2-[[ditert-butyl(hydroxy)silyl]oxymethyl]tetrahydrofuran-3-ol (51.7 mg, 0.062 mmol), formic acid (1.0 ml, 26.1 mmol), and saturated aqueous $KHSO_4$ (0.05 ml) were combined in a 25 ml flask. The reaction mixture was a yellow solution that was stirred at room temperature. After 4 hours, the reaction mixture was cooled to 0° C. in an ice bath. The pH of the reaction mixture was adjusted to pH 14 through the addition of 5 N NaOH (5.8 ml, 29.0 mmol). Then THF (2.0 ml) was added to the reaction mixture, which was removed from the ice bath and allowed to warm to room temperature. After 30 minutes, the pH of the reaction mixture was adjusted to pH 6 through the addition of 2 N HCl. The reaction mixture was partitioned between EtOAc (40 ml) and water (40 ml). The aqueous layer was extracted with EtOAc (2×20 ml). The organic layers were combined, washed with brine (1×20 ml), dried over $MgSO_4$, filtered, and evaporated under reduced pressure to give a yellow residue. TBAF 1.0 M in THF (1.0 ml, 1.000 mmol) was combined with the residue in a 25 ml flask. The reaction mixture was an amber solution that was heated to 60° C. with stirring. After 1 hour, the reaction mixture was cooled to room temperature before being partitioned between EtOAc (40 ml) and water (40 ml). The aqueous layer was extracted with EtOAc (2×20 ml). The organic layers were combined, washed with brine (1×20 ml), dried over $MgSO_4$, filtered, and evaporated under reduced pressure to give an amber residue. The residue was purified by preparative HPLC reverse phase (C-18), using a 30×150 mm Sunfire™ column and eluting with a 20%-100% acetonitrile/water+ 0.05% TFA gradient followed by a 100% acetonitrile+0.05% TFA flush. The product fractions were combined, evaporated under reduced pressure, and lyophilized from ethanol and benzene to give the title compound as a yellow solid. LC-MS: calculated for $C_{26}H_{29}ClN_6O_5$ 540.19. observed m/e: 541.16 $(M+H)^+$ (Rt 1.07/2 min). $^1H$ NMR δ (ppm) ($CD_3OD$): 8.16 (s, 1H), 7.61 (d, J=8.8 Hz, 2H), 7.52 (s, 1H), 6.83 (d, J=8.7 Hz, 2H), 5.41-5.42 (m, 1H), 4.52 (s, 4H), 4.35 (broad d, J=3.5 Hz, 1H), 4.23 (dd, J=4.1 Hz, J=11.2 Hz, 1H), 4.19 (d, J=10.6 Hz, 1H), 4.13 (s, 2H), 3.83 (qt, J=4.7 Hz, J=10.1 Hz, 1H), 3.76 (dd, J=4.3 Hz, J=11.8 Hz, 1H), 3.70 (dd, J=5.9 Hz, J=11.8 Hz, 1H), 1.21 (s, 6H).

Example 9

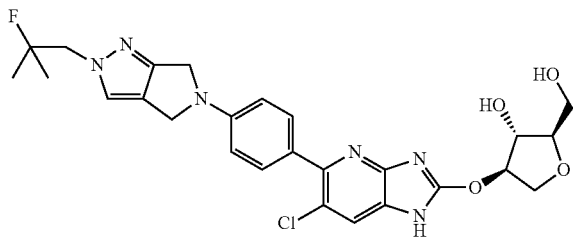 [SMILES: CC(C)(F)Cn1cc2c(n1)CN(c1ccc(-c3nc4nc(O[C@@H]5CO[C@H](CO)[C@H]5O)[nH]c4cc3Cl)cc1)C2]

(2R,3R,4R)-4-[[6-chloro-5-[4-[2-(2-fluoro-2-methyl-propyl)-4,6-dihydropyrrolo[3,4-c]pyrazol-5-yl]phenyl]-1H-imidazo[4,5-b]pyridin-2-yl]oxy]-2-(hydroxymethyl)tetrahydrofuran-3-ol Step A 2-(2-fluoro-2-methyl-propyl)-5,6-dihydro-4H-pyrrolo[3,4-c]pyrazole; 2,2,2-trifluoroacetic acid TFA (0.5 ml, 6.49 mmol) was added to a stirred solution of tert-butyl 2-(2-fluoro-2-methyl-propyl)-4,6-dihydropyrrolo[3,4-c]pyrazole-5-carboxylate (131.4 mg, 0.464 mmol) in DCM (0.5 ml). The reaction mixture was a colorless solution that was stirred at room temperature. After 1.5 hours, the reaction mixture was evaporated under reduced pressure to give the desired product as a colorless oil. This oil was used in the next step without further purification or characterization.

Step B 2-[[2-[[(4aR,7R,7aR)-2,2-ditert-butyl-4a,6,7,7a-tetrahydro-4H-furo[3,2-d][1,3,2]dioxasilin-7-yl]oxy]-6-chloro-5-[4-[2-(2-fluoro-2-methyl-propyl)-4,6-dihydropyrrolo[3,4-c]pyrazol-5-yl]phenyl]imidazo[4,5-b]pyridin-1-yl]methoxyl]ethyl-trimethyl-silane $Pd_2(dba)_3$ (18.9 mg, 0.021 mmol) and 2-(di-tert-butyl-phosphino)-1-phenyl-1H-pyrrole (13.1 mg, 0.046 mmol) were combined in an 8 ml vial, which was evacuated and back filled with nitrogen (3×). Dioxane (0.25 ml) was added to the vial to give a dark red/brown suspension that was stirred at room temperature. 2-[[2-[[(4aR,7R,7aR)-2,2-di-tert-butyl-4a,6,7,7a-tetrahydro-4H-furo[3,2-d][1,3,2]dioxasilin-7-yl]oxy]-5-(4-bromophenyl)-6-chloro-imidazo[4,5-b]pyridin-1-yl]methoxy]ethyl-trimethyl-silane (153.4 mg, 0.216 mmol), 2-(2-fluoro-2-methyl-propyl)-5,6-dihydro-4H-pyrrolo[3,4-c]pyrazole; 2,2,2-trifluoroacetic acid (the oil from Step A), tripotassium phosphate (360.4 mg, 1.698 mmol), dixoane (1.25 ml), and water (0.50 ml) were combined in a separate 8 ml vial. After 1 hour, the resulting hazy solution was added to the catalyst suspension, which was degassed (3×) and placed under nitrogen before being heated to 110° C. After 16.5 hours, the reaction mixture was cooled to room temperature. The reaction mixture was partitioned between EtOAc (40 ml) and water (40 ml). The aqueous layer was extracted with EtOAc (2×20 ml). The organic layers were combined, washed with brine (1×20 ml), dried over $MgSO_4$, filtered, and evaporated under reduced pressure to give an amber residue. The residue was dissolved in EtOAc and loaded onto three 500 micron 20 cm×20 cm silica gel plates, which were developed using 1:2 EtOAc/Hex. The silica containing the product band was collected and eluted with EtOAc (100 ml). The solvent was evaporated under reduced pressure to give the desired product as a light yellow solid. LC-MS: calculated for $C_{40}H_{58}ClFN_6O_5Si_2$ 812.37. observed m/e: 813.39 $(M+H)^+$ (Rt 1.51/2 min).

Step C (2R,3R,4R)-4-[[6-chloro-5-[4-[2-(2-fluoro-2-methyl-propyl)-4,6-dihydropyrrolo[3,4-c]pyrazol-5-yl]phenyl]-1H-imidazo[4,5-b]pyridin-2-yl]oxy]-2-(hydroxymethyl)tetrahydrofuran-3-ol 2-[[2-[[(4aR,7R,7aR)-2,2-ditert-butyl-4a,6,7,7a-tetrahydro-4H-furo[3,2-d][1,3,2]dioxasilin-7-yl]oxy]-6-chloro-5-[4-[2-(2-fluoro-2-methyl-propyl)-4,6-dihydropyrrolo[3,4-c]pyrazol-5-yl]phenyl]imidazo[4,5-b]pyridin-1-yl]methoxy]ethyl-trimethyl-silane (27.9 mg, 0.034 mmol), formic acid (1.0 ml, 26.1 mmol), and saturated aqueous $KHSO_4$ (0.05 ml) were combined in a 25 ml flask. The reaction mixture was a yellow suspension that was stirred at room temperature. After 1 hour, the reaction mixture was cooled to 0° C. in an ice bath. The pH of the reaction mixture was adjusted to pH 14 through the addition of 5 N NaOH (5.8 ml, 29.0 mmol). THF (2.0 ml) was added to the reaction mixture, which was removed from the ice bath and allowed to warm to room temperature. After 3 hours, the pH of the reaction mixture was adjusted to pH 6 through the addition of 2N HCl. The reaction mixture was partitioned between EtOAc (40 ml) and water (40 ml). The aqueous layer was extracted with EtOAc (2×20 ml). The organic layers were combined, washed with brine (1×20 ml), dried over $MgSO_4$, filtered, and evaporated under reduced pressure to give an orange residue. TBAF (1.0 M in THF, 1.0 ml, 1.000 mmol) was combined with the residue to give an amber solution that was heated to 60° C. with stirring. After 1 hour, the reaction mixture was cooled to room temperature before being partitioned between EtOAc (40 ml) and water (40 ml). The aqueous layer was extracted with EtOAc (2×20 ml). The organic layers were combined, washed with brine (1×20 ml), dried over MgSO$_4$, filtered, and evaporated under reduced pressure to give an amber residue. The residue was dissolved in EtOAc/MeOH and loaded onto a 500 micron 20 cm×20 cm silica gel plate, which was developed using a 90:9:1 DCM/MeOH/NH$_4$OH solvent mixture. The silica containing the product band was collected and eluted with a 90:9:1 DCM/MeOH/NH$_4$OH solvent mixture (~70 ml). The solvent was evaporated under reduced pressure and the resulting residue was lyophilized from ethanol and benzene to give the title compound as a pale yellow solid. LC-MS: calculated for C$_{26}$H$_{28}$ClFN$_6$O$_4$ 542.18. observed m/e: 543.30 (M+H)$^+$ (Rt 1.12/2 min). $^1$H NMR δ (ppm) (CD$_3$OD): 7.77 (s, 1H), 7.61 (d, J=8.6 Hz, 2H), 7.50 (s, 1H), 6.77 (d, J=8.6 Hz, 2H), 5.30-5.31 (m, 1H), 4.50 (s, 4H), 4.34 (d, J=20.7 Hz, 2H), 4.30 (broad d, J=4.5 Hz, 1H), 4.23 (dd, J=4.5 Hz, J=11.1 Hz, 1H), 4.16 (d, J=10.7 Hz, 1H), 3.82-3.86 (m, 1H), 3.76 (dd, J=4.5 Hz, J=11.7 Hz, 1H), 3.69 (dd, J=6.2 Hz, J=11.7 Hz, 1H), 1.35 (d, J=21.0 Hz, 6H).

Example 10

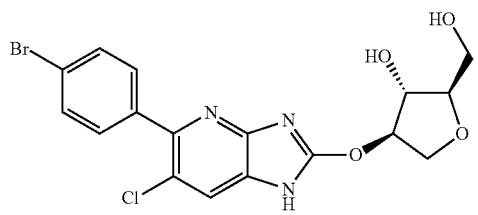 [SMILES: OC[C@H]1OC[C@@H](Oc2nc3nc(-c4ccc(Br)cc4)c(Cl)cc3[nH]2)[C@@H]1O]

(2R,3R,4R)-4-[[5-(4-bromophenyl)-6-chloro-1H-imidazo[4,5-b]pyridin-2-yl]oxy]-2-(hydroxymethyl)tetrahydrofuran-3-ol TFA (0.5 ml, 6.49 mmol) was added to a stirred solution of 2-[[2-[[(4aR,7R,7aR)-2,2-ditert-butyl-4a,6,7,7a-tetrahydro-4H-furo[3,2-d][1,3,2]dioxasilin-7-yl]oxy]-5-(4-bromophenyl)-6-chloro-imidazo[4,5-b]pyridin-1-yl]methoxy]ethyl-dimethyl-silane (64.8 mg, 0.091 mmol) in DCM (0.5 ml). The reaction mixture was a very pale yellow solution that was stirred at room temperature. After 2 hours, the reaction mixture was evaporated under reduced pressure to give a yellow oil. TBAF 1.0 M in THF (0.5 ml, 0.500 mmol) was combined with the oil to give a yellow solution that was heated to 60° C. with stirring. After 2 hours, the reaction mixture was cooled to room temperature. The reaction mixture was partitioned between EtOAc (40 ml) and water (40 ml). The aqueous layer was extracted with EtOAc (2×20 ml). The organic layers were combined, dried over MgSO$_4$, filtered, and evaporated under reduced pressure to give a colorless residue. The residue was purified by flash chromatography utilizing a 4 g silica RediSep R$_f$® column and employing a 0-100% EtOAc/hexane gradient followed by a 100% EtOAc hold. The product fractions were combined, evaporated under reduced pressure, and lyophilized from ethanol and benzene to give title compound as a white solid. LC-MS: calculated for C$_{17}$H$_{15}$BrClN$_3$O$_4$ 438.99, 440.99. observed m/e: 440.03, 442.06 (M+H)$^+$ (Rt 1.12/2 min). $^1$H NMR δ (ppm) (CD$_3$OD): 7.84 (s, 1H), 7.61 (abqt, J=8.5 Hz, J=24.0 Hz, 4H), 5.33-5.34 (m, 1H), 4.32 (broad d, J=3.6 Hz, 1H), 4.23 (dd, J=4.3 Hz, J=11.1 Hz, 1H), 4.17 (d, J=11.1 Hz, 1H), 3.84 (qt, J=4.6 Hz, J=10.2 Hz, 1H), 3.75 (dd, J=4.5 Hz, J=11.8 Hz, 1H), 3.69 (dd, J=5.9 Hz, J=11.8 Hz, 1H).

Example 11

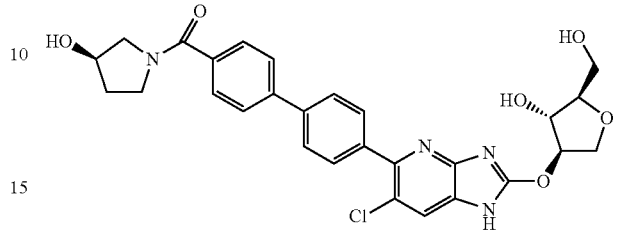

[4-[4-[6-chloro-2-[(1R,2R,3R)-2-hydroxy-3-(hydroxymethyl)cyclopentoxy]-1H-imidazo[4,5-b]pyridin-5-yl]phenyl]phenyl]-[(3R)-3-hydroxypyrrolidin-1-yl]methanone Step A [4-[4-[2-[[(4aR,7R,7aR)-2,2-ditert-butyl-4,4a,5,6,7,7a-hexahydrocyclopenta-[d][1,3,2]-dioxasilin-7-yl]oxy]-6-chloro-1-(2-trimethylsilylethoxymethyl)imidazo[4,5-b]pyridin-5-yl]-phenyl]phenyl]-[(3R)-3-(2-trimethylsilylethoxymethoxy)pyrrolidin-1-yl]methanone

[4-[4-[6-chloro-2-methylsulfonyl-1-(2-trimethylsilylethoxymethyl)-imidazo[4,5-b]pyridin-5-yl]phenyl]phenyl]-[(3R)-3-(2-trimethylsilylethoxymethoxy)-pyrrolidin-1-yl]methanone (120 mg, 0.158 mmol) was added to a stirred mixture of (4aR,7R,7aS)-2,2-ditert-butyl-4a,6,7,7a-tetrahydro-4H-furo[3,2-d][1,3,2]dioxasilin-7-ol (43.2 mg, 0.158 mmol) and cesium carbonate (56.8 mg, 0.174 mmol) in DMF (2 ml). The reaction mixture was stirred at room temperature overnight. In the morning, the reaction mixture was evaporated under reduced pressure. The resulting residue was purified by column chromatography on a silica gel Biotage™ 25M column, eluting with 10, 20-70% EtOAc/hexane to give the desired product as a colorless gum. LC-MS: calculated for C$_{48}$H$_{71}$ClN$_4$O$_8$Si$_3$ 950.43. observed m/e: 951.20 (M+H)$^+$ (Rt 4.99/5.5 min).

Step B [4-[4-[6-chloro-2-[(1R,2R,3R)-2-hydroxy-3-(hydroxymethyl)cyclopentoxy]-1H-imidazo[4,5-b]pyridin-5-yl]phenyl]phenyl]-[(3R)-3-hydroxypyrrolidin-1-yl]methanone

[4-[4-[2-[[(4aR,7R,7aR)-2,2-ditert-butyl-4,4a,5,6,7,7a-hexahydrocyclopenta[d][1,3,2]-dioxasilin-7-yl]oxy]-6-chloro-1-(2-trimethylsilylethoxymethyl)imidazo[4,5-b]pyridin-5-yl]phenyl]phenyl]-[(3R)-3-(2-trimethylsilylethoxymethoxyl)pyrrolidin-1-yl]methanone (115 mg, 0.121 mmol), formic acid (1.8 ml, 46.9 mmol) and saturated aqueous KHSO$_4$ (0.2 ml) were combined in a flask and stirred at room temperature overnight. In the morning, the reaction was quenched with MeOH (1 ml) and evaporated under reduced pressure. The residue was dissolved in THF and toluene, and evaporated under reduced pressure. The residue was combined with TBAF in THF 1.0 M (3 ml, 3.00 mmol) and heated to 60° C. After 2 hours, the reaction mixture was diluted with EtOAc (150 ml), washed with water (3×) and brine, dried over Na$_2$SO$_4$, and evaporated under reduced pressure. The resulting residue was purified by column chromatography on a silica gel Biotage™ 25M column, eluting with 2,4,6-8% MeOH/DCM. The material obtained off of the column was further purified by prep-TLC eluting with 10% MeOH in DCM to give the title compound as a colorless solid. LC-MS: calculated for $C_{28}H_{27}ClN_4O_6$ 550.16. observed m/e: 551.19 (M+H)$^+$ (Rt 1.47/4 min). $^1$H NMR δ (ppm) ((CD$_3$)$_2$SO): 7.97-7.63 (m, 9H), 5.67-5.65 (m, 1H), 5.28-4.81 (m, 3H), 4.34-4.00 (m, 4H), 3.64-3.13 (m, 7H), 1.98-1.90 (m, 2H).

Example 12

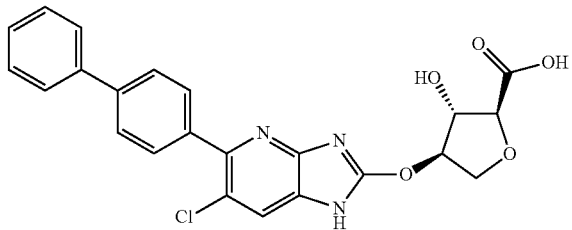 [SMILES: O=C(O)[C@H]1OC[C@@H](Oc2nc3nc(-c4ccc(-c5ccccc5)cc4)c(Cl)cc3[nH]2)[C@@H]1O]

(2S,3S,4R)-4-[[6-chloro-5-(4-phenylphenyl)-1H-imidazo[4,5-b]pyridin-2-yl]oxy]-3-hydroxy-tetrahydrofuran-2-carboxylic acid Step A (2S,3S,4R)-4-[5-(4-bromophenyl)-6-chloro-1-(2-trimethylsilylethoxymethyl)imidazo-[4,5-b]pyridin-2-yl]oxy-3-[ditert-butyl(hydroxy)silyl]oxy-tetrahydrofuran-2-carboxylic acid Sodium periodate (77.9 mg, 0.364 mmol) and ruthenium (III) chloride hydrate (2.4 mg, 10.65 μmol) were added to a stirred hazy solution of [(2R,3R,4R)-4-[5-(4-bromophenyl)-6-chloro-1-(2-trimethylsilylethoxymethyl)imidazo[4,5-b]pyridin-2-yl]oxy-3-[ditert-butyl(hydroxy)silyl]oxy-tetrahydrofuran-2-yl]methanol (83.8 mg, 0.115 mmol) in carbon tetrachloride (0.33 ml), acetonitrile (0.33 ml), and water (0.44 ml). The reaction mixture was a dark biphasic mixture that was stirred at room temperature overnight. The next day, the reaction mixture was partitioned between EtOAc (40 ml) and water (40 ml). The aqueous layer was extracted with EtOAc (2×20 ml). The organic layers were combined, dried over MgSO$_4$, filtered, and evaporated under reduced pressure to give a pale green residue. The residue was dissolved in EtOAc/MeOH and loaded onto two 500 micron 20 cm×20 cm silica gel plates, which were developed using a 40:59:1 hexane/EtOAc/AcOH solvent mixture. The silica containing the product band was collected and eluted with a 99:1 EtOAc/AcOH solvent mixture (80 ml). The solvent was evaporated under reduced pressure to give the desired product as a colorless residue. LC-MS: calculated for $C_{31}H_{45}BrClN_3O_7Si_2$ 741.17, 743.17. observed m/e: 742.31, 744.30 (M+H)$^+$ (Rt 1.49/2 min).

Step B methyl (2S,3S,4R)-4-[5-(4-bromophenyl)-6-chloro-1-(2-trimethylsilylethoxy-methyl)imidazo[4,5-b]pyridin-2-yl]oxy-3-[ditert-butyl(hydroxy)silyl]oxy-tetra-hydrofuran-2-carboxylate and methyl (2S,3S,4R)-4-[5-(4-bromophenyl)-6-chloro-1-(2-trimethylsilylethoxmethyl)imidazo[4,5-b]pyridin-2-yl]oxy-3-[ditert-butyl(trimethylsilyl-oxy)silyl]oxy-tetrahydrofuran-2-carboxylate TMS-Diazomethane (0.2 ml, 0.400 mmol) was added to a stirred solution of (2S,3S,4R)-4-[5-(4-bromophenyl)-6-chloro-1-(2-trimethylsilylethoxymethyl)imidazo[4,5-b]pyridin-2-yl]oxy-3-[di-tert-butyl(hydroxy)-silyl]oxy-tetra-hydrofuran-2-carboxylic acid (50.0 mg, 0.067 mmol) in DCM (0.7 ml). The reaction mixture was a yellow solution that was stirred at room temperature. After 2 days, the reaction mixture was evaporated under reduced pressure to give a mixture of the two products as a pale yellow foam. This material was used in the next step without further purification. LC-MS: calculated for $C_{32}H_{47}BrClN_3O_7Si_2$ 755.18, 757.18. observed m/e: 756.34, 758.36 (M+H)$^+$ (Rt 1.54/2 min). LC-MS: calculated for $C_{35}H_{55}BrClN_3O_7Si_3$ 827.22, 829.22. observed m/e: 828.44, 830.47 (M+H)$^+$ (Rt 1.63/2 min).

Step C methyl (2S,3S,4R)-4-[6-chloro-5-(4-phenylphenyl)-1-(2-trimethylsilyl-ethoxymethyl)imidazo[4,5-b]pyridin-2-yl]oxy-3-[ditert-butyl(hydroxy)silyl]oxy-tetrahydrofuran-2-carboxylate and methyl (2S,3S,4R)-4-[6-chloro-5-(4-phenylphenyl)-1-(2-trimethylsilylethoxymethyl)imidazo[4,5-b]pyridin-2-yl]oxy-3-[ditert-butyl(trimethyl-silyloxy)silyl]oxy-tetrahydrofuran-2-carboxylate Methyl (2S,3S,4R)-4-[5-(4-bromophenyl)-6-chloro-1-(2-trimethylsilylethoxymethyl)imidazo[4,5-b]pyridin-2-yl]oxy-3-[ditert-butyl(hydroxy)silyl]oxy-tetrahydrofuran-2-carboxylate and methyl (2S,3S,4R)-4-[5-(4-bromophenyl)-6-chloro-1-(2-trimethylsilylethoxymethyl)imidazo[4,5-b]pyridin-2-yl]oxy-3-[ditert-butyl(trimethylsilyloxy)silyl]oxy-tetrahydrofuran-2-carboxylate (all of the crude material from the previous step), phenylboronic acid (16.2 mg, 0.133 mmol), tripotassium phosphate (55.8 mg, 0.263 mmol), chloro(2-dicyclohexylphosphino-2',6'-dimethoxy-1,1'-biphenyl)[2-(2-aminoethylphenyl)]palladium(II)-methyl-t-butyl (5.6 mg, 7.36 μmol), and dioxane (0.7 ml) were combined in a vial. The reaction mixture was degassed (3×) and placed under nitrogen before being heated to 80° C. The reaction mixture was a pale yellow suspension. After 30 minutes, the reaction mixture had become a dark suspension. After an additional 2.5 hours, the reaction mixture was cooled to room temperature before being partitioned between EtOAc (40 ml) and water (40 ml). The aqueous layer was extracted with EtOAc (2×20 ml). The organic layers were combined, washed with brine (1×20 ml), dried over MgSO$_4$, filtered, and evaporated under reduced pressure to give a pale yellow residue. The residue was dissolved in EtOAc and loaded onto a 500 micron 20 cm×20 cm silica gel plate, which was developed using 20% EtOAc/Hex. The silica containing the product bands was collected and eluted with EtOAc (80 ml). The solvent was evaporated under reduced pressure to give a mixture of the two products as a colorless residue that was used in the next step. LC-MS: calculated for $C_{38}H_{52}ClN_3O_7Si_2$ 753.3. observed m/e: 754.46 (M+H)$^+$ (Rt 1.57/2 min). LC-MS: calculated for $C_{41}H_{60}ClN_3O_7Si_3$ 825.34. observed m/e: 826.61 (M+H)$^+$ (Rt 1.65/2 min).

Step D (2S,3S,4R)-4-[[6-chloro-5-(4-phenylphenyl)-1H-imidazo[4,5-b]pyridin-2-yl]oxy]-3-hydroxy-tetrahydrofuran-2-carboxylic acid TFA (0.5 ml, 6.49 mmol) was added to a stirred solution of methyl (2S,3S,4R)-4-[6-chloro-5-(4-phenylphenyl)-1-(2-trimethylsilylethoxy-methyl)imidazo[4,5-b]pyridin-2-yl]oxy-3-[ditert-butyl(hydroxy)-silyl]oxy-tetrahydrofuran-2-carboxylate and methyl (2S,3S,4R)-4-[6-chloro-5-(4-phenylphenyl)-1-(2-trimethylsilylethoxy-methyl)imidazo[4,5-b]pyridin-2-yl]oxy-3-[ditert-butyl(trimethylsilyloxy)silyl]oxytetrahydro-furan-2-carboxylate (entire sample from the previous step) in DCM (0.5 ml). The reaction mixture was a yellow solution that was stirred at room temperature. After 1 hour, the reaction mixture was evaporated under reduced pressure to give a pale yellow foam. TBAF 1.0 M in THF (0.75 ml, 0.750 mmol) was combined with the foam to give a yellow solution that was heated to 60° C. with stirring. After 1.5 hours, additional TBAF 1.0 M in THF (0.3 ml, 0.300 mmol) was added to the reaction mixture. After another hour, additional TBAF 1.0 M in THF (0.2 ml, 0.200 mmol) was added to the reaction mixture. After an additional 40 minutes, the reaction mixture was cooled to room temperature before being partitioned between EtOAc (40 ml) and water (40 ml). The aqueous layer was extracted with EtOAc (2×20 ml). The organic layers were combined, washed with brine (1×20 ml), dried over MgSO$_4$, filtered, and evaporated under reduced pressure to give a colorless residue. This material was purified by preparative HPLC reverse phase (C-18), using a 30×150 mm Sunfire™ column and eluting with a 20%-80% acetonitrile/water+0.05% TFA gradient followed by a 80% acetonitrile/water+0.05% TFA flush. The product fractions were combined, evaporated under reduced pressure, and lyophilized from ethanol and benzene to give the title compound as a yellow solid. LC-MS: calculated for C$_{23}$H$_{18}$ClN$_3$O$_5$ 451.09. observed m/e: 452.15 (M+H)$^+$ (Rt 1.16/2 min). $^1$H NMR δ (ppm) (CD$_3$OD): 7.87 (s, 1H), 7.72-7.76 (m, 4H), 7.71 (d, J=7.5 Hz, 2H), 7.48 (t, J=7.7 Hz, 2H), 7.38 (t, J=7.4 Hz, 1H), 5.36 (m, 1H), 4.75 (s, 1H), 4.45 (m, 1H), 4.39 (dd, J=3.6 Hz, J=11.0 Hz, 1H), 4.35 (d, J=10.9 Hz, 1H).

Example 13

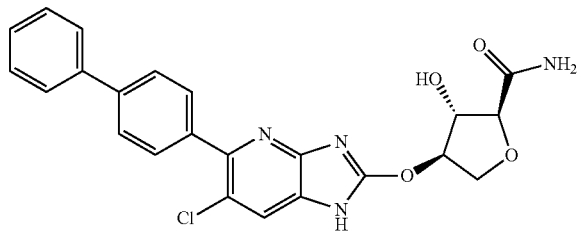 [SMILES: NC(=O)[C@H]1OC[C@@H](Oc2nc3nc(-c4ccc(-c5ccccc5)cc4)c(Cl)cc3[nH]2)[C@@H]1O]

(2S,3S,4R)-4-[[6-chloro-5-(4-phenylphenyl)-1H-imidazo[4,5-b]pyridin-2-yl]oxy]-3-hydroxy-tetrahydrofuran-2-carboxamide Triethylamine (6 µl, 0.043 mmol) was added to a stirred white suspension of (2S,3S,4R)-4-[[6-chloro-5-(4-phenylphenyl)-1H-imidazo[4,5-b]pyridin-2-yl]oxy]-3-hydroxy-tetrahydrofuran-2-carboxylic acid (4.4 mg, 9.74 µmol) in 1,2-dimethoxyethane (0.3 ml). The reaction mixture was cooled to 0° C. in an ice bath prior to the addition of ethyl chloroformate (4 µl, 0.042 mmol). The reaction mixture was a hazy white suspension. After 45 minutes, ammonia was blown into the reaction for 5 minutes. The reaction mixture was removed from the ice bath and allowed to warm to room temperature. After 1.5 hours, MeOH (0.2 ml) was added to the reaction mixture. After 3 days, potassium trimethylsilanolate (4.8 mg, 0.037 mmol) was added to the reaction mixture. After 2 hours, the reaction mixture was evaporated under reduced pressure to give a white residue. The residue was purified by preparative HPLC reverse phase (C-18), using a 30×150 mm Sunfire™ column and eluting with a 20%-100% acetonitrile/water+0.05% TFA gradient followed by a 100% acetonitrile+0.05% TFA flush. The product fractions were combined, evaporated under reduced pressure, and lyophilized from ethanol and benzene to give the title compound as a white solid. LC-MS: calculated for C$_{23}$H$_{19}$ClN$_4$O$_4$ 450.11. observed m/e: 451.16 (M+H)$^+$ (Rt 1.15/2 min). $^1$H NMR δ (ppm) (CD$_3$OD): 7.95 (s, 1H), 7.73-7.77 (m, 4H), 7.71 (d, J=7.8 Hz, 2H), 7.48 (t, J=7.7 Hz, 2H), 7.38 (t, J=7.2 Hz, 1H), 5.37 (d, J=3.0 Hz, 1H), 4.70 (s, 1H), 4.43 (d, J=11.1 Hz, 1H), 4.37 (dd, J=3.5 Hz, J=11.1 Hz, 1H), 4.33 (s, 1H).

Example 14

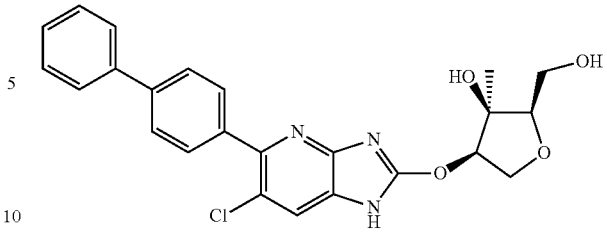

(2R,3S,4R)-4-[[6-chloro-5-(4-phenylphenyl)-1H-imidazo[4,5-b]pyridin-2-yl]oxy]-2-(hydroxymethyl)-3-methyl-tetrahydrofuran-3-ol Step A (2R,3S,4R)-4-[6-chloro-5-(4-phenylphenyl)-1-(2-trimethylsilylethoxy-methyl)imidazo[4,5-b]pyridin-2-yl]oxy-2-[[ditert-butyl(hydroxy)silyl]oxymethyl]-3-methyl-tetrahydrofuran-3-ol A stirred solution of (2R,4R)-4-[6-chloro-5-(4-phenylphenyl)-1-(2-trimethylsilylethoxymethyl)imidazo[4,5-b]pyridin-2-yl]oxy-2-[[ditert-butyl(hydroxy)silyl]oxymethyl]tetrahydrofuran-3-one (29.8 mg, 0.041 mmol) in THF (0.41 ml) was degassed (3×) and placed under nitrogen after being cooled to 0° C. in an ice bath. Methylmagnesium bromide 3.0 M in ether (35 µl, 0.105 mmol) was added to the reaction mixture dropwise. After 10 minutes, the reaction mixture was removed from the ice bath and allowed to warm to room temperature. After 1 hour, the reaction mixture was pipetted into saturated aqueous NaHCO$_3$ (15 ml) before being partitioned between EtOAc (30 ml) and water (15 ml). The aqueous layer was extracted with EtOAc (2×20 ml). The organic layers were combined, washed with brine (1×15 ml), dried over MgSO$_4$, filtered, and evaporated under reduced pressure to give a colorless residue. The residue was dissolved in EtOAc and loaded onto a 500 micron 20 cm×20 cm silica gel plate, which was developed using 35% EtOAc/Hex.

The silica containing the product band was collected and eluted with EtOAc (80 ml). The solvent was evaporated under reduced pressure to give the desired product as a colorless residue. LC-MS: calculated for C$_{38}$H$_{54}$ClN$_3$O$_6$Si$_2$ 739.32. observed m/e: 740.51 (M+H)$^+$ (Rt 1.49/2 min).

Step B (2R,3S,4R)-4-[[6-chloro-5-(4-phenylphenyl)-1H-imidazo[4,5-b]pyridin-2-yl]oxy]-2-(hydroxymethyl)-3-methyl-tetrahydrofuran-3-ol TFA (0.3 ml, 3.89 mmol) was added to a stirred solution of (2R,3S,4R)-4-[6-chloro-5-(4-phenylphenyl)-1-(2-trimethylsilylethoxy-methyl)imidazo[4,5-b]pyridin-2-yl]oxy-2-[[ditert-butyl(hydroxy)silyl]oxymethyl]-3-methyl-tetrahydrofuran-3-ol (18.3 mg, 0.025 mmol) in DCM (0.3 ml). The reaction mixture was a yellow solution that was stirred at room temperature. After 1.5 hours, the reaction mixture was evaporated under reduced pressure to give an amber residue. TBAF 1.0 M in THF (0.7 ml, 0.700 mmol) was combined with the residue to give a yellow solution that was heated to 60° C. with stirring. After 2 hours, the reaction mixture was cooled to room temperature before being partitioned between EtOAc (20 ml) and water (20 ml). The aqueous layer was extracted with EtOAc (2×10 ml). The organic layers were combined, washed with brine (1×10 ml), dried over MgSO$_4$, filtered, and evaporated under reduced pressure to give a colorless residue. This material was purified by preparative HPLC reverse phase (C-18), using a 30×150 mm Sunfire™ column and eluting with a 20%-100% acetonitrile/water+0.05% TFA gradient followed by a 100% acetonitrile+0.05% TFA flush. The product fractions were combined, evaporated under reduced pressure, and lyophilized from ethanol and benzene to give the title compound as a white solid. LC-MS: calculated for $C_{24}H_{22}ClN_3O_4$ 451.13. observed m/e: 452.19 $(M+H)^+$ (Rt 1.17/2 min). $^1$H NMR δ (ppm) ($CD_3OD$): 7.93 (s, 1H), 7.73-7.77 (m, 4H), 7.71 (d, J=7.8 Hz, 2H), 7.48 (t, J=7.6 Hz, 2H), 7.38 (t, J=7.1 Hz, 1H), 5.37-5.39 (m, 1H), 4.28 (dd, J=6.2 Hz, J=10.3 Hz, 1H), 4.07 (dd, J=4.3 Hz, J=10.2 Hz, 1H), 3.86 (dd, J=3.9 Hz, J=11.9 Hz, 1H), 3.80 (d, J=11.9 Hz, 1H), 3.75 (dd, J=4.0 Hz, J=6.4 Hz, 1H), 1.52 (s, 3H).

Example 15

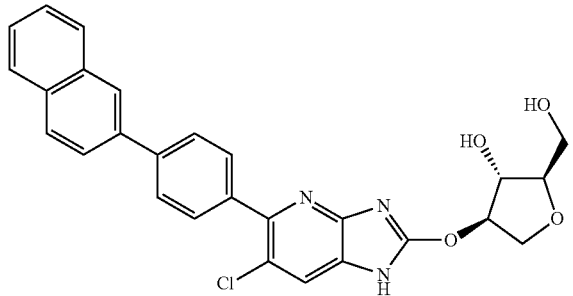 [SMILES: OC[C@H]1OC[C@@H](Oc2nc3nc(-c4ccc(-c5ccc6ccccc6c5)cc4)c(Cl)cc3[nH]2)[C@@H]1O]

(2R,3R,4R)-4-((6-chloro-5-(4-(naphthalen-2-yl)phenyl)-1H-imidazo[4,5-b]pyridin-2-yl)oxy)-2-(hydroxymethyl)tetrahydrofuran-3-ol 5-(4-bromophenyl)-6-chloro-2-(((4aR,7R,7aR)-2,2-di-tert-butyltetrahydro-4H-furo[3,2-d][1,3,2]dioxasilin-7-yl)oxy)-1-((2-(trimethylsilyl)ethoxy)-methyl)-1H-imidazo[4,5-b]pyridine (Intermediate 7, 50.0 mg, 0.070 mmol) and naphthalen-2-ylboronic acid (14.15 mg, 0.084 mmol) in anhydrous dioxane (0.4 ml) was purged with $N_2$ and then chloro[(tri-tert-butylphosphine)-2-(2-aminobiphenyl)]palladium(II) (7.2 mg, 0.014 mmol) and tripotassium phosphate (0.211 ml, 0.211 mmol) were added under $N_2$ flow. The mixture was heated to 60° C. overnight. The crude mixture was then extracted with $CH_2Cl_2$ and washed with water. The organic layer was transferred out to 2 dram vial and the solvent was evaporated under reduced pressure. To the resulting residue was added 1 ml of 1:1 $CH_2Cl_2$ and TFA and the mixture was stirred at 25° C. for two hours. The desired product formed by UPLC. The reaction mixture was evaporated under reduced pressure to give an amber residue. To the resulting residue was added TBAF 1.0 M in THF (0.211 ml, 0.211 mmol) and the reaction mixture was heated to 60° C. with stirring. After 1 hour, the reaction mixture was cooled to room temperature before being partitioned between $CH_2Cl_2$ (2 ml) and water (2 ml). The aqueous layer was separated and extracted with $CH_2Cl_2$ (2×1 ml). The combined organic layers were evaporated under reduced pressure to give an amber residue. The residue was dissolved with 1.5 ml DMSO, then filtered through a filter plate (0.45 micron) and submitted to High Throughput Purification group (HTP) for mass triggered reverse phase eluting with acetonitrile/water+0.1% TFA to give the title product. LC-MS: calculated for C27H27ClN3O4, 487.13. observed m/e: 488.13 $(M+H)^+$ (Rt 1.00/2.00 min).

TABLE 3

Compound 16-23 were prepared according to the methods in Example 15.

| Example | Structure | Exact Mass [M + H]+ |
|---|---|---|
| 16 | 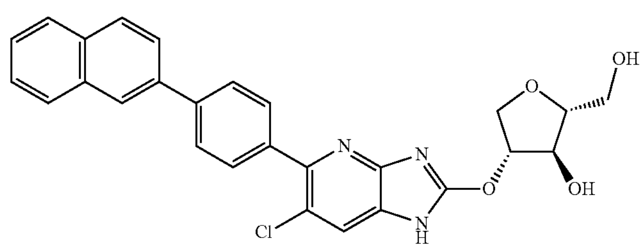 [SMILES: OC[C@H]1OC[C@@H](Oc2nc3nc(-c4ccc(-c5ccc6ccccc6c5)cc4)c(Cl)cc3[nH]2)[C@@H]1O] | 488.13 |
| 17 | 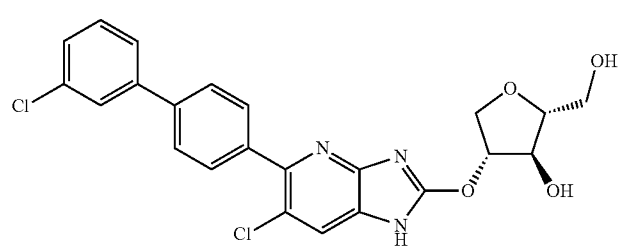 [SMILES: OC[C@H]1OC[C@@H](Oc2nc3nc(-c4ccc(-c5cccc(Cl)c5)cc4)c(Cl)cc3[nH]2)[C@@H]1O] | 472.08 |

TABLE 3-continued

Compound 16-23 were prepared according to the methods in Example 15.

| Example | Structure | Exact Mass [M + H]+ |
|---|---|---|
| 18 | 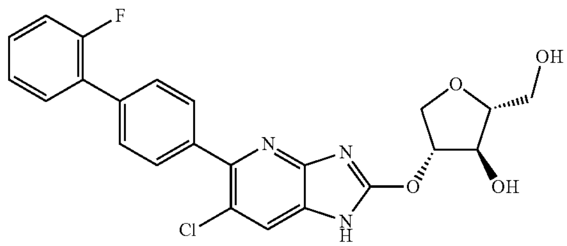 [SMILES: OC[C@H]1OC[C@@H](Oc2nc3nc(-c4ccc(-c5ccccc5F)cc4)c(Cl)cc3[nH]2)[C@@H]1O] | 456.11 |
| 19 | 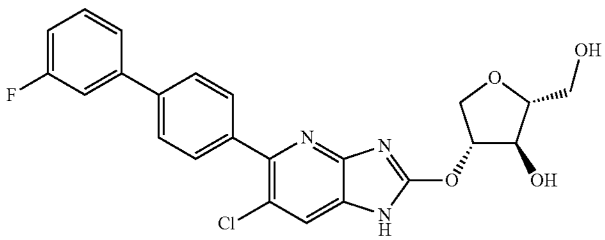 [SMILES: OC[C@H]1OC[C@@H](Oc2nc3nc(-c4ccc(-c5cccc(F)c5)cc4)c(Cl)cc3[nH]2)[C@@H]1O] | 456.11 |
| 20 | 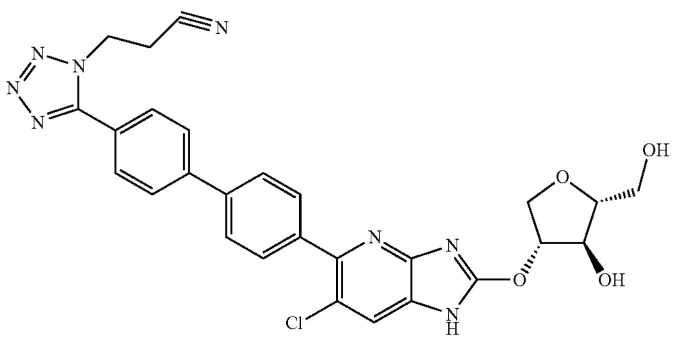 [SMILES: N#CCCn1nnnc1-c1ccc(-c2ccc(-c3nc4nc(O[C@@H]5CO[C@H](CO)[C@H]5O)[nH]c4cc3Cl)cc2)cc1] | 559.15 |
| 21 | 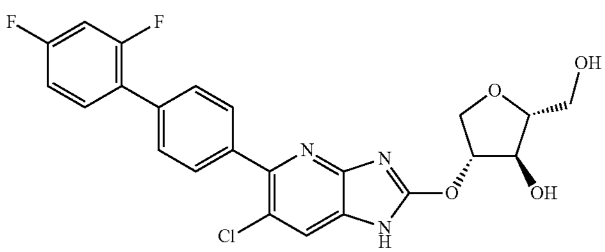 [SMILES: OC[C@H]1OC[C@@H](Oc2nc3nc(-c4ccc(-c5ccc(F)cc5F)cc4)c(Cl)cc3[nH]2)[C@@H]1O] | 474.1 |
| 22 | 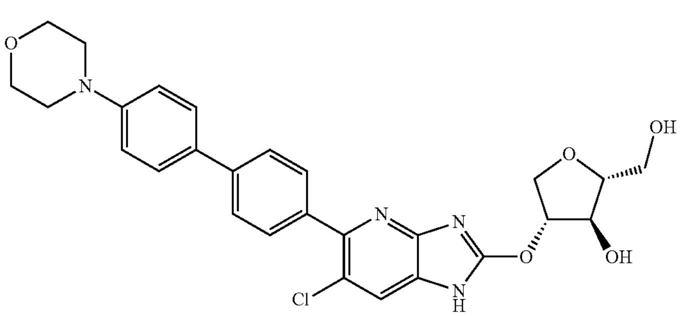 [SMILES: OC[C@H]1OC[C@@H](Oc2nc3nc(-c4ccc(-c5ccc(N6CCOCC6)cc5)cc4)c(Cl)cc3[nH]2)[C@@H]1O] | 523.17 |

TABLE 3-continued

Compound 16-23 were prepared according to the methods in Example 15.

| Example | Structure | Exact Mass [M + H]+ |
|---|---|---|
| 23 | 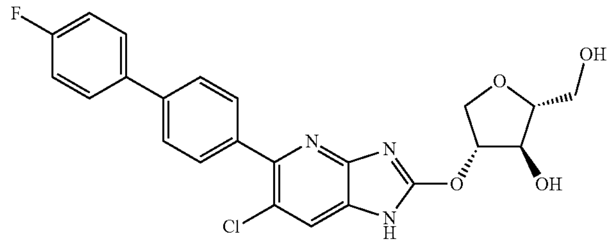 [SMILES: OC[C@H]1OC[C@@H](Oc2nc3nc(-c4ccc(-c5ccc(F)cc5)cc4)c(Cl)cc3[nH]2)[C@@H]1O] | 456.11 |

Example 24a and 24b

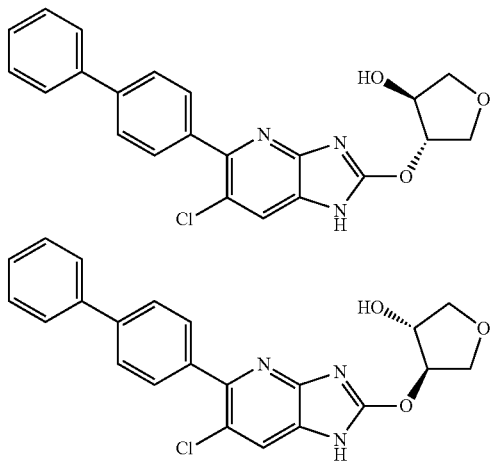

4-((5-([1,1'-biphenyl]-4-yl)-6-chloro-1H-imidazo[4,5-b]pyridin-2-yl)oxy)tetrahydrofuran-3-ol (trans)

Step A: 4-((5-([1,1'-biphenyl]-4-yl)-1-allyl-6-chloro-1H-imidazo[4,5-b]pyridin-2-yl)oxy)tetrahydrofuran-3-ol Cs$_2$CO$_3$ (480 mg, 1.473 mmol) and tetrahydro-furan-3,4-diol (217.8 mg, 2.092 mmol) were added to a stirred mixture of 5-([1,1'-biphenyl]-4-yl)-1-allyl-6-chloro-2-(methylsulfonyl)-1H-imidazo[4,5-b]pyridine (520.2 mg, 1.227 mmol) in DMF (5 ml) and the mixture was stirred at room temperature for 3 h. Water (100 mL) was added and the mixture was extracted with ethyl acetate (3×80 mL). The combined organic extracts were washed with brine (saturated, 50 mL), dried (Na$_2$SO$_4$), filtered and the solvent was evaporated under reduced pressure. The resulting residue was purified by column chromatography on silica gel Biotage™ 25M, eluting with EtOAc/isohexane (0-50% EtOAc in hexane) to give a mixture of isomers (trans, high Rf) and (trans, low Rf). LC-MS: calculated for C25H22ClN3O3 447.13. observed m/e: 447.83 (M+H)$^+$ (Rt 1.26/2 min).

Step B: 4-((5-([1,1'-biphenyl]-4-yl)-6-chloro-1H-imidazo[4,5-b]pyridin-2-yl)oxy)tetrahydrofuran-3-ol Tetrakis(triphenylphosphine)palladium (0) (25.1 mg, 0.022 mmol) was added to a stirred mixture of 4-((5-([1,1'-biphenyl]-4-yl)-1-allyl-6-chloro-1H-imidazo[4,5-b]pyridin-2-yl)oxy)tetrahydrofuran-3-ol, (trans, high Rf) (48.7 mg, 0.109 mmol), 1,3-dimethylbarbituric acid (34.0 mg, 0.217 mmol) in DMA (1.5 ml) under N$_2$ and the mixture was stirred at 80° C. for 48 h. The mixture was cooled, diluted with ethyl acetate (30 mL), washed with water (2×30 mL), brine (saturated, 2×30 mL), dried (Na$_2$SO$_4$), filtered and the solvent was evaporated under reduced pressure. The residue was purified by preparative TLC, eluting with EtOAc/isohexane (3:1), and then purified again by preparative HPLC Reverse phase (C-18), eluting with acetonitrile/water+0.1% TFA, to give the title compound. LC-MS: calculated for C22H18ClN3O3 407.10. observed m/e: 407.87 (M+H)$^+$ (Rt 1.17/2 min). $^1$H NMR δ (ppm) (CD$_3$OD): 7.91 (s, 1H), 7.74 (s, 4H), 7.69 (d, 2H), 7.47 (t, 2H), 7.37 (t, 1H), 5.53 (dd, 1H), 4.64 (dd, 1H), 4.21 (dd, 1H), 4.03 (m, 2H), 3.75 (dd, 1H).

TABLE 4

Compound 25 was prepared according to the procedures in Example 5.

| Example Number | Structure | HPLC-mass spectrum m/e |
|---|---|---|
| 25 | 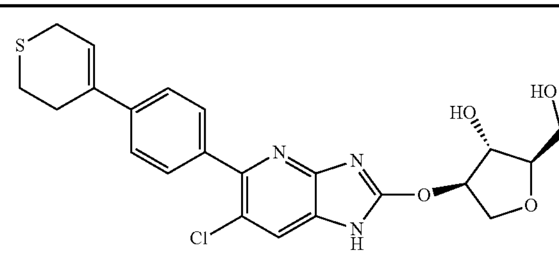 | 460.26 |

Example 26

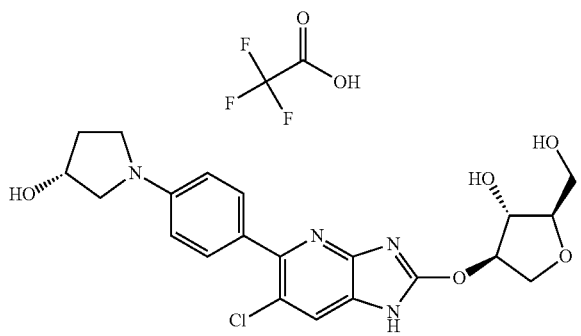

(3R)-1-[4-[6-chloro-2-[(3R,4R,5R)-4-hydroxy-5-(hydroxymethyl)tetrahydrofuran-3-yl]oxy-1H-imidazo[4,5-b]pyridin-5-yl]phenyl]pyrrolidin-3-ol 3.0 M aqueous lithium hydroxide (0.57 ml, 1.710 mmol) and 1,1'-bis(diphenylphosphino)-ferrocene-palladium(II)dichloride dichlormethane complex (47.1 mg, 0.058 mmol) were added to a stirred solution of (2R,3R,4R)-4-[(6-chloro-5-iodo-1H-imidazo[4,5-b]pyridin-2-yl)oxy]-2-(hydroxymethyl)tetrahydrofuran-3-ol (233.2 mg, 0.567 mmol) and (3R)-1-[4-(4,4,5,5-tetramethyl-1,3,2-dioxaborolan-2-yl) phenyl]pyrrolidin-3-ol (241.5 mg, 0.835 mmol) in dioxane (4.5 ml) and water (0.63 ml). The reaction mixture was degassed (3×) and placed under nitrogen and then heated to 80° C. After 3.5 hours, the reaction mixture was cooled to room temperature, and partitioned between EtOAc (50 ml), water (50 ml), and brine (a few ml). The aqueous layer was extracted with EtOAc until all product was extracted. The organic layers were combined, washed with brine (1×50 ml), dried over MgSO$_4$, filtered, and evaporated under reduced pressure to give a tan residue. This material was dissolved in DMSO and filtered (0.45 μm syringe filter) before being purified on a Waters Sunfire C18, 30×150 mm column eluting with acetonitrile/water+0.05% TFA at 20 ml/min using either a 12 or 15 minute 10-60% acetonitrile/water gradient. The product fractions were combined, frozen, and lyophlized to give the title compound as a yellow solid. LC-MS: calculated for $C_{21}H_{23}ClN_4O_5$ 446.14. observed m/e: 447.19 (M+H)$^+$ (Rt 0.96/4 min). $^1$H NMR δ (ppm) (400 MHz CD$_3$OD): δ 7.96 (s, 1H), 7.51-7.55 (m, 2H); 6.65-6.69 (m, 2H), 5.34 (dt, J=4.1, 1.8 Hz, 1H), 4.55 (tdd, J=4.7, 2.9, 2.1 Hz, 1H), 4.30 (dd, J=4.7, 1.8 Hz, 1H), 4.21 (dd, J=11.2, 4.2 Hz, 1H), 4.14-4.17 (m, 1H), 3.81 (dt, J=5.9, 4.5 Hz, 1H), 3.73 (dd, J=11.7, 4.4 Hz, 1H), 3.67 (dd, J=11.7, 5.9 Hz, 1H), 3.48-3.57 (m, 2H), 3.43 (td, J=8.8, 3.4 Hz, 1H), 3.27-3.33 (m, 1H), 2.13-2.22 (m, 1H), 2.06 (ddt, J=13.1, 7.0, 3.1 Hz, 1H).

TABLE 5

Examples 27-32 were prepared according to the methods in Example 26. Minor variations in conditions are noted.

| Example | Structure | HPLC-mass spectrum m/e | Conditions |
|---|---|---|---|
| 27 | 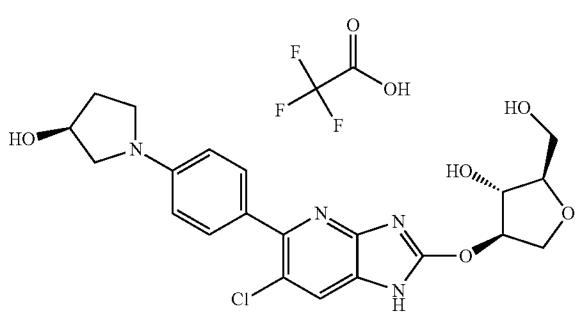 [SMILES: OC[C@H]1OC[C@@H](Oc2nc3nc(-c4ccc(N5CC[C@H](O)C5)cc4)c(Cl)cc3[nH]2)[C@@H]1O ; O=C(O)C(F)(F)F] | 447.32 | |
| 28 | 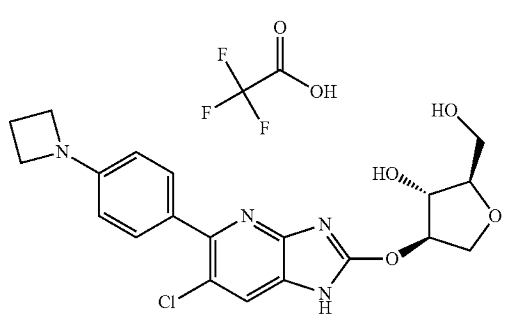 [SMILES: OC[C@H]1OC[C@@H](Oc2nc3nc(-c4ccc(N5CCC5)cc4)c(Cl)cc3[nH]2)[C@@H]1O ; O=C(O)C(F)(F)F] | 417.31 | Purified by reverse phase eluting with acetonitrile/water + 0.16% NH$_4$OH |

TABLE 5-continued
Examples 27-32 were prepared according to the methods in Example 26. Minor variations in conditions are noted.
| Example | Structure | HPLC-mass spectum m/e | Conditions |
|---|---|---|---|
| 29 | 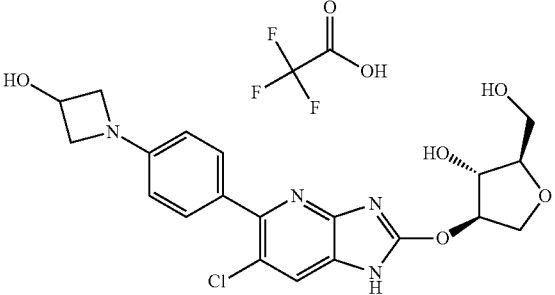 [SMILES: OC[C@H]1OC[C@@H](Oc2nc3nc(-c4ccc(N5CC(O)C5)cc4)c(Cl)cc3[nH]2)[C@@H]1O ; O=C(O)C(F)(F)F] | 433.29 | |
| 30 | 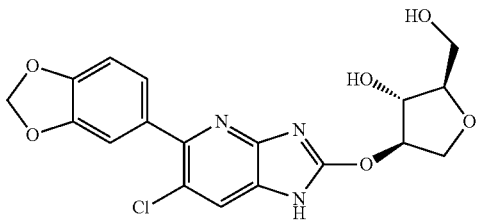 [SMILES: OC[C@H]1OC[C@@H](Oc2nc3nc(-c4ccc5c(c4)OCO5)c(Cl)cc3[nH]2)[C@@H]1O] | 406.23 | |
| 31 | 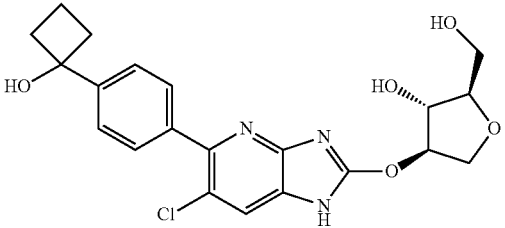 [SMILES: OC[C@H]1OC[C@@H](Oc2nc3nc(-c4ccc(C5(O)CCC5)cc4)c(Cl)cc3[nH]2)[C@@H]1O] | 432.34 | |
| 32 | 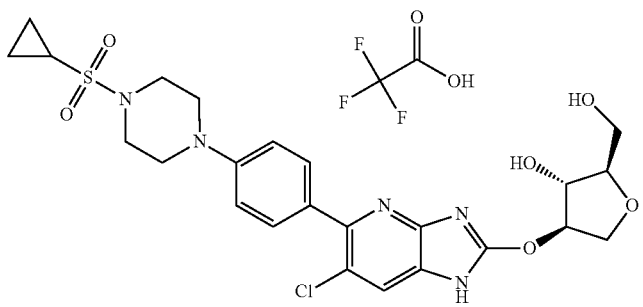 [SMILES: O=S(=O)(C1CC1)N1CCN(c2ccc(-c3nc4nc(O[C@@H]5CO[C@H](CO)[C@H]5O)[nH]c4cc3Cl)cc2)CC1 ; O=C(O)C(F)(F)F] | 550.5 | 3 eq. 2M K₃PO₄<br>0.1 eq Pd Catalyst<br>CAS: 1375325-71-5 |

Example 33

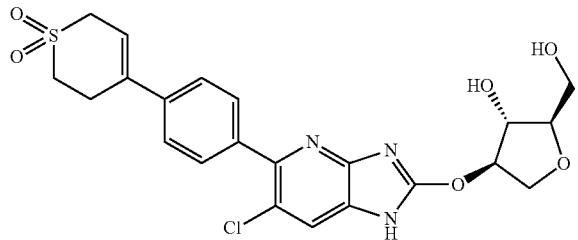 [SMILES: O=S1(=O)CC=C(c2ccc(-c3nc4nc(O[C@@H]5CO[C@H](CO)[C@H]5O)[nH]c4cc3Cl)cc2)CC1]

4-(4-(6-chloro-2-(((3R,4R,5R)-4-hydroxy-5-(hydroxymethyl)tetrahydrofuran-3-yl)oxy)-1H-imidazo[4,5-b]pyridin-5-yl)phenyl)-3,6-dihydro-2H-thiopyran 1,1-dioxide To a stirred solution of (2R,3R,4R)-4-((6-chloro-5-(4-(3,6-dihydro-2H-thiopyran-4-yl)phenyl)-1H-imidazo[4,5-b]pyridin-2-yl)oxy)-2-(hydroxymethyl)tetrahydrofuran-3-ol (Example 25, 70 mg, 0.152 mmol) in DCM (3.0 ml) under nitrogen at 0° C. was added portion wise m-CPBA (77% w/w, 136 mg, 0.608 mmol) over 1 hour. After 1.5 hours, the resultant oil was loaded onto a 24 g silica gel cartridge and chromatographed using an elution gradient of 0-10% methanol in DCM over 15 column volumes with a 4 column volume hold at 10% methanol. The desired product fractions were combined and concentrated under reduced pressure. The resultant residue was dissolved in acetonitrile/water, frozen at −78° C., and lyophilized to dryness to provide the title compound as a white solid. LC-MS: calculated for $C_{22}H_{22}ClN_3O_6S$ 491.09. observed m/e: 492.22 (M+H)$^+$ (Rt 1.05/4 min).

Biological Example 1

AMPKSAMSF (In Vitro AMPK Activation Assay)

The recombinant human AMPK complex 1 (containing α1β1γ1) or AMPK complex 7 (containing α2β1γ1) was obtained from baculovirus expression system. Recombinant viruses were generated by cotransfection of AMPK/pBac-Pak9 clones with Baculogold baculovirus DNA (Pharmingen) in *spodoptera frugiperda* 21 cells according to the manufacturer's instructions. Each round of virus amplification was performed for 5 days in Grace's medium containing 10% serum. Virus that had been subjected to three rounds of amplification was used for all protein production procedures. To express the AMPK complex, sf21 cells were adapted to serum free medium (SF900 II, Invitrogen) by sequential dilution from serum containing stocks into SF900II medium and maintained in shaker flasks at 90 rpm at 27° C. The recombinant AMPK enzyme complex was produced by triple infection, one recombinant virus for each of the subunits, in sf21 cells under serum free conditions. Cells were infected in log phase, 1×10$^6$ cells/ml, at a multiplicity of infection of ~5. Cells were harvested by centrifugation at 10,000×g for 15 minutes after 72 hours of infection with viruses. The insect cell pellet from 2 liters of culture was resuspended in 50 ml lysis buffer (20 mM Tris-HCl, 50 mM NaCl, 50 mM NaF, 30 mM Na PPi, 0.25 M sucrose, 10 mM ZnCl$_2$, 2 mM DTT, 0.4 mg/ml digitonin) and subjected to two cycles of freeze-thaw lysis in a dry-ice ethanol bath. Insoluble material was removed by centrifugation at 10,000×g and the supernatant was fractionated with use of polyethylene glycol (PEG). The protein fraction precipitating between 2.5 and 6% PEG was used for further purification using a Blue-Sepharose step (Zhou et al, J. Clin. Invest. 108, 1167-1174, 2001).

The in vitro AMPK activation assay is performed in a volume of 30 μl in a 384-well plate. Enzyme reactions were assembled in the microtiter plate by adding 15 μl of 2× enzyme in assay buffer (20 mM HEPES, pH 7.3, 5 mM MgCl$_2$, 3 mM DTT, 0.01% Brij 35 and CamK Kinase, to activate AMPK) to wells which contained either DMSO or compound. The reaction was initiated with the addition of 15 μl 2× substrate mixture containing 200 μM ATP, and 3.0 μM fluorescently labeled SAMS (5-FAM-HMRSAMSGL-HLVKRR-COOH) in assay buffer. After 45-minute incubation at 25° C., the reaction was stopped by the addition of 70 μl stop buffer (100 mM HEPES, pH 7.3, 40 mM EDTA, 0.015% Brij 35). Phosphorylated 5-FAM SAMS product is assessed using a Caliper EZ Reader LabChip microfluidics reader. Product conversion is determined by calculating the peak heights of the substrate and product and reporting the product/(product+substrate) peak ratio. The 10-point titration data were expressed as % maximum AMP activation. The results were plotted using 4 parameter fit and the inflection point reflecting 50% of the maximum activation was reported as the EC$_{50}$. The % maximum AMP activation for selected compounds is provided in the table below.

The compounds of present invention, including the compounds of Examples 1-24, were tested in the in vitro AMPK activation assay using recombinant human AMPK complex 1 (containing α1β1γ1) or AMPK complex 7 (containing α2β1γ1), and were found to have greater than 50% maximum AMP activation of human AMPK complex 1 (containing α1β1γ1) or AMPK complex 7 (containing α2β1γ1), and EC$_{50}$ values of less than 50 micromolar. Preferred compounds of the present invention were found to have EC$_{50}$ values of less than 0.1 micromolar in the in vitro AMPK activation assay using recombinant human AMPK complex 1 or AMPK complex 7.

| Maximum AMP Activation for Selected Compounds | | |
|---|---|---|
| Example No. | % Maximum AMP Activation of human AMPK Complex 7 | EC$_{50}$ (nM) |
| 1 | 188 | 16 |
| 2 | 315 | 4 |
| 3 | 338 | 13 |
| 4 | 206 | 20 |
| 5 | 261 | 2 |
| 6 | 268 | 5 |
| 7 | 282 | 3 |
| 8 | 332 | 9 |
| 9 | 294 | 11 |
| 10 | 209 | 3651 |
| 12 | 313 | 332 |
| 14 | 203 | 289 |
| 18 | 294 | 32 |
| 19 | 231 | 126 |
| 20 | 242 | 8 |
| 21 | 307 | 85 |
| 22 | 252 | 5 |
| 23 | 231 | 38 |

Biological Example 2

Phosphoroylation of Acetyl CoA Carboxylase by AMPK Activators in db/+ Mice

To assess the potential for AMPK activators to increase the phosphorylation of Acetyl COA Carboxylase (ACC) in liver and skeletal muscle, db/+ mice are dosed with AMPK activators at either 2 or 7 h prior to evaluation where phosphorylated ACC (p-ACC)/total ACC levels are compared in the tissues of vehicle and compound treated mice. Briefly, mice are anesthetized using gas anesthesia with 1-4% isoflurane administered to effect via nose cone. Once anesthetized, samples of liver and skeletal muscle (gastrocnemius) are removed, snap frozen in liquid nitrogen, and homogenized. Homogenates are analyzed for protein concentration and equal amounts of protein are assayed for total and phosphorylated ACC (p-ACC) levels using Meso Scale Discovery's Multi-array assay kit. MSD assay plates contain an electrode surface that is coated with streptavidin. Protein sample binds to streptavidin. The primary ACC or p-ACC specific antibody binds to protein and a secondary antibody labeled with MSD SULFO-TAG then binds to the primary antibody. The electrode surface of the MSD plate responds to an electrical stimulus and causes the SULFO-TAG labels bound to ACC and p-ACC to emit a light signal in proportion to the amount of p-ACC or total ACC present. The ratio of p-ACC/total ACC levels are determined for each sample and the ratio of p-ACC/total ACC levels for mice treated with AMPK activators is significantly elevated compared to the ratio of those treated with the vehicle control (significant elevations are described as differences where $p<0.05$).

Biological Example 3

Inhibition of Fatty Acid Synthesis (FAS) by AMPK Activators in db/+ Mice

To determine the effect of AMPK activators on Fatty Acid Synthesis (FAS) in the liver, the effect of oral pre-dosing of compounds on the amount of $^3H$ incorporated into hepatic triglyceride is determined as described by Sakurai T, Miyazawa S, Shindo Y, and T. Hashimoto (Biochim Biophys Acta. 1974 Sep. 19; 360 (3):275-88). Briefly, mice (db/+, Jackson Laboratory, Maine) are orally dosed with AMPK activators at time=−8 h. Then at time=−1 h, mice are injected with 0.5 ml of 0.15 M NaCl containing 0.2 mCi of $^3H$ water per 100 g of body weight. At time 0, mice are sacrificed via cervical dislocation and livers are harvested for FAS analysis. To analyze livers for FAS, samples of liver are heated at 90° C. for 5 hours in a 4 M KOH/50% ethanol solution. Then the alkaline hydrolysate of liver is extracted with hexane and acidified to a pH<2 with 10 M $H_2SO_4$. The fatty acids of liver are then extracted from acidified hydrolysate with additional hexane, dried down with a stream of warm air, then re-suspended in scintillation fluid, and counted on a beta counter. The amount of fatty acids synthesized per gram of liver is calculated based on the amount of $^3H$ incorporated into hepatic triglyceride. The amount of $^3H$ radiolabelled fatty acids synthesized in mice with treated with an AMPK activator is significantly less than the amount of $^3H$ radiolabelled fatty acids synthesized in the control mice.

Biological Example 4

In Vivo Study for Therapy with an AMPK Activator in Mice (Glucose Tolerance Test)

DIO mice are treated simultaneously with an effective dose of an AMPK-activated protein kinase activator. Materials and Methods: Male C57BL/6NT mice (Taconic, 16-18 weeks old at the beginning of the drug administration) are used. Mice are given water and high fat diet D12492 (Research Diet Inc.) ad libitum. They are kept in an animal room which is maintained at 23±2 C temperature, 55±15% relative humidity and on a 12-hr light-dark cycle (7:00-19:00) during a quarantine and acclimatization period of 1 week. Animals are then administered vehicle (5 ml/kg of 0.5% methylcellulose in distilled water) by oral gavage twice-daily at 9 AM and 5 PM. After 9 days, stable body weight is observed. The following day (day −1), the mice are fasted for 4 hours and tail bled to determine the glucose and insulin levels. Animals are sorted into groups based on plasma glucose, insulin levels and body weight (n=8). The body weight and food in the hopper are recorded on day 0 before compound dosing is initiated. One of the groups is orally administered vehicle while the second group is administered an AMPK-activated protein kinase activator of the present invention at a dose of 30 mg/kg (5 ml/kg) twice-daily for 12 days by gavage. Body weight and food intake are measured every other day. On day 5, the animals are fasted 4 hours for measuring plasma glucose and insulin levels after morning dosing. At day 12, body weight and food intake are measured and animals receive their last morning dose. Mice again are fasted 4 hours, blood is collected at a set time point (t=0 min), and then challenged with dextrose orally (2 g/kg) Plasma glucose and insulin levels are determined from tail bleeds taken at 20 and 90 minutes after dextrose challenge. The plasma glucose and insulin excursion profile from t=0 to t=90 min is used to integrate an area under the curve (AUC) for each treatment. Percent inhibition values for each treatment are generated from the AUC data normalized to the C57BL/6NT mice feed with D7012. Preferred compounds of the present invention significantly reduce day 12 glucose and/or insulin AUC during the Oral Glucose Tolerance Test after an oral dose in the range of 0.1 to 100 mg/kg.

Biological Example 5

Acute Food Intake Studies in Diet Induced Obese (DIO) Mice

General Procedure

Adult DIO mice are used in these studies. After at least 2 days of acclimation to the vivarium conditions (controlled humidity and temperature, lights on for 12 hours out of 24 hours) food (D12492 (Research Diet Inc.) is removed from rodent cages. An AMPK activator of the present invention or the vehicle is administered orally, intraperitoneally, subcutaneously or intravenously before the return of a known amount of food to cage. The optimal interval between dosing and food presentation is based on the half-life of the compound based on when brain concentrations of the compound is the highest. Food remaining is measured at several intervals. Food intake is calculated as grams of food eaten per gram of body weight within each time interval and the appetite-suppressant effect of the AMPK activator is compared to the effect of the vehicle. The food intake of mice treated with an AMPK activator is significantly less than the food intake of control mice.

Biological Example 6

Chronic Weight Reduction Studies in Diet Induced Obese (DIO) Mice

General Procedure

Adult DIO mice are used in these studies. Upon or soon after weaning, rats or mice are made obese due to exclusive access to diets containing fat and sucrose in higher proportions than in the control diet. The diet used to induce obesity is Research Diets D12451 chow (45% fat). The rodents ingest chow until they are significantly heavier and have a higher proportion of body fat than control diet rats, often 9 weeks. The rodents receive injections (1 to 4 per day) or continuous infusions of an AMPK activator of the present invention or the vehicle either orally, intraperitoneally, subcutaneously or intravenously. Food intake and body weights are measured daily or more frequently. Food intake is calculated as grams of food eaten per gram of body weight within each time interval and the appetite-suppressant and weight loss effect of the AMPK activator of the present invention is compared to the effect of the vehicle. The weight loss of mice treated with an AMPK activator is significantly greater than the weight loss of control mice.

Biological Example 7

Assay for Triglycerides

Adult DIO mice are used in these studies. Upon or soon after weaning, rats or mice are made obese due to exclusive access to diets containing fat and sucrose in higher proportions than in the control diet. The diet used to induce obesity is Research Diets D12451 chow (45% fat). The rodents ingest chow until they are significantly heavier and have a higher proportion of body fat than control diet rats, often 9 weeks. The rodents receive injections (1 to 4 per day) or continuous infusions of an AMPK activator of the present invention or the vehicle either orally, intraperitoneally, subcutaneously or intravenously. Food intake and body weights are measured daily or more frequently. Food intake is calculated as grams of food eaten per gram of body weight within each time interval and the appetite-suppressant and weight loss effect of the AMPK activator of the present invention is compared to the effect of the vehicle. The weight loss of mice treated with an AMPK activator is significantly greater than the weight loss of control mice.

Biological Example 8

Assay for Low HDL and/or High LDL

Adult DIO mice are used in these studies. Upon or soon after weaning, rats or mice are made obese due to exclusive access to diets containing fat and sucrose in higher proportions than in the control diet. The diet used to induce obesity is Research Diets D12451 chow (45% fat). The rodents ingest chow until they are significantly heavier and have a higher proportion of body fat than control diet rats, often 9 weeks. The rodents receive injections (1 to 4 per day) or continuous infusions of an AMPK activator of the present invention or the vehicle either orally, intraperitoneally, subcutaneously or intravenously. Food intake and body weights are measured daily or more frequently. Food intake is calculated as grams of food eaten per gram of body weight within each time interval and the appetite-suppressant and weight loss effect of the AMPK activator of the present invention is compared to the effect of the vehicle. The weight loss of mice treated with an AMPK activator is significantly greater than the weight loss of control mice.

Biological Example 9

Assay for Sarcopenia

Adult DIO mice are used in these studies. Upon or soon after weaning, rats or mice are made obese due to exclusive access to diets containing fat and sucrose in higher proportions than in the control diet. The diet used to induce obesity is Research Diets D12451 chow (45% fat). The rodents ingest chow until they are significantly heavier and have a higher proportion of body fat than control diet rats, often 9 weeks. The rodents receive injections (1 to 4 per day) or continuous infusions of an AMPK activator of the present invention or the vehicle either orally, intraperitoneally, subcutaneously or intravenously. Food intake and body weights are measured daily or more frequently. Food intake is calculated as grams of food eaten per gram of body weight within each time interval and the appetite-suppressant and weight loss effect of the AMPK activator of the present invention is compared to the effect of the vehicle. The weight loss of mice treated with an AMPK activator is significantly greater than the weight loss of control mice.

The scope of the claims should not be limited by the preferred embodiments set forth in the examples, but should be given the broadest interpretation consistent with the description as a whole.

While the invention has been described and illustrated with reference to certain particular embodiments thereof, those skilled in the art will appreciate that various changes, modifications and substitutions can be made therein without departing from the scope of the invention. For example, effective dosages other than the particular dosages as set forth herein above may be applicable as a consequence of variations in the responsiveness of the mammal being treated for any of the indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention.

What is claimed is:

1. A compound of structural formula I:

$$\begin{array}{c} \text{(I)} \\ \\ \underset{V \overset{W}{\diagdown} Z}{\overset{U \overset{T}{\diagup} N}{\diagdown}} Y \\ \phantom{V W Z} X \end{array}$$

or a pharmaceutically acceptable salt thereof, wherein:
T is N;
U is —$CR^1$—;
V is —$CR^2$—;
W is —$CR^4$—;
X is —O—;
Y is selected from:

$$\text{\Large —}\!\!\bigcirc\!\!\text{O}$$

wherein Y is unsubstituted or substituted with 1, 2, 3, 4 or 5 substituents selected from $R^b$;
Z is $NR^5$;

each R1 is independently selected from:
(1) —(CH$_2$)$_p$aryl-aryl, and
(2) —(CH$_2$)$_p$aryl-heteroaryl,
wherein each CH$_2$ is unsubstituted or substituted with 1 or 2 substituents selected from: halogen, CF$_3$, —OH, —NH$_2$, C$_{1-6}$alkyl, —OC$_{1-6}$alkyl, NHC$_{1-6}$alkyl, and —N(C$_{1-6}$alkyl)$_2$, and wherein each aryl and heteroaryl is unsubstituted or substituted with 1, 2, 3 or 4 substituents independently selected from R$^a$, provided that when Y is:

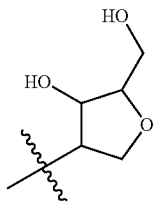 [SMILES: *C1COC(CO)C1O]

and R$^1$ is biphenyl, then R$^1$ is substituted with 1, 2, 3 or 4 substituents independently selected from R$^a$;
R$^2$ is selected from halogen;
R$^4$ is selected from hydrogen, halogen, and —C$_{1-6}$alkyl;
R$^5$ is selected from:
(1) hydrogen,
(2) —C$_{1-6}$alkyl,
(3) —C$_{1-6}$alkenyl,
(4) —(CH$_2$)$_u$OH,
(5) —CH$_2$CO$_2$H, and
(6) —CH$_2$CO$_2$C$_{1-6}$alkyl;
each R$^a$ is independently selected from the group consisting of:
(1) halogen,
(2) —(CH$_2$)$_m$OH,
(3) —C(O)R$^f$,
(4) —C$_{2-6}$cycloheteroalkyl,
(5) —SO$_2$—C$_{3-7}$cycloalkyl, and
(6) -heteroaryl,
wherein each CH$_2$ is unsubstituted or substituted with 1 or 2 substituents selected from: oxo, —OH, —(CH$_2$)$_{1-3}$OH, —CN, —NH$_2$, —NH(C$_{1-6}$alkyl), —N(C$_{1-6}$alkyl)$_2$, oxo, —C$_{1-6}$alkyl, —C$_{1-6}$alkyl substituted with 1-5 OH, —OC$_{1-6}$alkyl, halogen, —CH$_2$F, —CHF$_2$, —CF$_3$, —CO$_2$H, and —CO$_2$C$_{1-6}$alkyl, and wherein cycloheteroalkyl and heteroaryl are unsubstituted or substituted with 1, 2, 3 or 4 substituents selected from: oxo, —OH, —(CH$_2$)$_{1-5}$OH, —(CH$_2$)$_{1-5}$CN, —CN, —NH$_2$, —NH(C$_{1-6}$alkyl), —N(C$_{1-6}$alkyl)$_2$, —C$_{1-6}$alkyl substituted with 1-5 OH, —OC$_{1-6}$alkyl, halogen, —CH$_2$F, —CHF$_2$, —CF$_3$, —(CH$_2$)$_{1-5}$CF$_3$ optionally substituted with 1, 2 or 3 —OH, —CO$_2$H, —CO$_2$C$_{1-6}$alkyl, and —SO$_2$C$_{1-6}$alkyl;
each R$^b$ is independently selected from:
(1) hydrogen,
(2) —C$_{1-6}$alkyl,
(3) —C$_{1-6}$ alkenyl,
(4) —(CH$_2$)$_n$—C$_{3-10}$cycloalkyl,
(5) —(CH$_2$)$_n$—C$_{3-10}$cycloalkenyl,
(6) —(CH$_2$)$_n$—C$_{2-10}$cycloheteroalkyl,
(7) —(CH$_2$)$_n$—C$_{2-10}$cycloheteroalkenyl,
(8) —(CH$_2$)$_n$-aryl,
(9) —(CH$_2$)$_n$-heteroaryl,
(10) oxo,
(11) —(CH$_2$)$_n$—CF$_3$,
(12) —(CH$_2$)$_n$—CN,
(13) —(CH$_2$)$_r$-halogen,
(14) —(CH$_2$)$_s$—OH,
(15) —(CH$_2$)$_n$—NO$_2$,
(16) —(CH$_2$)$_n$—NH$_2$,
(17) —(CH$_2$)$_n$—NH(C$_{1-6}$alkyl),
(18) —(CH$_2$)$_n$—N(C$_{1-6}$alkyl)$_2$,
(19) —(CH$_2$)$_n$—NHCO$_2$H,
(20) —(CH$_2$)$_n$—OC$_{1-6}$alkyl,
(21) —(CH$_2$)$_n$—OC$_{1-6}$alkenyl,
(22) —(CH$_2$)$_n$—COC$_{1-6}$alkyl,
(23) —(CH$_2$)$_n$—CO$_2$H,
(24) —(CH$_2$)$_n$—OCOH,
(25) —(CH$_2$)$_n$—CO$_2$R$^i$,
(26) —(CH$_2$)$_n$—OC(O)R$^i$,
(27) —(CH$_2$)$_q$C(O)N(R$^e$)$_2$,
(28) —(CH$_2$)$_q$CO$_2$N(R$^e$)$_2$,
(29) —(CH$_2$)$_n$C(O)(CH$_2$)$_n$N(R$^g$)$_2$,
(30) —(CH$_2$)$_n$OC(O)(CH$_2$)$_n$N(R$^g$)$_2$,
(31) —(CH$_2$)$_n$N(R$^e$)C(O)C$_{1-6}$alkyl,
(32) —(CH$_2$)$_n$N(R$^e$)SO$_2$R$^i$,
(33) —(CH$_2$)$_n$SO$_2$C$_{1-6}$alkyl,
(34) —(CH$_2$)$_n$SO$_2$N(R$^e$)R$^g$,
(35) —(CH$_2$)$_n$SO$_2$N(R$^e$)C(O)R$^i$,
(36) —(CH$_2$)$_n$SO$_2$N(R$^e$)CO$_2$R$^i$,
(37) —(CH$_2$)$_n$SO$_2$N(R$^e$)CON(R$^g$)$_2$,
(38) —(CH$_2$)$_n$C(O)N(R$^e$)SO$_2$R$^i$,
(39) —(CH$_2$)$_n$N(R$^e$)C(O)N(R$^g$)$_2$,
(40) =N(OH), and
(41) =N(OC$_{1-6}$alkyl),
wherein each CH$_2$ is unsubstituted or substituted with 1 or 2 substituents selected from: —C$_{1-6}$alkyl, —OH, halogen and —NH$_2$ wherein each NH is unsubstituted or substituted with 1 substituent selected from R$^c$, and wherein each alkyl, cycloalkyl, cycloalkenyl, cycloheteroalkyl, cycloheteroalkenyl, aryl and heteroaryl is unsubstituted or substituted with 1, 2, 3 or 4 substituents selected from R$^c$;
each R$^c$ is independently selected from:
(1) halogen,
(2) oxo,
(3) —(CH$_2$)$_r$OH,
(4) —(CH$_2$)$_r$N(R$^e$)$_2$,
(5) —(CH$_2$)$_r$CN,
(6) —C$_{1-6}$alkyl,
(7) —CF$_3$,
(8) —C$_{1-6}$alkyl-OH,
(9) —OCH$_2$OC$_{1-6}$alkyl,
(10) —(CH$_2$)$_r$OC$_{1-6}$alkyl,
(11) —OCH$_2$aryl,
(12) —(CH$_2$)$_r$SC$_{1-6}$alkyl,
(13) —(CH$_2$)$_r$C(O)R$^f$,
(14) —(CH$_2$)$_r$C(O)N(R$^e$)$_2$,
(15) —(CH$_2$)$_r$CO$_2$H,
(16) —(CH$_2$)$_r$CO$_2$R$^f$,
(17) —(CH$_2$)$_r$C$_{3-7}$cycloalkyl,
(18) —(CH$_2$)$_r$C$_{2-6}$cycloheteroalkyl,
(19) —(CH$_2$)$_r$aryl, and
(20) —(CH$_2$)$_r$heteroaryl,
wherein each CH$_2$ is unsubstituted or substituted with 1 or 2 substituents selected from: oxo, —OH, —CN, —N(R$^h$)$_2$, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl and heteroaryl, and wherein alkyl, cycloalkyl, cycloheteroalkyl, aryl and heteroaryl are unsubstituted or substituted with 1, 2, 3 or 4 substituents selected from: oxo, —OH, —CN, —N(R$^h$)$_2$, —C$_{1-6}$alkyl, —OC$_{1-6}$ alkyl, halogen, —CH$_2$F, —CHF$_2$, —CF$_3$, —CO$_2$H, —CO$_2$C$_{1-6}$alkyl, —C$_{3-7}$cycloalkyl and heteroaryl;
each R$^e$, R$^g$ and R$^h$ is independently selected from:
(1) hydrogen,
(2) —C$_{1-6}$alkyl, and
(3) —O—C$_{1-6}$alkyl,
wherein alkyl is unsubstituted or substituted with 1, 2, 3 or 4 substituents selected from: —OH, oxo, halogen, C$_{1-6}$alkyl, —OC$_{1-6}$alkyl, —NH$_2$, —NH(C$_{1-6}$alkyl), and —N(C$_{1-6}$alkyl)$_2$;
each Rj is independently selected from:
(1) hydrogen,
(2) C$_{1-6}$alkyl,
(3) C$_{3-6}$cycloalkyl,
(4) —C(O)R$^i$,
(5) —CO$_2$R$^i$, and
(6) —SO$_2$R$^i$,
wherein alkyl and cycloalkyl are unsubstituted or substituted with 1, 2, 3 or 4 substituents selected from: —OH, oxo, halogen, C$_{1-6}$alkyl, —OC$_{1-6}$alkyl, —NH$_2$, —NH(C$_{1-6}$alkyl), and —N(C$_{1-6}$alkyl)$_2$;
each R$^f$ and R$^i$ is independently selected from:
(1) C$_{1-6}$alkyl,
(2) —(CH$_2$)$_r$C$_{4-7}$cycloalkyl,
(3) —(CH$_2$)$_r$C$_{4-7}$cycloalkenyl,
(4) —(CH$_2$)$_r$C$_{3-7}$cycloheteroalkyl,
(5) —(CH$_2$)$_r$C$_{3-7}$cycloheteroalkenyl,
(6) —(CH$_2$)$_r$aryl, and
(7) —(CH$_2$)$_r$heteroaryl,
wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl, and heteroaryl;
n is 0, 1, 2, 3 or 4;
m is 0, 1, 2, 3 or 4;
p is 0, 1, 2, or 3;
q is 0, 1, 2, 3 or 4;
r is 0, 1 or 2;
s is 0, 1, 2, 3 or 4;
t is 0, 1, 2, 3 or 4; and
u is 0, 1, 2, 3 or 4.

2. The compound according to claim 1, wherein Y is selected from:

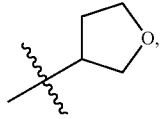

wherein Y is substituted with 1, 2, 3, 4 or 5 substituents selected from R$^b$; or
a pharmaceutically acceptable salt thereof.

3. The compound according to claim 1, wherein Y is:

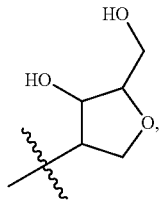

wherein Y is unsubstituted or substituted with 1, 2 or 3 substituents selected from R$^b$; or a pharmaceutically acceptable salt thereof.

4. The compound according to claim 1, wherein each R$^1$ is independently selected from:
(1) biphenyl,
(2) phenyl-naphthalene,
(3) phenyl-pyridine, and
(4) phenyl-dihydropyrrolopyrazole,
wherein each phenyl, naphthalene, pyridine and dihydropyrrolopyrazole is unsubstituted or substituted with 1, 2, 3 or 4 substituents independently selected from R$^a$, and wherein each biphenyl is substituted with 1, 2, 3 or 4 substituents independently selected from R$^a$; and
R$^2$ is selected from halogen;
or a pharmaceutically acceptable salt thereof.

5. The compound according to claim 1, wherein
R$^1$ is biphenyl, wherein each phenyl is substituted with 1, 2, 3 or 4 substituents independently selected from R$^a$; and
R$^2$ is halogen;
or a pharmaceutically acceptable salt thereof.

6. The compound according to claim 1, wherein
R$^3$ is hydrogen or absent; R$^4$ is hydrogen; and R$^5$ is hydrogen; or a pharmaceutically acceptable salt thereof.

7. The compound according to claim 1, wherein
R$^3$ is hydrogen or absent; R$^4$ is hydrogen; R$^5$ is hydrogen; and R$^2$ is halogen; or a pharmaceutically acceptable salt thereof.

8. The compound according to claim 1 wherein:
T is N;
U is —CR$^1$—;
V is —CR$^2$—;
W is —CR$^4$—;
X is —O—;
Y is selected from:

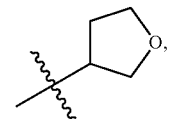

wherein Y is unsubstituted or substituted with 1, 2, 3, 4 or 5 substituents selected from R$^b$;
Z is NR$^5$;
R$^2$ is halogen;
R$^4$ is hydrogen;
R$^5$ is hydrogen;
or a pharmaceutically acceptable salt thereof.

9. The compound according to claim 1 wherein:
T is N;
U is —CR$^1$—;
V is —CR$^2$—;
W is —CR$^4$—;
X is —O—;
Y is:

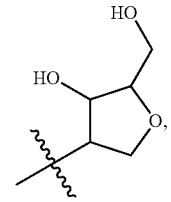

wherein Y is unsubstituted or substituted with 1, 2 or 3 substituents selected from R$^b$;

Z is $NR^5$;
$R^2$ is halogen;
$R^4$ is hydrogen; and
$R^5$ is hydrogen;
or a pharmaceutically acceptable salt thereof.

10. A compound selected from:

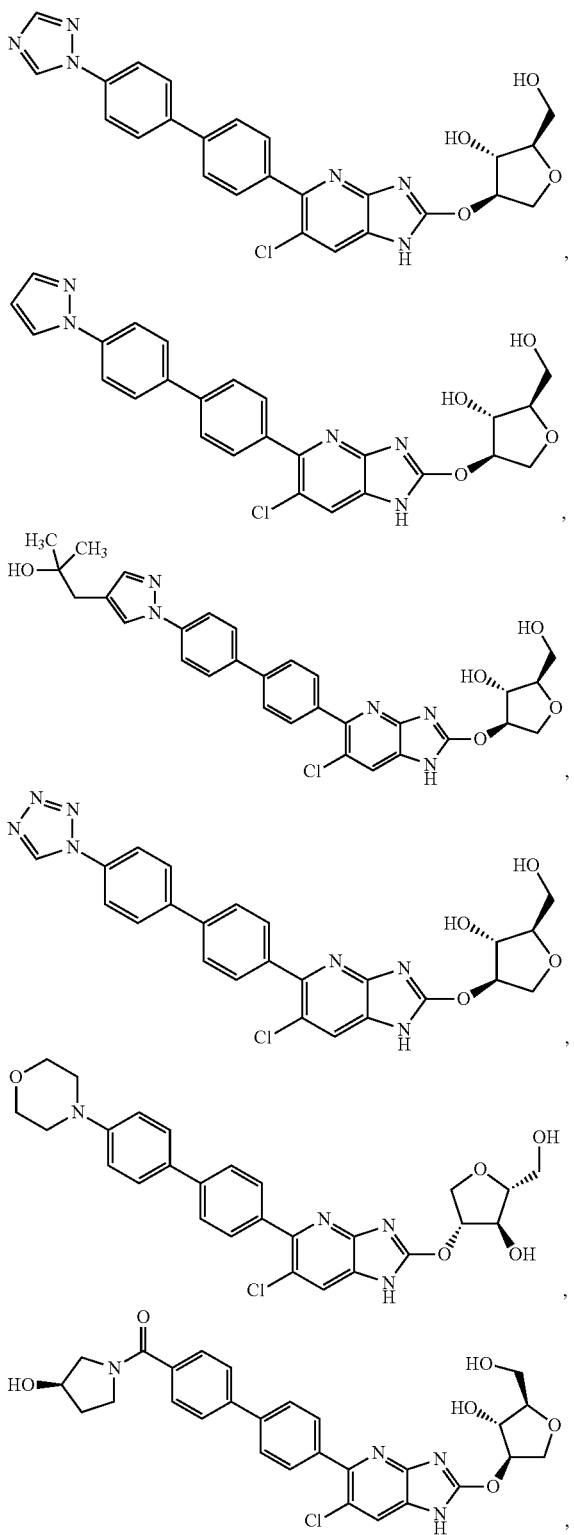

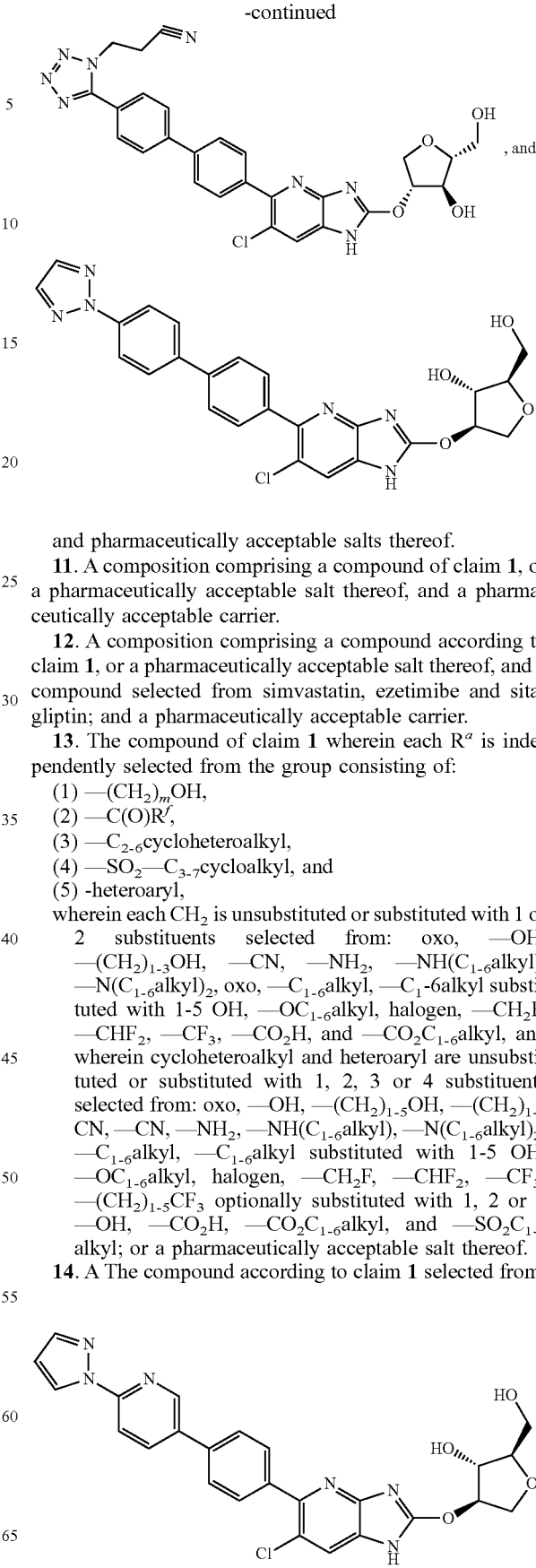

and pharmaceutically acceptable salts thereof.

11. A composition comprising a compound of claim 1, or a pharmaceutically acceptable salt thereof, and a pharmaceutically acceptable carrier.

12. A composition comprising a compound according to claim 1, or a pharmaceutically acceptable salt thereof, and a compound selected from simvastatin, ezetimibe and sitagliptin; and a pharmaceutically acceptable carrier.

13. The compound of claim 1 wherein each $R^a$ is independently selected from the group consisting of:
(1) —$(CH_2)_m$OH,
(2) —C(O)$R^f$,
(3) —$C_{2-6}$cycloheteroalkyl,
(4) —$SO_2$—$C_{3-7}$cycloalkyl, and
(5) -heteroaryl,
wherein each $CH_2$ is unsubstituted or substituted with 1 or 2 substituents selected from: oxo, —OH, —$(CH_2)_{1-3}$OH, —CN, —$NH_2$, —NH($C_{1-6}$alkyl), —N($C_{1-6}$alkyl)$_2$, oxo, —$C_{1-6}$alkyl, —$C_1$-6alkyl substituted with 1-5 OH, —$OC_{1-6}$alkyl, halogen, —$CH_2F$, —$CHF_2$, —$CF_3$, —$CO_2H$, and —$CO_2C_{1-6}$alkyl, and wherein cycloheteroalkyl and heteroaryl are unsubstituted or substituted with 1, 2, 3 or 4 substituents selected from: oxo, —OH, —$(CH_2)_{1-5}$OH, —$(CH_2)_{1-5}$CN, —CN, —$NH_2$, —NH($C_{1-6}$alkyl), —N($C_{1-6}$alkyl)$_2$, —$C_{1-6}$alkyl, —$C_{1-6}$alkyl substituted with 1-5 OH, —$OC_{1-6}$alkyl, halogen, —$CH_2F$, —$CHF_2$, —$CF_3$, —$(CH_2)_{1-5}CF_3$ optionally substituted with 1, 2 or 3 —OH, —$CO_2H$, —$CO_2C_{1-6}$alkyl, and —$SO_2C_{1-6}$alkyl; or a pharmaceutically acceptable salt thereof.

14. A The compound according to claim 1 selected from:

123
-continued
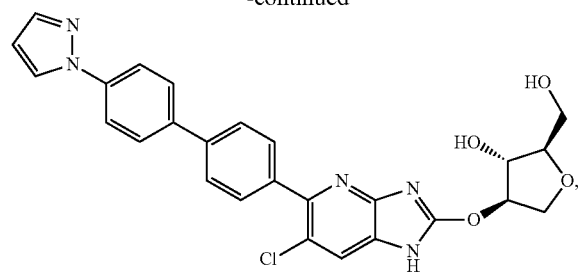
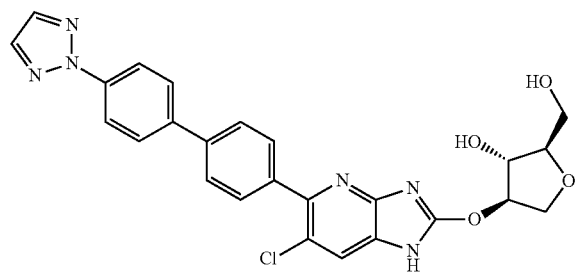
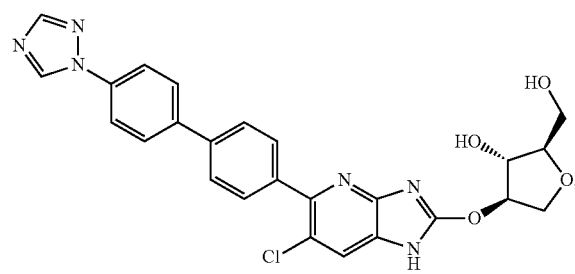
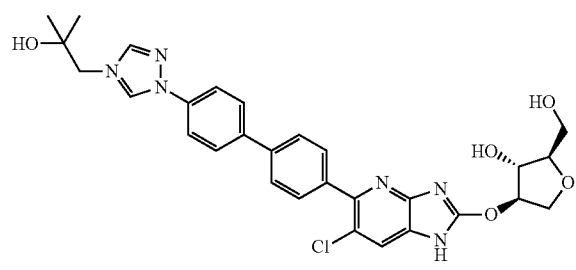
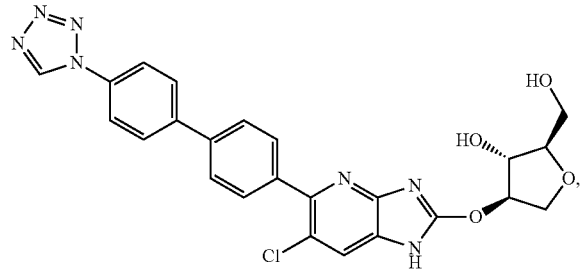
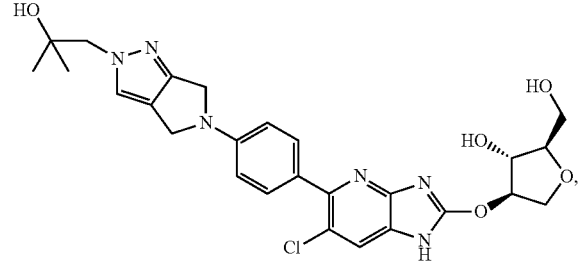
124
-continued
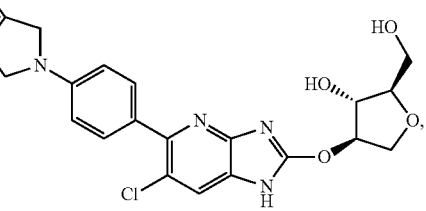
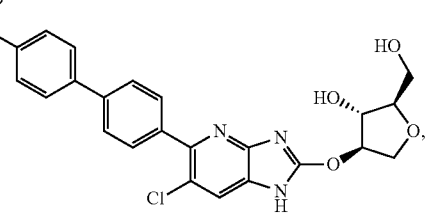
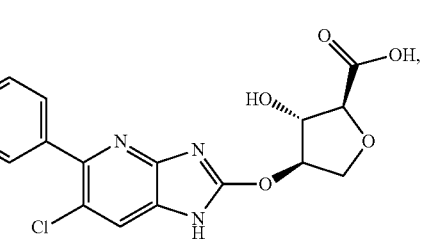
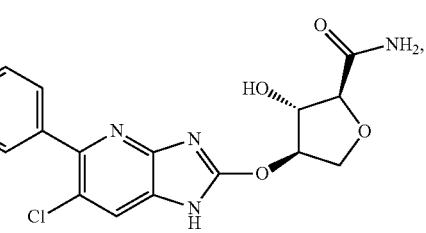
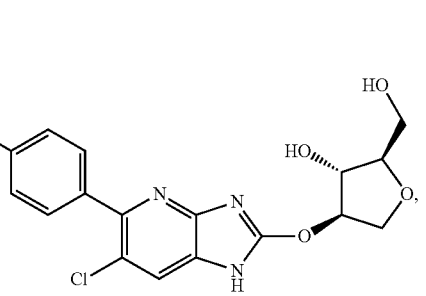
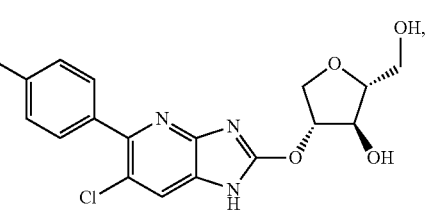

-continued
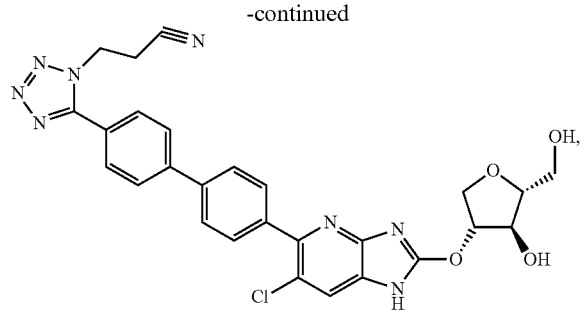
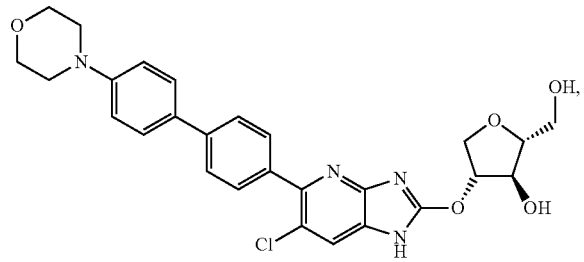
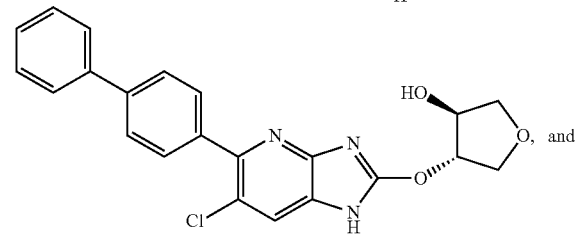
or a pharmaceutically acceptable salt thereof.
15. A compound selected from:
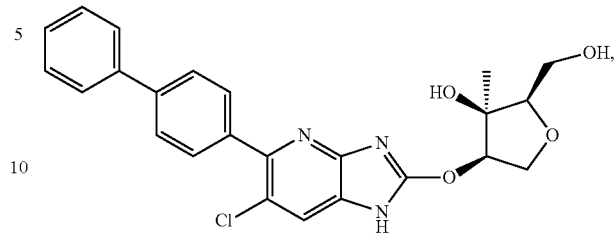
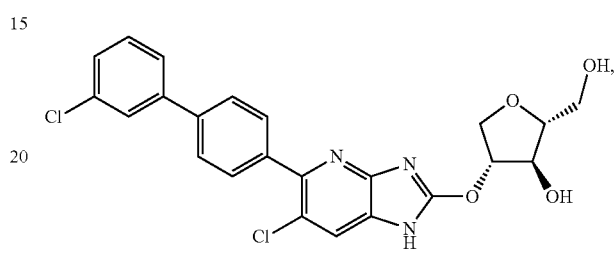
and
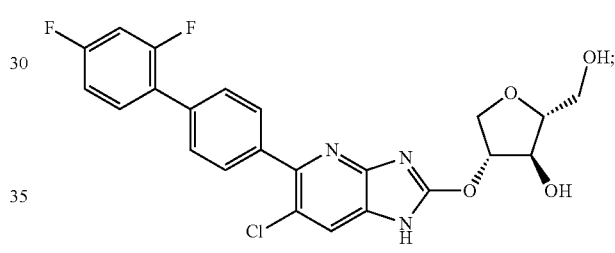
or a pharmaceutically acceptable salt thereof.
* * * * *